US012806296B2

(12) United States Patent
Bénard et al.

(10) Patent No.: US 12,806,296 B2
(45) Date of Patent: Nov. 24, 2026

(54) RADIOLABELLED CXCR4-TARGETING COMPOUNDS FOR DIAGNOSIS AND THERAPY

(71) Applicants: PROVINCIAL HEALTH SERVICES AUTHORITY, Vancouver (CA); THE UNIVERSITY OF BRITISH COLUMBIA, Vancouver (CA)

(72) Inventors: François Bénard, Vancouver (CA); Kuo-Shyan Lin, Richmond (CA); Etienne Rousseau, Sherbrooke (CA); Zhengxing Zhang, Vancouver (CA); Daniel Kwon, Coquitlam (CA); Joseph Lau, Richmond (CA); Carlos Uribe Munoz, Surrey (CA); Jerome Lozada, Vancouver (CA); David Perrin, Vancouver (CA)

(73) Assignees: PROVINCIAL HEALTH SERVICES AUTHORITY, Vancouver (CA); THE UNIVERSITY OF BRITISH COLUMBIA, Vancouver (CA)

( * ) Notice: Subject to any disclaimer, the term of this patent is extended or adjusted under 35 U.S.C. 154(b) by 1361 days.

(21) Appl. No.: 17/604,708

(22) PCT Filed: Apr. 17, 2020

(86) PCT No.: PCT/CA2020/050521

§ 371 (c)(1),
(2) Date: Oct. 18, 2021

(87) PCT Pub. No.: WO2020/210919

PCT Pub. Date: Oct. 22, 2020

(65) Prior Publication Data

US 2022/0218852 A1 Jul. 14, 2022

Related U.S. Application Data

(60) Provisional application No. 62/835,733, filed on Apr. 18, 2019.

(51) Int. Cl.

| | |
|---|---|
| ***A61K 51/08*** | (2006.01) |
| ***A61K 51/04*** | (2006.01) |
| ***A61P 35/00*** | (2006.01) |

(52) U.S. Cl.

CPC ........ *A61K 51/088* (2013.01); *A61K 51/0482* (2013.01); *A61P 35/00* (2018.01)

(58) Field of Classification Search

CPC ...... A61K 51/00; A61K 51/08; A61K 51/088; A61K 51/04; A61K 51/0482; A61K 51/0402; A61K 51/0497

See application file for complete search history.

(56) References Cited

U.S. PATENT DOCUMENTS

| | | | |
|---|---|---|---|
| 5,650,134 | A | 7/1997 | Albert et al. |
| 6,166,226 | A | 12/2000 | Buchwald et al. |
| 7,041,859 | B1 | 5/2006 | Kabalka |
| 8,114,381 | B2 | 2/2012 | Perrin et al. |
| 8,153,101 | B2 | 4/2012 | McBride et al. |
| 8,574,546 | B2 | 11/2013 | Perrin et al. |
| 8,691,761 | B2 | 4/2014 | Rivier et al. |
| 10,150,804 | B2 | 12/2018 | Benard et al. |

(Continued)

FOREIGN PATENT DOCUMENTS

| | | |
|---|---|---|
| CA | 2267153 | 4/1998 |
| CA | 2710923 | 2/2010 |

(Continued)

OTHER PUBLICATIONS

Suzuki et al, Scientific Reports, Oct. 25, 2019, vol. 9, 15284, 10 pages (Year: 2019).*

Extended European Search Report for European Application No. 21881418.4 mailed Nov. 5, 2024, 18 pages.

Merriam-Webster Inc, "Definition of Derivative" [online]. Retrieved from: http://beta.www.merriam-webster.com/dictionary/derivative; retrieved on Dec. 9, 2015; 10 pages.

Antunes et al., "Influence of Different Spacers on the Biological Profile of a DOTA-Somatostatin Analogue," Bioconjugate Chemistry, 2007, vol. 18, pp. 84-92.

Bagutski et al. "Improved method for the conversion of pinacolboronic esters into trifluoroborate salts: facile synthesis of chiral secondary and tertiary trifluoroborates," Tetrahedron 2009, 65, pp. 9956-9960.

Banerjee et al., "Clinical applications of Gallium-68," Applied Radiation and Isotopes, 2013, vol. 76, pp. 2-13.

Berge et al., "Pharmaceutical Salts," J. Pharm Sci, 1977, vol. 66, No. 1, pp. 1-19.

(Continued)

*Primary Examiner* — D. L. Jones

(74) *Attorney, Agent, or Firm* — Thompson Coburn LLP

(57) ABSTRACT

This application relates to compounds of Formula (I): [targeting peptide]-N($R^1$)—$X^1$($R^2$)$L^1$-[linker]-$R^X_{n1}$ (I). The targeting peptide is cyclo[L-Phe-L-Tyr-L-Lys(iPr)-D-Arg-L-2-Nal-Gly-D-Glu]-L-Lys(iPr). $R^1$ is H or methyl. $X^1$ is an optionally substituted $C_1$-$C_{15}$ hydrocarbon optionally comprising heteroatoms. $R^2$ is C(O)OH or C(O)$NH_2$. $L^1$ is a linkage (thiolether, amide, maleimide-thiol, triazole). The linker has a net negative charge at physiological pH and is a linear or branched chain of 1-10 units of $X^2L^2$ and/or $X^2(L^2)_2$, wherein: each $X^2$ is, independently, an optionally substituted $C_1$-$C_{15}$ hydrocarbon optionally comprising heteroatoms; and each $L^2$ is a linkage. The linker optionally further comprises an albumin binder bonded to an $L^2$. Each $R^X$ is a radiolabelling group linked through a separate $L^2$, selected from: a metal chelator; a prosthetic group containing trifluoroborate ($BF_3$); or a prosthetic group containing a silicon-fluorine-acceptor moiety. The compounds may be useful for imaging CXCR4-expressing tissues or for treating CXCR4-associated diseases or conditions (e.g. cancer).

31 Claims, 6 Drawing Sheets

(56) References Cited

U.S. PATENT DOCUMENTS

| | | | |
|---|---|---|---|
| 10,556,023 B2 | 2/2020 | Perrin et al. | |
| 11,207,432 B2 | 12/2021 | Perrin et al. | |
| 12,427,209 B2 * | 9/2025 | Perrin | A61K 51/0497 |
| 2006/0128664 A1 | 6/2006 | Holmes-Farley et al. | |
| 2008/0300177 A1 | 12/2008 | Kohn et al. | |
| 2009/0028791 A1 | 1/2009 | Balatoni et al. | |
| 2014/0147381 A1 | 5/2014 | Espenan | |
| 2016/0311858 A1 | 10/2016 | Kariyuki et al. | |
| 2016/0333068 A1 | 11/2016 | Bénard et al. | |
| 2020/0222563 A1 | 7/2020 | Perrin et al. | |
| 2021/0024605 A1 | 1/2021 | Perrin et al. | |
| 2022/0062445 A1 | 3/2022 | Perrin et al. | |
| 2022/0062446 A1 | 3/2022 | Perrin et al. | |
| 2024/0100203 A1 | 3/2024 | Bénard et al. | |
| 2024/0342321 A1 | 10/2024 | Bénard | |
| 2025/0242064 A1 | 7/2025 | Bénard et al. | |

FOREIGN PATENT DOCUMENTS

| | | | | |
|---|---|---|---|---|
| CA | 2810241 | 3/2012 | | |
| CA | 2931554 | 6/2015 | | |
| CN | 102066974 A | 5/2011 | | |
| CN | 105636924 A | 6/2016 | | |
| CN | 106967152 A | 7/2017 | | |
| CN | 108699087 A | 10/2018 | | |
| CN | 109517039 A | 3/2019 | | |
| EP | 1027316 A1 | 8/2000 | | |
| EP | 1089305 A2 | 4/2001 | | |
| EP | 2226328 A1 | 9/2010 | | |
| EP | 2555796 A1 | 2/2013 | | |
| EP | 3459559 A1 * | 3/2019 | | A61K 38/10 |
| WO | WO 2005/077967 A1 | 8/2005 | | |
| WO | WO 2007/032005 A2 | 3/2007 | | |
| WO | WO-2008150689 A1 | 12/2008 | | |
| WO | WO 2009/012596 A1 | 1/2009 | | |
| WO | WO-2009135015 A2 | 11/2009 | | |
| WO | WO 2011/124931 A1 | 10/2011 | | |
| WO | WO 2012/094334 A1 | 7/2012 | | |
| WO | WO 2012/118909 A1 | 9/2012 | | |
| WO | WO 2014/134716 A1 | 9/2014 | | |
| WO | WO-2015055318 A1 | 4/2015 | | |
| WO | WO 2015/100498 A1 | 7/2015 | | |
| WO | WO-2017117687 A1 | 7/2017 | | |
| WO | WO 2019/050564 A1 | 3/2019 | | |
| WO | WO-2019057445 A1 | 3/2019 | | |
| WO | WO 2020/009093 A1 | 1/2020 | | |
| WO | WO-2020018700 A1 | 1/2020 | | |
| WO | WO-2020210919 A1 | 10/2020 | | |
| WO | WO-2021168567 A1 | 9/2021 | | |
| WO | WO-2022082312 A1 | 4/2022 | | |
| WO | WO-2023201435 A1 | 10/2023 | | |

OTHER PUBLICATIONS

Bernard-Gauthier et al., "18F-Labeled Silicon-Based Fluoride Acceptors: Potential Opportunities for Novel Positron Emitting Radiopharmaceuticals," Biomed Res Int, 2014, vol. 2014, Article ID: 454503, 20 pages.

Bernard-Gauthier, V. et al., "From Unorthodox to Established: The Current Status of 18F-Trifluoroborate- and 18F-SIFA-Based Radiopharmaceuticals in PET Nuclear Imaging," Bioconjugate Chemistry, 2016, vol. 27, pp. 267-279.

Bleul et al., "The HIV coreceptors CXCR4 and CCR5 are differentially expressed and regulated on human T lymphocytes," PNAS, 1997, vol. 94, pp. 1925-1930.

Boutourine et al., "Rapid Routes of Synthesis of Chemically Reactive and Highly Radioactive Labeled α- and β-Oligonucleotide Derivatives for in Vivo Studies," Bioconjungate Chemistry, 1:350-356, (1990).

Breeman et al., "Somatostatin receptor-mediated imaging and therapy: basic science, current knowledge, limitations and future perspectives," European Journal of Nuclear Medicine, Sep. 2001, vol. 28, No. 9, pp. 1421-1429.

Buchmann et al., "Comparison of 68Ga-DOTATOC PET and 111In-DTPAOC (Octreoscan)SPECT in patients with neuroendocrine tumours," Eur J Nucl Med Mol Imaging., 2007, vol. 34, pp. 1617-1626.

Cai et al., "RGD-based PET tracers for imaging receptor integrin αvβ3 expression," Journal of Labelled Compounds and Radiopharmaceuticals, 2013, vol. 56, pp. 264-279.

Chatterjee et al., "The Intricate Role of CXCR4 in Cancer," Adv Cancer Res, 2014, 124:31-82.

Chin et al., "First Experience with Clinical-Grade [18F]FP-P(RGD)2: An Automated Multi- step Radiosynthesis for Clinical PET Studies," Mol Imaging Biol., 2012, vol. 14, pp. 88-195.

ClinicalTrials.gov, "LY2510924, Idarubicin and Cytarabine in Patients With Relapsed or Refractory Acute Myeloid Leukemia," ClinicalTrials.gov identifier: NCT02652871, Jan. 12, 2016, 9 pages.

De Clerq, "The AMD3100 story: the path to the discovery of a stem cell mobilizer (Mozobil)," Biochem Pharmacol, 2009, vol. 77, No. 11, pp. 1655-1664 (32 pages total).

Demmer et al., "PET Imaging of CXCR4 Receptors in Cancer by a New Optimized Ligand," ChemMedChem, 2011, vol. 6, pp. 1789-1791.

Doring et al., "The CXCL12/CXCR4 chemokine ligand/receptor axis in cardiovascular disease," Front Physiol., 2014, vol. 5, Article 212, 23 pages.

Duda et al., "CXCL12 (SDF1a)-CXCR4/CXCR7 Pathway Inhibition: An Emerging Sensitizer for Anticancer Therapies?" Clin Cancer Res, 2011, vol. 17, No. 8, pp. 2074-2080.

Dumas et al., "Synthesis of Acyltrifluoroborates," Organic Letters, 14:2138-2141, (2012).

Eberl et al., "High beam current operation of a PETtraceTM cyclotron for 18F production," Applied Radiation and Isotopes, 2012, vol. 70, pp. 922-930.

EP Office Action mailed Mar. 10, 2020 in corresponding European Appln No. 14759809.8 (20 page).

Extended European Search Report for EP2964658 mailed Oct. 4, 2016, 12 pages.

Extended Search Report for European Patent Application No. 15733077.0, dated Jun. 19, 2017, 6 pages.

Fani et al., "Unexpected Sensitivity of sst2 Antagonists to N-Terminal Radiometal Modifications," The Journal of Nuclear Medicine, Sep. 2012, vol. 53, No. 9, pp. 1481-1489.

Feng et al., "HIV-1 Entry Cofactor: Functional cDNA Cloning of a Seven-Transmembrane, G Protein-Coupled Receptor," Science, 1996, 272:872-877, Abstract, 6 pages.

Gabriel et al., "68Ga-DOTA-Tyr3-Octreotide PET in Neuroendocrine Tumors: Comparison with Somatostatin Receptor Scintigraphy and CT," The Journal of Nuclear Medicine, Apr. 2007, vol. 48, No. 4, pp. 508-518.

Gabriel et al., "An Intrapatient Comparison of 99mTc-EDDA/HYNIC-TOC with 111In-DTPA Octreotide for Diagnosis of Somatostatin Receptor-Expressing Tumors," The Journal of Nuclear Medicine, May 2003, vol. 44, No. 5, pp. 708-716.

Ginj et al., "Design, Synthesis, and Biological Evaluation of Somatostatin-Based Radiopeptides," Chemistry & Biology, Oct. 2006, vol. 13, pp. 1081-1090.

Gourni et al., "PET of CXCR4 Expression by a 68Ga-Labeled Highly Specific Targeted Contrast Agent," J. Nucl. Med., 2011, vol. 52, No. 11, pp. 1803-1810.

Guo et al., "Preparation and Biological Evaluation of 64Cu Labeled Tyr3-Octreotate using a Phosphonic Acid-Based Cross-Bridged Macrocyclic Chelator," Bioconjugate Chemistry, 2012, vol. 23, pp. 1470-1477.

Harwig, C.W., et al., "Synthesis and characterization of 2,6-difluoro-4-carboxyphenylboronic acid and a biotin derivative thereof as captors of anionic aqueous [18F]-fluoride for the preparation of [18F/19F]-labeled aryltrifluoroborates with high kinetic stability," Tetrahedron Letters, 2008, vol. 49, pp. 3152-3156.

Henze et al., "PET Imaging of Somatostatin Receptors Using [68GA]DOTA-D-Phe1-Tyr3-Octreotide: First Results in Patients with Meningiomas," The Journal of Nuclear Medicine, Jul. 2001, vol. 42, No. 7, pp. 1053-1056.

Herrmann et al., "First-in-Human Experience of CXCR4-Directed Endoradiotherapy with 177Lu- and 90Y-Labeled Pentixather in

(56) References Cited

OTHER PUBLICATIONS

Advanced-Stage Multiple Myeloma with Extensive Intra- and Extramedullary Disease," J Nucl Med, 2016, vol. 57, No. 2, pp. 248-251.
Imahori et al., "Positron Emission Tomography-based Boron Neutron Capture Therapy Using Boronophenylalanine for High-Grade Gliomas: Part I," Clinical Cancer Research, vol. 4, Aug. 1998, pp. 1825-1832.
Imahori et al., "Positron Emission Tomography-based Boron Neutron Capture Therapy Using Boronophenylalanine for High-Grade Gliomas: Part II," Clinical Cancer Research, vol. 4, Aug. 1998, pp. 1833-1841.
International Search Report and Written Opinion for International (PCT) Patent Application No. PCT/CA2015/000002, mailed May 4, 2015, 10 pages.
International Search Report and Written Opinion of the International Searching Authority for International Application No. PCT/CA2019/051853, dated Feb. 18, 2020, 8 pages.
International Search Report and Written Opinion of the International Searching Authority for International Application No. PCT/CA2020/050521, dated Jul. 29, 2020, 7 pages.
International Preliminary Report Patentability, dated Aug. 14, 2006, corresponding to PCT/CA2005/000195, 6 pages.
Ishiwata et al., "4-Borono-2[18F]-D,L,phenylalanine: A Possible Tracer for Melanoma Diagnosis with PET," International Journal of Radiation Applications and Instrumentation. Part B, Nuclear Medicine and Biology, 1992, vol. 19, No. 3, pp. 311-318.
Ishiwata et al., "A unique in vivo assessment of 4-[10B] borono-L-phenylalanine in tumour tissues for boron neutron capture therapy of malignant melanomas using positron emission tomography and 4-borono-2-[18F]fluoro-L-phenylalanine," Melanoma Research, 1992, vol. 2, pp. 171-179.
Kabalka, G., et al., "Evaluation of Fluorine-18-BPA-Fructose for Boron Neutron Capture Treatment Planning," The Journal of Nuclear Medicine, vol. 38, No. 11, Nov. 1997, pp. 1762-1767.
Kabalka, G., et al., "The Development of Boron Neutron Capture Agents Utilizing Positron Emission Tomography," Special publication Royal Society of Chemistry (Great Britain), vol. 253, (2000), Contemporary Boron Chemistry—Medicinal Applications, pp. 120-126.
Kayani "A Comparison of 68Ga-DOTATATE and 18F-FDG PET/CT in Pulmonary Neuroendocrine Tumors," The Journal of Nuclear Medicine, Dec 2009, vol. 50, No. 12, pp. 1927-1932.
Keenan et al., "RADAR Realistic Animal Model Series for Dose Assessment," J Nucl Med, 2010, vol. 51, No. 3, pp. 471-476.
Kemerink et al., "Effect of the positron range of 18F, 68Ga and 1241 on PET/CT in lung equivalent materials," Eur J Nucl Med Mol Imaging, 2011, vol. 38, pp. 940-948.
Kirkham et al. "Synthesis of Ynone Trifluoroborates toward Functionalized Pyrazoles," Org. Letters, 2012, vol. 14, No. 20, pp. 5354-5357.
Kostikov et al., "Oxalic Acid Supported Si-18F-Radiofluorination: One-Step Radiosynthesis of N-Succinimidyl 3-(Di-tert-butyl[18F]fluorosilyl) benzoate ([18F]SiFB) for Protein Labeling," Bioconjug Chem, 2012, vol. 23, pp. 106-114.
Kostikov et al., "Synthesis of [18F]SiFB: a prosthetic group for direct protein radiolabeling for application in positron emission tomography," Nature Protocols, 2012, vol. 7, pp. 1956-1963, Abstract, 9 pages.
Krausz et al., "SPECT/CT hybrid imaging with 111In-pentetreotide in assessment of neuroendocrine tumours," Clinical Endocrinology, 2003, vol. 59, pp. 565-573.
Kuo et al., "One-Step 18F-Labeling and Preclinical Evaluation of Prostate-Specific Membrane Antigen Trifluoroborate Probes for Cancer Imaging," J Nucl Med, 2019, vol. 60, No. 8, pp. 1160-1166.
Kwekkeboom et al. "Peptide Receptor Radionuclide Therapy in Patients With Gastroenteropancreatic Neuroendocrine Tumors," Seminars in Nuclear Medicine, Mar. 2010, vol. 40, No. 2, pp. 78-88.
Kwekkeboom et al. "Somatostatin receptor-based imaging and therapy of gastroenteropancreatic neuroendocrine tumors," Endocr Relat Cancer., 2010, vol. 17, pp. R53-R73.
Laforest et al. "Image quality with non-standard nuclides in PET," QJ Nucl Med Mol Imaging, 2008, vol. 52, pp. 151-158.
Lau et al., "[68Ga]Ga/[177Lu]Lu-BL01, a Novel Theranostic Pair for Targeting C-X-C Chemokine Receptor 4," J et al. Mol. Pharmaceutics 2019, 16, 11, 4688-4695.
Laverman et al., "A Novel Facile Method of Labeling Octreotide with $^{18}$F-Fluorine, " The Journal of Nuclear Medicine, Mar. 2010, vol. 51(3), pp. 454-461.
Laverman et al., "Optimized labeling of NOTA-conjugated octreotide with F-18," Tumor Biol., 2012, vol. 33, pp. 427-434.
Laverman et al., "Radiolabelled peptides for oncological diagnosis," Eur J Nucl Med Mol Imaging, 2012, 39 Suppl 1(Suppl 1):S78-S92.
Lawrence et al. "Regiospecific Functionalized of Methyl C—H Bonds of Alkyl Groups in Reagents with Heteroatom Functionality," J. Am. Chem. Soc, 2004, vol. 126, pp. 15334-15335.
Lennox et al., "Organotrifluoroborate Hydrolysis: Boronic Acid Release Mechanism and an Acid-Base Paradox in Cross-Coupling," J. Am. Chem. Soc, 134:7431-7441, (2012).
Leyton et al., "Targeting Somatostatin Receptors: Preclinical Evaluation of Novel $^{18}$F-Fluoroethyltriazole-Tyr$^3$-Octreotate Analogs for PET," The Journal of Nuclear Medicine, Sep. 2011, vol. 52(9), pp. 1441-1448.
Li et al. "Hydrolytic stability of nitrogenous-heteroaryltrifluoroborates under aqueous conditions at near neutral pH," Journal of Fluorine Chemistry, 130:377-382, (2009).
Li et al., "One-step and one-pot-two-step radiosynthesis of cyclo-RGD-$^{18}$F-aryltrifluoroboronate conjugates for functional imaging," Am. J. Nucl. Med. Mol. Imaging, 2013, vol. 3(1), pp. 44-56.
Liu et al., "'Kit-like' radiosynthesis and biological evaluation of an F-labeled 4-(2-Aminoethyl)- benzenesulfonamide (AEBS) trimer for imaging carbonic anhydrase IX expression with positron emission tomography," World Molecular Imaging Congress, Sep. 19, 2013—poster, 1 page.
Liu et al., "(18)F-trifluoroborate derivatives of [des-arg(10)]kallidin for imaging bradykinin b1 receptor expression with positron emission tomography," Molecular Pharmaceutics, 2015, vol. 12, No. 3, pp. 974-982.
Liu et al., "An Organotrifluoroborate for Broadly Applicable One-Step 18F-Labeling," Angew Chem Int Ed., 2014, vol. 53, pp. 11876-11880.
Liu et al., "Facile synthesis and biological evaluation of an 18F-labeled 4-(2-aminoethyl) benzenesulfonamide (AEBS) trimer for imaging carbonic anhydrase IX expression with positron emission tomography," World Molecular Imaging Congress, Sep. 19, 2013, Presentation No. LBAP 029, 2 pages.
Liu et al., "Kit-like 18F-labeling of RGD-19F-Arytrifluroborate in high yield and at extraordinarily high specific activity with preliminary in vivo tumor imaging," Nuclear Medicine and Biology, vol. 40, 2013, pp. 841-849.
Liu et al., "Preclinical evaluation of a high affinity 18F-trifluoroborate octreotate derivative for somatostatin receptor imaging—poster," University of British Columbia, 2014, 1 page.
Liu et al., "Preclinical Evaluation of a High-Affinity $^{18}$F-Trifluoroborate Octreotate Derivative for Somatostatin Receptor Imaging," Journal of Nuclear Medicine, Sep. 2014, vol. 55(9), pp. 1499-1505.
Liu et al., "Preclinical Evaluation of a Novel 18F-Labelled Somatostatin Receptor-Binding Peptide—Abstract Proof," ScholarOne, Inc, 2014, Control ID: 1931699, 4 pages.
Liu et al., "Preclinical evaluation of a novel F-labelled somatostatin receptor-binding peptide," The Journal of Nuclear Medicine, 2014, vol. 55 (Supplement 1):1089, 1 page.
Liu et al., "Rapid, one-step, high yielding 18F-labeling of an aryltrifluoroborate bioconjugate by isotope exchange at very high specific activity," Journal of Labelled Compounds and Radiopharmaceuticals, 2012, vol. 55, pp. 491-496.
Liu et al., "Stoichiometric Leverage: Rapid 18F-Aryltrifluoroborate Radiosynthesis at High Specific Activity for Click Conjugation," Angew. Chem. Int. Ed., 2013, vol. 52, pp. 2303-2307.
Liu et al., "One-step 18F labeling of biomolecules using organotrifluoroborates," Nat Protoc, 2015, vol. 10, No. 9, pp. 1423-1432.

(56) References Cited

OTHER PUBLICATIONS

Matteson et al., "Iodomethaneboronic Esters and Aminomethaneboronic Esters," Journal of Organometallic Chemistry, 1979, vol. 170, pp. 259-264.
Means et al. "Chemical Modifications of Proteins: History and Applications," Bioconjugate Chemistry, 1990, vol. 1, No. 1, pp. 2-12.
Molander et al., "Functionalization of Organotrifluoroborates: Reductive Amination," J. Org. Chem., 2008, vol. 73, pp. 3885-3891.
Molander et al., "Synthesis of an Acyltrifluoroborate and its Fusion with Azides to Form Amides," J. Org. Chem., 75: 4304-4306, (2010).
Molander et al., "Synthesis of Functionalized Organotriflurorborates via the 1,3-Dipolar Cycloaddition of Azides," Organic Letters, 8:2031-2034, (2006).
Na Sun et al., "Biorelevant pKa (37 °C) predicted from the 2D structure of the molecule and its pKa at 25 °C," Journal of Pharmaceutical and Biomedical Analysis, vol. 56, No. 2, 2011, pp. 173-182.
Nichols, T., et al., "Improved treatment planning for boron neutron capture therapy for glioblastoma multiforme using fluorine-18 labeled boronophenylalanine and positron tomography," Med. Phys., vol. 29, No. 10, Oct. 2002, pp. 2351-2358.
Office Action for European Application No. 14759809.8 dated Oct. 10, 2018, 17 pages.
Okarvi, "Recent Progress in Fluorine-18 labelled peptide radiopharmaceuticals," European Journal of Nuclear Medicine, (2001), vol. 28, pp. 929-938.
Onufriev et al., "A Novel View Of pH Titration in Biomolecules," Biochemistry, vol. 40, No. 12, Mar. 27, 2001 (7 pages).
Peng et al., "Identification of LY2510924, a novel cyclic peptide CXCR4 antagonist that exhibits antitumor activities in solid tumor and breast cancer metastatic models," Mol Cancer Ther, 2015, 14(2):480-490.
Poeppel et al., "$^{68}$GA-DOTATOC Versus $^{68}$Ga-DOTATATE PET/CT in Functional Imaging of Neuroendocrine Tumors," The Journal of Nuclear Medicine, Dec 2011, vol. 52(12), pp. 1864-1870.
Poethko et al., "Two-Step Methodology for High-Yield Routine Radiohalogenation of Peptides: 18F-Labeled RGD and Octreotide Analogs," The Journal of Nuclear Medicine, May 2004, vol. 45 No. 5, pp. 892-902.
Poole et al., "Radiotracers in Fluorine Chemistry. Part IV. Fluorine-18 Exchange between labelled Alkyfluorosilanes and Fluorides or Fluoride Methoxides, of Tungsten(vi), Molybdenum,(vi), Tellurium(vi), and lodine(v)," J. Chem. Soc, Dalton Trans., (1976), pp. 1557-1560.
Poty et al., "AMD3100: A Versatile Platform for CXCR4 Targeting (68)Ga-Based Radiopharmaceuticals," Bioconjug Chem, 2016, 27(3):752-761.
Pourghisian et al., "(18)F-AmBF3-MJ9: a novel radiofluorinated bombesin derivative for prostate cancer imaging," Bioorganic & Medicinal Chemistry, 2015, vol. 23, No. 7, pp. 1500-1506.
Raushel et al. "Reinvestigation of Aminomethyltrifluoroborates and Their Application in Suzuki-Miyaura Cross-Coupling Reactions," J. Org. Chem, 2011, vol. 76, pp. 2762-2769.
Reubi et al., "Affinity profiles for human somatostatin receptor subtypes SST1-SST5 of somatostatin radiotracers selected for scintigraphic and radiotherapeutic use," European Journal of Nuclear Medicine, Mar. 2000, vol. 27, No. 3, pp. 273-282.
Roxin et al. "Preliminary evaluation of 18F-labeled LLP2A-trifluoroborate conjugates as VLA-4 (α4β1 integrin) specific radiotracers for PET imaging of melanoma," Nuclear Medicine and Biology 61 (2018) 11-20.
Roxin et al., "A metal-free DOTA-conjugated $^{18}$F-labeledradiotracer: [$^{18}$F]DOTA-AMBF3 LLP2A for imaging VLA-4 Over-expression in murine melanoma with improved tumor uptake and greatly enhanced renal clearance," Bioconjugate Chem. 2019, 30, 1210-1219.
Salgia et al., "A randomized phase II study of LY2510924 and carboplatin/etoposide versus carboplatin/etoposide in extensive-disease small cell lung cancer," Lung Cancer, 2017, 105:7-13, Abstract, 10 pages.
Schirrmacher et al., "18F-labeling of peptides by means of an organosilicon-based fluoride acceptor," Angew. Chem. Int. Ed., 2006, vol. 45, pp. 1-5.
Schottelius et al., "[177Lu]pentixather: Comprehensive Preclinical Characterization of a First CXCR4-directed Endoradiotherapeutic Agent," Theranostics, 2017, vol. 7, Issue 9, pp. 2350-2362.
Shoup et al., "Synthesis of Fluorine-18-Labeled Biotin Derivatives: Biodistribution and Infection Localization," The Journal of Nuclear Medicine, (1994), vol. 35, pp. 1685-1690.
Smith, M. et al., "March's Advanced Organic Chemistry: Reactions, Mechanisms, and Structure," 7th ed., Jun. 13, 2013, John Wiley & Sons, vol. 116, pp. 334-346.
Sprague et al., "Preparation and Biological Evaluation of Copper-64-Labeled Tyr3-Octreotate Using a Cross-Bridged Macrocyclic Chelator," Clinical Cancer Research, Dec. 2004, vol. 10, pp. 8674-8682.
Stabin et al., "OLINDA/EXM: The Second-Generation Personal Computer Software for Internal Dose Assessment in Nuclear Medicine," J Nucl Med, 2005, vol. 46, No. 6, pp. 1023-1027.
Stabin et al., "RADAR Reference Adult, Pediatric, and Pregnant Female Phantom Series for Internal and External Dosimetry," J Nucl Med, 2012, vol. 53, No. 11, pp. 1807-1813.
Storch et al., "Evaluation of [99mTc/EDDA/HYNICO]Octreotide Derivatives Compared with [111In-DOTA0,Tyr3,Thr8]Octreotide and [111In-DTPA0]Octreotide: Does Tumor or Pancreas Uptake Correlate with the Rate of Internalization?" The Journal of Nuclear Medicine, Sep. 2005, vol. 46, No. 9, pp. 1561-1569.
Supplemental European Search Report dated Mar. 26, 2010 for EP05706491.7, 4 pages.
Suzuki et al., "C-terminal-modified LY2510924: a versatile scaffold for targeting C-X-C chemokine receptor type 4," Scientific Reports 9, Article No. 15284 (2019), 10 pages.
Ting et al. "Capturing aqueous [18F]-fluoride with an arylboronic ester for PET: Synthesis and aqueous stability of a fluorescent [18F]-labeled aryltrifluoroborate," Journal of Fluorine Chemistry, 129:349-358, (2008).
Ting et al. "Toward [18F]-Labeled Aryltrifluoroborate Radiotracers: In Vivo Positron Emission Tomography Imaging of Stable Aryltrifluoroborate Clearance in Mice," J. Am. Chem. Soc, 130:12045-12055, (2008).
Ting et al., "Arylfluoroborates and Alkylfluorosilicates as Potential PET Imaging Agents: High-Yielding Aqueous Biomolecular 18F-Labeling," J. Am. Chem. Soc, 127:13094-13095, (2005).
Ting et al., "Substituent effects on aryitrifluoroborate solvolysis in water: Implications for Suzuki-Miyaura coupling and the design of stable 18F-labeled aryitrifluoroborates for use in PET imaging," J. Org. Chem., 73:4662-4670, (2008).
Toyokuni et al., "Synthesis of a New Heterobiofunctional Linker, N-[4-(Aminooxy)butyl] maleimide, for Facile Access to a Thiol-Reactive 18F-Labeling Agent," Bioconjugate Chem, 2003, vol. 14, pp. 1253-1259.
Vag et al., "PET imaging of chemokine receptor CXCR4 in patients with primary and recurrent breast carcinoma," European Journal of Nuclear Medicine and Molecular Imaging Research, 2018, vol. 8, No. 90, 9 pages.
Vallabhajosula et al., "Preclinical Evaluation of Technetium-99m-Labeled Somatostatin Receptor-Binding Peptides," The Journal of Nuclear Medicine, Jun. 1996, vol. 37, No. 6, pp. 1016-1022.
Virgolini et al. "Somatostatin Receptor Subtype Specificity and in Vivo Binding of a Novel Tumor Tracer. 99mTc-P8291," Cancer Research, Mav 1998, vol. 58, pp. 1850-1859.
Walenkamp et al., "CXCR4 Ligands: The Next Big Hit?," J Nucl Med, 2017, vol. 58, No. 9 (Suppl. 2), pp. 77S-82S.
Wängler et al., "One-Step $^{18}$F-Labeling of Carbohydrate-Conjugated Octreotate-Derivatives Containing a Silicon-Fluoride-Acceptor (SiFA): In Vitro and in Vivo Evaluation as Tumor Imaging Agents for Positron Emission Tomography," Bioconjugate Chem., 2010, vol. 21(12), pp. 2289-2296.

(56) References Cited

OTHER PUBLICATIONS

Weiss et al., Molecular Imaging of Chemokine Receptor CXCR4, Theranostics, 2013, vol. 3, Issue 1, pp. 76-84.
Wester et al., "PET imaging of somatostatin receptors: design, synthesis and preclinical evaluation of a novel 18F-labelled, carbohydrated analogue of octreotide," European Journal of Nuclear Medicine and Molecular Imaging, Jan. 2003, vol. 30, No. 1, pp. 117-122.
International Preliminary Report on Patentability for International Application No. PCT/CA2014/000200, issued Sep. 8, 2015, 5 pages.
International Search Report for International Application No. PCT/CA2014/000200, mailed Jun. 11, 2014, 5 pages.
Written Opinion of the International Searching Authority for International Application No. PCT/CA2014/000200, mailed Jun. 11, 2014, 4 pages.
Zhan et al., "Hydration of the Fluoride Anion: Structures and Absolute Hydration Free Energy from First-Principles Electronic Structure Calculations," J Phys Chem A., 2004, vol. 108, pp. 2020-2029.
European Patent Application No. 21881418.4: Partial Supplementary European Search Report, dated Aug. 13, 2024, 20 pages.
Kwon, D. et al. "[18F]Trifluoroborate-based CXCR4-targeting PET Agents Based on a Potent and Novel Pharmacophore," Journal of Nuclear Medicine, Aug. 2022:63(supplement 2):Abstract 2579 [online]. Retrieved from the Internet: URL:https://jnm.snmjournals.org/content/63 /supplement_2/2579, 4 pages.
Kwon, D. et al., "A CXCR4-Targeting Radiotheranostic Based on a Potent Novel Peptide Antagonist", Journal of Nuclear Medicine, Aug. 2022:63(supplement 2):Abstract 2566 [online]. Retrieved from the Internet: URL:https://jnm.snmjournals.org/content/63 /supplement_2/2566, 4 pages.
Kwon, D. et al. "High-Contrast CXCR4-Targeted 18F-PET Imaging Using a Potent and Selective Antagonist," Mol Pharm. Jan. 4, 2021;18(1):187-197. doi: 10.1021/acs.molpharmaceut.0c00785. Epub Nov. 30, 2020.
Balkwill, F, "Cancer and the chemokine network," Nat. Rev. Cancer, Jul. 2004, vol. 4, pp. 540-550.
Clayden et al., "The definition of pKa" Organic Chemistry. Oxford University Press, 2001, pp. 185-188.
Domanska, U.M. et al. "A review on CXCR4/CXCL12 axis in oncology: No place to hide" Eur J Cancer, 2013, vol. 49, pp. 219-230.
Dumas, A.M. et al., "Amide-Forming Ligation of Acyltrifluorborates and Hydroxylamines in Water," Angew Chem Int Ed Engl, 51:5683-5686 (Jun. 2012).
Extended European Search Report for Application No. 19900988.7, dated Oct. 31, 2022, 7 pages.
Extended European Search Report for Application No. 20791838.4, dated Dec. 20, 2022, 10 pages.
Fujii, N. et al. "Molecular-Size Reduction of a Potent CXCR4-Chemokine Antagonist Using Orthogonal Combination of Conformation- and Sequence-Based Libraries," Angew. Chemie Int. Ed., 42, 3251-3253 (2003).
George, G.P.C. et al., "Positron Emission Tomographic Imaging of CXCR4 in Cancer: Challenges and Promises," Mol. Imaging, 2014, vol. 13, pp. 1-19, DOI: 10.2310/7290.2014.00041.
George, J. et al. "Transfer of Endothelial Progenitor and Bone Marrow Cells Influences Atherosclerotic Plaque Size and Composition in Apolipoprotein E Knockout Mice," Arterioscler. Thromb. Vasc. Biol., 25, 2636-2641 (2005).
Griffith, J.W. et al., "Chemokines and Chemokine Receptors: Positioning Cells for Host Defense and Immunity," Annu. Rev. Immunol., 2014, vol. 32, pp. 659-702.
Guo, F. et al. "CXCL12/CXCR4: a symbiotic bridge linking cancer cells and their stromal neighbors in oncogenic communication networks," Oncogene, 2016, vol. 35, pp. 816-826.
Huang. S. et al., "Improving the Biodistribution of PSMA-targeting tracers with a highly negatively charged linker", The Prostate, Feb. 24, 2014, vol. 74, No. 7, pp. 702-713.
International Preliminary Report on Patentability for International Application No. PCT/CA2008/001368, mailed on Feb. 4, 2010, 8 pages.
International Search Report and Written Opinion for International Application No. PCT/CA2021/051486, mailed Jan. 20, 2022, 11 pages.
International Search Report and Written Opinion for International Application No. PCT/CA2023/050538 dated Jul. 9, 2023, 15 pages.
Jacobson, O. and Weiss, I.D., "CXCR4 chemokine receptor overview: biology, pathology and applications in imaging and therapy," Theranostics, 2013, vol. 3, pp. 1-2.
Kuil, J. et al., "Imaging agents for the chemokine receptor 4 (CXCR4)," Chem. Soc. Rev., 2012, 41, 5239-5261.
Lepage, M., et al., "Toward 18 F-Labeled Theranostics: A Single Agent that Can Be Labeled with 18F, 64Cu, or 177Lu," Chembiochem, 2020, vol. 21, No. 7, pp. 943-947.
Lin, K-S. et al., "In vivo radioimaging of bradykinin receptor b1, a widely overexpressed molecule in human cancer," Cancer Res. Jan. 2015;75(2):387-393. doi:10.1158/0008-5472.CAN-14-1603.
Murdoch, C. "CXCR4: chemokine receptor extraordinaire," Immunol. Rev., 177, 175-184 (2000).
Poschenrieder. A. et al., "The influence of different metal-chelate conjugates of pentixafor on the CXCR4 affinity", EJNMMI Research, Dec. 26, 2016; 6:36, 8 pages.
Price, E. W. and C. Orvig, "Matching chelators to radiometals for radiopharmaceuticals," Chem Soc Rev, vol. 43, pp. 260-290 (2014).
Ratajczak, M. Z. et al. "The pleiotropic effects of the SDF-1-CXCR4 axis in organogenesis, regeneration and tumorigenesis," Leukemia, 20, 1915-1924 (2006).
Segars, William Paul. Development and application of the new dynamic NURBS-based cardiac-torso (NCAT) phantom. Dissertation, The University of North Carolina at Chapel Hill, 2001; 24 pages.
Sprik and Ciccotti, "Free energy from constrained molecular dynamics," J Chem Phys, 109(18):7737-7744, (Nov. 1998).
Tamamura, H. et al. "A Low-Molecular-Weight Inhibitor against the Chemokine Receptor CXCR4: A Strong Anti-HIV Peptide T140," Biochem. Biophys. Res. Commun. 253, 877-882 (1998).
Todorovic, M. et al., "Fluorescent Isoinodole Crosslink (FlICK) Chemistry: A Rapid, User-friendly Stapling Reaction", Angewandte Chemie, 2019, 58(40), 14120-14124.
Walsh, J.C. et al., "Application of Silicon-Fluoride Chemistry to Fluorine-18 Labeling Agents for Biomolecules: A Preliminary Note," J. Labelled Cpd. Radiopharm., 1999, vol. 42 (Suppl. 1), pp. S1-S3.
Wang, A. et al. "CXCR4/CXCL12 Hyperexpression Plays a Pivotal Role in the Pathogenesis of Lupus," J. Immunol., Apr. 2009;182:4448-4458.
Wang, A. et al. "Dysregulated expression of CXCR4/CXCL12 in subsets of patients with systemic lupus erythematosus," Arthritis Rheum., Nov. 2010;62:3436-3446.
Woodard, L.E. & Nimmagadda, S. "CXCR4-Based Imaging Agents," J. Nucl. Med., 52, 1665-1669 (2011).
Yang, H. et al., "Synthesis and Evaluation of a Macrocyclic Actinium-225 Chelator, Quality Control and In Vivo Evaluation of 225Ac-crown-aMSH Peptide", Chem Eur J, 2020, 26, 11435-11440.
Zhao, H. et al. "CXCR4 over-expression and survival in cancer: a system review and meta-analysis," Oncotarget, 6, 5022-5040 (2015).
Zlotnik, A. et al. "Homeostatic chemokine receptors and organ-specific metastasis," Nat. Rev. Immunol., 11, 597-606 (2011).
Roxin et al., "The case for DOTA as a pharmacokinetic modulator for 18F-labeled peptides: DOTA-[18F]AMBF3-LLP2A for improved PET imaging of VLA-4 over-expression in murine melanoma," Journal of Nuclear Medicine. May 2019; 60 (supplement 1):1008, 2 pages.

* cited by examiner

RADIOLABELLED CXCR4-TARGETING COMPOUNDS FOR DIAGNOSIS AND THERAPY

CROSS-REFERENCE TO RELATED APPLICATIONS

This application is a U.S. National Stage Application under 35 U.S.C. § 371 of International Application No. PCT/CA2020/050521, filed Apr. 17, 2020, which claims priority to U.S. Provisional Application No. 62/835,733, filed Apr. 18, 2019, the disclosures of which are hereby incorporated by reference in their entireties for all purposes.

FIELD OF INVENTION

The present invention relates to radiolabelled compounds for selective imaging or treatment, particularly compounds that target CXCR4.

BACKGROUND OF THE INVENTION

C-X-C chemokine receptor type 4 (CXCR4) is a G protein-coupled receptor involved in chemotaxis and leukocyte trafficking. CXCR4 was identified as a co-receptor for HIV entry into T cells, establishing itself as a prominent target for pharmaceutical development (Feng et al., *Science.* 1996, 272:872-7; Bleul et al., *Proc Natl Acad Sci.* 1997, 94:1925-1930). The expression of CXCR4 is also associated with autoimmune disorders, cardiovascular disease and cancer (Doring et al., *Front Physiol.* 2014, 5:212; Chatterjee et al., *Adv Cancer Res.* 2014, 124:31-82), including the observed overexpression of CXCR4 in 23 human cancers including hematological and solid cancers (Chatterjee et al., ibid). The α-chemokine stromal cell-derived factor 1 (SDF-1a) signals through CXCR4 to promote cancer cell proliferation and to potentiate metastatic behavior (Duda et al., *Clin Cancer Res.* 2011, 17:2074-2080). Plerixafor, also known as AMD3100, developed originally for HIV treatment, received FDA approval (De Clercq, *Biochem Pharmacol.* 2009, 77:1655-1664) to mobilize hematopoietic stem cells into peripheral blood for collection and autologous transplantation.

Radiolabeled monoclonal antibodies, cyclam inhibitors, and peptides have been used as pharmacophores for CXCR4-targeted imaging in nuclear medicine (Weiss et al., *Theranostics.* 2013, 3:76-84; Walenkamp et al., *J Nucl Med.* 2017, 58:77S-82S). To date, [$^{68}$Ga]Ga-Pentixafor, a cyclic pentapeptide adapted by the Wester group (Demmer et al., *Chem Med Chem.* 2011, 6:1789-1791; Gourni et al., *J Nucl Med.* 2011, 52:1803-1810), is the most investigated CXCR4 radiopharmaceutical in the clinic. [$^{68}$Ga]Ga-Pentixafor has been used to image patients with leukemia, lymphoma, multiple myeloma, adrenocortical carcinoma, small cell lung carcinoma, or breast carcinoma (Walenkamp et al., supra; Vag et al., *EJNMMI Res.* 2018, 8:90). Pentixather, a derivative of Pentixafor with an iodinated tyrosine, is the companion therapeutic agent (radiolabeled with $^{177}$Lu-lutetium or $^{90}$Y-yttrium) for endoradiotherapy (Schottelius et al., *Theranostics.* 2017, 7:2350-2362; Herrmann et al., *J Nucl Med.* 2016, 57:248-251). Preliminary data with [$^{177}$Lu]Lu/[$^{90}$Y]Y-Pentixather on a compassionate-use basis was reported for three patients with refractory multiple myeloma (Herrmann et al., ibid). Based on [$^{18}$F]FDG imaging, one patient had partial response and one had complete response. The third patient failed to undergo [$^{18}$F]FDG restaging due to sepsis following autologous stem cell transplantation. Pending more studies, [$^{177}$Lu]Lu/[$^{90}$Y]Y-Pentixather appears to be a promising radiotherapeutic agent.

LY2510924 (cyclo[Phe-Tyr-Lys(iPr)-D-Arg-2-Nal-Gly-D-Glu]-Lys(iPr)-$NH_2$) is a novel cyclic peptide that can block SDF-1a binding to CXCR4 with an $IC_{50}$ value of 79 pM (Peng et al., *Mol Cancer Ther.* 2015, 14:480-490). The authors demonstrated that LY2510924 was able to inhibit growth of non-Hodgkin lymphoma, renal cell carcinoma, lung cancer, colorectal cancer, and breast cancer xenograft models. LY2510924 failed to improve treatment efficacy of carboplatin/etoposide chemotherapy for small cell lung cancer patients (Salgia et al., *Lung Cancer.* 2017, 105:7-13); however, it is currently being evaluated in a phase II study in combination with idarubicin and cytarabine for patients with relapsed or refractory acute myeloid leukemia (ClinicalTrials.gov Identifier: NCT02652871). In this regimen, LY2510924 is expected to mobilize cancer cells from bone marrow to enter the bloodstream, where they can be acted upon by the combination of chemotherapeutics.

There is therefore an unmet need in the field for improved imaging agents (e.g. PET imaging agents) and radiotherapeutic compositions for in-vivo diagnosis and treatment of cancers and other diseases/disorders characterized by expression of CXCR4

No admission is necessarily intended, nor should it be construed, that any of the preceding information constitutes prior art against the present invention.

SUMMARY OF THE INVENTION

Disclosed herein are novel compounds targeting CXCR4.

This disclosure provides a compound, wherein the compound has Formula I (shown below) or is a salt or a solvate of Formula I $$[\text{targeting peptide}]\text{-N}(R^1)\text{—}X^1(R^2)L^1\text{-}[\text{linker}]\text{-}R^X_{n1} \quad (I),$$

wherein:

the targeting peptide is cyclo[L-Phe-L-Tyr-L-Lys(iPr)-D-Arg-L-2-Nal-Gly-D-Glu]-L-Lys(iPr) which is C-terminally bonded to —N($R^1$)—;

$R^1$ is H or methyl;

$X^1$ is a linear, branched, and/or cyclic $C_1$-$C_{15}$ alkylenyl, alkenylenyl or alkynylenyl wherein 0-6 carbons are independently replaced by N, S, and/or O heteroatoms, and substituted with 0-3 groups independently selected from one or a combination of oxo, hydroxyl, sulfhydryl, halogen, guanidino, carboxylic acid, sulfonic acid, sulfinic acid, and/or phosphoric acid;

$R^2$ is C(O)OH or C(O)$NH_2$;

$L^1$ is —S—, —NHC(O)—, —C(O)NH—, —N($CH_3$)C(O)—, —C(O)N($CH_3$)—,

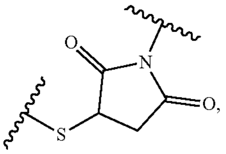

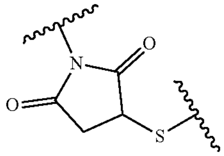
,

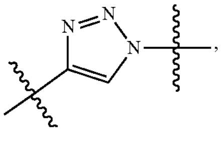
, or

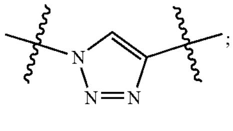
;

the linker is a linear or branched chain of 1-10 units of $X^2L^2$ and/or $X^2(L^2)_2$, wherein:

each $X^2$ is, independently, a linear, branched, and/or cyclic $C_1$-$C_{15}$ alkylenyl, alkenylenyl or alkynylenyl wherein 0-6 carbons are independently replaced by N, S, and/or O heteroatoms, and substituted with 0-3 groups independently selected from one or a combination of oxo, hydroxyl, sulfhydryl, halogen, guanidino, carboxylic acid, sulfonic acid, sulfinic acid, and/or phosphoric acid;

each $L^2$ is independently —S—, —NHC(O)—, —C(O)NH—, —$N(CH_3)C(O)$—, —$C(O)N(CH_3)$—,

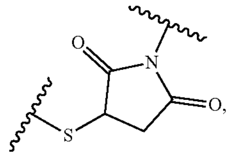

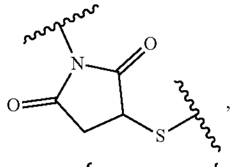
,

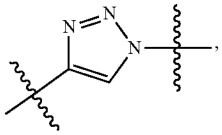
, or

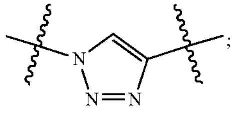
;

the linker comprises at least one carboxylic acid, sulfonic acid, sulfinic acid, or phosphoric acid, and has a net negative charge at physiological pH;

the linker optionally further comprises an albumin binder bonded to an $L^2$ of the linker, wherein the albumin binder is: —$(CH_2)_{n2}$—$CH_3$ wherein n2 is 8-20; —$(CH_2)_{n3}$—C(O)OH wherein n3 is 8-20, or

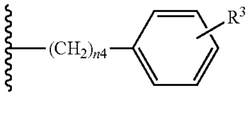

wherein n4=1-4 and $R^3$ is I, Br, F, Cl, H, OH, $OCH_3$, $NH_2$, $NO_2$ or $CH_3$;

n1 is 1 or 2; and each $R^X$ is a radiolabelling group linked through a separate $L_2$ of the linker, and is independently selected from: a metal chelator optionally in complex with a radiometal or radioisotope-bound metal; a prosthetic group containing trifluoroborate ($BF_3$); or a prosthetic group containing a silicon-fluorine-acceptor moiety.

This summary of the invention does not necessarily describe all features of the invention.

BRIEF DESCRIPTION OF THE DRAWINGS

These and other features of the invention will become more apparent from the following description in which reference is made to the appended drawings wherein.

DETAILED DESCRIPTION

Figure 1:
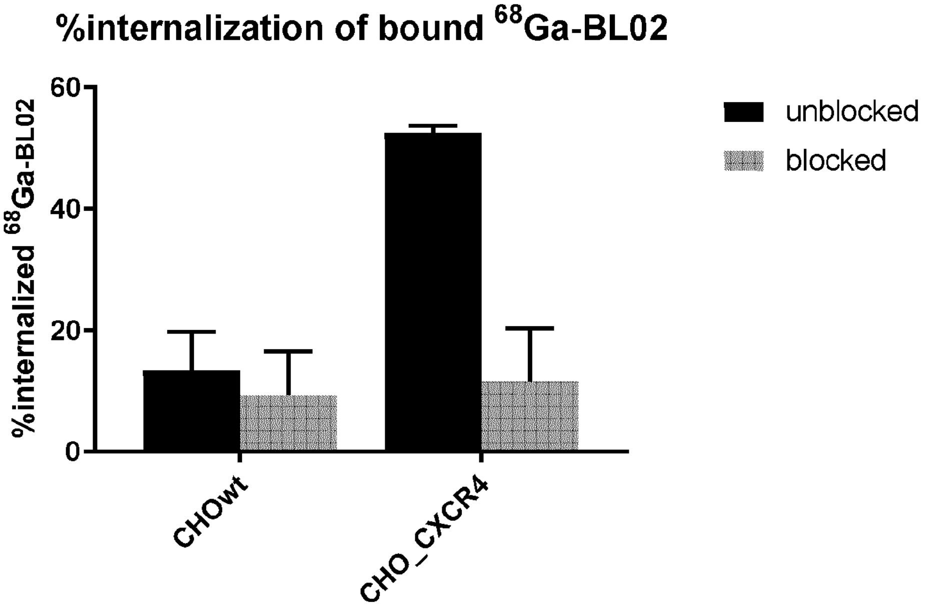
FIG. 1 shows a graph of the percentage internalization of the bound [$^{68}$Ga]Ga-BL02 in CHO:CXCR4 and CHO:WT cells.

As used herein, the terms "comprising," "having", "including" and "containing," and grammatical variations thereof, are inclusive or open-ended and do not exclude additional, unrecited elements and/or method steps. The term "consisting essentially of" if used herein in connection with a composition, use or method, denotes that additional elements and/or method steps may be present, but that these additions do not materially affect the manner in which the recited composition, method or use functions. The term "consisting of" if used herein in connection with a composition, use or method, excludes the presence of additional elements and/or method steps. A composition, use or method described herein as comprising certain elements and/or steps may also, in certain embodiments consist essentially of those elements and/or steps, and in other embodiments consist of those elements and/or steps, whether or not these embodiments are specifically referred to. A use or method described herein as comprising certain elements and/or steps may also, in certain embodiments consist essentially of those elements and/or steps, and in other embodiments consist of those elements and/or steps, whether or not these embodiments are specifically referred to.

A reference to an element by the indefinite article "a" does not exclude the possibility that more than one of the elements is present, unless the context clearly requires that there be one and only one of the elements. The singular forms "a", "an", and "the" include plural referents unless the content clearly dictates otherwise. The use of the word "a" or "an" when used herein in conjunction with the term "comprising" may mean "one," but it is also consistent with the meaning of "one or more," "at least one" and "one or more than one."

Unless otherwise specified, "certain embodiments", "various embodiments", "an embodiment" and similar terms includes the particular feature(s) described for that embodiment either alone or in combination with any other embodiment or embodiments described herein, whether or not the other embodiments are directly or indirectly referenced and regardless of whether the feature or embodiment is described in the context of a method, product, use, composition, compound, et cetera.

As used herein, the terms "treat", "treatment", "therapeutic" and the like includes ameliorating symptoms, reducing disease progression, improving prognosis and reducing recurrence (e.g. reducing cancer recurrence).

As used herein, the term "diagnostic agent" includes an "imaging agent". As such, a "diagnostic radiometal" includes radiometals that are suitable for use in imaging agents and "diagnostic radioisotope" includes radioisotopes that are suitable for use in imaging agents.

The term "subject" refers to an animal (e.g. a mammal or a non-mammal animal). The subject may be a human or a non-human primate. The subject may be a laboratory mammal (e.g., mouse, rat, rabbit, hamster and the like). The subject may be an agricultural animal (e.g., equine, ovine, bovine, porcine, camelid and the like) or a domestic animal (e.g., canine, feline and the like). In some embodiments, the subject is a human.

The compounds disclosed herein may also include base-free forms, salts or pharmaceutically acceptable salts thereof. Unless otherwise specified, the compounds claimed and described herein are meant to include all racemic mixtures and all individual enantiomers or combinations thereof, whether or not they are explicitly represented herein.

The compounds disclosed herein may be shown as having one or more charged groups, may be shown with ionizable groups in an uncharged (e.g. protonated) state or may be shown without specifying formal charges. As will be appreciated by the person of skill in the art, the ionization state of certain groups within a compound (e.g. without limitation, carboxylic acid, sulfonic acid, sulfinic acid, phosphoric acid and the like) is dependent, inter alia, on the pKa of that group and the pH at that location. For example, but without limitation, a carboxylic acid group (i.e. COOH) would be understood to usually be deprotonated (and negatively charged) at neutral pH and at most physiological pH values, unless the protonated state is stabilized. Likewise, sulfonic acid groups, sulfinic acid groups, and phosphoric acid groups would generally be deprotonated (and negatively charged) at neutral and physiological pH values.

As used herein, the terms "salt" and "solvate" have their usual meaning in chemistry. As such, when the compound is a salt or solvate, it is associated with a suitable counter-ion. It is well known in the art how to prepare salts or to exchange counter-ions. Generally, such salts can be prepared by reacting free acid forms of these compounds with a stoichiometric amount of a suitable base (e.g. without limitation, Na, Ca, Mg, or K hydroxide, carbonate, bicarbonate, or the like), or by reacting free base forms of these compounds with a stoichiometric amount of a suitable acid. Such reactions are generally carried out in water or in an organic solvent, or in a mixture of the two. Counter-ions may be changed, for example, by ion-exchange techniques such as ion-exchange chromatography. All zwitterions, salts, solvates and counter-ions are intended, unless a particular form is specifically indicated.

In certain embodiments, the salt or counter-ion may be pharmaceutically acceptable, for administration to a subject. More generally, with respect to any pharmaceutical composition disclosed herein, non-limiting examples of suitable excipients include any suitable buffers, stabilizing agents, salts, antioxidants, complexing agents, tonicity agents, cryoprotectants, lyoprotectants, suspending agents, emulsifying agents, antimicrobial agents, preservatives, chelating agents, binding agents, surfactants, wetting agents, non-aqueous vehicles such as fixed oils, or polymers for sustained or controlled release. See, for example, Berge et al. 1977. (*J. Pharm Sci.* 66:1-19), or Remington—The Science and Practice of Pharmacy, 21st edition (Gennaro et al editors. Lippincott Williams & Wilkins Philadelphia), each of which is incorporated by reference in its entirety.

As used herein, the expression "Cy-Cz", where y and z are integers (e.g. $C_1$-$C_{15}$, $C_1$-$C_5$, and the like), refers to the number of carbons in a compound, R-group or substituent, or refers to the number of carbons plus heteroatoms when a certain number of carbons are specified as being replaced by heteroatoms. Heteroatoms may include any, some or all possible heteroatoms. For example, in some embodiments, the heteroatoms are selected from N, O, S, P and Se. In some embodiments, the heteroatoms are selected from N, S and O. Unless otherwise specified, such embodiments are non-limiting.

Unless explicitly stated otherwise, the term "alkyl" includes any reasonable combination of the following: (1) linear or branched; (2) acyclic or cyclic, the latter of which may include multi-cyclic (fused rings, multiple non-fused rings or a combination thereof; and (3) unsubstituted or substituted. In the context of the expression "alkyl, alkenyl or alkynyl" and similar expressions, the "alkyl" would be understood to be a saturated alkyl. As used herein, the term "linear" may be used as it is normally understood to a person of skill in the art and generally refers to a chemical entity that comprises a skeleton or main chain that does not split off into more than one contiguous chain. Non-limiting examples of linear alkyls include methyl, ethyl, n-propyl, and n-butyl. As used herein, the term "branched" may be used as it is normally understood to a person of skill in the art and generally refers to a chemical entity that comprises a skeleton or main chain that splits off into more than one contiguous chain. The portions of the skeleton or main chain that split off in more than one direction may be linear, cyclic or any combination thereof. Non-limiting examples of a branched alkyl group include tert-butyl and isopropyl.

The term "alkylenyl" refers to a divalent analog of an alkyl group. In the context of the expression "alkylenyl, alkenylenyl or alkynylenyl", and similar expressions, the "alkylenyl" would be understood to be a saturated alkylenyl.

As used herein, the term "saturated" when referring to a chemical entity may be used as it is normally understood to a person of skill in the art and generally refers to a chemical entity that comprises only single bonds, and may include linear, branched, and/or cyclic groups. Non-limiting examples of a saturated $C_1$-$C_{20}$ alkyl group may include methyl, ethyl, n-propyl, i-propyl, sec-propyl, n-butyl, i-butyl, sec-butyl, t-butyl, n-pentyl, i-pentyl, sec-pentyl, t-pentyl, n-hexyl, i-hexyl, 1,2-dimethylpropyl, 2-ethylpropyl, 1-methyl-2-ethylpropyl, I-ethyl-2-methylpropyl, 1,1,2-trimethylpropyl, 1,1,2-triethylpropyl, 1,1-dimethylbutyl, 2,2-dimethylbutyl, 2-ethylbutyl, 1,3-dimethylbutyl, 2-methylpentyl, 3-methylpentyl, sec-hexyl, t-hexyl, n-heptyl, i-heptyl, sec-heptyl, t-heptyl, n-octyl, i-octyl, sec-octyl, t-octyl, n-nonyl, i-nonyl, sec-nonyl, t-nonyl, n-decyl, i-decyl, sec-decyl, t-decyl, cyclopropanyl, cyclobutanyl, cyclopentanyl, cyclohexanyl, cycloheptanyl, cyclooctanyl, cyclononanyl, cyclodecanyl, and the like. Unless otherwise specified, a $C_1$-$C_{20}$ alkylenyl therefore encompasses, without limitation, all divalent analogs of the above-listed saturated alkyl groups.

As used herein, the term "unsaturated" when referring to a chemical entity may be used as it is normally understood to a person of skill in the art and generally refers to a chemical entity that comprises at least one double or triple bond, and may include linear, branched, and/or cyclic groups. Non-limiting examples of a $C_2$-$C_{20}$ alkenyl group may include vinyl, allyl, isopropenyl, I-propene-2-yl, 1-butene-1-yl, 1-butene-2-yl, 1-butene-3-yl, 2-butene-1-yl, 2-butene-2-yl, octenyl, decenyl, cyclopropenyl, cyclobutenyl, cyclopentenyl, cyclohexenyl, cycloheptenyl, cyclooctenyl, cyclononanenyl, cyclodecanenyl, and the like. Unless otherwise specified, a $C_1$-$C_{20}$ alkenylenyl therefore encompasses, without limitation, all divalent analogs of the above-listed alkenyl groups. Non-limiting examples of a $C_2$-$C_{20}$ alkynyl group may include ethynyl, propynyl, butynyl, pentynyl, hexynyl, heptynyl, octynyl, nonynyl, decynyl, and the like. Unless otherwise specified, a $C_1$-$C_{20}$ alkynylenyl therefore encompasses, without limitation, all divalent analogs of the above-listed alkynyl groups.

Where it is specified that 1 or more carbons in an alkyl, alkenyl, alkynyl, alkylenyl, alkenylenyl, alkynylenyl, etc., are independently replaced by a heteroatom, the person of skill in the art would understand that various combinations of different heteroatoms may be used. Non-limiting examples of non-aromatic heterocyclic groups include aziridinyl, azetidinyl, diazetidinyl, pyrrolidinyl, pyrrolinyl, piperidinyl, piperazinyl, imidazolinyl, pyrazolidinyl, imidazolydinyl, phthalimidyl, succinimidyl, oxiranyl, tetrahydropyranyl, oxetanyl, dioxanyl, thietanyl, thiepinyl, morpholinyl, oxathiolanyl, and the like. The expression "a linear, branched, and/or cyclic . . . alkyl, alkenyl or alkynyl" includes, inter alia, aryl groups. Unless further specified, an "aryl" group includes both single aromatic rings as well as fused rings containing at least one aromatic ring. non-limiting examples of $C_3$-$C_{20}$ aryl groups include phenyl (Ph), pentalenyl, indenyl, naphthyl and azulenyl. Non-limiting examples of $X_3$-$X_{20}$ aromatic heterocyclic groups include pyrrolyl, imidazolyl, pyrazolyl, pyridinyl, pyridazinyl, pyrimidinyl, pirazinyl, quinolinyl, isoquinolinyl, acridinyl, indolyl, isoindolyl, indolizinyl, purinyl, carbazolyl, indazolyl, phthalazinyl, naphthyridinyl, quinoxalinyl, quinazolinyl, cinnolinyl, pteridinyl, phenanthridinyl, phenazinyl, phenanthrolinyl, perimidinyl, furyl, dibenzofuryl, xanthenyl, benzofuryl, thiophenyl, thianthrenyl, benzothiophenyl, phosphorinyl, phosphinolinyl, phosphindolyl, thiazolyl, oxazolyl, isoxazolyl, and the like. Likewise, the expression "a linear, branched, and/or cyclic . . . alkylenyl, alkenylenyl or alkynylenyl" includes, interalia, divalent analogs of the above-defined linear, branched, and/or cyclic alkyl, alkenyl or alkynyl groups, including all aryl groups encompassed therein.

As used herein, the term "substituted" is used as it would normally be understood to a person of skill in the art and generally refers to a compound or chemical entity that has one chemical group replaced with a different chemical group. Unless otherwise specified, a substituted alkyl is an alkyl in which one or more hydrogen atom(s) are independently each replaced with an atom that is not hydrogen. For example, chloromethyl is a non-limiting example of a substituted alkyl, more particularly an example of a substituted methyl. Aminoethyl is another non-limiting example of a substituted alkyl, more particularly an example of a substituted ethyl. Unless otherwise specified, a substituted compound or group (e.g. alkyl, alkylenyl, aryl, and the like) may be substituted with any chemical group reasonable to the person of skill in the art. For example, but without limitation, a hydrogen bonded to a carbon or heteroatom (e.g. N) may be substituted with halide (e.g. F, I, Br, Cl), amine, amide, oxo, hydroxyl, thiol (sulfhydryl), phosphate (or phosphoric acid), phosphonate, sulfate, $SO_2H$ (sulfinic acid), $SO_3H$ (sulfonic acid), alkyls, aryl, ketones, carboxaldehyde, carboxylic acid, carboxamides, nitriles, guanidino, monohalomethyl, dihalomethyl or trihalomethyl.

As used herein, the term "unsubstituted" is used as it would normally be understood to a person of skill in the art. Non-limiting examples of unsubstituted alkyls include methyl, ethyl, tert-butyl, pentyl and the like. The expression "optionally substituted" is used interchangeably with the expression "unsubstituted or substituted".

In the structures provided herein, hydrogen may or may not be shown. In some embodiments, hydrogens (whether shown or implicit) may be protium (i.e. $^1H$), deuterium (i.e. $^2H$) or combinations of $^1H$ and $^2H$. Methods for exchanging $^1H$ with $^2H$ are well known in the art. For solvent-exchangeable hydrogens, the exchange of $^1H$ with $^2H$ occurs readily in the presence of a suitable deuterium source, without any catalyst. The use of acid, base or metal catalysts, coupled with conditions of increased temperature and pressure, can facilitate the exchange of non-exchangeable hydrogen atoms, generally resulting in the exchange of all $^1H$ to $^2H$ in a molecule.

The compounds disclosed herein incorporate amino acids, e.g. as residues in a peptide chain (linear or branched) or as amino acids that are otherwise part of a compound. Amino acids have both an amino group and a carboxylic acid group, either or both of which can be used for covalent attachment. In attaching to the remainder of the compound, the amino group and/or the carboxylic acid group may be converted to an amide or other structure; e.g. a carboxylic acid group of a first amino acid is converted to an amide (e.g. a peptide bond) when bonded to the amino group of a second amino acid. As such, amino acid residues may have the formula —$N(R^a)R^bC(O)$—, where $R^a$ and $R^b$ are R-groups. $R^a$ will typically be hydrogen or methyl. The amino acid residues of a peptide may comprise typical peptide (amide) bonds and may further comprise bonds between side chain functional groups and the side chain or main chain functional group of another amino acid. For example, the side chain carboxylate of one amino acid residue in the peptide (e.g. Asp, Glu, etc.)

may be bonded to and the amine of another amino acid residue in the peptide (e.g. Dap, Dab, Orn, Lys). Further details are provided below. The term "amino acid" includes proteinogenic and nonproteinogenic amino acids. Non-limiting examples of nonproteinogenic amino acids are shown in Table 1 and include: D-amino acids (including without limitation any D-form of the following amino acids), ornithine (Orn), 3-(1-naphtyl)alanine (Nal), 3-(2-naphtyl)alanine (2-Nal), α-aminobutyric acid, norvaline, norleucine (Nle), homonorleucine, beta-(1,2,3-triazol-4-yl)-L-alanine, 1,2,4-triazole-3-alanine, Phe(4-F), Phe(4-CI), Phe(4-Br), Phe(4-1), Phe(4-$NH_2$), Phe(4-$NO_2$), homoarginine (hArg), 2-amino-4-guanidinobutyric acid (Agb), 2-amino-3-guanidinopropionic acid (Agp), B-alanine, 4-aminobutyric acid, 5-aminovaleric acid, 6-aminohexanoic acid, 7-aminoheptanoic acid, 8-aminooctanoic acid, 9-aminononanoic acid, 10-aminodecanoic acid, 2-aminooctanoic acid, 2-amino-3-(anthracen-2-yl)propanoic acid, 2-amino-3-(anthracen-9-yl) propanoic acid, 2-amino-3-(pyren-1-yl)propanoic acid, Trp (5-Br), Trp(5-$OCH_3$), Trp(6-F), Trp(5-OH) or Trp(CHO), 2-aminoadipic acid (2-Aad), 3-aminoadipic acid (3-Aad), propargylglycine (Pra), homopropargylglycine (Hpg), beta-homopropargylglycine (Bpg), 2,3-diaminopropionic acid (Dap), 2,4-diaminobutyric acid (Dab), azidolysine (Lys ($N_3$)), azido-ornithine (Orn($N_3$)), 2-amino-4-azidobutanoic acid Dab($N_3$), Dap($N_3$), 2-(5'-azidopentyl)alanine, 2-(6'-azidohexyl)alanine, 4-amino-1-carboxymethyl-piperidine (Pip), 4-(2-aminoethyl)-1-carboxymethyl-piperazine (Acp), and tranexamic acid. If not specified as an L- or D-amino acid, an amino acid shall be understood to encompass both L- and D-amino acids.

TABLE 1

List of non-limiting examples of non-proteinogenic amino acids.

| | |
|---|---|
| Any D-amino acid of a proteinogenic amino acid | 10-aminodecanoic acid |
| ornithine (Orn) | 2-aminooctanoic acid |
| 3-(1-naphtyl)alanine (Nal) | 2-amino-3-(anthracen-2-yl)propanoic acid |
| 3-(2-naphtyl)alanine (2-Nal) | 2-amino-3-(anthracen-9-yl)propanoic acid |
| α-aminobutyric acid | 2-amino-3-(pyren-1-yl)propanoic acid |
| norvaline | Trp(5-Br), |
| norleucine (Nle) | Trp(5-$OCH_3$), |
| homonorleucine | Trp(6-F), |
| beta-(1,2,3-triazol-4-yl)-L-alanine | Trp(5-OH) |
| 1,2,4-triazole-3-alanine | Trp(CHO), |
| Phe(4-F), | 2-aminoadipic acid (2-Aad) |
| Phe(4-Cl), | 3-aminoadipic acid (3-Aad) |
| Phe(4-Br), | propargylglycine (Pra) |
| Phe(4-I), | homopropargylglycine (Hpg) |
| Phe(4-$NH_2$), | beta-homopropargylglycine (Bpg) |
| Phe(4-$NO_2$), | 2,3-diaminopropionic acid (Dap) |
| homoarginine (hArg) | 2,4-diaminobutyric acid (Dab) |
| 4-(2-aminoethyl)-1-carboxymethyl-piperazine (Acp) | azidolysine (Lys($N_3$)) |
| 2-(5'-azidopentyl)alanine | azido-ornithine (Orn($N_3$)) |
| 2-(6'-azidohexyl)alanine | amino-4-azidobutanoic acid Dab($N_3$) |
| 2-amino-4-guanidinobutyric acid (Agb) | tranexamic acid |
| 2-amino-3-guanidinopropionic acid (Agp) | 4-amino-1-carboxymethyl-piperidine (Pip) |
| β-alanine | $NH_2(CH_2)_2O(CH_2)_2C(O)OH$ |
| 4-aminobutyric acid | $NH_2(CH_2)_2[O(CH_2)_2]_2C(O)OH$ |
| 5-aminovaleric acid | $NH_2(CH_2)_2[O(CH_2)_2]_3C(O)OH$ |
| 6-aminohexanoic acid | $NH_2(CH_2)_2[O(CH_2)_2]_4C(O)OH$ |
| 7-aminoheptanoic acid | $NH_2(CH_2)_2[O(CH_2)_2]_5C(O)OH$ |
| 8-aminooctanoic acid | $NH_2(CH_2)_2[O(CH_2)_2]_6C(O)OH$ |
| 9-aminononanoic acid | |

The wavy line "〰" symbol shown through or at the end of a bond in a chemical formula (e.g. in the definitions $L^1$, $L^2$, etc.) is intended to define the R group on one side of the wavy line, without modifying the definition of the structure on the opposite side of the wavy line. Where an R group is bonded on two or more sides (e.g. certain definitions of $X^1$, $X^2$, etc.), any atoms shown outside the wavy lines are intended to clarify orientation of the R group. As such, only the atoms between the two wavy lines constitute the definition of the R group. When atoms are not shown outside the wavy lines, or for a chemical group shown without wavy lines but does have bonds on multiple sides (e.g. —C(O)NH—, and the like.), the chemical group should be read from left to right matching the orientation in the formula that the group relates to (e.g. for formula —$R^a$—$R^b$—$R^c$—, the definition of $R^b$ as —C(O)NH— would be incorporated into the formula as —$R^a$—C(O)NH—$R^c$— not as —$R^a$—NHC(O)—$R^c$—).

In various aspects, there is disclosed a compound, wherein the compound has Formula I or is a salt or a solvate of Formula I:

$$[\text{targeting peptide}]\text{-N}(R^1)\text{—}X^1(R^2)L^1\text{-[linker]-}R^X_{n1} \quad (1),$$

wherein:

the targeting peptide is cyclo[L-Phe-L-Tyr-L-Lys(iPr)-D-Arg-L-2-Nal-Gly-D-Glu]-L-Lys(iPr) which is C-terminally bonded to —N($R^1$)—;

$R^1$ is H or methyl;

$X^1$ is a linear, branched, and/or cyclic $C_1$-$C_{15}$ hydrocarbon (e.g. alkylenyl, alkenylenyl or alkynylenyl) wherein 0-6 carbons are independently replaced by N, S, and/or O heteroatoms, and substituted with 0-3 groups independently selected from one or a combination of oxo, hydroxyl, sulfhydryl, halogen, guanidino, carboxylic acid, sulfonic acid, sulfinic acid, and/or phosphoric acid; $R^2$ is C(O)OH or C(O)$NH_2$;

$L^1$ is —S—, —NHC(O)—, —C(O)NH—, —N(CH$_3$)C(O)—, —C(O)N(CH$_3$)—,

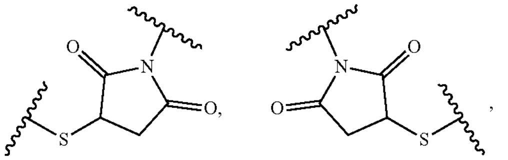

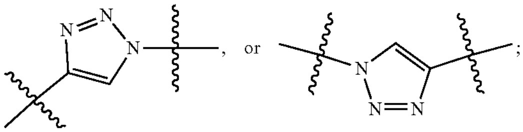

the linker is a linear or branched chain of 1-10 units of $X^2L^2$ and/or $X^2(L^2)_2$, wherein:

each $X^2$ is, independently, a linear, branched, and/or cyclic $C_1$-$C_{15}$ hydrocarbon (e.g. alkylenyl, alkenylenyl or alkynylenyl) wherein 0-6 carbons are independently replaced by N, S, and/or O heteroatoms, and substituted with 0-3 groups independently selected from one or a combination of oxo, hydroxyl, sulfhydryl, halogen, guanidino, carboxylic acid, sulfonic acid, sulfinic acid, and/or phosphoric acid;

each $L^2$ is independently —S—, —NHC(O)—, —C(O)NH—, —N(CH$_3$)C(O)—, —C(O)N(CH$_3$)—,

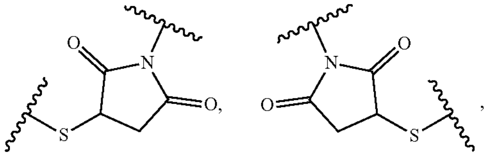

-continued

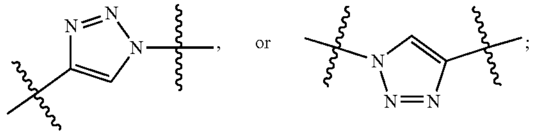

the linker comprises at least one carboxylic acid, sulfonic acid, sulfinic acid, or phosphoric acid, and has a net negative charge at physiological pH;

the linker optionally further comprises an albumin binder bonded to an $L_2$ of the linker, wherein the albumin binder is: —(CH$_2$)$_{n2}$—CH$_3$ wherein n2 is 8-20; —(CH$_2$)$_{n3}$—C(O)OH wherein n3 is 8-20, or

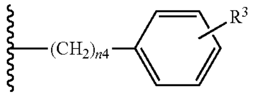

wherein n4=1-4 and $R^3$ is I, Br, F, Cl, H, OH, OCH$_3$, NH$_2$, NO$_2$ or CH$_3$;

n1 is 1 or 2; and each $R^X$ is a radiolabelling group linked through a separate $L_2$ of the linker, and is independently selected from: a metal chelator optionally in complex with a radiometal or radioisotope-bound metal; a prosthetic group containing trifluoroborate (BF$_3$); or a prosthetic group containing a silicon-fluorine-acceptor moiety.

The targeting peptide has the structure of Formula II or is a salt or solvate of Formula II:

(II)

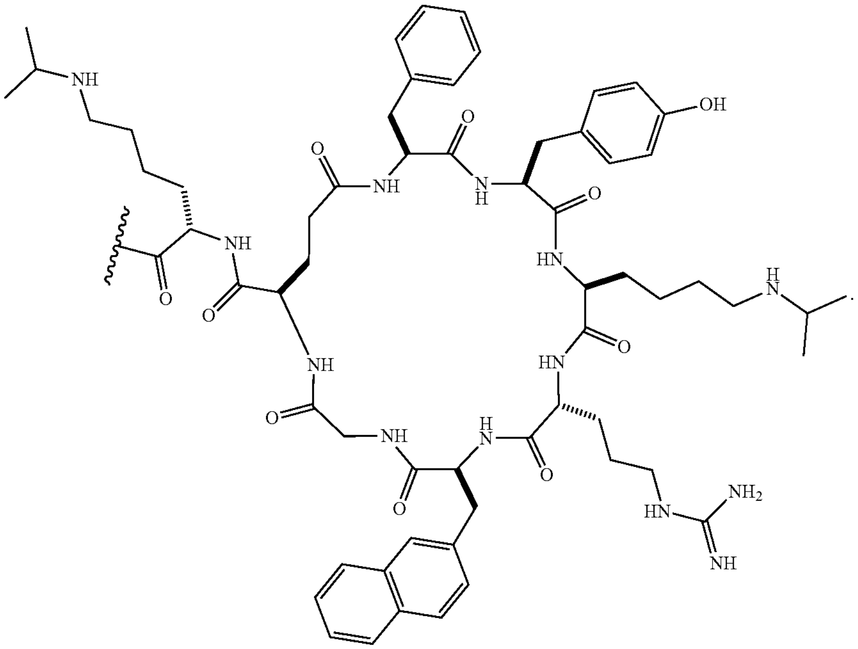

In some embodiments, $R^1$ is H. In other embodiments, $R^1$ is methyl.

$X^1$ is a linear, branched, and/or cyclic $C_1$-$C_{15}$ hydrocarbon (e.g. alkylenyl, alkenylenyl or alkynylenyl) wherein 0-6 carbons are independently replaced by N, S, and/or O heteroatoms, and substituted with 0-3 groups independently selected from one or a combination of oxo, hydroxyl, sulfhydryl, halogen, guanidino, carboxylic acid, sulfonic acid, sulfinic acid, and/or phosphoric acid. In some embodiments, the hydrocarbon is an alkylenyl. In some embodiments, the hydrocarbon is an alkenylenyl. In some embodiments, the hydrocarbon is an alkynylenyl. In some embodiments, the hydrocarbon is linear. In some embodiments, the hydrocarbon is branched. In some embodiments, the hydrocarbon is cyclic. The term "cyclic" in this context includes single ring, multi-ring or fused ring systems, each of which can individually be aromatic, partially aromatic or non-aromatic. In some embodiments, the hydrocarbon is linear and cyclic. In some embodiments, the hydrocarbon is branched and cyclic.

In some embodiments, $X^1$ is a linear, branched, and/or cyclic $C_1$-$C_{15}$ alkylenyl. In some embodiments, $X^1$ is a linear alkylenyl. In some embodiments, $X^1$ is

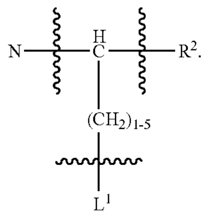

In some embodiments, $X^1$ is

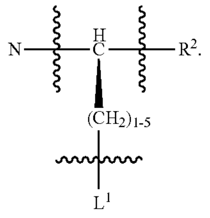

In some embodiments, $X^1$ is

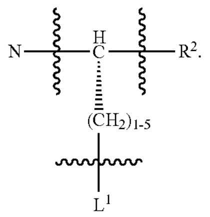

In some embodiments, $-N(R^1)-X^1(R^2)L^1$- forms a sidechain-linked amino acid residue. In some embodiments, the sidechain-linked amino acid residue is Lys, ornithine, 2,3-diaminopropionic acid (Dap), 2,4-diaminobutyric acid (Dab), Glu, Asp, or 2-aminoadipic acid (2-Aad). In some embodiments, the sidechain-linked amino acid residue is an L-amino acid. In some embodiments, the sidechain-linked amino acid residue is a D-amino acid. In some embodiments, the sidechain-linked amino acid residue is L-Lys. In some embodiments, the sidechain-linked amino acid residue is D-Lys.

In some embodiments, $R^2$ is C(O)OH. In other embodiments, $R^2$ is $C(O)NH_2$.

$L^1$ is a linkage selected from —S—, —NHC(O)—, —C(O)NH—, $-N(CH_3)C(O)-$, $-C(O)N(CH_3)-$,

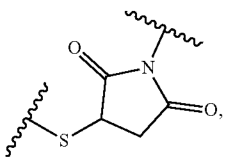
,
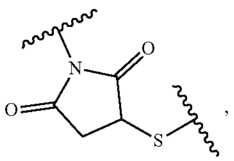
,
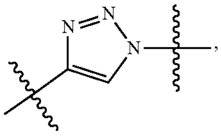
, or
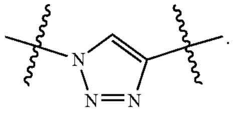
.

In some embodiments, $L^1$ is —S—. In some embodiments, $L^1$ is —NHC(O)—. In some embodiments, $L^1$ is —C(O)NH—. In some embodiments, $L^1$ is $-N(CH_3)C(O)-$. In some embodiments, $L^1$ is $-C(O)N(CH_3)-$. In some embodiments, $L^1$ is

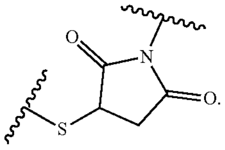 [SMILES: *SC1CC(=O)N(*)C1=O]

In some embodiments, $L^1$ is

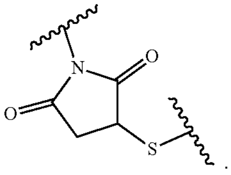 [SMILES: *SC1CC(=O)N(*)C1=O]

In some embodiments, $L^1$ is

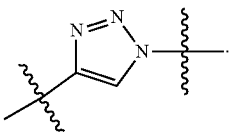

In some embodiments, $L^1$ is

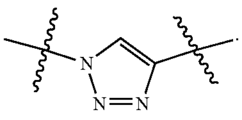

The "linker" is a linear or branched chain of 1-10 units of $X^2L^2$ and/or $X^2(L^2)_2$, including any combination or configuration of $X^2L^2$ and/or $X^2(L^2)_2$. In some embodiments, the linker consists only of $X^2L^2$ units (e.g. 1-10 units of $X^2L^2$ and zero units of $X^2(L^2)_2$). In some embodiments, the linker has 3 units of $X^2L^2$. In some embodiments, the linker has 1 unit of $X^2(L^2)_2$. In some embodiments, the linker has 2 units of $X^2(L^2)_2$. In some embodiments, the linker has 3 units of $X^2(L^2)_2$. In some embodiments, the linker has 1-8 units of $X^2L^2$ and 0-2 units of $X^2(L^2)_2$. In some embodiments, the linker has 1-3 units of $X^2L^2$ and 0 units of $X^2(L^2)_2$. In some embodiments, the linker has 3 units of $X^2L^2$ and 0 units of $X^2(L^2)_2$. In some embodiments, the linker has 4 units of $X^2L^2$ and 0 units of $X^2(L^2)_2$. In some embodiments, the linker has 1 units of $X^2L^2$ and 1 unit of $X^2(L^2)_2$. In some embodiments, the linker has 2 units of $X^2L^2$ and 1 unit of $X^2(L^2)_2$. In some embodiments, the linker has 3 units of $X^2L^2$ and 1 unit of $X^2(L^2)_2$. In some embodiments, the linker has 4 units of $X^2L^2$ and 1 unit of $X^2(L^2)_2$. In some embodiments, the linker has 5 units of $X^2L^2$ and 1 unit of $X^2(L^2)_2$. In some embodiments, the linker has 6 units of $X^2L^2$ and 1 unit of $X^2(L^2)_2$. In some embodiments, the linker has 7 units of $X^2L^2$ and 1 unit of $X^2(L^2)_2$. In some embodiments, the linker has 1-8 units of $X^2L^2$ and 2 units of $X^2(L^2)_2$.

Each $X^2$ is, independently, a linear, branched, and/or cyclic $C_1$-$C_{15}$ hydrocarbon (e.g. alkylenyl, alkenylenyl or alkynylenyl) wherein 0-6 carbons are independently replaced by N, S, and/or O heteroatoms, and substituted with 0-3 groups independently selected from one or a combination of oxo, hydroxyl, sulfhydryl, halogen, guanidino, carboxylic acid, sulfonic acid, sulfinic acid, and/or phosphoric acid. In some embodiments, one or more hydrocarbon is an alkylenyl. In some embodiments, one or more hydrocarbon is an alkenylenyl. In some embodiments, one or more hydrocarbon is an alkynylenyl. In some embodiments, one or more hydrocarbon is linear and cyclic. In some embodiments, one or more hydrocarbon is branched and cyclic. The term "cyclic" in this context includes single ring, multi-ring or fused ring systems, each of which can individually be aromatic, partially aromatic or non-aromatic. In some embodiments, each hydrocarbon is linear.

In some embodiments, each $X^2$ in each $X^2L^2$ unit is independently a linear, branched, and/or cyclic $C_1$-$C_{15}$ alkylenyl. In some embodiments, each $X^2$ in each $X^2L^2$ unit is, independently, a linear or branched $C_1$-$C_{15}$ alkylenyl substituted with 0-1 group independently selected from carboxylic acid, sulfonic acid, sulfinic acid, and/or phosphoric acid. In some embodiments, each $X^2$ in each $X^2L^2$ unit is, independently, a linear or branched $C_2$-$C_6$ alkylenyl substituted with 0-1 group independently selected from carboxylic acid, sulfonic acid, sulfinic acid, and/or phosphoric acid. In some embodiments, each $X^2$ in each $X^2L^2$ unit is, independently, a linear or branched $C_2$-$C_6$ alkylenyl substituted with 0-1 carboxylic acid group.

In some embodiments, each $X^2$ in each $X^2L^2$ unit is independently a linear, branched, and/or cyclic $C_1$-$C_{15}$ alkylenyl. In some embodiments, each $X^2$ in each $X^2(L^2)_2$ unit is, independently, a linear or branched $C_1$-$C_{15}$ alkylenyl. In some embodiments, each $X^2$ in each $X^2(L^2)_2$ unit is, independently, a linear or branched $C_2$-$C_6$ alkylenyl.

In some embodiments, each $X^2$ is independently: —CH(R)— wherein each R is independently H or $C_1$-$C_3$ linear or branched alkyl;

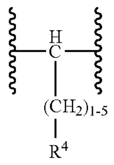

wherein each $R^4$ is independently hydrogen, carboxylic acid, sulfonic acid, sulfinic acid, or phosphoric acid; or

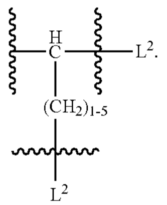

In some embodiments, each $X^2$ is independently: —CH—;

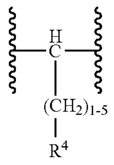

wherein each $R^4$ is independently carboxylic acid, sulfonic acid, sulfinic acid, or phosphoric acid; or

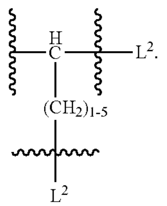

In some embodiments, each $X^2$ is independently: —CH—;

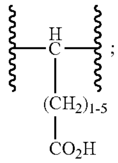

; or

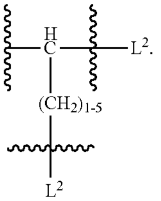

Each $L^2$ is a linkage independently selected from —S—, —NHC(O)—, —C(O)NH—, —N($CH_3$)C(O)—, —C(O)N($CH_3$)—,

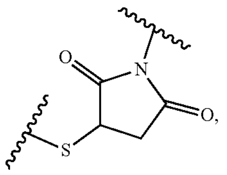 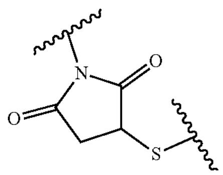 ,

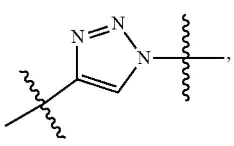 , or 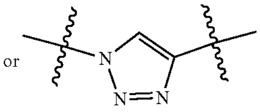 .

In some embodiments, each $L^2$ between two $X^2$ groups is independently —NHC(O)—, —C(O)NH—, —$N(CH_3)C$(O)—, or —$C(O)N(CH_3)$—, and each $L^2$ linking $R^X$ is independently —S—, —NHC(O)—, —C(O)NH—,

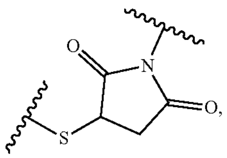 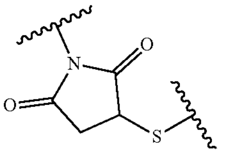 ,

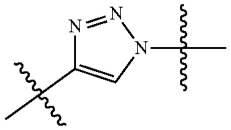 , or

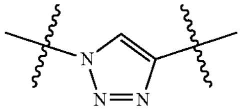 .

In some such embodiments, each $L^2$ linking $R^X$ is independently-NHC(O)—, —C(O)NH—, —$N(CH_3)C(O)$—, —$C(O)N(CH_3)$—,

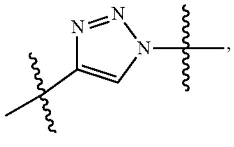 , or 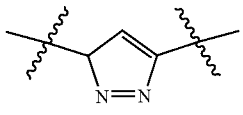 .

In some such embodiments, each $L^2$ linking $R^X$ is independently-NHC(O)—, —C(O)NH—,

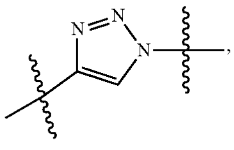 , or 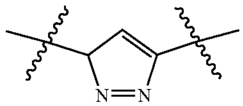 .

In some such embodiments, each $L^2$ between two $X^2$ groups is an unmethylated amide. In some such embodiments, 1, 2, 3, 4, or 5 instances of $L^2$ between two $X^2$ groups is a methylated amide.

In some embodiments, the linker (when including the —C(O)— of $L^1$) corresponds to a linear or branched peptide of amino acid residues selected from proteinogenic amino acid residues and/or nonproteinogenic amino acid residues (e.g. as listed in Table 1), and wherein each $L^2$ between two $X^2$ groups is methylated or unmethylated, and wherein each $L^2$ linking an $R^X$ is independently —S—, —NHC(O)—, —C(O)NH—, —$N(CH_3)C(O)$—, —$C(O)N(CH_3)$—,

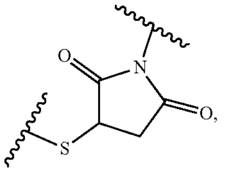 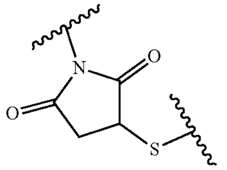 ,

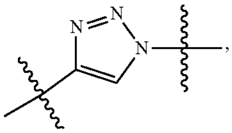 , or 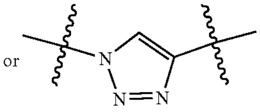 .

In some such embodiments, each $L^2$ between two $X^2$ groups is an unmethylated amide. In some such embodiments, 1, 2, 3, 4, or 5 instances of $L^2$ between two $X^2$ groups is a methylated amide.

The amino acid residues in the linker may be all L-amino acids, all D-amino acids, or a combination of L- and D-amino acids. In some embodiments, all amino acids in the linker are L-amino acids. In some embodiments, all amino acids in the linker are D-amino acids.

In some embodiments, the linker comprises 2-7 amino acid residues selected from one or a combination of: Glu, Asp, and/or 2-aminoadipic acid (2-Aad). In some embodiments, the linker comprises 2 amino acid residues selected from one or a combination of: Glu, Asp, and/or 2-Aad. In some embodiments, the linker comprises 3 amino acid residues selected from one or a combination of: Glu, Asp, and/or 2-Aad. In some embodiments, the linker comprises 4 amino acid residues selected from one or a combination of: Glu, Asp, and/or 2-Aad. In some embodiments, the linker comprises 5 amino acid residues selected from one or a combination of: Glu, Asp, and/or 2-Aad. In some embodiments, the linker comprises 2 or 3 consecutive Glu, Asp, and/or 2-Aad residues. In some embodiments, the linker comprises 3 consecutive Glu residues. In some embodiments, the linker (when including the —C(O)— of $L^1$) consists of a linear peptide of 3 Glu/Asp/2-Aad residues (see compounds BL02, BL08, BL09, BL17, BL20, BL25).

In some embodiments, the linker has a net negative charge of −1 to −5 at physiological pH. In some embodiments, the linker has a net negative charge of −2 to −5 at physiological pH. In some embodiments, the linker has a net negative charge of −1 at physiological pH. In some embodiments, the linker has a net negative charge of −2 at physiological pH. In some embodiments, the linker has a net negative charge of −3 at physiological pH. In some embodiments, the linker has a net negative charge of −4 at physiological pH. In some embodiments, the linker has a net negative charge of −5 at physiological pH.

In some embodiments, the linker has the structure of the linker of any one of BL02, BL03, BL04, BL07, BL08, BL09, BL17, BL18, BL19, BL20, BL21, BL22, BL23, BL24, BL25, BL26, BL27, BL28, or BL29, or wherein the linker is a salt or solvate of a linker of the foregoing.

In some embodiments, the compound has the structure of any one of BL02, BL03, BL04, BL07, BL08, BL09, BL17, BL18, BL19, BL20, BL21, BL22, BL23, BL24, BL25, BL26, BL27, BL28, or BL29, or which is a salt or solvate thereof, wherein DOTA is optionally in complex with a radioisotope or wherein the prosthetic group containing $BF_3$ optionally comprises $^{18}F$.

In some embodiments, the linker further comprises an albumin binder bonded to an $L^2$ of the linker. In some embodiments, the albumin binder is: $-(CH_2)_{n2}-CH_3$ wherein n2 is 8-20. In some embodiments, n2 is 12-18. In some embodiments, n2 is 14-18. In some embodiments, n2 is 16. In some embodiments, the albumin binder is $-(CH_2)_{n3}-C(O)OH$ wherein n3 is 8-20. In some embodiments, n3 is 12-18. In some embodiments, n3 is 14-18. In some embodiments, n3 is 16. In some embodiments, the albumin binder is

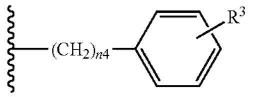

wherein n4=1-4 and $R^3$ is I, Br, F, Cl, H, OH, $OCH_3$, $NH_2$, $NO_2$ or $CH_3$. In some embodiments, n4 is 1. In some embodiments, n4 is 2. In some embodiments, n4 is 3. In some embodiments, n4 is 4. In some embodiments, $R^3$ is H, I, Cl, F, $OCH_3$, or $CH_3$. In some embodiments, n4 is 3 and $R^3$ is H, I, Cl, F, $OCH_3$, or $CH_3$. In some embodiments, the $L^2$ incorporating the albumin binder into the linker is an amide.

In some embodiments, n1 is 1. In other embodiments, n1 is 2; i.e. the compound has two radiolabeling groups attached to the linker. In some embodiments, the two radiolabeling groups are different. In some embodiments, the two radiolabeling groups are the same.

In some embodiments, an $R^X$ comprises a metal chelator optionally in complex with a radiometal (e.g. $^{68}Ga$ or $^{177}Lu$) or in complex with a radioisotope-bound metal (e.g. $Al^{18}F$). The chelator may be any metal chelator suitable for binding to the radiometal or to the metal-containing prosthetic group bonded to the radioisotope (e.g. polyaminocarboxylates and the like). Many suitable chelators are known, e.g. as summarized in Price and Orvig, *Chem. Soc. Rev.,* 2014, 43, 260-290, which is incorporated by reference in its entirety. Non-limiting examples of suitable chelators include those selected from the group consisting of: DOTA and derivatives; DOTAGA; NOTA; NODAGA; NODASA; CB-DO2A; 3p-C-DEPA; TCMC; DO3A; DTPA and DTPA analogues optionally selected from CHX-A"-DTPA and 1B4M-DTPA; TETA; NOPO; Me-3,2-HOPO; CB-TE1A1P; CB-TE2P; MM-TE2A; DM-TE2A; sarcophagine and sarcophagine derivatives optionally selected from SarAr, SarAr-NCS, diamSar, AmBaSar, and BaBaSar; TRAP; AAZTA; DATA and DATA derivatives; H2-macropa or a derivative thereof; $H_2$dedpa, $H_4$octapa, $H_4$py4pa, $H_4$Pypa, $H_2$azapa, Hsdecapa, and other picolinic acid derivatives; CP256; PCTA; C-NETA; C-NE3TA; HBED; SHBED; BCPA; CP256; YM103; desferrioxamine (DFO) and DFO derivatives; and $H_6$phospa. Exemplary non-limiting examples of suitable chelators and example radioisotopes (radiometals) chelated by these chelators are shown in Table 2. In alternative embodiments, an $R^X$ comprises a chelator selected from those listed above or in Table 2, or is any other suitable chelator. One skilled in the art could replace any of the chelators listed herein with another chelator.

TABLE 2

Exemplary chelators and exemplary isotopes which bind said chelators.

| Chelator | Isotopes |
|---|---|
| 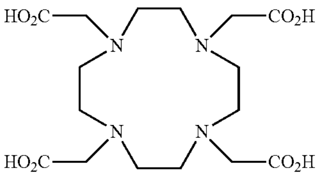 [SMILES: O=C(O)CN1CCN(CC(=O)O)CCN(CC(=O)O)CCN(CC(=O)O)CC1]<br>DOTA 1,4,7,10-tetraazacyclododecane-1,4,7,10-tetraacetic acid | Cu-64/67<br>Ga-67/68<br>In-111<br>Lu-177<br>Y-86/90<br>Bi-203/212/213<br>Pb-212<br>Ac-225<br>Gd-159<br>Yb-175<br>Ho-166<br>As-211<br>Sc-44/47<br>Pm-149<br>Pr-142<br>Sn-117m<br>Sm-153<br>Tb-149/161<br>Er-165<br>Ra-223/224<br>Th-227 |
| 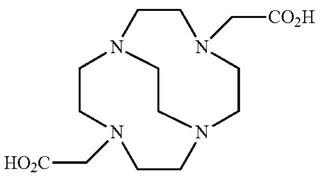<br>CB-DO2A, 4,10-bis(carboxymethyl)-1,4,7,10-tetraazabicyclo[5.5.2]tetradecane | Cu-64/67 |

TABLE 2-continued
| Exemplary chelators and exemplary isotopes which bind said chelators. | |
|---|---|
| Chelator | Isotopes |
| 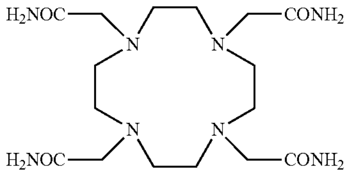 [SMILES: NC(=O)CN1CCN(CC(N)=O)CCN(CC(N)=O)CCN(CC(N)=O)CC1] TCMC, 1,4,7,10-tetrakis(carbamoylmethyl)-I,4,7,10-tetraazacyclododecane | Pb-212 |
| 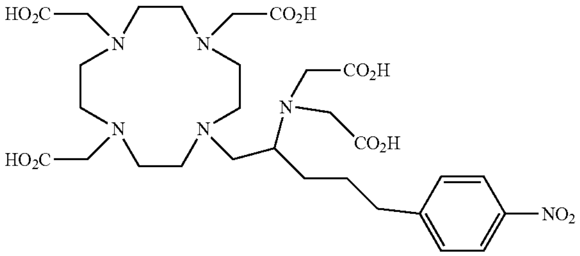 [SMILES: O=C(O)CN1CCN(CC(=O)O)CCN(CC(CCCc2ccc([N+](=O)[O-])cc2)N(CC(=O)O)CC(=O)O)CCN(CC(=O)O)CC1] 3p-C-DEPA | Bi-212/213 |
| 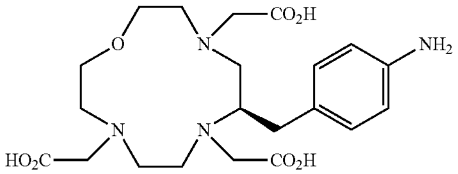 [SMILES: Nc1ccc(C[C@@H]2CN(CC(=O)O)CCOCCN(CC(=O)O)CCN2CC(=O)O)cc1] p-$NH_2$-Bn-Oxo-DO3A | Cu-64/67 |
| 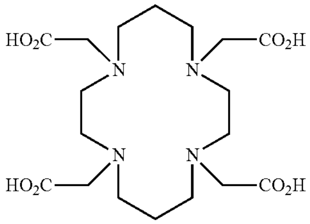 [SMILES: O=C(O)CN1CCCN(CC(=O)O)CCN(CC(=O)O)CCCN(CC(=O)O)CC1] TETA, 1,4,8,11-tetraazacyclotetradecane-1,4,8,11-tetraacetic acid | Cu-64/67 |
| 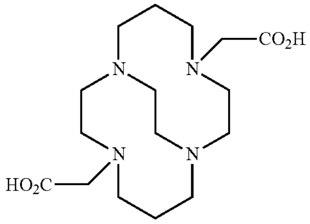 [SMILES: O=C(O)CN1CCCN2CCN(CCCN(CC(=O)O)CC2)CC1] CB-TE2A, 4,11-bis-(carboxymethyl)-1,4,8,11-tetraazabicyclo[6.6.2]-hexadecane | Cu-64/67 |

TABLE 2-continued

| Exemplary chelators and exemplary isotopes which bind said chelators. | |
|---|---|
| Chelator | Isotopes |
| 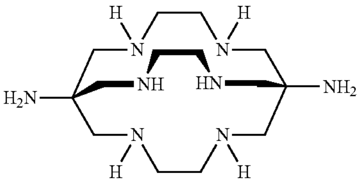<br>Diamsar | Cu-64/67 |
| 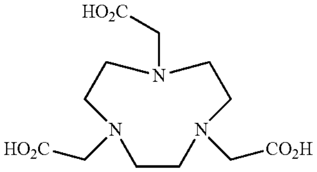 [SMILES: O=C(O)CN1CCN(CC(=O)O)CCN(CC(=O)O)CC1]<br>NOTA, 1,4,7-triazacyclononane-1,4,7-triacetic acid | Cu-64/67<br>Ga-68<br>In-111<br>Sc-44/47 |
| 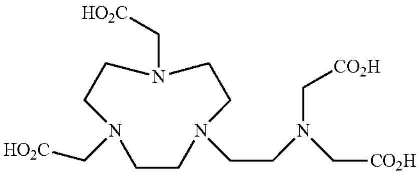 [SMILES: O=C(O)CN1CCN(CCN(CC(=O)O)CC(=O)O)CCN(CC(=O)O)CC1]<br>NETA, {4-[2-(bis-carboxymethylamino)-ethyl]-7-carboxymethyl-[1,4,7]triazonan-1-yl}-acetic acid | Cu-64/67<br>Ga-68<br>Lu-177<br>Y-86/90<br>Bi-213<br>Pb-212 |
| 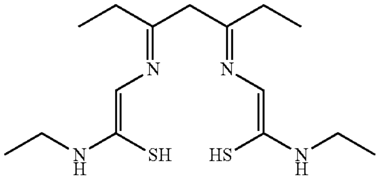 [SMILES: CCN/C(S)=C/N=C(\CC)C/C(CC)=N/C=C(\S)NCC]<br>HxTSE | Au-198/199 |
| 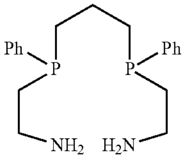<br>$P_2N_2Ph_2$ | Rh-105 |
| 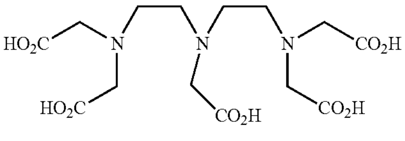 [SMILES: O=C(O)CN(CCN(CC(=O)O)CC(=O)O)CCN(CC(=O)O)CC(=O)O]<br>DTPA, diethylenetriaminepentaacetic acid | In-111<br>Sc-44/47<br>Lu-177<br>Y-86/90<br>Sn-117m<br>Pd-109 |
| 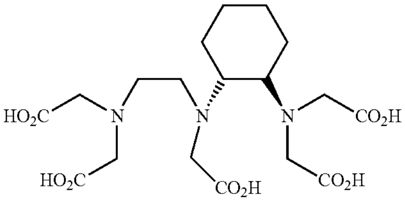 | In-111<br>Lu-177<br>Y-86/90<br>Bi-212/213 |

TABLE 2-continued

| Exemplary chelators and exemplary isotopes which bind said chelators. | |
|---|---|
| Chelator | Isotopes |
| CHX-A00-DTPA, 2-(p-isothiocyanatobenzyl)-cyclohexyldiethylenetriaminepentaacetic acid | |
| 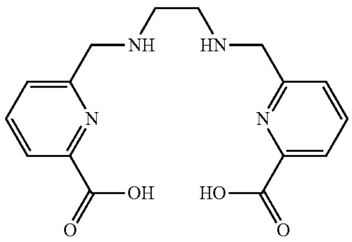 [SMILES: O=C(O)c1cccc(CNCCNCc2cccc(C(=O)O)n2)n1] $H_2$dedpa, 1,2-[[6-(carboxy)-pyridin-2-yl]-methylamino]ethane | Cu-64/67 |
| 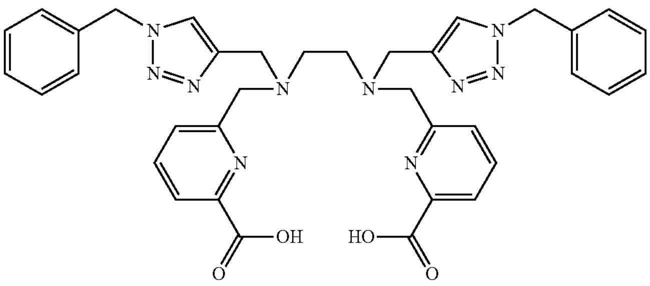 [SMILES: O=C(O)c1cccc(CN(CCN(Cc2cn(Cc3ccccc3)nn2)Cc2cccc(C(=O)O)n2)Cc2cn(Cc3ccccc3)nn2)n1] $H_2$azapa, N,N0-[1-benzyl-1,2,3-triazole-4-yl]methyl-N,N0-[6-(carboxy)pyridin-2-yl]-1,2-diaminoethane | Cu-64/67 |
| 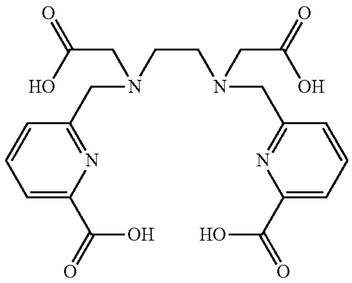 [SMILES: O=C(O)CN(CCN(CC(=O)O)Cc1cccc(C(=O)O)n1)Cc1cccc(C(=O)O)n1] $H_4$octapa | In-111<br>Lu-177<br>Y-86/90<br>Ac-225 |
| 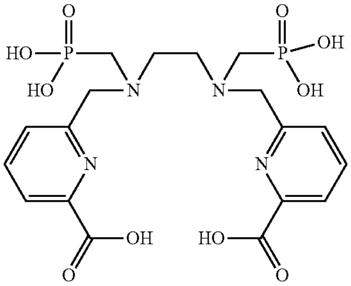 [SMILES: O=C(O)c1cccc(CN(CCN(Cc2cccc(C(=O)O)n2)CP(=O)(O)O)CP(=O)(O)O)n1] $H_6$phospa | Ac-225 |

TABLE 2-continued
Exemplary chelators and exemplary isotopes which bind said chelators.
| Chelator | Isotopes |
|---|---|
| 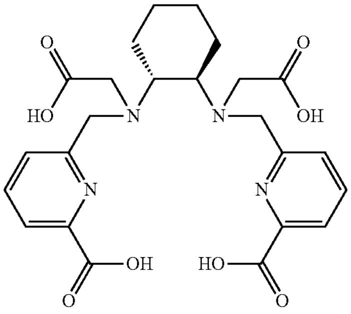 [SMILES: O=C(O)CN(Cc1cccc(C(=O)O)n1)[C@@H]1CCCC[C@H]1N(CC(=O)O)Cc1cccc(C(=O)O)n1]<br>$H_4CHXoctapa$ | In-111<br>Ac-225 |
| 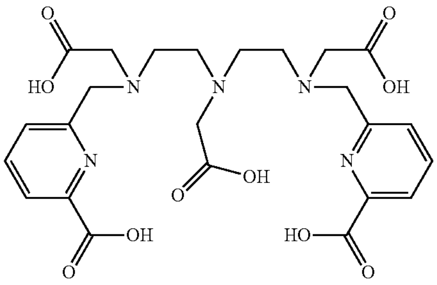 [SMILES: O=C(O)CN(CCN(CC(=O)O)Cc1cccc(C(=O)O)n1)CCN(CC(=O)O)Cc1cccc(C(=O)O)n1]<br>$H_5decapa$ | In-111<br>Lu-177<br>Ac-225 |
| 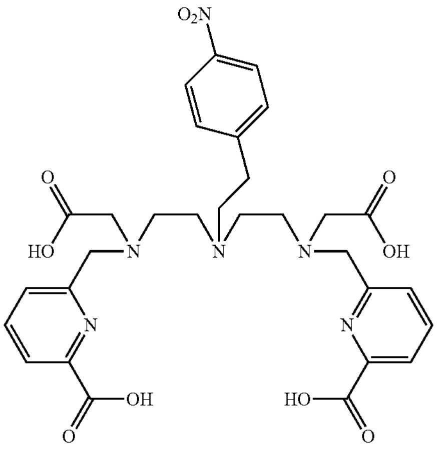 [SMILES: O=C(O)CN(CCN(CCc1ccc([N+](=O)[O-])cc1)CCN(CC(=O)O)Cc1cccc(C(=O)O)n1)Cc1cccc(C(=O)O)n1]<br>$H_4neunpa$-p-Bn-$NO_2$ | In-111<br>Lu-177<br>Ac-225 |
| 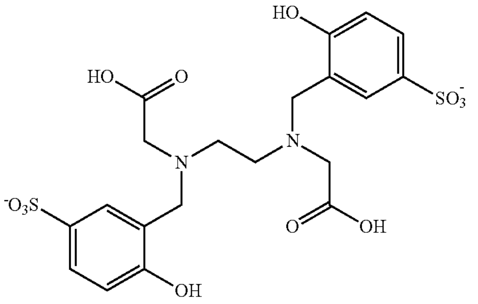<br>SHBED, N,N0-bis(2-hydroxy-5-sulfobenzyl)-ethylenediamine-N,N0-diacetic acid | In-111<br>Ga-68 |

TABLE 2-continued

Exemplary chelators and exemplary isotopes which bind said chelators.

| Chelator | Isotopes |
| --- | --- |
| 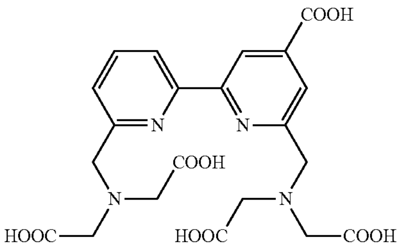 BPCA | In-111 |
| 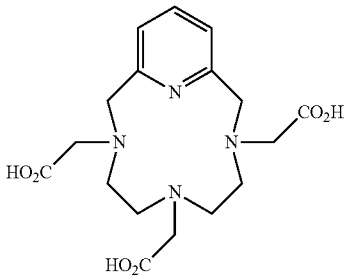 PCTA, 3,6,9,15-tetraazabicyclo[9.3.1]-pentadeca-1(15),11,13-triene-3,6,9,-tri-acetic acid | Cu-64/67 |
| H2-MACROPA (N,N'-bis[(6-carboxy-2-pyridil)methyl]-4,13-diaza-18-crown-6) | Ac-225 |

In some embodiments, an $R^X$ of the compound is a polyaminocarboxylate chelator. In some such embodiments, the chelator is attached through an amide bond. In some embodiments, $R^X$ is: DOTA or a derivative thereof; TETA or a derivative thereof; SarAr or a derivative thereof; NOTA or a derivative thereof; TRAP or a derivative thereof; HBED or a derivative thereof; 2,3-HOPO or a derivative thereof; PCTA (3,6,9,15-tetraazabicyclo[9.3.1]-pentadeca-1(15),11,13-triene-3,6,9,-triacetic acid) or a derivative thereof; DFO or a derivative thereof; DTPA or a derivative thereof; OCTAPA (N,N0-bis(6-carboxy-2-pyridylmethyl)-ethylenediamine-N,N0-diacetic acid) or a derivative thereof; or H2-MACROPA or a derivative thereof. In some embodiments, an $R^X$ is DOTA. In some embodiments, an $R^X$ is a chelator moiety in complex with radioisotope X wherein X is $^{64}$Cu, $^{67}$Cu, $^{90}$Y, $^{111}$In, $^{114m}$In $^{117m}$Sn, $^{153}$Sm, $^{149}$Tb, $^{161}$Tb, $^{177}$Lu $^{225}$Ac, $^{213}$Bi, $^{224}$Ra, $^{212}$Bi, $^{212}$Pb, $^{227}$Th, $^{223}$Ra, $^{47}$Sc, $^{186}$Re or $^{188}$Re. In some embodiments, X is $^{177}$Lu. In some embodiments, an $R^X$ is a chelator moiety in complex with radioisotope X wherein X is $^{64}$Cu, $^{68}$Ga, $^{86}$Y, $^{111}$In, $^{94m}$Tc, $^{44}$Sc, $^{89}$Zr, or $^{99m}$Tc. In some embodiments, X is $^{68}$Ga.

In some embodiments, the chelator is conjugated with a radioisotope. The conjugated radioisotope may be, without limitation, $^{68}$Ga, $^{61}$Cu, $^{64}$Cu, $^{67}$Ga, $^{99m}$Tc, $^{111}$In, $^{44}$Sc, $^{86}$Y, $^{89}$Zr, $^{90}$Nb, $^{177}$Lu, $^{117m}$Sn, $^{165}$Er, $^{90}$Y, $^{227}$Th, $^{225}$Ac, $^{213}$Bi, $^{212}$Bi, $^{211}$As, $^{203}$Pb, $^{212}$Pb, $^{47}$Sc, $^{166}$Ho, $^{188}$Re, $^{186}$Re, $^{149}$Pm, $^{159}$Gd, $^{105}$Rh, $^{109}$Pd, $^{198}$Au, $^{199}$Au, $^{175}$Yb, $^{142}$Pr, $^{14m}$In, and the like. In some embodiments, the chelator is a chelator from Table 2 and the conjugated radioisotope is a radioisotope indicated in Table 2 as a binder of the chelator.

In some embodiments, the chelator is not conjugated to a radioisotope.

In some embodiments, the chelator is: DOTA or a derivative thereof, conjugated with $^{177}$Lu, $^{111}$In, $^{213}$Bi, $^{68}$Ga, $^{67}$Ga, $^{203}$Pb, $^{212}$Pb, $^{44}$Sc, $^{47}$Sc, $^{90}$Y, $^{86}$Y, $^{225}$Ac, $^{117m}$Sn, $^{153}$Sm, $^{149}$Tb, $^{161}$Tb, $^{165}$Er, $^{224}$Ra, $^{212}$Bi, $^{227}$Th, $^{223}$Ra, $^{64}$Cu or $^{67}$Cu; H2-MACROPA conjugated with $^{225}$Ac; Me-3,2-HOPO conjugated with $^{227}$Th; $H_4$py4pa conjugated with $^{225}$Ac, $^{227}$Th or $^{177}$Lu; $H_4$pypa conjugated with $^{177}$Lu; NODAGA conjugated with $^{68}$Ga; DTPA conjugated with $^{111}$In; or DFO conjugated with $^{89}$Zr.

In some embodiments, the chelator is TETA, SarAr, NOTA, TRAP, HBED, 2,3-HOPO, PCTA, DFO, DTPA, OCTAPA or another picolinic acid derivative.

In some embodiments, an $R^X$ is a chelator for radiolabelling with $^{99m}$Tc, $^{94m}$Tc, $^{186}$Re, or $^{188}$Re, such as mercaptoacetyl, hydrazinonicotinamide, dimercaptosuccinic acid, 1,2-ethylenediylbis-L-cysteine diethyl ester, methylenediphosphonate, hexamethylpropyleneamineoxime and hexakis(methoxy isobutyl isonitrile), and the like. In some embodiments, an $R^X$ is a chelator, wherein the chelator is mercaptoacetyl, hydrazinonicotinamide, dimercaptosuccinic acid, 1,2-ethylenediylbis-L-cysteine diethyl ester, methylenediphosphonate, hexamethylpropyleneamineoxime or hexakis(methoxy isobutyl isonitrile). In some of these embodiments, the chelator is bound by a radioisotope. In some such embodiments, the radioisotope is $^{99m}$Tc, $^{94m}$Tc, $^{186}$Re, or $^{188}$Re.

In some embodiments, an $R^X$ is a chelator that can bind $^{18}$F-aluminum fluoride ([$^{18}$F]AIF), such as 1,4,7-triazacyclononane-1,4-diacetate (NODA) and the like. In some embodiments, the chelator is NODA. In some embodiments, the chelator is bound by [$^{18}$F]AIF.

In some embodiments, an $R^X$ is a chelator that can bind $^{72}$As or $^{77}$As, such as a trithiol chelate and the like. In some embodiments, the chelator is a trithiol chelate. In some embodiments, the chelator is conjugated to $^{72}As$. In some embodiments, the chelator is conjugated to $^{77}As$.

In some embodiments, an $R^X$ is a prosthetic group containing a trifluoroborate ($BF_3$), capable of $^{18}F/^{19}F$ exchange radiolabeling. Such an $R^X$ group may be the only $R^X$ (n1=1), or may be in addition to second $R^X$ (n1=2), wherein the second $R^X$ is the same or different as the first $R^X$. The prosthetic group may be $R^6R^7BF_3$, wherein $R^6$ is independently $-(CH_2)_{1-5}-$ and the group $-R^7BF_3$ may independently be selected from one or a combination of those listed in Table 3 (below), Table 4 (below), or

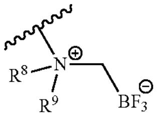

wherein $R^8$ and $R^9$ are independently $C_1$-$C_5$ linear or branched alkyl groups. For Tables 3 and 4, the R in the pyridine substituted with —OR, —SR, —NR—, —NHR or $-NR_2$ groups is $C_1$-$C_5$ branched or linear alkyl. In some embodiments, $-R^7BF_3$ is selected from those listed in Table 3. In some embodiments, $-R^7BF_3$ is independently selected from one or a combination of those listed in Table 4. In some embodiments, one fluorine is $^{18}F$. In some embodiments, all three fluorines are $^{19}F$.

TABLE 3

| Exemplary $R^7BF_3$ groups. | |
|---|---|
| 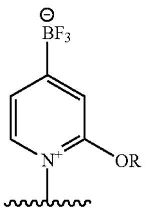 | 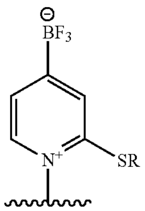 |
| 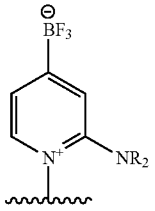 | 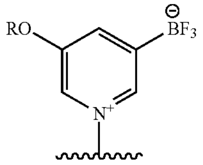 |
| 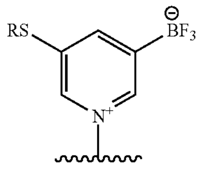 | 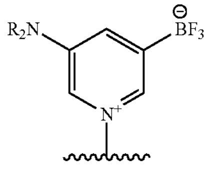 |
| 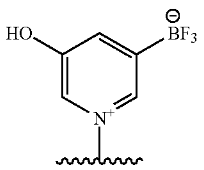 | 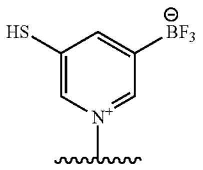 |

TABLE 3-continued

| Exemplary $R^7BF_3$ groups. | |
|---|---|
| 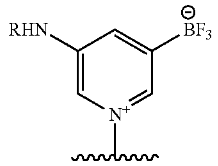 | 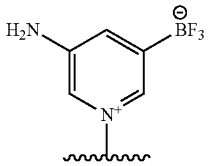 |
| 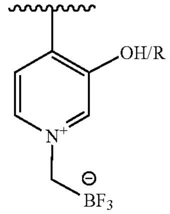 | 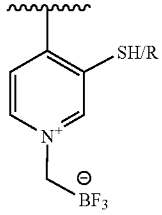 |
| 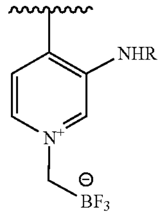 | 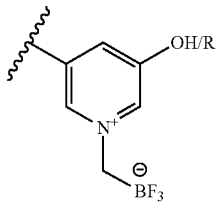 |
| 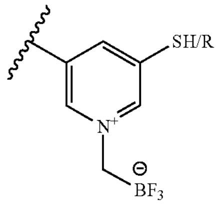 | 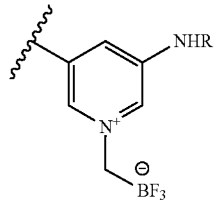 |
| 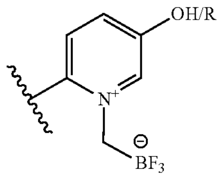 | 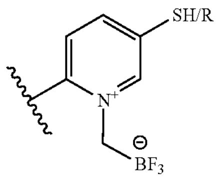 |
| 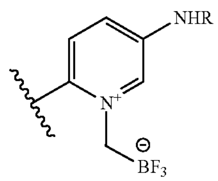 | 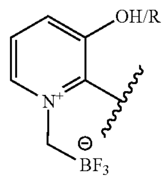 |
| 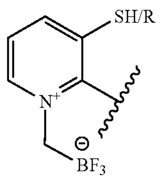 | 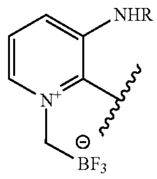 |

TABLE 3-continued
| Exemplary $R^7BF_3$ groups. | |
|---|---|
| 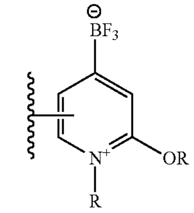 | 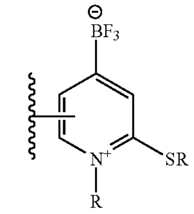 |
| 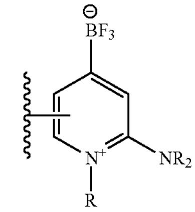 | 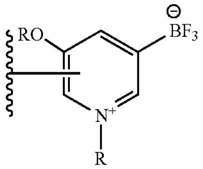 |
| 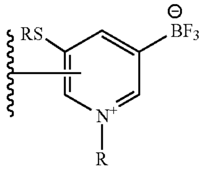 | 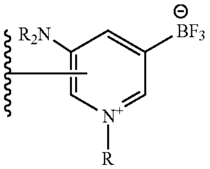 |
| 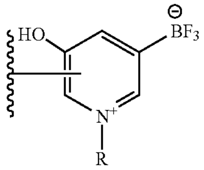 | 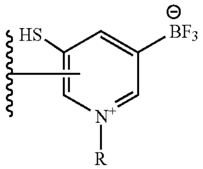 |
| 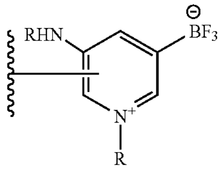 | 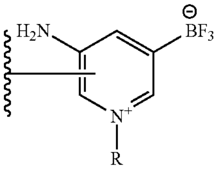 |
| 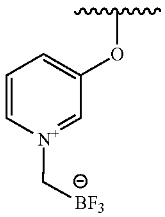 | 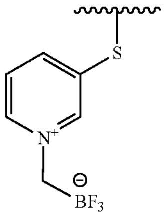 |
| 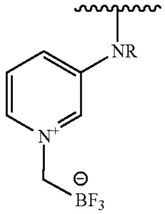 | 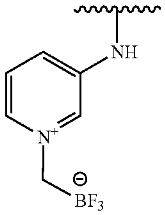 |
TABLE 3-continued
| Exemplary $R^7BF_3$ groups. | |
|---|---|
| 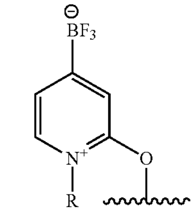 | 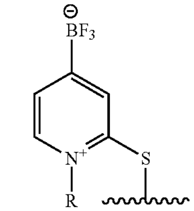 |
| 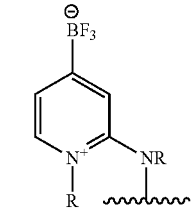 | 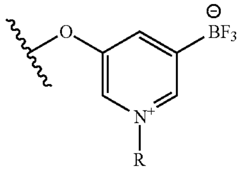 |
| 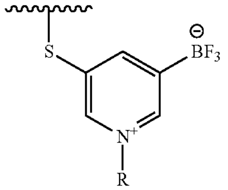 | 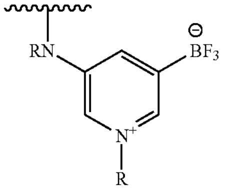 |
| 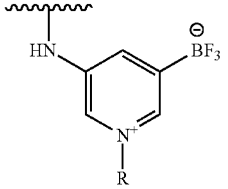 | 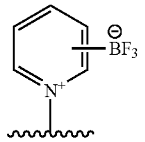 |
TABLE 4
| Exemplary $R^7BF_3$ groups. | |
|---|---|
| 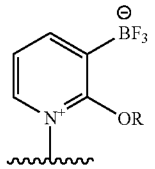 | 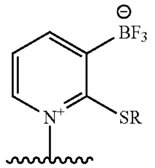 |
| 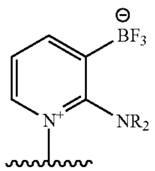 | 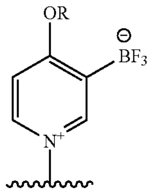 |
| 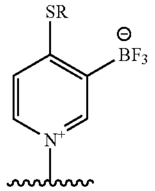 | 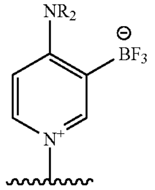 |

TABLE 4-continued
| Exemplary $R^7BF_3$ groups. | |
|---|---|
| 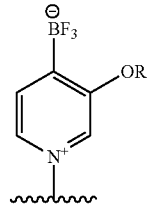 | 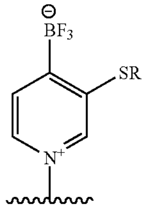 |
| 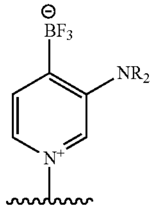 | 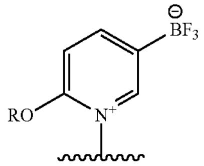 |
| 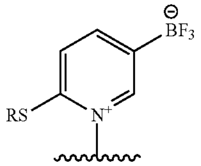 | 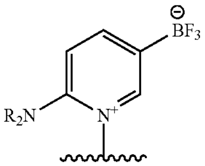 |
| 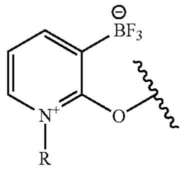 | 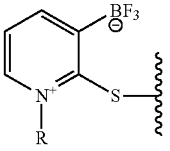 |
| 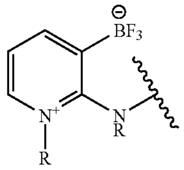 | 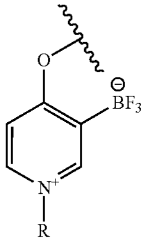 |
| 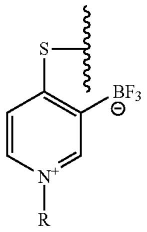 | 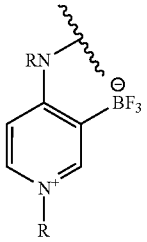 |
| 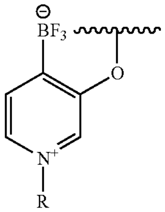 | 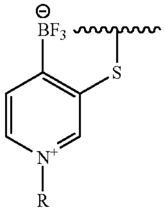 |
TABLE 4-continued
| Exemplary $R^7BF_3$ groups. | |
|---|---|
| 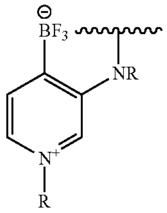 | 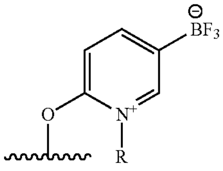 |
| 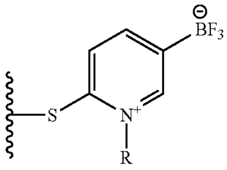 | 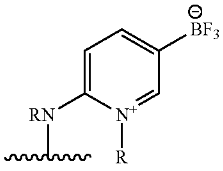 |
| 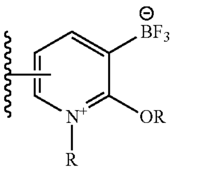 | 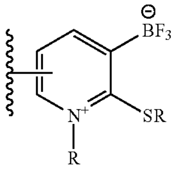 |
| 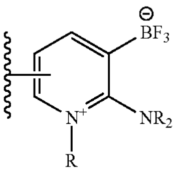 | 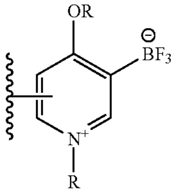 |
| 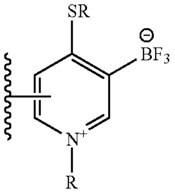 | 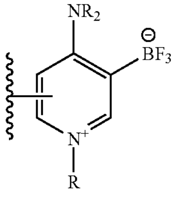 |
| 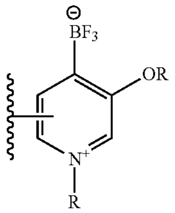 | 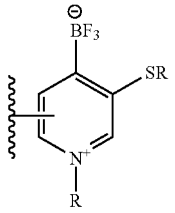 |
| 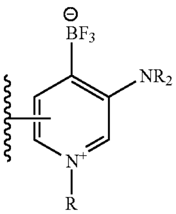 | 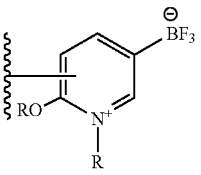 |

TABLE 4-continued
| Exemplary $R^7BF_3$ groups. | |
|---|---|
| 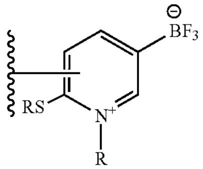 | 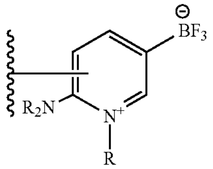 |
| 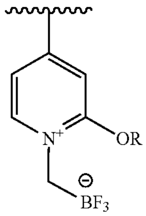 | 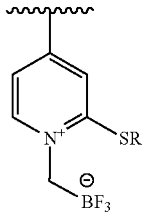 |
| 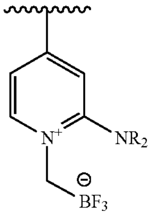 | 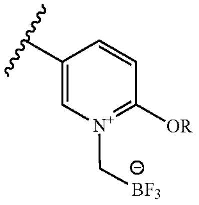 |
| 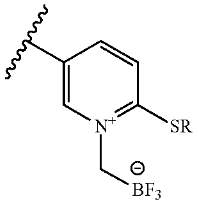 | 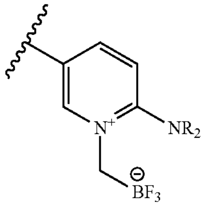 |
| 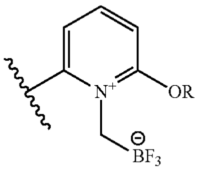 | 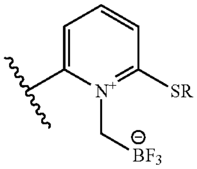 |
| 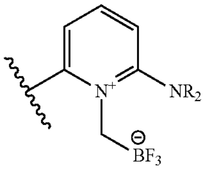 | 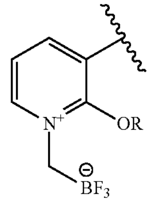 |
| 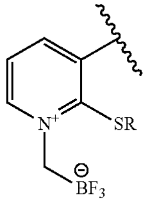 | 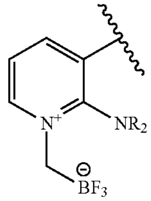 |
TABLE 4-continued
| Exemplary $R^7BF_3$ groups. | |
|---|---|
| 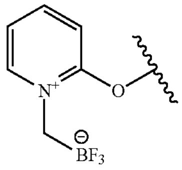 | 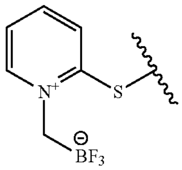 |
| 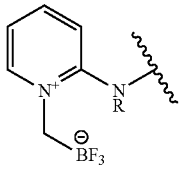 | 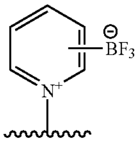 |
In some embodiments, $R^7BF_3$ may form
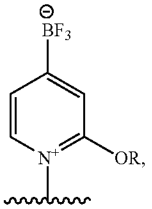
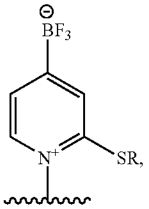
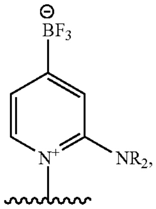
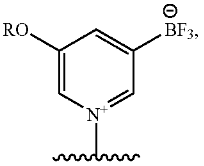
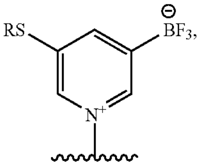
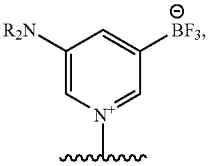
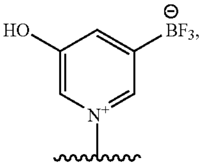
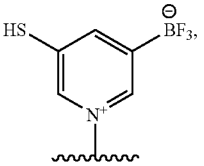
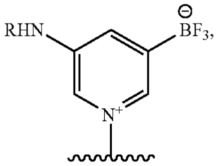
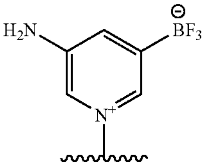
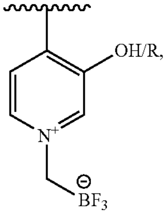
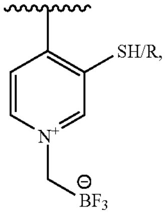
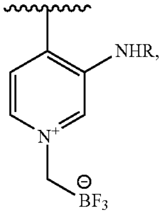

-continued

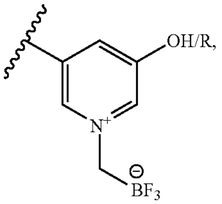
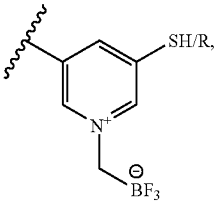
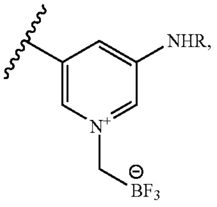
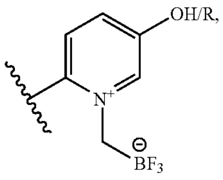
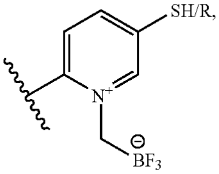
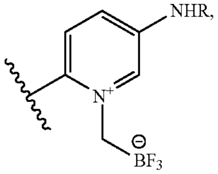
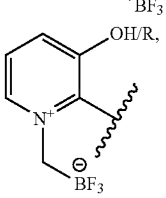
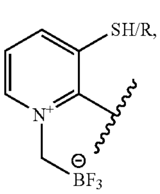
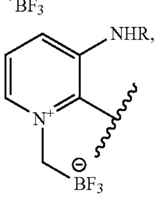
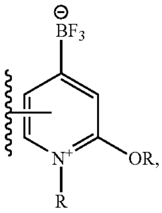
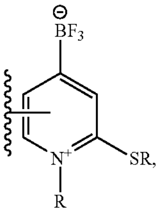
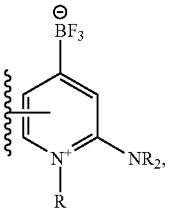
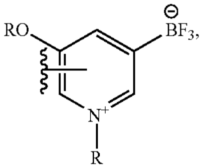
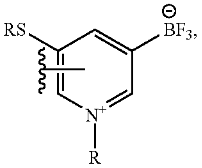
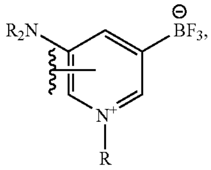
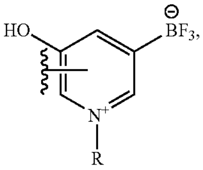
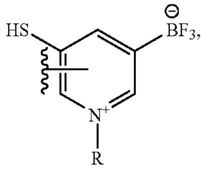
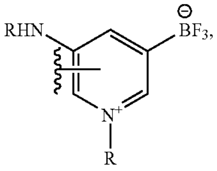
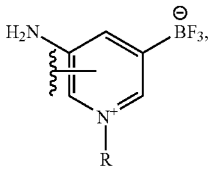
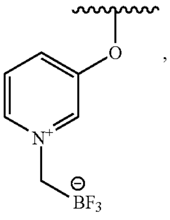
, -continued

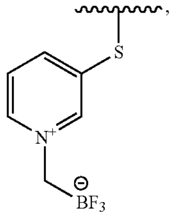
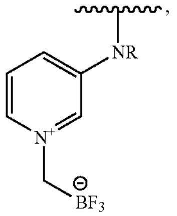
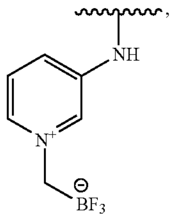
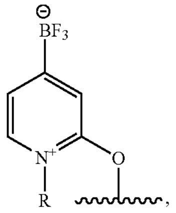
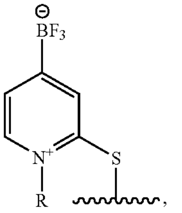
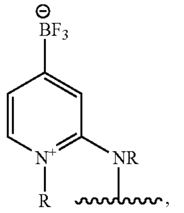
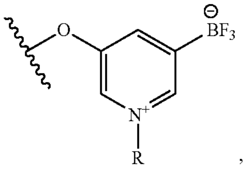
,
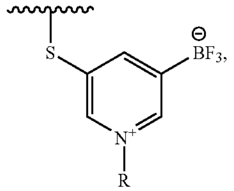
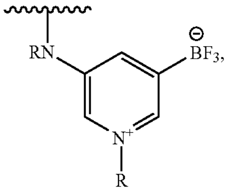
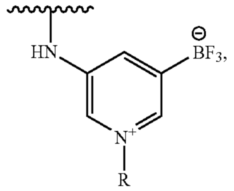
or
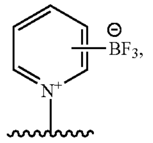

in which the R (when present) in the pyridine substituted —OR, —SR, —NR—, —NHR or —$NR_2$ is a branched or linear $C_1$-$C_5$ alkyl. In some embodiments, R is a branched or linear $C_1$-$C_5$ saturated alkyl. In some embodiments, R is methyl. In some embodiments, R is ethyl. In some embodiments, R is propyl. In some embodiments, R is isopropyl. In some embodiments, R is n-butyl. In some embodiments, one fluorine is $^{18}F$. In some embodiments, all three fluorines are $^{19}F$.

In some embodiments, $R^7BF_3$ may form
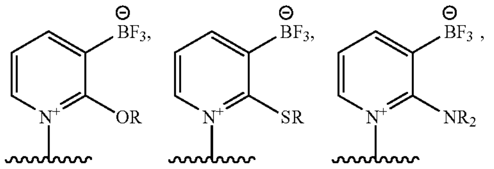
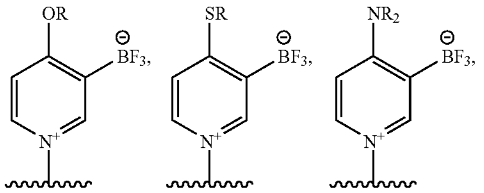
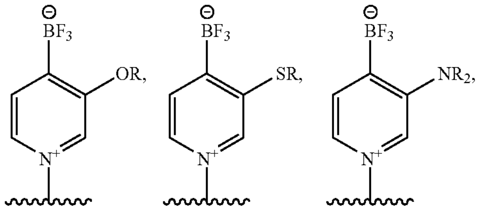
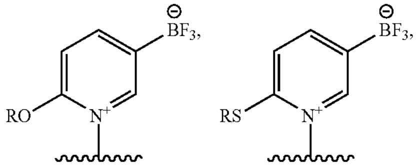
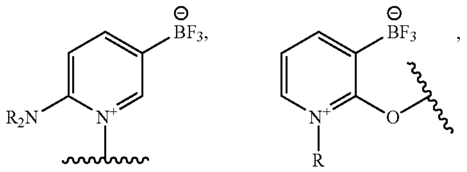
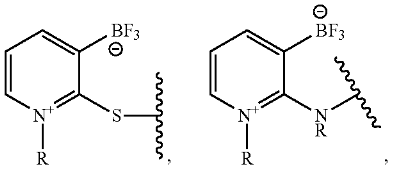
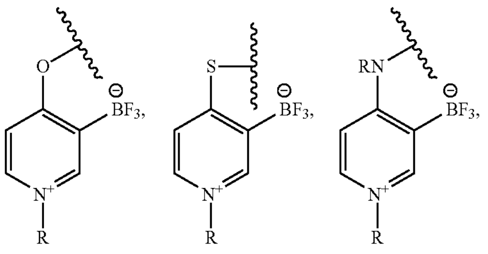
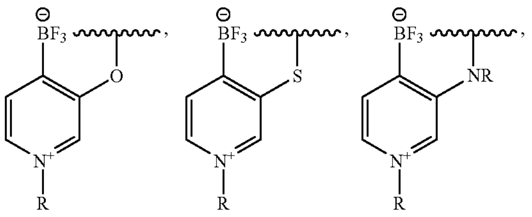
-continued
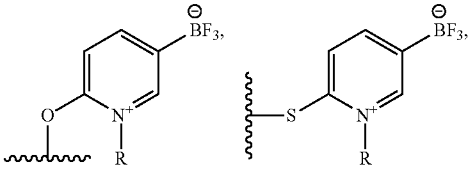
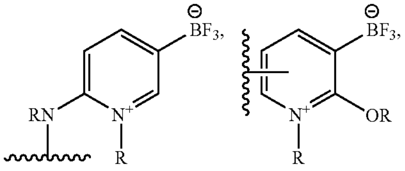
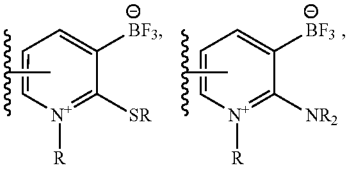
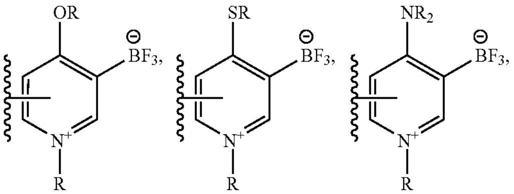
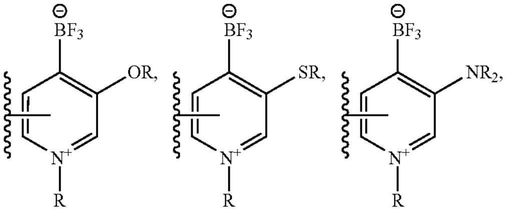
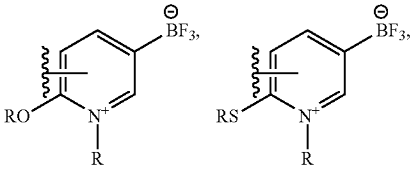
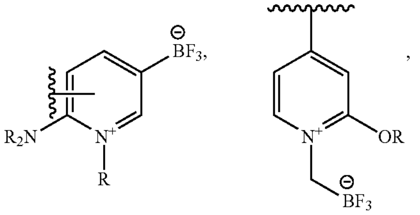
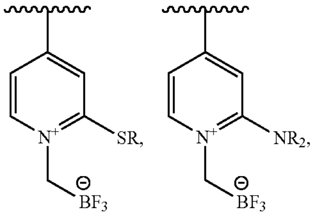
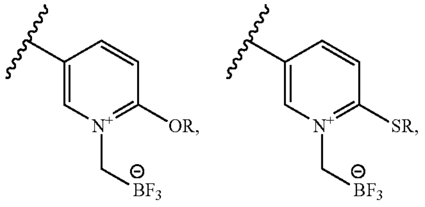

-continued

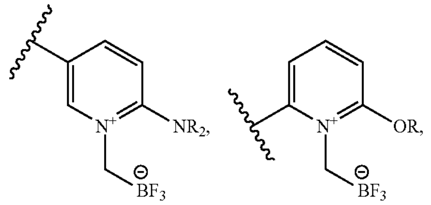

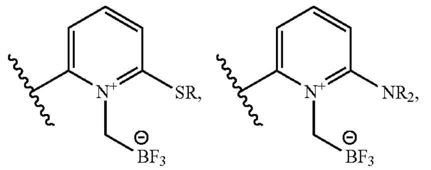

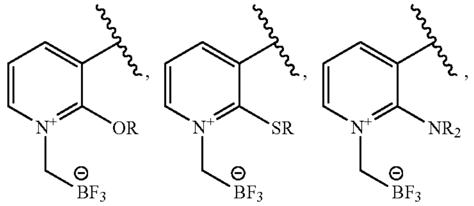

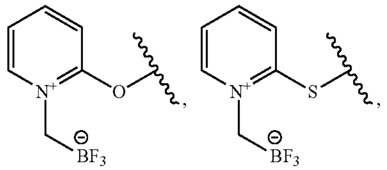

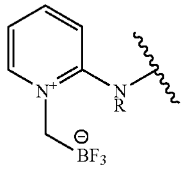

or

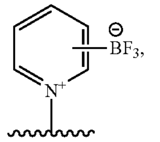

in which the R (when present) in the pyridine substituted —OR, —SR, —NR— or —$NR_2$ is branched or linear $C_1$-$C_5$ alkyl. In some embodiments, R is a branched or linear $C_1$-$C_5$ saturated alkyl. In some embodiments, R is methyl. In some embodiments, R is ethyl. In some embodiments, R is propyl. In some embodiments, R is isopropyl. In some embodiments, R is n-butyl. In some embodiments, —$R^7BF_3$ is

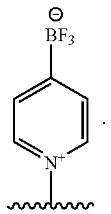

In some embodiments, one fluorine is $^{18}F$. In some embodiments, all three fluorines are $^{19}F$.

In some embodiments, —$R^7BF_3$ is

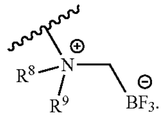

In some embodiments, $R^8$ is methyl. In some embodiments, $R^8$ is ethyl. In some embodiments, $R^8$ is propyl. In some embodiments, $R^8$ is isopropyl. In some embodiments, $R^8$ is butyl. In some embodiments, $R^8$ is n-butyl. In some embodiments, $R^8$ is pentyl. In some embodiments, $R^9$ is methyl. In some embodiments, $R^9$ is ethyl. In some embodiments, $R^9$ is propyl. In some embodiments, $R^9$ is isopropyl. In some embodiments, $R^9$ is butyl. In some embodiments, $R^9$ is n-butyl. In some embodiments, $R^9$ is pentyl. In some embodiments, $R^8$ and $R^9$ are both methyl. In some embodiments, one fluorine is $^{18}F$. In some embodiments, all three fluorines are $^{19}F$.

In some embodiments, an $R^X$ is a prosthetic group containing a silicon-fluorine-acceptor moiety. In some embodiments, the fluorine of the silicon-fluorine acceptor moiety is $^{18}F$. The prosthetic groups containing a silicon-fluorine-acceptor moiety may be independently selected from one or a combination of the following:

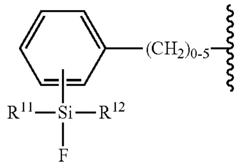

or

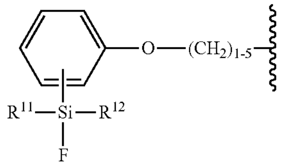

wherein $R^{11}$ and $R^{12}$ are independently a linear or branched, cyclic or acyclic, and/or aromatic or non-aromatic $C_1$-$C_{10}$ alkyl, alkenyl or alkynyl group. In some embodiments, $R^{11}$ and $R^{12}$ are independently selected from the group consisting of phenyl, tert-butyl, sec-propyl or methyl. In some embodiments, the prosthetic group is

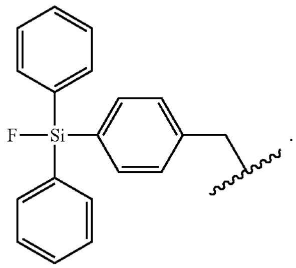 [SMILES: *Cc1ccc([Si](F)(c2ccccc2)c2ccccc2)cc1]

In some embodiments, the prosthetic group is

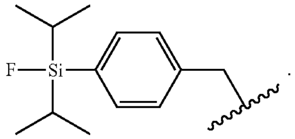 [SMILES: *Cc1ccc([Si](F)(C(C)C)C(C)C)cc1]

In some embodiments, the prosthetic group is

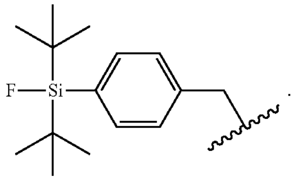 [SMILES: *Cc1ccc([Si](F)(C(C)(C)C)C(C)(C)C)cc1]

In some embodiments, the prosthetic group is

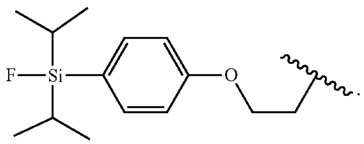 [SMILES: *CCOc1ccc([Si](F)(C(C)C)C(C)C)cc1]

The overexpression of CXCR4 has been observed in over 23 types of malignancies, including brain, breast, and prostate cancers. Moreover, leukemia, lymphoma and myeloma have significant CXCR4 expression. Retrospective studies have shown that CXCR4 expression is correlated with lowered survival for prostate and melanoma patients. Furthermore, CXCR4 expression is a prognostic factor of disease relapse for acute and chronic myeloid leukemia, acute myelogenous leukemia and multiple myeloma. The SDF-1/CXCR4 axis mediates cancer growth, potentiates metastasis, recruits stromal and immune cells to support malignant growth, and confers chemotherapeutic resistance. Radiolabeled CXCR4 probes could be used in the early diagnosis of solid and hematological malignancies that express CXCR4. Such imaging agents could be used to confirm the diagnostic of malignancy, or guide focal ablative treatment if the disease is localized. Such ligands could also be used to monitor response to therapy, by providing an independent assessment of the residual cellular content of a tumour known to overexpress CXCR4. [$^{68}$Ga]Ga-Pentixafor has been used by the Wester group for cancer imaging and to identify potential responders to endoradiotherapy.

Dysregulation of the SDF-1/CXCR4 axis also mediates a number of inflammatory conditions. In rheumatoid arthritis (RA), SDF-1/CXCR4 signaling is responsible for the pro-inflammatory migration of activated T-cells into the site of inflammation; specifically, the synovium of patients with RA showed that the presence of T-cells with increased expression of CXCR4. Given the burden of RA on the population with respect to morbidity and mortality, there is a significant amount of research into developing therapeutics to mediate the inflammatory response, especially with novel biologics being approved by the FDA in the past few years. Radiolabeled CXCR4 probes for positron emission tomography imaging would enable diagnosis and prognosis of the rheumatoid arthritis and also be used to monitor therapy of emerging disease-modifying antirheumatic drugs in clinical trials. CXCR4 expression has been detected with PET imaging using [r$^{8}$Ga]Ga-Pentixafor in diseases with an inflammatory component, including infectious bone diseases, urinary tract infections as a complication after kidney transplantation, myocardial infarctions, and ischemic strokes. CXCR4 imaging may have a significant role in diagnosing and monitoring other inflammatory diseases in the future.

In the setting of cardiac pathology, inflammatory diseases of the cardiac vessel walls are mediated in part by the dysregulation of the SDF-1/CXCR4 axis. In the early stages of atherosclerosis, the SDF-1/CXCR4 axis recruits endothelial progenitor cells towards sites of peripheral vascular damage, thereby initiating plaque formation, though there is some evidence towards an atheroprotective effect. Atherosclerotic plaques are characterized by the presence of hypoxia, which has been shown to upregulate the expression of CXCR4 and influence cell trafficking. Finally, in a rabbit model of atherosclerosis, [$^{68}$Ga]Ga-Pentixafor enabled visualization of atherosclerotic plaques by PET. In the same study, atherosclerotic plaques were identified in patients with a history of atherosclerosis using [$^{68}$Ga]Ga-Pentixafor. As such, PET diagnostic agents targeting CXCR4 are potentially viable as an alternative method of diagnosing and obtaining prognostic information about atherosclerosis.

In certain embodiments, the compound is conjugated with a radioisotope for positron emission tomography (PET) or single photon emission computed tomography (SPECT) imaging of a CXCR4-expressing tissue or for imaging an inflammatory condition or disease (e.g. rheumatoid arthritis or cardiovascular disease), wherein the compound is conjugated with a radioisotope that is a positron emitter or a gamma emitter. Without limitation, the positron or gamma emitting radioisotope may be $^{68}$Ga, $^{67}$Ga, $^{61}$Cu, $^{64}$Cu, $^{99m}$Tc, $^{110m}$In, $^{111}$In, $^{44}$Sc, $^{86}$Y $^{89}$Zr, $^{90}$Nb, $^{18}$F, $^{131}$I, $^{123}$I, $^{124}$I or $^{72}$As.

When the radioisotope (e.g. X) is a diagnostic radioisotope, there is disclosed use of certain embodiments of the compound for preparation of a radiolabelled tracer for imaging. There is also disclosed a method of imaging CXCR4-expressing tissues or an inflammatory condition or disease in a subject, in which the method comprises: administering to the subject a composition comprising certain embodiments of the compound and a pharmaceutically acceptable excipient; and imaging the subject, e.g. using positron emission tomography (PET). When the tissue is a diseased tissue (e.g. a CXCR4-expressing cancer), CXCR4-targeted treatment may then be selected for treating the subject. There is therefore disclosed the use of certain compounds of the invention in imaging a CXCR4-expressing cancer in a subject, wherein $R^X$ comprises or is complexed with a diagnostic or imaging radioisotope. In some embodiments, the subject is human.

Given the broad expression of CXCR4 in cancers, there has been a significant push to develop CXCR4-targeting therapeutics. While CXCR4 inhibitors have demonstrated efficacy in tumor models in mice, in both treating tumors and preventing metastasis, very few pharmaceutical agents have demonstrated efficacy in clinical trials. Plerixafor, also known as AMD3100, developed originally for HIV treatment, is the lone CXCR4 antagonist to receive FDA approval to date. AMD3100 is given to lymphoma and multiple myeloma patients to mobilize hematopoietic stem cells into peripheral blood for collection and autologous transplantation, and not as a method of direct treatment. There is an unmet clinical need for treating CXCR4-expressing cancers, many of which are resistant to the standard of care available today.

Cancers that are CXCR4 positive could be susceptible to endoradiotherapy. In this application, a peptide targeting CXCR4 is radiolabeled with a radioisotope, usually a β- or α-particle emitter, to deliver a high local dose of radiation to lesions. These radioactive emissions usually inflict DNA damage, thereby inducing cellular death. This method of therapy has been exploited in oncology, with the somatostatin receptor (for neuroendocrine tumors) and prostate-specific membrane antigen (for metastatic castration-resistant prostate cancer) being two examples. Unlike external beam radiation therapy, this systemic treatment can be effective even in the metastatic setting. Therapeutic radioisotopes include but are not restricted to $^{177}$Lu, $^{90}$Y, $^{225}$Ac and $^{64}$Cu.

With respect to cardiac pathologies, a small retrospective study with endoradiotherapy by [$^{90}$Y]Y— or [$^{177}$Lu]Lu-Pentixather demonstrated regression of CXCR4 expression and activity in patients with previously identified atherosclerotic plaques. Therefore, radionuclide therapy may present a novel route of therapy for inflammatory diseases such as atherosclerosis.

In certain embodiments the compound is conjugated with a radioisotope that is used for therapy (e.g. cancer therapy). This includes radioisotopes such as $^{165}$Er, $^{212}$Bi, $^{211}$At, $^{166}$Ho, $^{149}$Pm, $^{159}$Gd, $^{105}$Rh, $^{109}$Pd $^{198}$Au, $^{199}$Au, $^{175}$Yb, $^{142}$Pr, $^{177}$Lu (β-emitter, $t_{2/1}$=6.65 d), $^{111}$In, $^{213}$Bi, $^{203}$Pb, $^{212}$Pb, $^{47}$Sc, $^{90}$Y (β-emitter, $t_{2/1}$=2.66 d), $^{117m}$Sn, $^{153}$Sm, $^{149}$Tb, $^{161}$Tb, $^{224}$Ra, $^{225}$Ac (α-emitter, $t_{2/1}$=9.95 d), $^{227}$Th, $^{223}$Ra, $^{77}$As, $^{131}$I, $^{64}$Cu or $^{67}$Cu.

When the radioisotope (e.g. X) is a therapeutic radioisotope, there is disclosed use of certain embodiments of the compound (or a pharmaceutical composition thereof) for the treatment of a disease or condition characterized by expression of CXCR4 in a subject. Accordingly, there is provided use of the compound in preparation of a medicament for treating a disease or condition characterized by expression of CXCR4 in a subject. There is also provided a method of treating a disease or condition characterized by expression of CXCR4 in a subject, in which the method comprises: administering to the subject a composition comprising the compound and a pharmaceutically acceptable excipient. For example, but without limitation, the disease may be a CXCR4-expressing cancer (e.g. non-Hodgkin lymphoma, lymphoma, multiple myeloma, leukemia, adrenocortical cancer, lung cancer, breast cancer, renal cell cancer, colorectal cancer). There is therefore disclosed the use of certain compounds of the invention for treating a CXCR4-expressing cancer in a subject, wherein $R^X$comprises or is complexed with a therapeutic radioisotope. In some embodiments, the subject is human.

The compounds presented herein incorporate peptides, which may be synthesized by any of a variety of methods established in the art. This includes but is not limited to liquid-phase as well as solid-phase peptide synthesis using methods employing 9-fluorenylmethoxycarbonyl (Fmoc) and/or t-butyloxycarbonyl (Boc) chemistries, and/or other synthetic approaches.

Solid-phase peptide synthesis methods and technology are well-established in the art. For example, peptides may be synthesized by sequential incorporation of the amino acid residues of interest one at a time. In such methods, peptide synthesis is typically initiated by attaching the C-terminal amino acid of the peptide of interest to a suitable resin. Prior to this, reactive side chain and alpha amino groups of the amino acids are protected from reaction by suitable protecting groups, allowing only the alpha carboxyl group to react with a functional group such as an amine group, a hydroxyl group, or an alkyl halide group on the solid support. Following coupling of the C-terminal amino acid to the support, the protecting group on the side chain and/or the alpha amino group of the amino acid is selectively removed, allowing the coupling of the next amino acid of interest. This process is repeated until the desired peptide is fully synthesized, at which point the peptide can be deprotected and cleaved from the support, and purified. A non-limiting example of an instrument for solid-phase peptide synthesis is the Aapptec Endeavor 90 peptide synthesizer.

To allow coupling of additional amino acids, Fmoc protecting groups may be removed from the amino acid on the solid support, e.g. under mild basic conditions, such as piperidine (20-50% v/v) in DMF. The amino acid to be added must also have been activated for coupling (e.g. at the alpha carboxylate). Non-limiting examples of activating reagents include without limitation 2-(1H-benzotriazol-1-yl)-1,1,3,3-tetramethyluronium hexafluorophosphate (HBTU), 2-(1H-benzotriazol-1-yl)-1,1,3,3-tetramethyluronium tetrafluoroborate (TBTU), 2-(7-Aza-1H-benzotriazole-1-yl)-1,1,3,3-tetramethyluronium hexafluorophosphate (HATU), benzotriazole-1-yl-oxy-tris(dimethylamino)phosphoniumhexafluorophosphate (BOP), benzotriazole-1-yl-oxy-tris(pyrrolidino)phosphoniumhexafluorophosphate (PyBOP). Racemization is minimized by using triazoles, such as 1-hydroxy-benzotriazole (HOBt) and 1-hydroxy-7-aza-benzotriazole (HOAt). Coupling may be performed in the presence of a suitable base, such as N,N-diisopropylethylamine (DIPEA/DIEA) and the like. For long peptides or if desired, peptide synthesis and ligation may be used.

Apart from forming typical peptide bonds to elongate a peptide, peptides may be elongated in a branched fashion by attaching to side chain functional groups (e.g. carboxylic acid groups or amino groups), either: side chain to side chain; or side chain to backbone amino or carboxylate. Coupling to amino acid side chains may be performed by any known method, and may be performed on-resin or off-resin. Non-limiting examples include: forming an amide between an amino acid side chain containing a carboxyl group (e.g. Asp, D-Asp, Glu, D-Glu, Aad, and the like) and an amino acid side chain containing an amino group (e.g. Lys, D-Lys, Orn, D-Orn, Dab, D-Dab, Dap, D-Dap, and the like) or the peptide N-terminus; forming an amide between an amino acid side chain containing an amino group (e.g. Lys, D-Lys, Orn, D-Orn, Dab, D-Dab, Dap, D-Dap, and the like) and either an amino acid side chain containing a carboxyl group (e.g. Asp, D-Asp, Glu, D-Glu, and the like) or the peptide C-terminus; and forming a 1, 2, 3-triazole via click chemistry between an amino acid side chain containing an azide group (e.g. Lys($N_3$), D-Lys($N_3$), and the like) and an alkyne group (e.g. Pra, D-Pra, and the like). The protecting groups on the appropriate functional groups must be selectively removed before amide bond formation, whereas the reaction between an alkyne and an azido groups via the click reaction to form an 1,2,3-triazole does not require selective deprotection. Non-limiting examples of selectively removable protecting groups include 2-phenylisopropyl esters (O-2-PhiPr) (e.g. on Asp/Glu) as well as 4-methyltrityl (Mtt), allyloxycarbonyl (alloc), 1-(4,4-dimethyl-2,6-dioxocyclohex-1-ylidene))ethyl (Dde), and 1-(4,4-dimethyl-2, 6-dioxocyclohex-1-ylidene)-3-methylbutyl (ivDde) (e.g. on Lys/Orn/Dab/Dap). O-2-PhiPr and Mtt protecting groups can be selectively deprotected under mild acidic conditions, such as 2.5% trifluoroacetic acid (TFA) in DCM. Alloc protecting groups can be selectively deprotected using tetrakis(triphenylphosphine)palladium(0) and phenylsilane in DCM. Dde and ivDde protecting groups can be selectively deprotected using 2-5% of hydrazine in DMF. Deprotected side chains of Asp/Glu (L- or D-forms) and Lys/Orn/Dab/Dap (L- or D-forms) can then be coupled, e.g. by using the coupling reaction conditions described above.

Peptide backbone amides may be N-methylated (i.e. alpha amino methylated). This may be achieved by directly using Fmoc-N-methylated amino acids during peptide synthesis. Alternatively, N-methylation under Mitsunobu conditions may be performed. First, a free primary amine group is protected using a solution of 4-nitrobenzenesulfonyl chloride (Ns-Cl) and 2,4,6-trimethylpyridine (collidine) in NMP. N-methylation may then be achieved in the presence of triphenylphosphine, diisopropyl azodicarboxylate (DIAD) and methanol. Subsequently, N-deprotection may be performed using mercaptoethanol and 1,8-diazabicyclo[5.4.0]undec-7-ene (DBU) in NMP. For coupling protected amino acids to N-methylated alpha amino groups, HATU, HOAt and DIEA may be used.

The formation of the thioether (—S—) linkages (e.g. for $L^1$ or $L^2$) can be achieved either on solid phase or in solution phase. For example, the formation of thioether (—S—) linkage can be achieved by coupling between a thiol-containing compound (such as the thiol group on cysteine side chain) and an alkyl halide (such as 3-(Fmoc-amino) propyl bromide and the like) in an appropriate solvent (such as N,N-dimethylformamide and the like) in the presence of base (such as N,N-diisopropylethylamine and the like). If the reactions are carried out in solution phase, the reactants used are preferably in equivalent molar ratio (1 to 1), and the desired products can be purified by flash column chromatography or high performance liquid chromatography (HPLC). If the reactions are carried out on solid phase, meaning one reactant has been attached to a solid phase, then the other reactant is normally used in excess amount (>3 equivalents of the reactant attached to the solid phase). After the reactions, the excess unreacted reactant and reagents can be removed by sequentially washing the solid phase (resin) using a combination of solvents, such as N,N-dimethylformamide, methanol and dichloromethane, for example.

The formation of the linkage (e.g. for $L^1$ or $L^2$) between a thiol group and a maleimide group can be performed using the conditions described above for the formation of the thioether (—S—) linkage simply by replacing the alkyl halide with a maleimide-containing compounds. Similarly, this reaction can be conducted in solid phase or solution phase. If the reactions are carried out in solution phase, the reactants used are preferably in equivalent molar ratio (1 to 1), and the desired products can be purified by flash column chromatography or high performance liquid chromatography (HPLC). If the reactions are carried out on solid phase, meaning one reactant has been attached to a solid phase, then the other reactant is normally used in excess amount (>3 equivalents of the reactant attached to the solid phase). After the reactions, the excess unreacted reactant and reagents can be removed by sequentially washing the solid phase (resin) using a combination of solvents, such as N,N-dimethylformamide, methanol and dichloromethane, for example.

Non-peptide moieties (e.g. radiolabeling groups, albumin-binding groups and/or linkers) may be coupled to the peptide N-terminus while the peptide is attached to the solid support. This is facile when the non-peptide moiety comprises an activated carboxylate (and protected groups if necessary) so that coupling can be performed on resin. For example, but without limitation, a bifunctional chelator, such as 1,4,7,10-tetraazacyclododecane-1,4,7,10-tetraacetic acid (DOTA) tris(tert-butyl ester) may be activated in the presence of N-hydroxysuccinimide (NHS) and N,N'-dicyclohexylcarbodiimide (DCC) for coupling to a peptide. Alternatively, a non-peptide moiety may be incorporated into the compound via a copper-catalyzed click reaction under either liquid or solid phase conditions. Copper-catalyzed click reactions are well established in the art. For example, 2-azidoacetic acid is first activated by NHS and DCC and coupled to a peptide. Then, an alkyne-containing non-peptide moiety may be clicked to the azide-containing peptide in the presence of $Cu^{2+}$ and sodium ascorbate in water and organic solvent, such as acetonitrile (ACN) and DMF and the like. Non-peptide moieties may also be added in solution phase, which is routinely performed.

The synthesis of chelators is well-known and many chelators are commercially available (e.g. from Sigma-Aldrich™/Milipore Sigma™ and others). Protocols for conjugation of radiometals to the chelators are also well known (e.g. see Example 1, below). The synthesis of the silicon-fluorine-acceptor moieties can be achieved following previously reported procedures (e.g. Bernard-Gauthier et al. *Biomed Res Int.* 2014 2014:454503; Kostikov et al. *Nature Protocols* 2012 7:1956-1963; Kostikov et al. *Bioconjug Chem.* 2012 18:23:106-114; each of which is incorporated by reference in its entirety).

The synthesis or acquisition of radioisotope-substituted aryl groups is likewise facile. The synthesis of the $R^6R^7BF_3$ component on the compounds can be achieved following previously reported procedures (e.g.: Liu et al. *Angew Chem Int Ed* 2014 53:11876-11880; Liu et al. *J Nucl Med* 2015 55:1499-1505; Liu et al. *Nat Protoc* 2015 10:1423-1432; Kuo et al., *J Nucl Med* 2019 60:1160-1166; each of which is incorporated by reference in its entirety). Generally, the $BF_3$-containing motif can be coupled to the linker via click chemistry by forming a 1,2,3-triazole ring between a $BF_3$-containing azido (or alkynyl) group and an alkynyl (or azido) group on the linker, or by forming an amide linkage between a $BF_3$-containing carboxylate and an amino group on the linker. To make the $BF_3$-containing azide, alkyne or carboxylate, a boronic acid ester-containing azide, alkyne or carboxylate is first prepared following by the conversion of the boronic acid ester to $BF_3$ in a mixture of HCl, DMF and $KHF_2$. For alkyl $BF_3$, the boronic acid ester-containing azide, alkyne or carboxylate can be prepared by coupling boronic acid ester-containing alkyl halide (such as iodomethylboronic acid pinacol ester) with an amine-containing azide, alkyne or carboxylate (such as N,N-dimethylpropargylamine). For aryl $BF_3$, the boronic acid ester can be prepared via Suzuki coupling using aryl halide (iodine or bromide) and bis(pinacolato)diboron.

$^{18}F$-Fluorination of the $BF_3$-containing compounds via $^{18}F$-$^{19}F$ isotope exchange reaction can be achieved following previously published procedures (Liu et al. *Nat Protoc* 2015 10:1423-1432, incorporated by reference in its entirety). Generally, ~100 nmol of the $BF_3$-containing compound is dissolved in a mixture of 15 μl of pyridazine-HCl buffer (pH=2.0-2.5, 1 M), 15 μl of DMF and 1 μl of a 7.5 mM $KHF_2$ aqueous solution. $^{18}F$-Fluoride solution (in saline, 60 μl) is added to the reaction mixture, and the resulting solution is heated at 80° C. for 20 min. At the end of the reaction, the desired product can be purified by solid phase extraction or by reversed high performance liquid chromatography (HPLC) using a mixture of water and acetonitrile as the mobile phase.

When the peptide has been fully synthesized on the solid support, the desired peptide may be cleaved from the solid support using suitable reagents, such as TFA, tri-isopropylsilane (TIS) and water. Side chain protecting groups, such as Boc, pentamethyldihydrobenzofuran-5-sulfonyl (Pbf), trityl (Trt) and tert-butyl (tBu) are simultaneously removed (i.e. deprotection). The crude peptide may be precipitated and collected from the solution by adding cold ether followed by centrifugation. Purification and characterization of the peptides may be performed by standard separation techniques, such as high performance liquid chromatography (HPLC) based on the size, charge and polarity of the peptides. The identity of the purified peptides may be confirmed by mass spectrometry or other similar approaches.

The present invention will be further illustrated in the following examples for the synthesis and evaluation of specific compounds.

EXAMPLES

Experimental Methods and Procedures

Chemical Synthesis

Reagents and solvents were purchased from commercial sources and used without further purification, unless otherwise stated. High performance liquid chromatography (HPLC) was performed on 1) an Agilent 1260 infinity system equipped with a model 1200 quaternary pump, a model 1200 UV absorbance detector and a Bioscan NaI scintillation detector or 2) an Agilent 1260 Infinity II Preparative System equipped with a model 1260 Infinity II preparative binary pump, a model 1260 Infinity variable wavelength detector (set at 220 nm), and a 1290 Infinity II preparative open-bed fraction collector. The HPLC column used for purification was a preparative column (Gemini, NX-C18, 5 μm, 110 Å, 50×30 mm) purchased from Phenomenex. The HPLC column used for radiosynthesis was a Phenomenex Luna C18semi-preparative column (5μ, 250×10 mm) and for quality control was a Phenomenex Luna C18 analytical column (5μ, 250×4.6 mm). The identities of peptides were confirmed by mass analysis using an AB SCIEX 4000 QTRAP mass spectrometer system with an ESI ion source or a Waters 2695 Separation module and Waters-Micromass ZQ mass spectrometer system. A Bruker 300 Ultrashield NMR system was used to obtain the $^{1}H$, $^{19}F$, $^{11}B$, and $^{13}C$ NMR Data.

Unless otherwise noted, amino acid couplings were performed using 4/8/4 equivalents of the Fmoc-Amino Acid/DIC/Oxyma for 6 mins at 90° C. using the CEM Liberty Blue Microwave Peptide Synthesizer. Fmoc groups were removed after amino acid couplings were completed using a 20% piperidine solution in DMF for 1 min at 90° C. unless otherwise noted. The resin was washed three times with 3 mL DMF after each deprotection. Peptides were deprotected and simultaneously cleaved from the resin using a 92.5/5/2.5 TFA/TIS/$H_2O$ cocktail unless otherwise stated.

Synthesis of BL02

The chemical structure of BL02 is below.

BL02

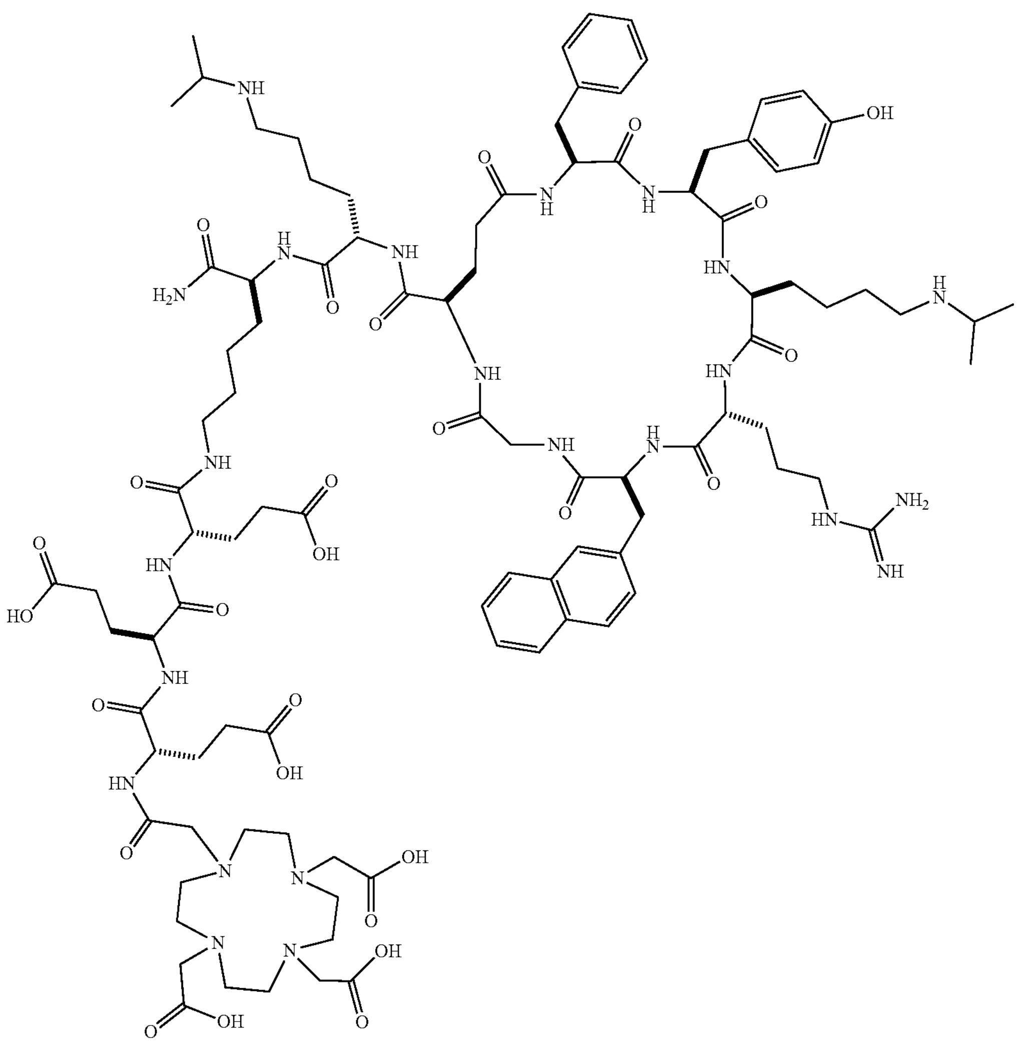

Fmoc-Rink Amide ProTide resin (CEM, 0.25 mmol, 0.58 mmol/g) was deprotected with 20% v/v piperidine in DMF for 1 min at 90° C. twice. Fmoc-Lys(ivDde)-OH was then coupled to the resin. The resin was then capped using 1-acetylimidazole in DMF (0.1 w/v) at room temperature for 30 minutes. Fmoc-Lys(iPr,Boc)-OH, Fmoc-D-Glu(OAll)-OH, Fmoc-Gly-OH (coupled twice), Fmoc-2Nal-OH (coupled twice), Fmoc-D-Arg-OH (coupled twice for 4 mins each), Fmoc-Lys(iPr,Boc)-OH, Fmoc-Tyr(tBu)-OH, and Fmoc-Phe-OH (coupled twice) were sequentially coupled to the peptidyl resin. At a 0.1 mmol scale, the —OAllyl protecting group on D-Glu was removed using $Pd(PPh_3)_4$ (25 mg)/Phenylsilane (600 μL) in DCM (5 mL) (2×5 min at 35° C.). The Na-Fmoc on Phe was then removed, and cyclization was performed using DIC/HOBt in DMF (3×10 min at 90° C.). Following cyclization, the ivDde protecting group was removed by 2% v/v hydrazine in DMF (5×5 min at RT). The resin (0.025 mmol) was coupled with three Fmoc-Glu(OtBu)-OH sequentially. Afterwards, the chelator DOTA tri-t-butyl ester (4 equiv.) in DMF was coupled to the terminal amine with HATU/DIEA (4/8 equiv.) for 10 minutes at 50° C., with two coupling cycles. The peptide was deprotected and cleaved at 3.5 h at 35° C. and the crude peptide mixture was concentrated and precipitated in cold diethyl ether. The suspension was centrifuged at 2500 RPM for 7 minutes, the supernatant diethyl ether was discarded, and the solids were diluted into water, frozen and lyophilized to yield a white powder. The reaction mixture was purified by HPLC using the preparative column eluted with first 10-18% acetonitrile in water with 0.1% TFA for 0-16 mins, then 18-22% acetonitrile for 16-20 mins, then 22-25% acetonitrile in 20-25 mins at a flow rate of 30 mL/min. The retention time was 22.4 min, and the yield of the peptide was 9.0%. ESI-MS: calculated $[M+2H]^{2+}$ for BL02 $C_{99}H_{147}N_{23}O_{27}$ 1046.5508; found $[M+2H]^{2+}$ 1046.2185.

Synthesis of Ga-BL02

For Ga-BL02, a solution of BL02 (1.89 mg, 0.90 μmol) and $GaCl_3$ (0.8 mg, 4.5 μmol) in 400 μL sodium acetate buffer (0.1 M, pH 4.2) was incubated at 70° C. for 15 min. The reaction mixture was purified by HPLC using the preparative column eluted with first 10-18% acetonitrile in water with 0.1% TFA for 0-16 min, then 18-22% acetonitrile for 16-20 min, then 22-25% acetonitrile in 20-25 min at a flow rate of 30 mL/min. The retention time of Ga-BL02 was 23.2 min, and the yield of the peptide was 80%. ESI-MS: calculated $[M+2H]^{2+}$ for Ga-BL02 $C_{99}H_{147}GaN_{23}O_{27}$ 1080.0058; found $[M+2H]^{2+}$ 1080.1585.

Synthesis of Lu-BL02

For Lu-BL02, a solution of BL02 (1.1 mg, 0.53 μmol) and $LuCl_3$ (0.76 mg, 2.7 μmol) in 500 μL sodium acetate buffer (0.1 M, pH 4.2) was incubated at 90° C. for 20 min. The reaction mixture was purified by HPLC using the preparative column eluted with 13-33% acetonitrile in water with 0.1% TFA over 20 mins at a flow rate of 30 mL/min. The retention time of Lu-BL02 was 11.6 min, and the yield of the peptide was 42%. ESI-MS: calculated $[M+3H]^{3+}$ for Lu-BL02 $C_{99}H_{148}LuN_{23}O_{27}$ 755.6780; found $[M+3H]^{3+}$ 755.0988.

Synthesis of BL03

The chemical structure of BL03 is below.

BL03

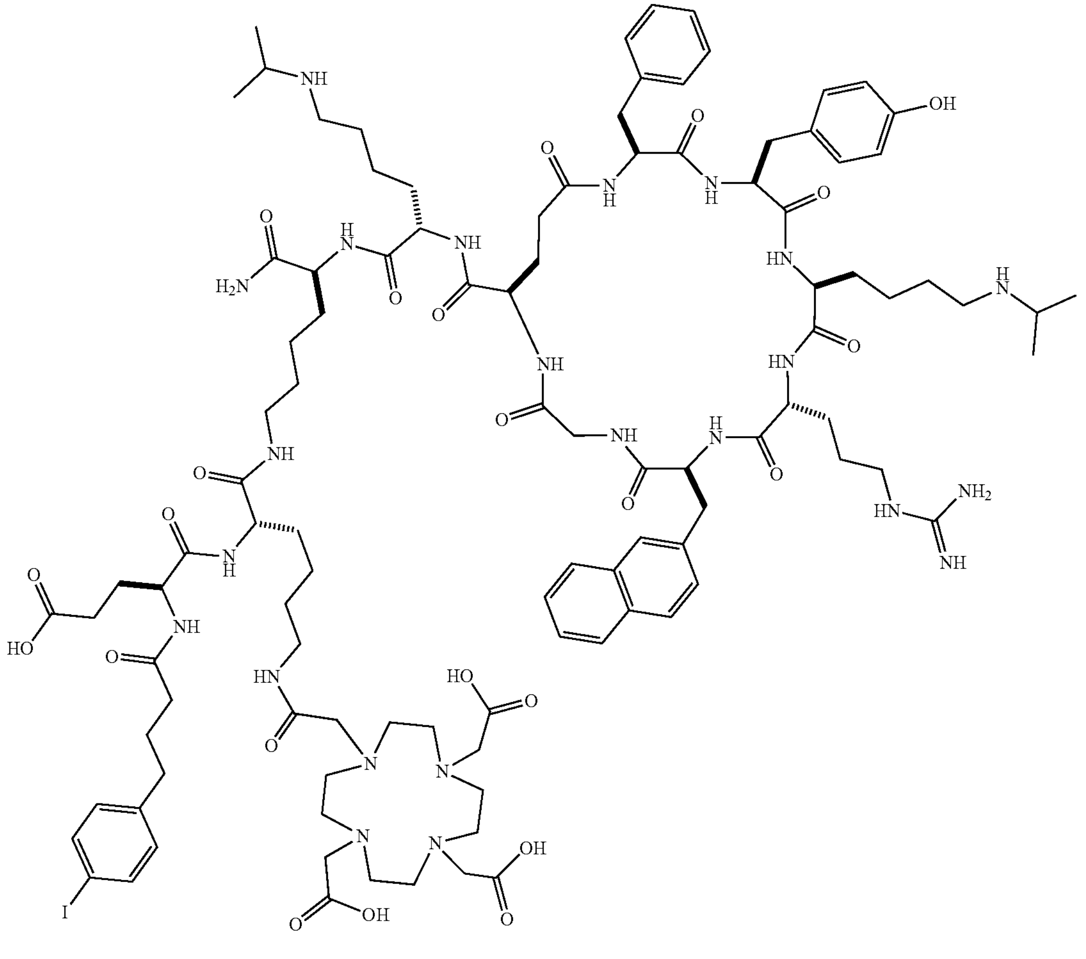

From the synthesis of BL02, following the removal of the ivDde group at a 0.025 mmol scale, Fmoc-Lys(ivDde)-OH, Fmoc-Glu(OtBu)-OH, and 4-(p-iodophenyl)butyric acid were coupled sequentially with using 4/8/4 equiv. of Fmoc-AA-OH/DIC/Oxyma in DMF for 4 min at 90° C. After each coupling, the Fmoc group was removed with 20% v/v piperidine in DMF for 1 min at 90° C. and the resin washed three times. The ivDde protecting group was then removed by 3% v/v hydrazine in DMF (5×5 min at RT). The chelator DOTA tri-t-butyl ester (4 equiv.) in DMF was coupled twice to the ε-amine group on the Lys side-chain with HATU/DIEA (4/8 equiv.) for 10 min at 50° C. The peptide was deprotected and simultaneously cleaved from the resin by treating with a cocktail solution of 92.5/5/2.5 TFA/TIS/$H_2O$ for 3 h at 35° C. The crude peptide mixture was worked up as previously described. The reaction mixture was purified by HPLC using the preparative column eluted with calculated $[M+2H]^{2+}$ for BL03 $C_{105}H_{156}IN_{23}O_{23}$ 1117.5406; found $[M+2H]^{2+}$ 1117.6880.

Synthesis of Lu-BL03

For Lu-BL03, a solution of BL03 (2.77 mg, 1.23 μmol) and $LuCl_3$ (1.74 mg, 6.17 μmol) in 400 μL sodium acetate buffer (0.1 M, pH 4.2) was incubated at 80° C. for 15 min. The reaction mixture was purified by HPLC using the preparative column eluted with 20-30% acetonitrile in water with 0.1% TFA for 0-20 min at a flow rate of 30 mL/min. The retention time of Lu-BL03 was 19.11 min, and the yield of the peptide was 59%. ESI-MS: calculated $[M+3H]^{3+}$ for Lu-BL03 $C_{105}H_{155}LuN_{23}O_{23}$ 803.0045; found $[M+3H]^{3+}$ 803.2280.

Synthesis of BL04

The chemical structure of BL04 is below.

BL04

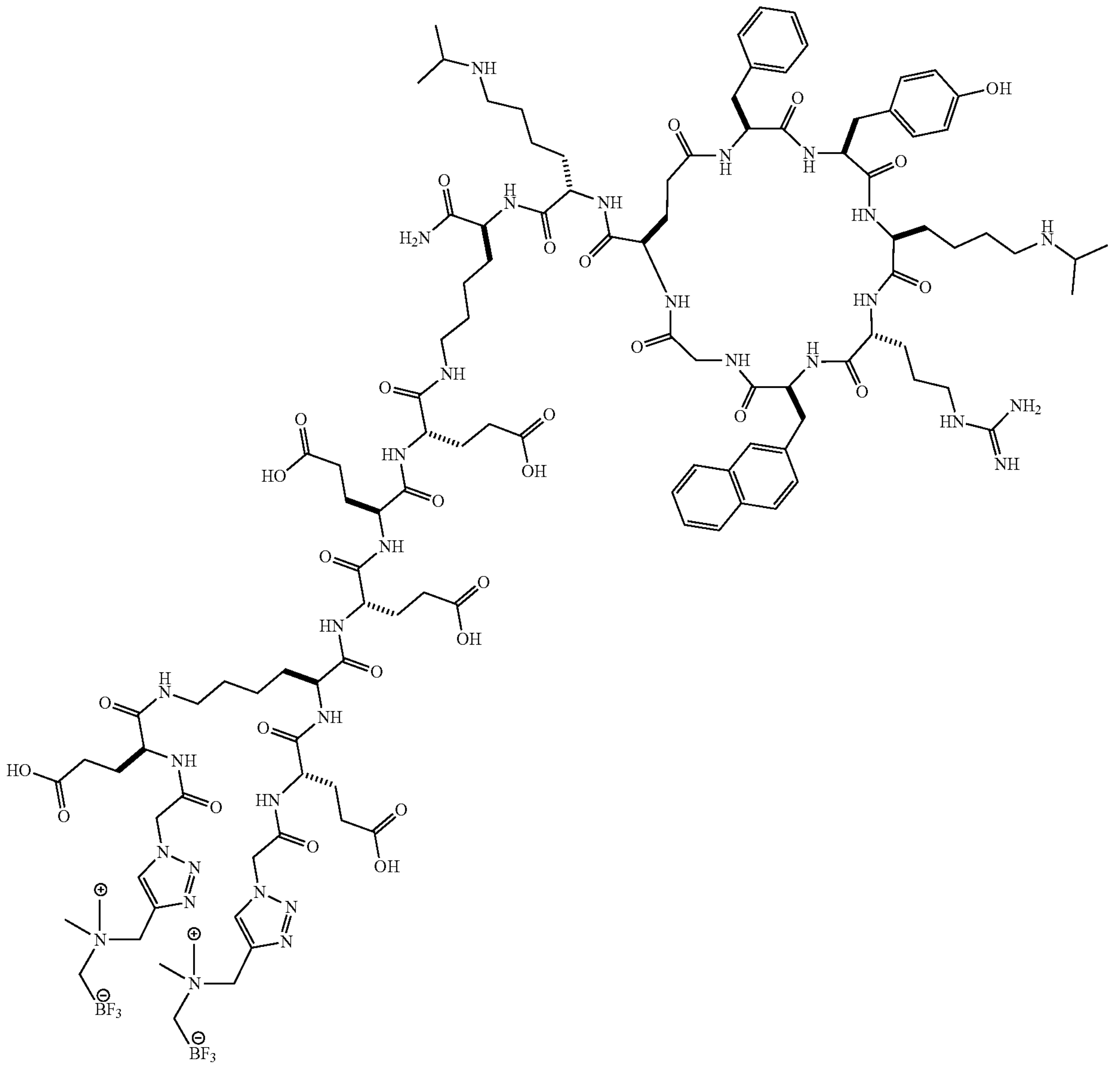

15-33.75% acetonitrile in water with 0.1% TFA for 0-25 mins at a flow rate of 30 mL/min. The retention time was 19.98 min, and the yield of the peptide was 6.7%. ESI-MS:

From the synthesis of BL02, following the coupling of the triglutamate linker at a 0.025 mmol scale, Fmoc-Lys (ivDde)-OH, Fmoc-Glu(OtBu)-OH and 2-azidoacetic acid were coupled on sequentially. The ivDde protecting group was then removed by 2% v/v hydrazine in DMF (5x5 min at RT), and Fmoc-Glu(OtBu)-OH and 2-azidoacetic acid were coupled on sequentially. The peptide was deprotected and cleaved for 4 h at 35° C. and the crude peptide mixture was worked up as previously described. The reaction mixture was purified by HPLC using the preparative column eluted with 20-30% acetonitrile in water with 0.1% TFA for 0-15 mins at a flow rate of 30 mL/min. The retention time was 10.19 min. The fractions were collected and lyophilized. The yield of the peptide was 5.2%. The azido precursor (0.825 mg, 0.37 μmol) was dissolved in 3 mL of $H_2O$. 5 μL of 1 M $CuSO_4$, 5 μL of 1 M propargyl-$AMBF_3$, 500 μL of 0.1 M $NH_4OH$ solution, and 6 μL of 1 M sodium ascorbate were added sequentially and heated to 45° C. until the reaction mixture turned clear and starting material was consumed based on HPLC. The reaction mixture was purified again by HPLC using the preparative column eluted with 10-30% acetonitrile in water with 0.1% formic acid for 0-15 mins at a flow rate of 30 mL/min. The retention time was 8.14 min and the yield of the peptide was 65%.

Synthesis of BL05

The chemical structure of BL05 is below.

From the synthesis of BL02, following the removal of the ivDde group at a 0.025 mmol scale, the resin containing the macrocyclic peptide was coupled three times using 4/8/4 equiv. of Fmoc-D-Arg(Pbf)-OH/DIC/Oxyma in DMF for 4 min at 90° C., with two coupling cycles for each coupling. After each double coupling, the Fmoc group was removed with 20% v/v piperidine in DMF for 1 min at 90° C. and the resin washed three times before the next coupling. Afterwards, the chelator DOTA tri-t-butyl ester (4 equiv.) in DMF was coupled to the terminal amine with HATU/DIEA (4/8 equiv.) for 10 minutes at 50° C., with two coupling cycles. The peptide was deprotected and simultaneously cleaved from the resin by treating with a cocktail solution of 92.5/5/2.5 TFA/TIS/$H_2O$ for 4.5 h at 40° C. and the crude peptide mixture was worked up as previously described. The reaction mixture was purified by HPLC using the preparative column eluted with first 10-15% acetonitrile in water with 0.1% TFA for 0-5 mins, then 15% acetonitrile for 5-10 mins, then 15-25% acetonitrile in 10-20 mins at a flow rate of 30 mL/min. The retention time was 18.3 min, and the yield of the peptide was 5.0%. ESI-MS: calculated $[M+3H]^{3+}$ for BL05 $C_{102}H_{165}N_{32}O_{21}$ 725.0948; found $[M+3H]^{3+}$ 725.5924.

BL05

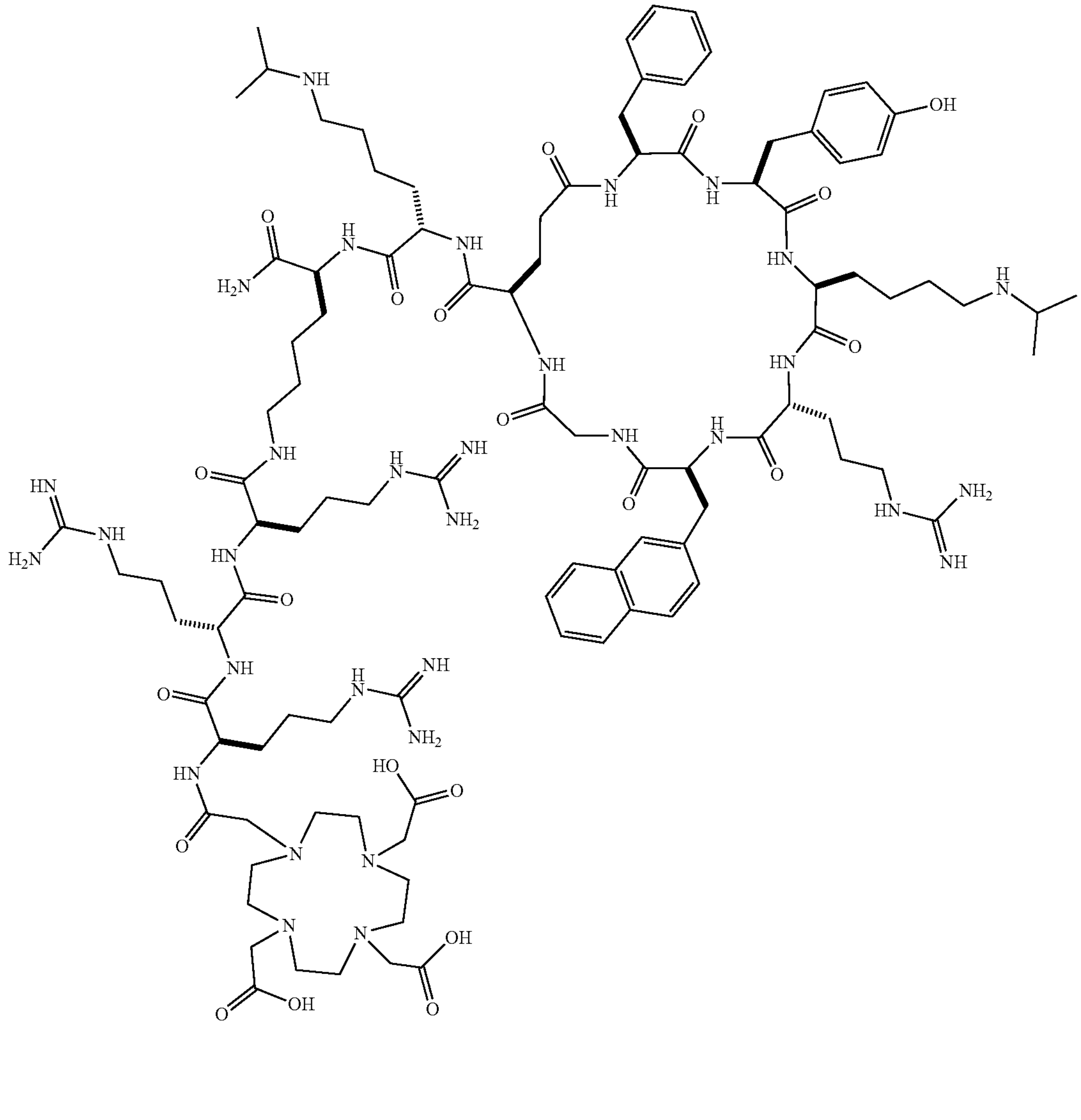

Synthesis of Ga-BL05

For Ga-BL05, a solution of BL05 (1.0 mg, 0.46 μmol) and $GaCl_3$ (0.56 mg, 3.2 μmol) in 300 μL sodium acetate buffer (0.1 M, pH 4.2) was incubated at 80° C. for 15 min. The reaction mixture was purified by HPLC using the preparative column eluted with first 10-15% acetonitrile in water with 0.1% TFA for 0-5 mins, then 15% acetonitrile for 5-10 mins, then 15-25% acetonitrile in 10-20 mins at a flow rate of 30 mL/min. The retention time of Ga-BL05 was 18.7 min, and the yield of the peptide was 89%. ESI-MS: calculated $[M+3H]^{3+}$ for Ga-BL05 $C_{102}H_{163}GaN_{32}O_{21}$ 747.3981; found $[M+3H]^{3+}$ 747.6309.

Synthesis of BL06

The chemical structure of BL06 is below.

BL06

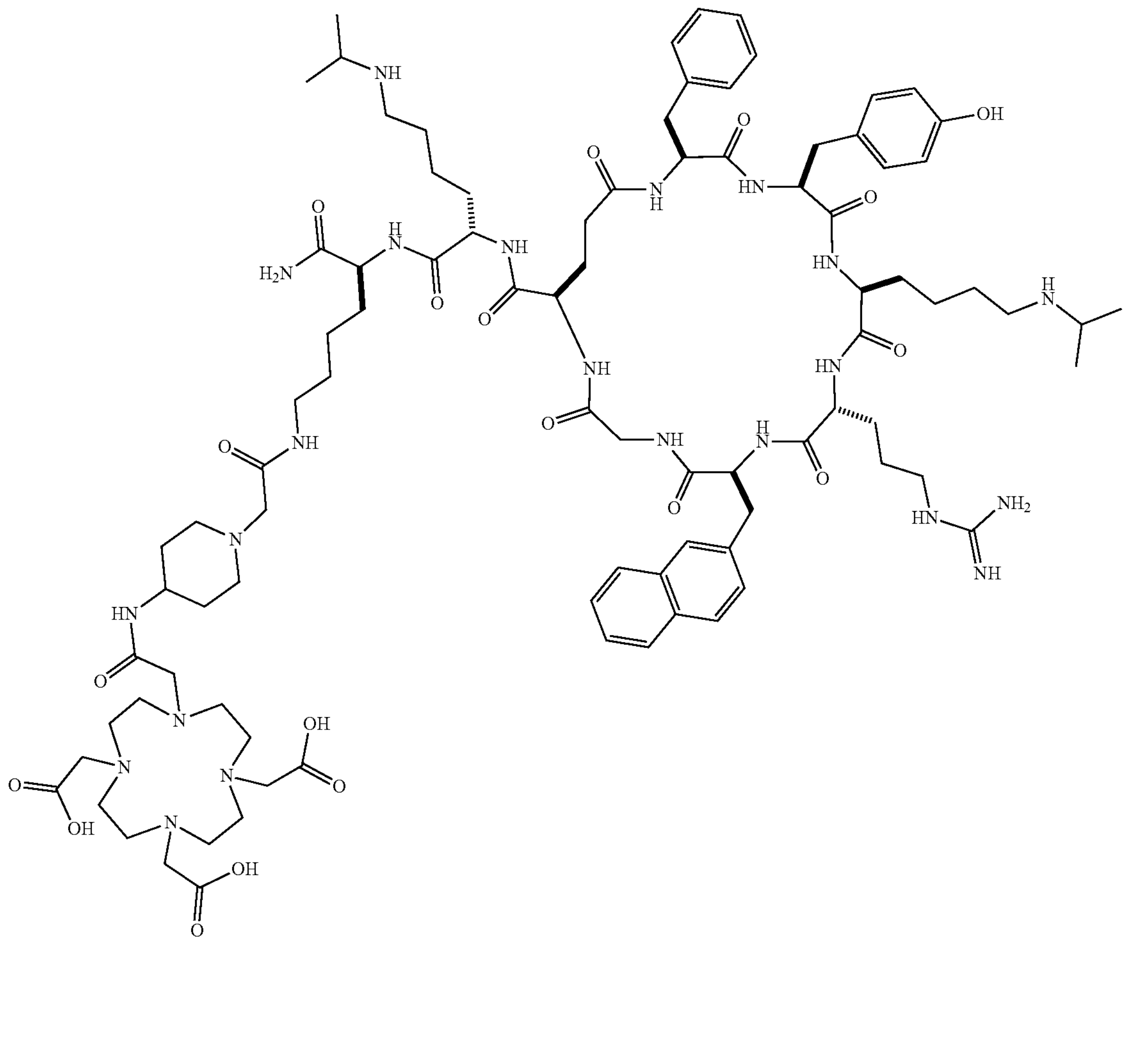

From the synthesis of BL02, following the removal of the ivDde group, the resin (0.025 mmol) containing the macrocyclic peptide was coupled with Fmoc-Pip-OH/HATU/DIEA in DMF for 10 min at 50° C. for two cycles. The chelator DOTA tri-t-butyl ester (4 equiv.) in DMF was coupled to the terminal amine with HATU/DIEA (4/8 equiv.) for 10 minutes at 50° C., with two coupling cycles. The peptide was deprotected and cleaved for 4 h at 35° C. and the crude peptide mixture was worked up as previously described. The reaction mixture was purified by HPLC using the preparative column eluted with 10-25% acetonitrile in water with 0.1% TFA for 0-15 mins at a flow rate of 30 mL/min. The retention time was 14.0 min, and the yield of the peptide was 9.0%. ESI-MS: calculated $[M+2H]^{2+}$ for BL06 $C_{91}H_{140}N_{22}O_{19}$ 922.5327; found $[M+2H]^{2+}$ 922.8853.

Synthesis of Ga-BL06

For Ga-BL06, a solution of BL06 (1.54 mg, 0.84 μmol) and $GaCl_3$ (1.0 mg, 5.85 μmol) in 500 μL sodium acetate buffer (0.1 M, pH 4.2) was incubated at 80° C. for 15 min. The reaction mixture was purified by HPLC using the preparative column eluted with 10-25% acetonitrile in water with 0.1% TFA for 0-15 min at a flow rate of 30 mL/min. The retention time of Ga-BL06 was 13.6 min, and the yield of the peptide was 87%. ESI-MS: calculated $[M+2H]^{2+}$ for Ga-BL06 $C_{91}H_{138}GaN_{22}O_{19}$ 955.9877; found $[M+2H]^{2+}$ 956.8644.

Synthesis of Lu-BL07

The chemical structure of Lu-BL07 is below.

Lu-BL07

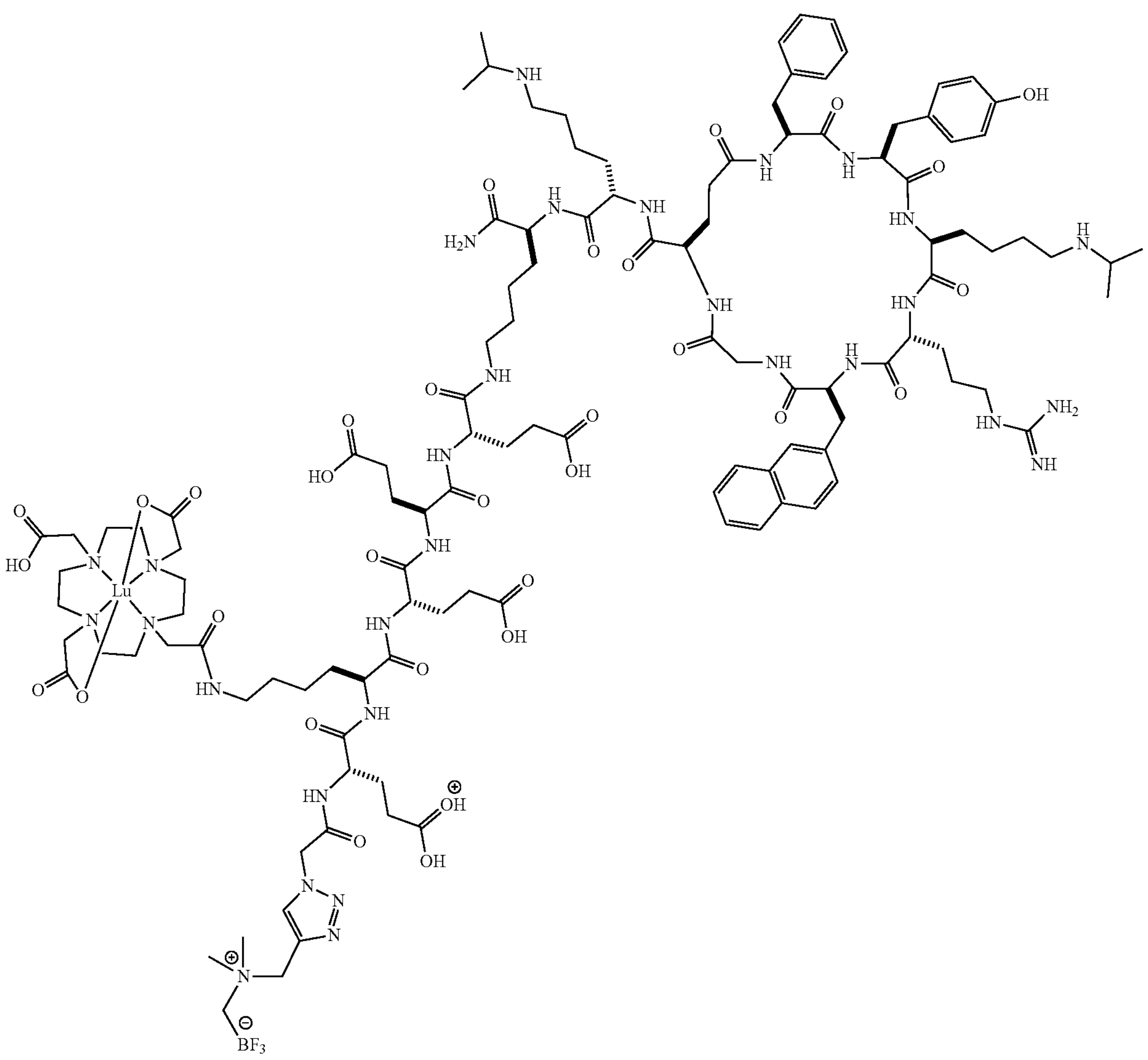

From the synthesis of BL02, following the removal of the ivDde group, the resin (0.025 mmol) containing the macrocyclic peptide was coupled with three Fmoc-Glu(OtBu)-OH, a Fmoc-Lys(ivDde)-OH and a Fmoc-Glu(OtBu)-OH sequentially. 2-Azidoacetic acid was then coupled for 10 min at 90° C., with two cycles. The ivDde protecting group was then removed by 2% v/v hydrazine in DMF (5×5 min at RT). The peptide was deprotected and cleaved for 4 h at 35° C. and the crude peptide mixture was worked up as previously described and purified by HPLC. The fractions were collected and lyophilized and dissolved in 3 mL of $H_2O$. 5 uL of 1 M $CuSO_4$,5 uL of 1 M propargyl-$AMBF_3$, 500 uL of 0.1 M $NH_4OH$ solution, and 6 uL of 1 M sodium ascorbate were added sequentially and heated to 45° C. until the reaction mixture turned clear and starting material was consumed based on HPLC. The reaction mixture was purified by HPLC and the fractions collected and lyophilized. The chelator DOTA NHS-ester (0.93 mg, 1.22 μmol) in DMF and DIEA (0.72 μL, 4.1 umol), was coupled to the terminal amine of the peptide (0.9 mg, 0.41 μmol). After completion of the reaction in 3 hours as determined by HPLC, the reaction mixture was diluted in water and purified via preparative HPLC. The reaction yield was 74%. To the unchelated peptide (0.65 mg, 0.23 μL), $LuCl_3$ (0.28 mg, 1 μmol) was added in 500 μL sodium acetate buffer (0.1 M, pH 4.2) and incubated at 90° C. for 15 min. The reaction mixture was purified by HPLC using the preparative column eluted with 5-25% acetonitrile in water with 0.1% formic acid for 0-20 mins at a flow rate of 30 mL/min. The retention time was 13.9 min, and the overall yield of the peptide was 1.4%. ESI-MS: calculated $[M+3H]^{3+}$ for Lu-BL07 $C_{118}H_{179}BF_3LuN_{30}O_{32}$ 923.7579; found $[M+3H]^{3+}$ 923.2525.

Synthesis of BL08

The chemical structure of BL08 is below.

BL08

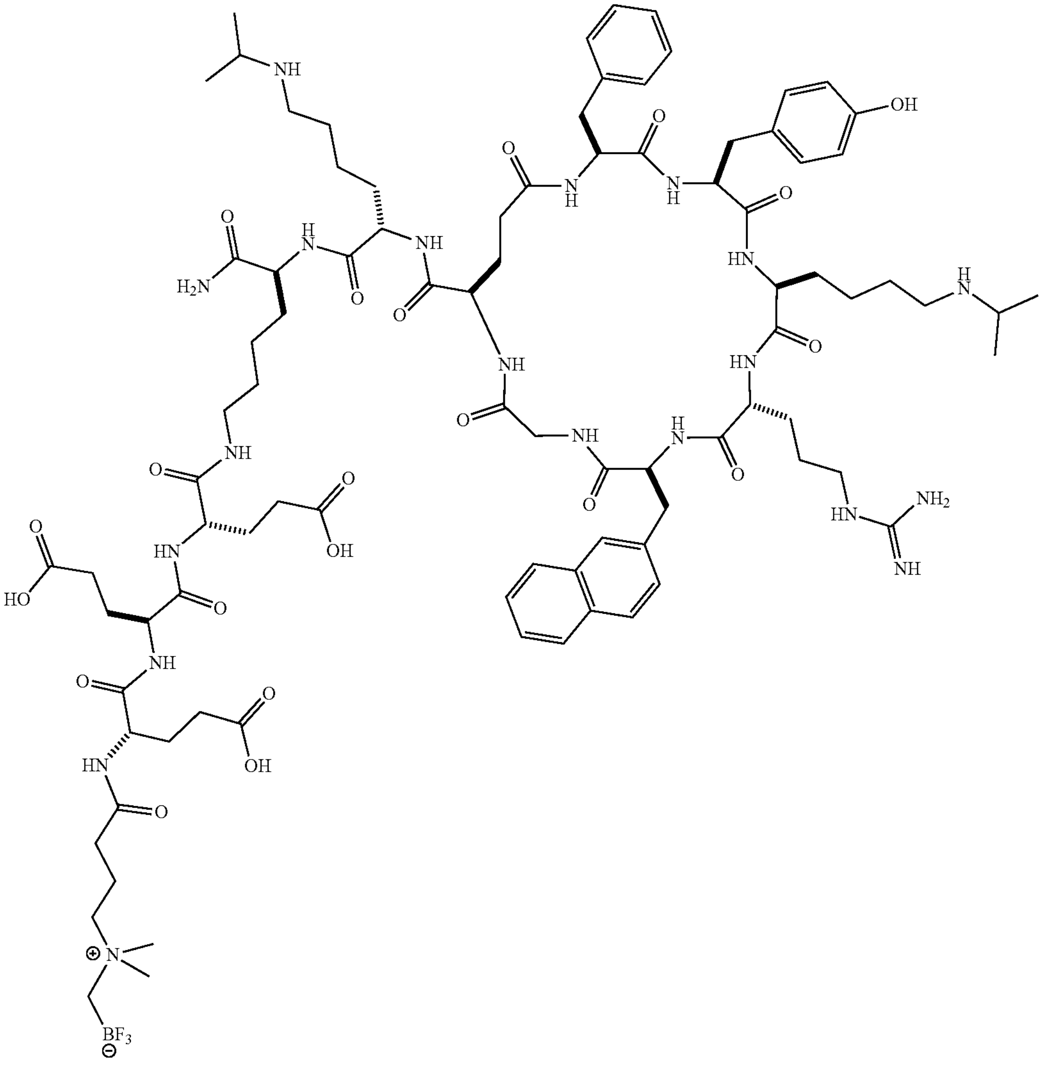

From the synthesis of BL02, following the removal of the ivDde group, the resin (0.025 mmol) was coupled with three Fmoc-Glu(OtBu)-OH sequentially. After the final Fmoc deprotection, the resin washed three times before the next coupling. The resin was placed into a spin column and was swelled using degassed and freshly distilled DMF (10 mL) for 30 minutes. The solution was then drained and rinsed with DCM. At a 0.025 mmol scale, PepBF3 JL3 (see below) (32 mg, 149 μmol) was dissolved in DMF (5 mL) and was transferred to the spin column. HBTU (54.5 mg, 144 μmol) was directly added to the bead solution followed by DIPEA (52 μL, 609 μmol). The mixture was mixed for 4 hours using a tube rotator. The solution was drained and rinsed with DCM, DMF, and DCM three times in 10 mL portions each and dried in vacuo for 16 hours. The dried beads were transferred into a falcon tube and were suspended in 500 μL DCM and added with 50 μL TIPS, 10 μL $H_2O$, and a stir bar. $KHF_2$ (200 mg) was placed into a separate falcon tube. TFA (1 mL) was added to the falcon tube using a hypodermic needle and 1 mL syringe. The tube was then sealed and sonicated until all the solids were observed to completely dissolve. After complete dissolution, the mixture was added to the falcon tube containing the beads. The mixture was stirred uncapped for 1 hour. Afterwards, the mixture was cooled then diluted with $H_2O$ (1 mL) in an ice bath followed by the slow addition of excess $NH_4OH$ until basic. ACN was then added to the mixture and the solution was filtered and concentrated at low heat. The resulting mixture was diluted into water, frozen, and lyophilized to yield a white powder. This was then triturated with ACN and centrifuged. The supernatant was collected and concentrated to yield the crude peptide mixture which was purified by HPLC using the preparative column, eluted with 10-20% acetonitrile in water with 0.1% formic acid over 15 mins at a flow rate of 30 mL/min. The retention time was 9.12 min, and the yield of BL08 was 5.8%. ESI-MS: calculated $[M+2H]^{2+}$ for $C_{90}H_{136}BF_3N_{20}O_{21}$ 950.5112, found 950.6130.

Synthesis of BL09

The chemical structure of BL09 is below.

BL09

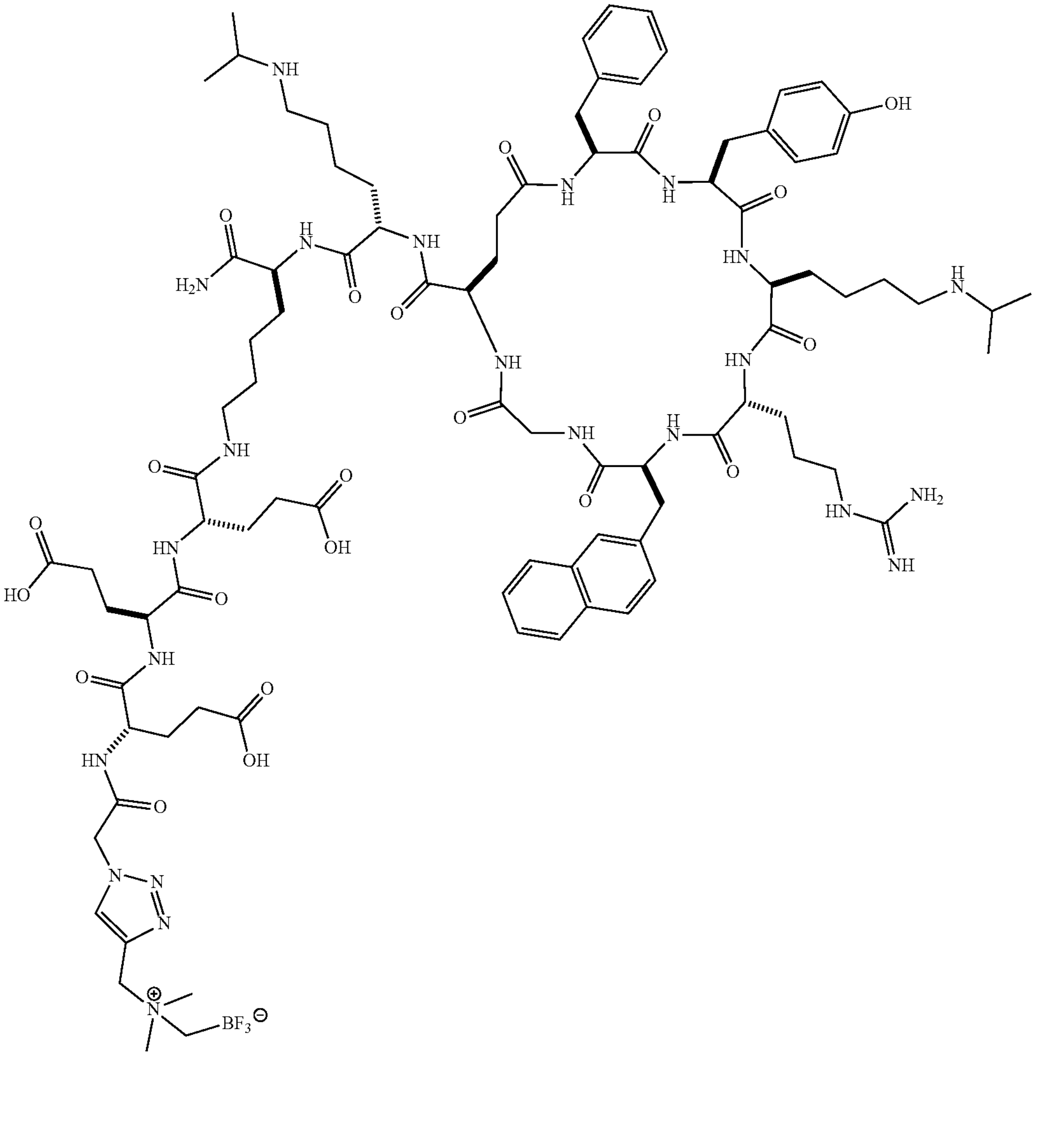

From the synthesis of BL08, following the removal of the Fmoc group after the third coupling of Fmoc-Glu(OtBu)-OH, 2-Azidoacetic acid was coupled for 10 min at 90° C., with two cycles. The peptide was deprotected and cleaved for 3 h at 35° C. and the crude peptide mixture was worked up as previously described. The reaction mixture was purified by HPLC using the preparative column eluted with 18-28% acetonitrile in water with 0.1% TFA over 15 mins at a flow rate of 30 mL/min. The retention time was 11.87 min and the yield of the peptide was 11.2%. The fractions were collected and lyophilized and dissolved in 3 mL of $H_2O$. 5 uL of 1 M $CuSO_4$, 5 uL of 1 M propargyl-$AMBF_3$, 500 uL of 0.1 M $NH_4OH$ solution, and 6 uL of 1 M sodium ascorbate were added sequentially and heated to 45° C. until the reaction mixture turned clear and starting material was consumed based on HPLC. The reaction mixture was purified again by HPLC using the preparative column eluted with 10-20% acetonitrile in water with 0.1% formic acid over 15 mins at a flow rate of 30 mL/min. The retention time was 8.73 min and the yield of BL09 was 47%. ESI-MS: calculated $[M+2H]^{+2}$ $C_{91}H_{135}BF_3N_{23}O_{21}$ 977.0119, found 977.1859.

Synthesis of BL17

The chemical structures of BL17, BL20 and BL25 are below.

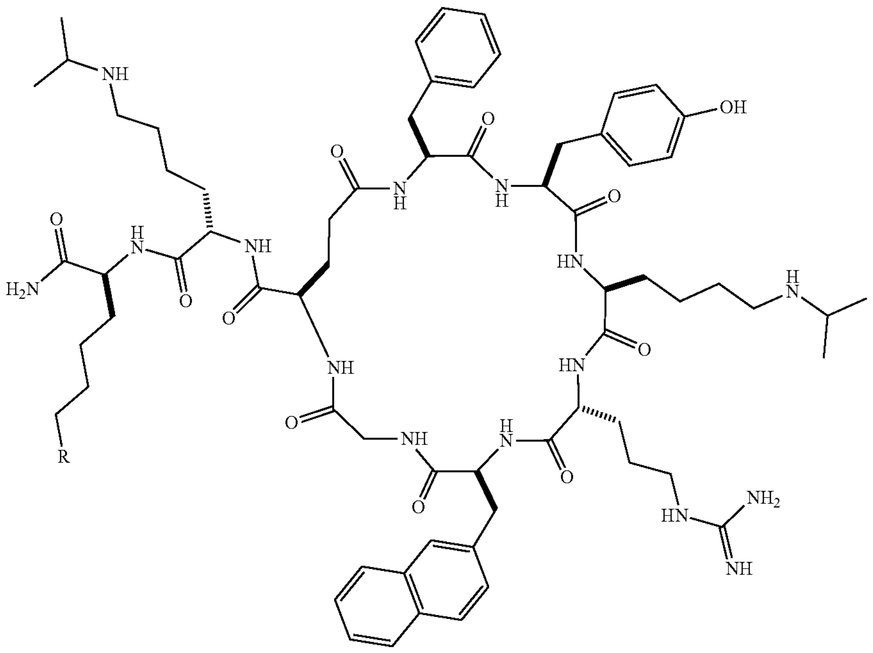
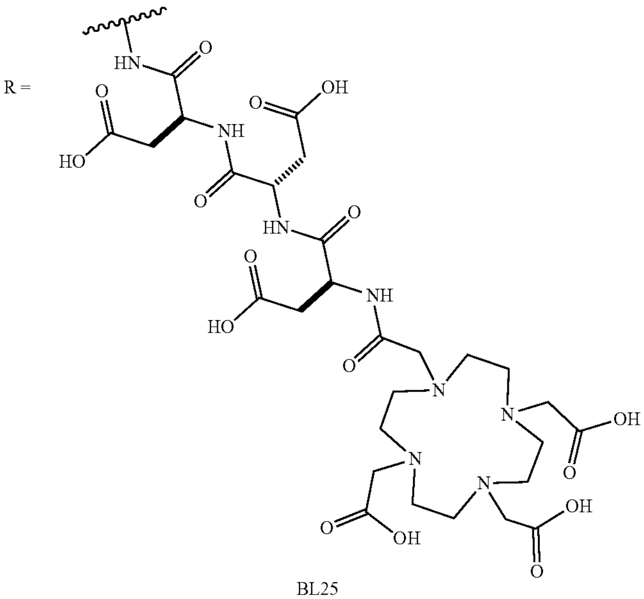
BL25

-continued

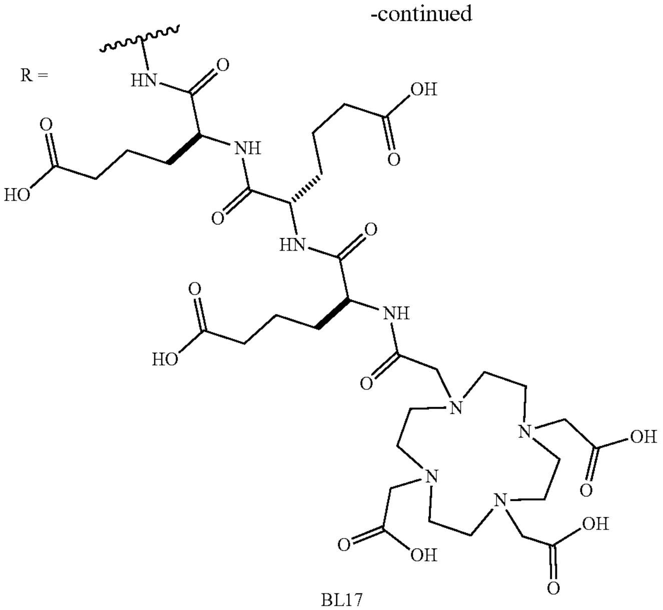

BL17

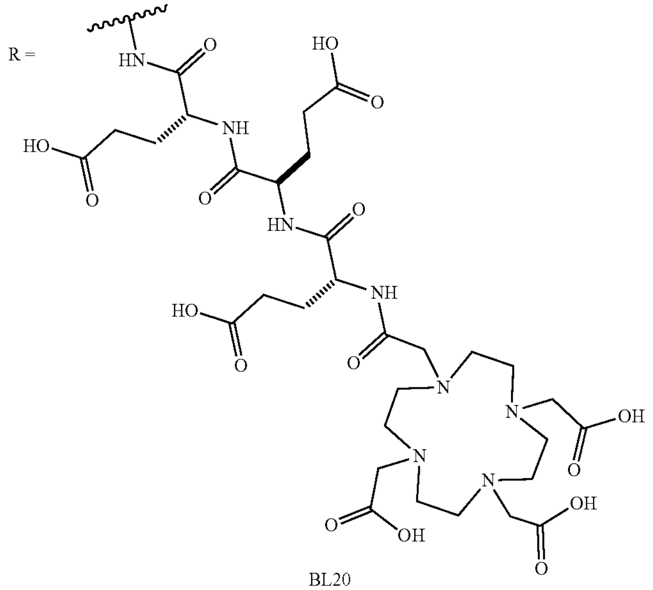 [SMILES: *NC(=O)[C@@H](CCC(=O)O)NC(=O)[C@@H](CCC(=O)O)NC(=O)[C@@H](CCC(=O)O)NC(=O)CN1CCN(CC(=O)O)CCN(CC(=O)O)CCN(CC(=O)O)CC1]

BL20

From the synthesis of BL02, following the removal of the ivDde group, the resin (0.025 mmol) was coupled with three Fmoc-Aad(OtBu)-OH sequentially. Afterwards, the chelator DOTA tri-t-butyl ester (4 equiv.) in DMF was coupled to the terminal amine with HATU/DIEA (4/8 equiv.) for 18 hours at room temperature. The peptide was deprotected and cleaved for 3.5 h at 35° C. and the crude peptide mixture was worked up as previously described. The reaction mixture was purified by HPLC using the preparative column eluted with 10-30% acetonitrile in water with 0.1% TFA over 20 mins at a flow rate of 30 mL/min. The retention time was 14.3 min and the yield of the peptide was 7.2%. ESI-MS: calculated $[M+2H]^{2+}$ for BL17 $C_{102}H_{155}N_{23}O_{27}$ 1067.5743; found $[M+2H]^{2+}$ 1067.4061.

Synthesis of Ga-BL17

For Ga-BL17, a solution of BL17 (2.3 mg, 1.1 μmol) and $GaCl_3$ (0.95 mg, 5.4 μmol) in 500 μL sodium acetate buffer (0.1 M, pH 4.2) was incubated at 90° C. for 20 min. The reaction mixture was purified by HPLC using the preparative column eluted with 10-30% acetonitrile in water with 0.1% TFA over 20 mins at a flow rate of 30 mL/min. The retention time of Ga-BL17 was 14.6 min, and the yield of the peptide was 86%. ESI-MS: calculated $[M+2H]^{2+}$ for Ga-BL17 $C_{102}H_{153}GaN_{23}O_{27}$ 1101.0292; found $[M+2H]^{2+}$ 1100.9840.

Synthesis of BL18

The chemical structure of BL18 is below.

BL18

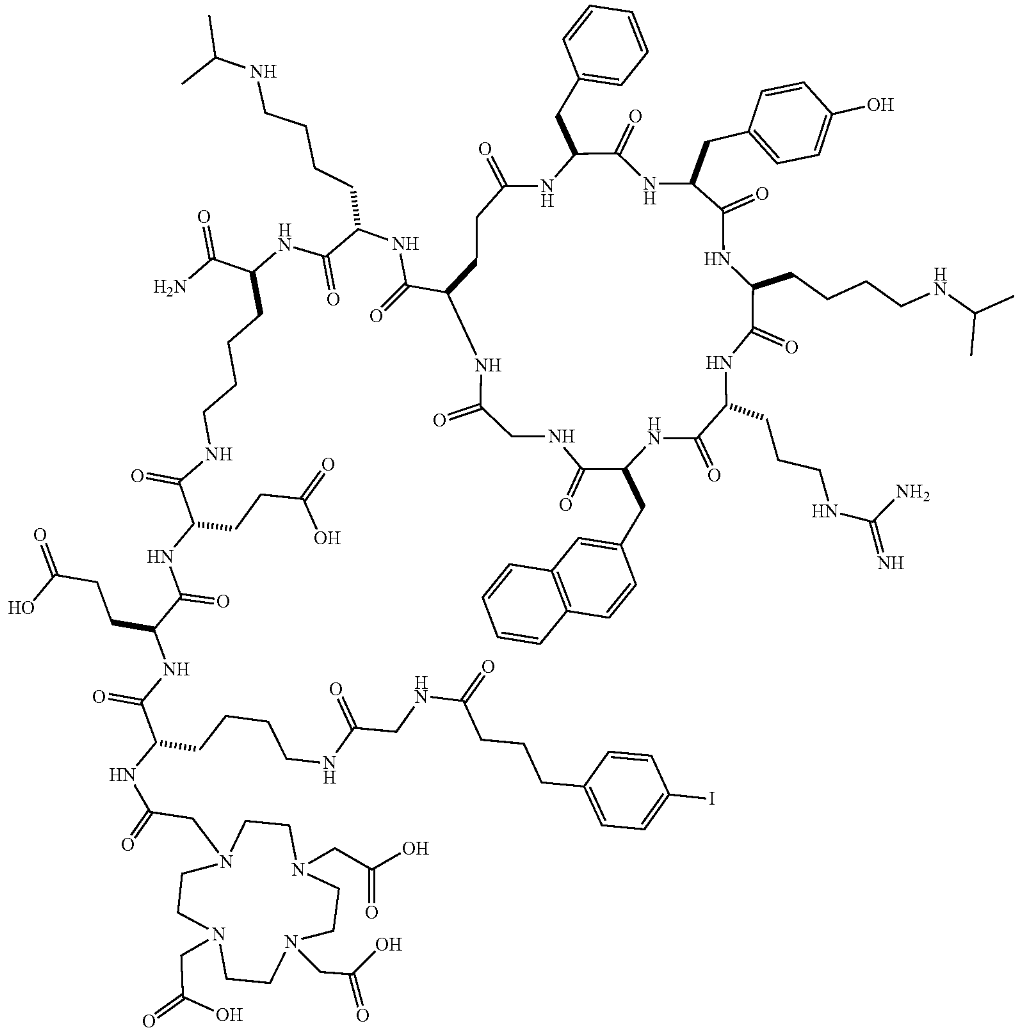

From the synthesis of BL02, following the removal of the ivDde group, the resin (0.025 mmol) was coupled with Glu(OtBu), Glu(OtBu) and Lys(ivDde) sequentially. Afterwards, the chelator DOTA tri-t-butyl ester (4 equiv.) in DMF was coupled to the terminal amine with HATU/DIEA (4/8 equiv.) for 18 hours at room temperature. The ivDde protecting group was removed by 2% v/v hydrazine in DMF (5×5 min at RT). Fmoc-Gly-OH was then coupled. Afterwards, following removal of the Fmoc group, 4-(p-iodophenyl)butyric acid (4 equiv.) was coupled using HATU and DIEA (4 and 8 equiv.) for 10 minutes at 50° C. The peptide was deprotected and cleaved for 3.5 h at 35° C. and the crude peptide mixture was worked up as previously described. The reaction mixture was purified by HPLC using the preparative column eluted with 20-40% acetonitrile in water with 0.1% TFA over 15 mins at a flow rate of 30 mL/min. The retention time was 9.1 min, and the yield of the peptide was 4.0%. ESI-MS: calculated $[M+3H]^{3+}$ for BL18 $C_{112}H_{167}N_{25}O_{27}$ 807.3842; found $[M+3H]^{2+}$ 807.1577.

Synthesis of Lu-BL18

For Lu-BL18, a solution of BL18 (1.8 mg, 0.74 μmol) and $LuCl_3$ (1.0 mg, 3.6 μmol) in 500 μL sodium acetate buffer (0.1 M, pH 4.2) was incubated at 80° C. for 15 min. The reaction mixture was purified by HPLC using the preparative column eluted with 20-40% acetonitrile in water with 0.1% TFA over 15 mins at a flow rate of 30 mL/min. The retention time of Lu-BL17 was 9.3 min, and the yield of the peptide was 75%.

Synthesis of BL19

The chemical structure of BL19 is below.

BL19

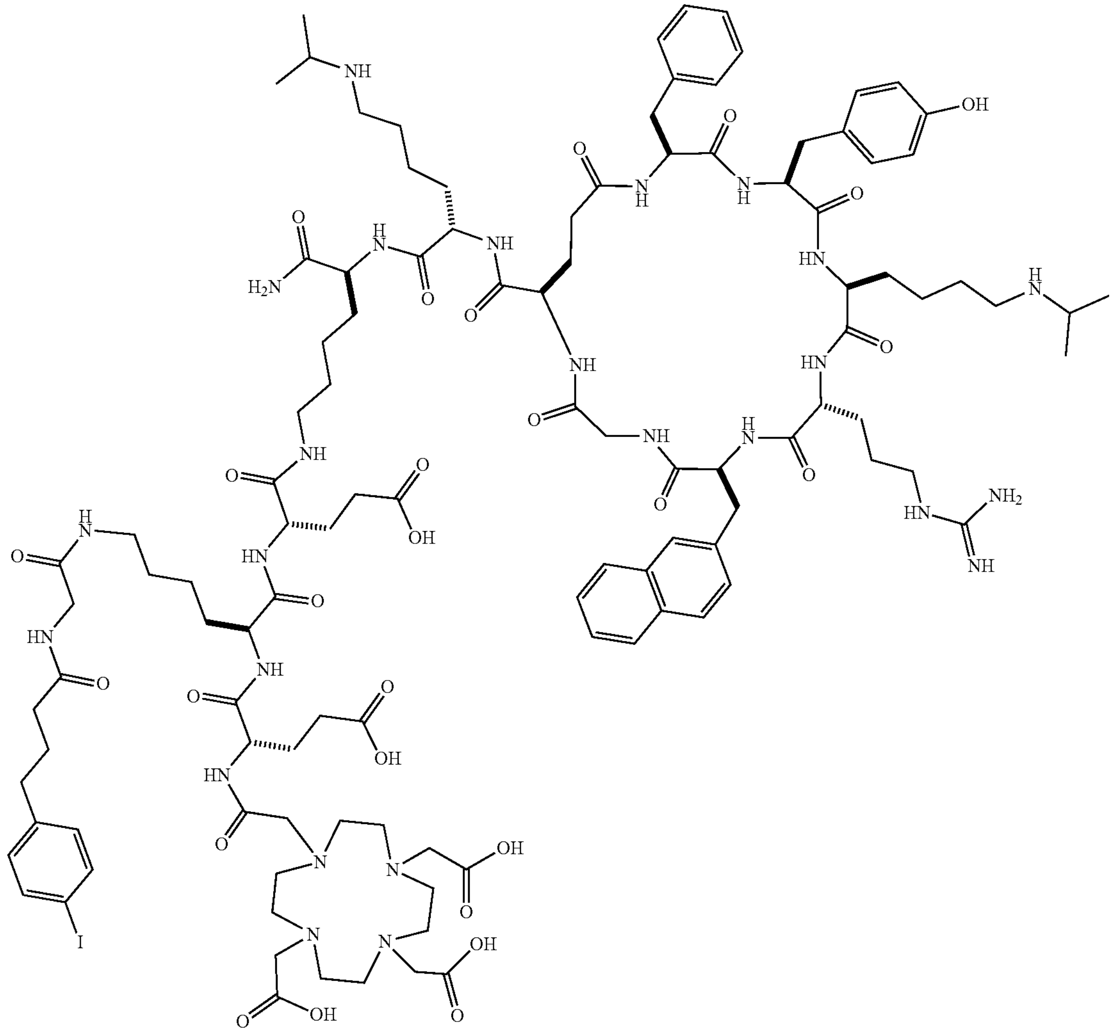

From the synthesis of BL02, following the removal of the ivDde group, the resin (0.025 mmol) was coupled with Glu(OtBu), Lys(ivDde) and Glu(OtBu) sequentially. Afterwards, the chelator DOTA tri-t-butyl ester (4 equiv.) in DMF was coupled to the terminal amine with HATU/DIEA (4/8 equiv.) for 18 hours at room temperature. The ivDde protecting group was removed by 2% v/v hydrazine in DMF (5×5 min at RT). Fmoc-Gly-OH was then coupled. Afterwards, following removal of the Fmoc group, 4-(p-iodophenyl)butyric acid (4 equiv.) was coupled using HATU and DIEA (4 and 8 equiv.) for 10 minutes at 50° C. The peptide was deprotected and cleaved for 3.5 h at 35° C. and the crude peptide mixture was worked up as previously described. The reaction mixture was purified by HPLC using the preparative column eluted with 20-40% acetonitrile in water with 0.1% TFA over 15 mins at a flow rate of 30 mL/min. The retention time was 9.1 min, and the yield of the peptide was 4.6%. ESI-MS: calculated $[M+3H]^{3+}$ for BL19 $C_{112}H_{167}N_{25}O_{27}$ 807.3842; found $[M+3H]^{3+}$ 807.3602.

Synthesis of Lu-BL19

For Lu-BL19, a solution of BL19 (1.34 mg, 0.55 μmol) and $LuCl_3$ (0.78 mg, 2.76 μmol) in 500 μL sodium acetate buffer (0.1 M, pH 4.2) was incubated at 80° C. for 15 min. The reaction mixture was purified by HPLC using the preparative column eluted with 20-40% acetonitrile in water with 0.1% TFA over 15 mins at a flow rate of 30 mL/min. The retention time of Lu-BL19 was 9.3 min, and the yield of the peptide was 71%. ESI-MS: calculated $[M+3H]^{3+}$ for Lu-BL19 $C_{112}H_{165}ILuN_{25}O_{27}$ 865.0259; found $[M+3H]^{3+}$ 864.5719.

Synthesis of BL20

The chemical structure of BL20 is shown above.

From the synthesis of BL02, following the removal of the ivDde group, the resin (0.025 mmol) was coupled with three Fmoc-D-Glu(OtBu)-OH sequentially. Afterwards, the chelator DOTA tri-t-butyl ester (4 equiv.) in DMF was coupled to the terminal amine with HATU/DIEA (4/8 equiv.) for 18 hours at room temperature. The peptide was deprotected and cleaved for 3.5 h at 35° C. and the crude peptide mixture was worked up as previously described. The reaction mixture was purified by HPLC using the preparative column eluted with 11-31% acetonitrile in water with 0.1% TFA over 20 mins at a flow rate of 30 mL/min. The retention time was 13.3 min, and the yield of the peptide was 5.9%. ESI-MS: calculated $[M+2H]^{2+}$ for BL20 $C_{99}H_{147}N_{23}O_{27}$ 1046.5508; found $[M+2H]^{2+}$ 1045.9112.

Synthesis of Ga-BL20

For Ga-BL20, a solution of BL20 (0.94 mg, 0.45 μmol) and $GaCl_3$ (0.46 mg, 2.6 μmol) in 500 μL sodium acetate buffer (0.1 M, pH 4.2) was incubated at 80° C. for 15 min. The reaction mixture was purified by HPLC using the preparative column eluted with 11-31% acetonitrile in water with 0.1% TFA for 30 min at a flow rate of 30 mL/min. The retention time of Ga-BL20 was 13.4 min, and the yield of the peptide was 85%. ESI-MS: calculated $[M+2H]^{2+}$ for Ga-BL20 $C_{99}H_{147}GaN_{23}O_{27}$ 1080.0058; found $[M+2H]^{2+}$ 1079.3370.

Synthesis of BL21

The chemical structure of BL21 is below.

BL21

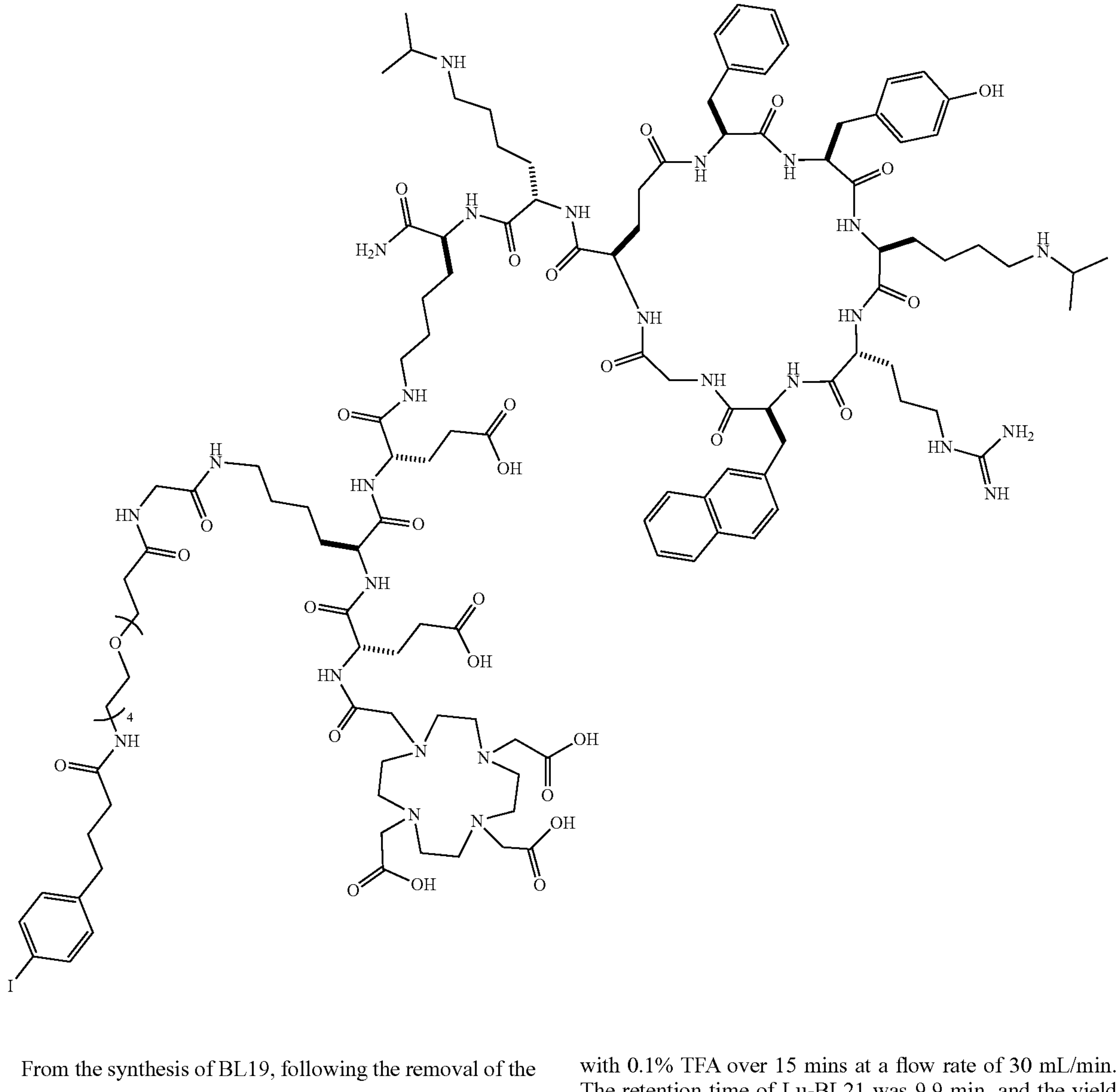

From the synthesis of BL19, following the removal of the second ivDde group, Fmoc-Gly-OH and Fmoc-NH-PEG$_4$-COOH and was coupled sequentially. Afterwards, following removal of the Fmoc group, 4-(p-iodophenyl)butyric acid (4 equiv.) was coupled using HATU and DIEA (4 and 8 equiv.) for 10 minutes at 50° C. The peptide was deprotected and cleaved for 3.5 h at 35° C. and the crude peptide mixture was worked up as previously described. The reaction mixture was purified by HPLC using the preparative column eluted with 20-40% acetonitrile in water with 0.1% TFA over 15 mins at a flow rate of 30 mL/min. The retention time was 9.5 min, and the yield of the peptide was 6.1%.

Synthesis of Lu-BL21

For Lu-BL21, a solution of BL21 (1.51 mg, 0.57 μmol) and $LuCl_3$ (0.80 mg, 2.82 μmol) in 500 μL sodium acetate buffer (0.1 M, pH 4.2) was incubated at 80° C. for 15 min. The reaction mixture was purified by HPLC using the preparative column eluted with 20-40% acetonitrile in water with 0.1% TFA over 15 mins at a flow rate of 30 mL/min. The retention time of Lu-BL21 was 9.9 min, and the yield of the peptide was 97%.

Synthesis of BL22

The chemical structures of BL22, BL23, BL26, BL27, BL28 and BL29 are below.

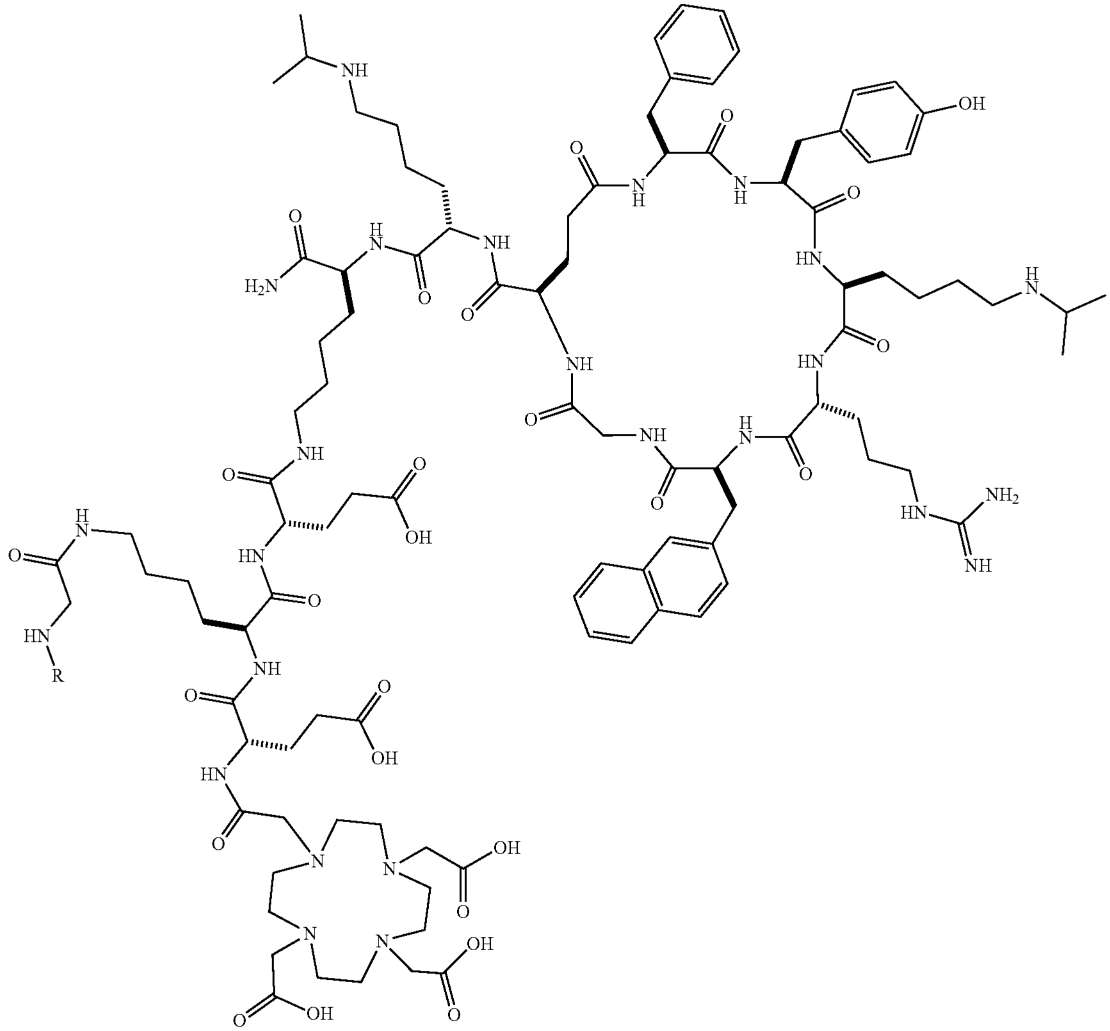

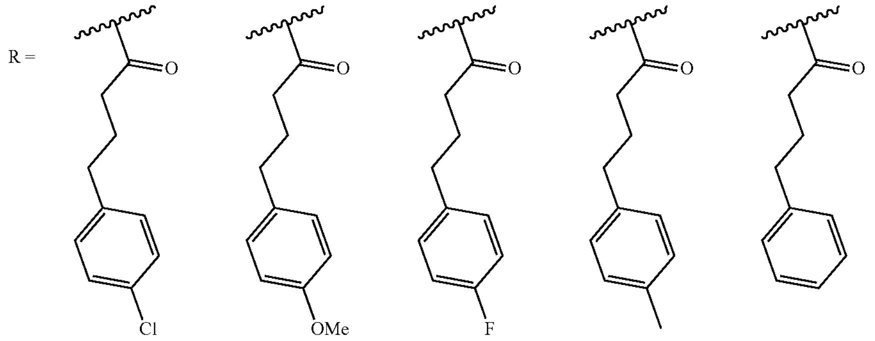

BL22 BL23 BL27 BL28 BL29

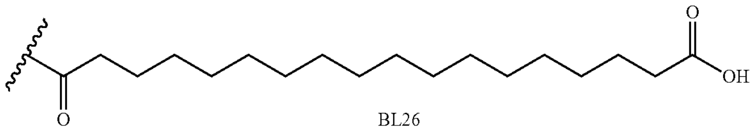

BL26

From the synthesis of BL19, following the coupling of Fmoc-Gly-OH, the Fmoc group was removed and 4-(p-chlorophenyl)butyric acid (4 equiv.) was coupled using HATU and DIEA (4 and 8 equiv.) for 10 minutes at 50° C. with two cycles. The peptide was deprotected and cleaved for 3.5 h at 35° C. and the crude peptide mixture was worked up as previously described. The reaction mixture was purified by HPLC using the preparative column eluted with 20-40% acetonitrile in water with 0.1% TFA for 0-15 min at a flow rate of 30 mL/min. The retention time was 8.2 min, and the yield of the peptide was 8.2%. ESI-MS: calculated $[M+2H]^{2+}$ for BL22 $C_{112}H_{116}ClN_{25}O_{27}$ 1164.6048; found $[M+2H]^{2+}$ 1164.7199.

Synthesis of Ga-BL22

For Ga-BL22, a solution of BL22 (1.41 mg, 6.0 μmol) and $GaCl_3$ (0.53 mg, 3.0 μmol) in 500 μL sodium acetate buffer (0.1 M, pH 4.2) was incubated at 80° C. for 15 min. The reaction mixture was purified by HPLC using the preparative column eluted with 20-40% acetonitrile in water with 0.1% TFA for 0-15 min at a flow rate of 30 mL/min. The retention time was 8.4 min, and the yield of the peptide was 75%. ESI-MS: calculated $[M+3H]^{3+}$ for Ga-BL22 $C_{112}H_{166}ClGaN_{25}O_{27}$ 799.3782; found $[M+3H]^{3+}$ 799.0323.

Synthesis of BL23

The chemical structure of BL23 is above.

From the synthesis of BL19, following the coupling of Fmoc-Gly-OH, the Fmoc group was removed and 4-(4-methoxyphenyl)butyric acid (4 equiv.) was coupled using HATU and DIEA (4 and 8 equiv.) for 10 minutes at 50° C. with two cycles. The peptide was deprotected and cleaved for 3.5 h at 35° C. and the crude peptide mixture was worked up as previously described. The reaction mixture was purified by HPLC using the preparative column eluted with 20-40% acetonitrile in water with 0.1% TFA for 0-15 min at a flow rate of 30 mL/min. The retention time was 7.0 min, and the yield of the peptide was 7.9%. ESI-MS: calculated $[M+3H]^{3+}$ for BL23 $C_{113}H_{170}N_{25}O_{28}$ 775.4221; found $[M+3H]^{3+}$ 775.4712.

Synthesis of Ga-BL23

For Ga-BL23, a solution of BL23 (0.91 mg, 0.39 μmol) and $GaCl_3$ (0.33 mg, 1.89 μmol) in 500 μL sodium acetate buffer (0.1 M, pH 4.2) was incubated at 80° C. for 15 min. The reaction mixture was purified by HPLC using the preparative column eluted with 20-40% acetonitrile in water with 0.1% TFA for 0-15 min at a flow rate of 30 mL/min. The retention time was 7.8 min, and the yield of the peptide was 98%.

Synthesis of Lu-BL23

For Lu-BL23, a solution of BL23 (0.80 mg, 0.34 μmol) and $LuCl_3$ (0.47 mg, 1.67 μmol) in 500 μL sodium acetate buffer (0.1 M, pH 4.2) was incubated at 80° C. for 15 min. The reaction mixture was purified by HPLC using the preparative column eluted with 20-40% acetonitrile in water with 0.1% TFA over 15 mins at a flow rate of 30 mL/min. The retention time was 7.5 min, and the yield of the peptide was 84%.

Synthesis of BL24

The chemical structure of BL24 is below.

BL24

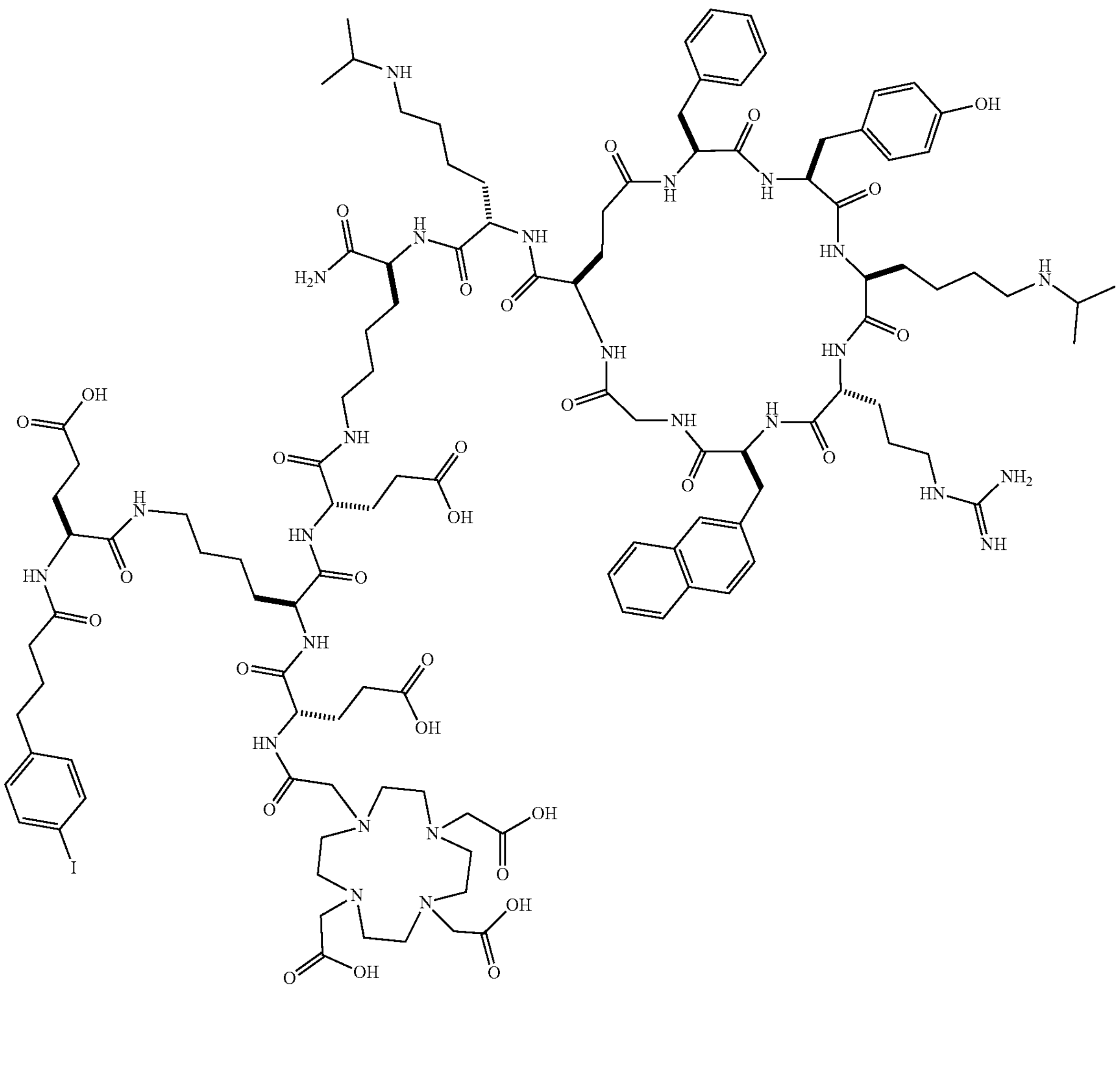

From the synthesis of BL19, following the removal of the second ivDde group, Fmoc-Glu(OtBu)-OH was coupled. Afterwards, following removal of the Fmoc group, 4-(p-iodophenyl)butyric acid (4 equiv.) was coupled using HATU and DIEA (4 and 8 equiv.) for 10 minutes at 50° C. The peptide was deprotected and cleaved for 3.5 h at 35° C. and the crude peptide mixture was worked up as previously described. The reaction mixture was purified by HPLC using the preparative column eluted with 20-40% acetonitrile in water with 0.1% TFA over 15 mins at a flow rate of 30 mL/min. The retention time was 8.9 min, and the yield of the peptide was 6.1%.

Synthesis of Ga-BL24

For Ga-BL24, a solution of BL24 (0.95 mg, 0.38 μmol) and $GaCl_3$ (0.34 mg, 1.94 μmol) in 500 μL sodium acetate buffer (0.1 M, pH 4.2) was incubated at 80° C. for 15 min. The reaction mixture was purified by HPLC using the preparative column eluted with 20-40% acetonitrile in water with 0.1% TFA over 15 mins at a flow rate of 30 mL/min. The retention time was 9.3 min, and the yield of the peptide was 86%.

Synthesis of BL25

The chemical structure of BL25 is shown above.

From the synthesis of BL02, following the removal of the ivDde group, the resin (0.025 mmol) was coupled with three Fmoc-D-Asp(OBno)-OH sequentially using a 2/4/2 equiv. of amino acid/DIC/Oxyma. The Fmoc was deprotected at room temperature for 5 minutes between couplings. Afterwards, the chelator DOTA tri-t-butyl ester (4 equiv.) in DMF was coupled to the terminal amine with HATU/DIEA (4/8 equiv.) for 18 hours at room temperature. The peptide was deprotected and cleaved for 3.5 h at 35° C. and the crude peptide mixture was worked up as previously described. The reaction mixture was purified by HPLC using the preparative column eluted with 12-32% acetonitrile in water with 0.1% TFA for 0-20 min at a flow rate of 30 mL/min. The retention time was 12.0 min, and the yield of the peptide was 5.3%. ESI-MS: calculated $[M+2H]^{2+}$ for BL25 $C_{96}H_{143}N_{23}O_{27}$ 1025.5273; found $[M+2H]^{2+}$ 1024.9492.

Synthesis of Ga-BL25

For Ga-BL25, a solution of BL25 (2.06 mg, 1.0 μmol) and $GaCl_3$ (0.97 mg, 5.55 μmol) in 500 μL sodium acetate buffer (0.1 M, pH 4.2) was incubated at 80° C. for 15 min. The reaction mixture was purified by HPLC using the preparative column eluted with 12-32% acetonitrile in water with 0.1% TFA for 0-20 min at a flow rate of 30 mL/min. The retention time was 12.3 min, and the yield of the peptide was 76%. ESI-MS: calculated $[M+3H]^{3+}$ for Ga-BL25 $C_{96}H_{143}GaN_{23}O_{27}$ 706.6599; found $[M+3H]^{3+}$ 706.1981.

Synthesis of BL26

The chemical structure of BL26 is shown above.

From the synthesis of BL19, the coupling of Fmoc-Gly-OH, the Fmoc group was removed and 1,18-octadecanedioic acid mono-tert-butyl ester (4 equiv.) was coupled using HATU and DIEA (4 and 8 equiv.) for 10 minutes at 50° C. with two cycles. The peptide was deprotected and cleaved for 3.5 h at 35° C. and the crude peptide mixture was worked up as previously described. The reaction mixture was purified by HPLC using the preparative column eluted with 20-40% acetonitrile in water with 0.1% TFA over 15 mins at a flow rate of 30 mL/min. The retention time was 13.5 min, and the yield of the peptide was 10.5%.

Synthesis of Ga-BL26

For Ga-BL26, a solution of BL26 (1.43 mg, 0.57 μmol) and $GaCl_3$ (4.8 mg, 2.75 μmol) in 500 μL sodium acetate buffer (0.1 M, pH 4.2) was incubated at 80° C. for 15 min. The reaction mixture was purified by HPLC using the preparative column eluted with 22-44% acetonitrile in water with 0.1% TFA over 15 mins at a flow rate of 30 mL/min. The retention time was 12.5 min, and the yield of the peptide was 92%.

Synthesis of BL27

The chemical structure of BL27 is shown above.

From the synthesis of BL19, following the coupling of Fmoc-Gly-OH, the Fmoc group was removed and 4-(4-fluorophenyl)butyric acid (4 equiv.) was coupled using HATU and DIEA (4 and 8 equiv.) for 10 minutes at 50° C. with two cycles. The peptide was deprotected and cleaved for 3.5 h at 35° C. and the crude peptide mixture was worked up as previously described. The reaction mixture was purified by HPLC using the preparative column eluted with 20-40% acetonitrile in water with 0.1% TFA over 15 mins at a flow rate of 30 mL/min. The retention time was 7.8 min, and the yield of the peptide was 9.7%.

Synthesis of Ga-BL27

For Ga-BL27, a solution of BL27 (0.98 mg, 0.41 μmol) and $GaCl_3$ (0.35 mg, 2.1 μmol) in 500 μL sodium acetate buffer (0.1 M, pH 4.2) was incubated at 80° C. for 15 min. The reaction mixture was purified by HPLC using the preparative column eluted with 20-40% acetonitrile in water with 0.1% TFA over 15 mins at a flow rate of 30 mL/min. The retention time was 7.6 min, and the yield of the peptide was 91%.

Synthesis of BL28

The chemical structure of BL28 is shown above.

From the synthesis of BL19, following the coupling of Fmoc-Gly-OH, the Fmoc group was removed and 4-(4-methylphenyl)butyric acid (4 equiv.) was coupled using HATU and DIEA (4 and 8 equiv.) for 10 minutes at 50° C. with two cycles. The peptide was deprotected and cleaved for 3.5 h at 35° C. and the crude peptide mixture was worked up as previously described. The reaction mixture was purified by HPLC using the preparative column eluted with 20-40% acetonitrile in water with 0.1% TFA over 15 mins at a flow rate of 30 mL/min. The retention time was 7.9 min, and the yield of the peptide was 9.3%.

Synthesis of Ga-BL28

For Ga-BL28, a solution of BL28 (1.1 mg, 0.46 μmol) and $GaCl_3$ (4.0 mg, 2.3 μmol) in 500 μL sodium acetate buffer (0.1 M, pH 4.2) was incubated at 80° C. for 15 min. The reaction mixture was purified by HPLC using the preparative column eluted with 20-40% acetonitrile in water with 0.1% TFA over 15 mins at a flow rate of 30 mL/min. The retention time was 8.0 min, and the yield of the peptide was 72%.

Synthesis of BL29

The chemical structure of BL29 is shown above.

From the synthesis of BL19, following the coupling of Fmoc-Gly-OH, the Fmoc group was removed and 4-phenylbutyric acid (4 equiv.) was coupled using HATU and DIEA (4 and 8 equiv.) for 10 minutes at 50° C. with two cycles. The peptide was deprotected and cleaved for 3.5 h at 35° C. and the crude peptide mixture was worked up as previously described. The reaction mixture was purified by HPLC using the preparative column eluted with 20-40% acetonitrile in water with 0.1% TFA over 15 mins at a flow rate of 30 mL/min. The retention time was 7.1 min, and the yield of the peptide was 7.0%.

Chemical Synthesis of the $PepBF_3$ Synthon

Synthesis of $PepBF_3$ JL3

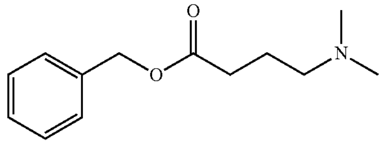 [SMILES: CN(C)CCCC(=O)OCc1ccccc1]

4-Dimethylamino-butyric acid benzyl ester (JL1). A round bottom flask charged with γ-aminobutyric acid (2 g, 19.4 mmol, 1 equiv.), formaldehyde (9 mL, 37% in solution v/v, 121 mmol, 6 equiv.), and formic acid (6 mL, 90% in solution, 143 mmol, 7 equiv.) and was stirred at 80° C. for 48 h. The reaction was monitored by TLC (10% MeOH in DCM, $R_f$ of intermediate=0.45, stained with bromocresol green). The reaction mixture was cooled to room temperature and HCl (6 mL, 4 M, 24.4 mmol, 1.25 equiv.) was added. The reaction solution was dried down by rotary evaporation to give a yellow solid intermediate 4-Dimethylamino-butyric acid to which, benzyl alcohol (10 mL, 100 mmol, 5 equiv.), and 4-toluenesuphonic acid monohydrate (3.5 g, 20.9 mmol, 1.05 equiv.) was added. The reaction was refluxed at 90° C. for 2 h and the reaction solution was cooled to room temperature. The toluene phase was extracted with $H_2O$ (4×100 mL) and NaOH (1 M) was added to the pooled aqueous phase until basic. The aqueous phase was then extracted with EtOAc (3×100 mL). The EtOAc extract was then washed with brine, dried with $MgSO_4$, filtered, and evaporated to give 3.31 g of crude orange oil which was then purified via silica chromatography by using basified silica and saturating the column in pet ether (PE) and the fractions monitored by TLC (10% MeOH in DCM, $R_f$ of intermediate=0.3). The compound was loaded directly onto the silican and rinsed with PE, elutions were performed at 5 column volumes (CV) of PE, 1:1; PE:EtOAc, EtOAc, DCM, 10% MeOH in DCM to give JL1 in good yields (2.332 g, 52% over two steps). $^1H$ NMR (300 MHz, $CDCl_3$) δ (ppm): 7.37 (m, 5H), 5.14 (s, 2H), 2.42 (t, 2H), 2.35 (t, 2H), 2.26 (s, 6H), 1.85 (quint, 2H).

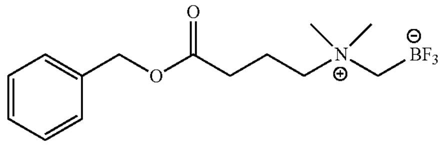

(3-Benzyloxycarbonyl-propyl)-dimethyl-ammonium-methylenetrifluoroborate (JL2). 4-Dimethylamino-butyric acid benzyl ester JL1 (2.5 g, 11.2 mmol) was dissolved in $Et_2O$ (50 mL) and DCM (50 mL). Iodomethyl-boronylpinacolate (1.92 mL, 10.64 mmol, 0.95 equiv.) was added drop-wise to the stirring mixture and the solution as allowed to stir for 2 hours and was then placed into a 50° C. bath and stirred for 30 hours. The reaction was cooled and the solvents were removed by rotovap to yield thick orange oil. The oil was dissolved in ACN (100 mL) and diluted with 50 mL of water and was combined with an aqueous solution of $AgNO_3$ (100 mL, 0.18 M, 1.5 equiv.), then brine (0.12 mL, 0.71 mmol, 1.5 equiv.), producing yellow precipitates and white precipitates respectively. The mixture was filtered over celite and concentrated by rotovap. The resulting white solids were triturated with ACN (100 mL), sonicated for 30 mins, filtered through celite, and the filtrate was concentrated to 15 mL and transferred to a plastic bottle. To fluorinate, $KHF_2$ (14 mL, 4 M, 112 mmol, 10 equiv.) and HCl (37 mL, 3 M, 112 mmol, 10 equiv.) were added to the solution. The reaction was allowed to fluorinate for 1 hour and was quenched by adding concentrated $NH_4OH$ until basic. The mixture was frozen and lyophilized to give white solids that were extracted with acetone (3×300 mL), and the pooled extract was dried down by rotary evaporation to give the crude product as white solids which was purified by silica chromatography. Column purification was performed by using basified silica and saturating the column in DCM and the fractions monitored by TLC (40% ACN in DCM, Rf=0.4). The compound was dissolved with MeOH and was dry loaded onto silica. The silica bound compound was placed into the column, and gradient elutions were performed at 5 CVs of 0, 5, 10, 20% ACN in DCM to yield the pure compound JL2 in good yields (2.7655 g, 86% over two steps). $^1H$ NMR (300 MHz, ACN) δ (ppm): 7.37 (m, 5H), 5.13 (s, 2H), 3.30 (m, 2H), 3.03 (s, 6H), 2.48 (t, 2H), 2.45 (m, 2H), 2.09 (m, 2H). $^{19}F$ NMR (300 MHz, ACN) δ (ppm): −141.02. $^{11}B$ NMR (300 MHz, ACN) δ (ppm): −2.09.

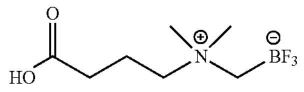

(3-Carboxy-propyl)-dimethyl-ammonium-methylenetrifluoroborate (JL3). (3-Benzyloxycarbonyl-propyl)-dimethyl-ammonium-methylenetrifluoroborate JL2 (2.65 g, 8.7 mmol) was placed in a round bottom flask and the moisture was evacuated under reduced pressure and a warm water bath. Argon was flushed through the flask and freshly distilled THE (100 mL) was added into the flask and sonicated to achieve dissolution. Palladium on charcoal (1.4 g, 10% Pd/C, 0.50 mmol, 0.11 equiv.) was added to the reaction vessel. The flask was capped and stirred under $H_2$(g) for 16 hours. Reaction progress was monitored with TLC (40% ACN in DCM, Rf=0.4, UV, HBQ and BCG stain active). Upon complete consumption of starting material, the mixture was filtered through celite to remove the charcoal and washed with methanol (3×50 mL). The solution was dried down by rotary evaporation to give white solids (1.095 g, 60% overall yield). $^1H$ NMR (300 MHz, $D_2O$) δ (ppm): 3.21 (m, 2H), 2.97 (s, 6H), 2.42 (m, 2H), 2.39 (t, 2H), 2.08 (m, 2H). $^{19}F$ NMR (300 MHz, $D_2O$) δ (ppm): −140.91. $^{11}B$ NMR (300 MHz, $D_2O$) δ (ppm): 2.08. $^{13}C$ NMR (300 MHz, MeOD) δ (ppm): 174.26, 65.69, 52.37, 29.85, 18.19. ESI-MS (−): $C_7H_{15}BF_3NO_2$ calculated exact mass 213.11 m/z; found [2M-H]−=425.2 m/z.

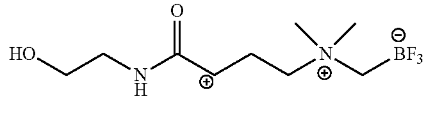

[3-(2-Hydroxy-ethylcarbamoyl)-propyl]-dimethyl-ammonium-methylenetrifluoroborate (JL4). (3-Carboxy-propyl)-dimethyl-ammonium-methylenetrifluoroborate JL3 (50 mg, 0.23 mmol) was charged into a round bottom flask and was dissolved in DMF (5 mL). 3-aminopropanol (19.8 μL, 0.25 mmol, 1.1 equiv.) was added into the mixture followed by the addition of HBTU (97.9 mg, 0.25 mmol, 1.1 equiv.) and DIPEA (61 μL, 0.35 mmol, 1.5 equiv.) and was allowed to stir for 16 hours. The reaction was monitored using TLC (10% MeOH in DCM, Rf=0.2, product is $KMnO_4$ and HBQ stain active). Upon complete consumption of the starting material, the reaction was dried down and was purified by silica chromatography. Column purification was performed by using basified silica and saturating the column in DCM. The crude mixture was dissolved with MeOH and was dry loaded onto silica. The silica bound compound was placed into the column, and gradient elutions were performed at 5 CVs of 0, 5 and 10% MeOH in DCM to yield the pure compound JL4 (8 mg, 13%). $^1$H NMR (300 MHz, $D_2O$) δ (ppm): 3.60 (t, 2H), 3.29 (m, 4H), 3.06 (s, 6H), 2.43 (m, 2H), 2.28 (t, 2H), 2.08 (m, 2H), 1.73 (quint, 2H). $^{19}$F NMR (300 MHz, D20) δ (ppm): −141.23. $^{11}$B NMR (300 MHz, D20) δ (ppm): 2.05.

Radiochemical Synthesis $^{18}$F-Labeling: No-carrier-added [$^{18}$F]fluoride was obtained by bombardment of $H_2{}^{18}O$ with 18-MeV protons (Advanced Cyclotron Systems Inc) followed by trapping on an anion exchange resin column (pre-activated with brine and washed with DI water, without $HCO_3^-$ preconditioning). The [$^{18}$F]fluoride was then eluted from the column using HCl-pyridazine buffer (pH 2.0). Unlabeled trifluoroborate precursors (100 nmol) was suspended in DMF (15 μL). The eluted [$^{18}$F]fluoride (30-100 GBq) was added into a reaction vessel containing the solution of BL08 or BL09. The vial was heated at 80° C. for 20 minutes on a heating block and quenched upon the addition of 1 mL of water. [31,32] The mixture was purified by semi-prep HPLC and quality control was performed via analytical HPLC with the co-injection of the unlabeled standard with a one-twelfth of the radiotracer. Radiochemical yields (decay-corrected) were >10% and radiochemical purities were >95%.

$^{68}$Ga-Labeling: [$^{68}$Ga]$GaCl_3$ was eluted from an iThemba Labs generator with a total of 4 mL of 0.1 M HCl. The eluted [$^{68}$Ga]$GaCl_3$ solution was added to 2 mL of concentrated HCl. This radioactive mixture was then added to a DGA resin column and washed with 3 mL of 5 M HCl. The column was then dried with air and the [$^{68}$Ga]$GaCl_3$ (0.10-0.50 GBq) was eluted with 0.5 mL of water into a vial containing a solution of the unlabeled precursor (25 μg) in 0.7 mL HEPES buffer (2 M, pH 5.3). The reaction mixture was heated in a microwave oven (Danby; DMW7700WDB) for 1 min at power setting 2. The mixture was purified by semi-prep HPLC and quality control was performed via analytical HPLC with the co-injection of the unlabeled standard with a one-twelfth of the radiotracer. Radiochemical yields (decay-corrected) were >50% and radiochemical purities were >95%.

$^{177}$Lu-Labeling: [$^{177}$Lu]$LuCl_3$ was purchased from ITM Isotopen Technologien Munchen AG. [$^{177}$Lu]$LuCl_3$ (100-1000 MBq) in 0.04 M HCl (10-100 μL) was added to a solution of the unlabeled precursor (25 μg) in 0.5 mL of NaOAc buffer (0.1 M, pH 4.5). The reaction mixture was incubated at 100° C. for 15 min. The mixture was purified by semi-prep HPLC and quality control was performed via analytical HPLC with the co-injection of the unlabeled standard with a one-twelfth of the radiotracer. Radiochemical yields (decay-corrected) were >50% and radiochemical purities were >95%.

Competition Binding Assay

The binding affinities of nonlabelled peptides for CXCR4 were determined using a competition binding assay using the CHO:CXCR4 cells. Briefly, CHO:CXCR4 cells (200,000 cells/well) were plated in a 24-well BioCoat™ Poly-D-Lysine Multiwell Plates (Corning) the previous night. The next day, each well was incubated with RPMI-1640 medium (Life Technologies Corporations) supplemented with 20 mM HEPES and 2 mg/mL BSA, [$^{125}$I]SDF-1α (0.01 nM, Perkin Elmer) and competing non-radioactive ligands (10 μM to 1 μM) and incubated for 1-1.5 hours at 27° C. with moderate shaking. After incubation, the cells were washed with ice-cold PBS twice, trypsinized and counted on a Perkin Elmer WIZARD 2480 gamma counter. IC50 values were determined by a nonlinear regression analysis to fit a logistic equation to the competition data using GraphPad Prism 7.

Internalization

2×10$^6$ cells/well are seeded in complete growth medium in a 24 well Poly-D-Lysine plate (Corning BioCoat™, Ref No. 354414) 24-48 hours prior to the assay. Reactions are performed in triplicate, an unblocked and a blocked set for both CHOwt and CHO::CXCR4 cells. For the assay, the growth medium is replaced with 400 μl of reaction medium (RPMI, 2 mg/ml BSA, 20 mM HEPES). For blocked sets, cells are preincubated for 1 hour with 1 μM LY2510924 at 37° C. and 5% $CO_2$. 0.8 MBq of 68Ga-BL02 per well is added to both unblocked and blocked wells and incubated at 27° C. with mild shaking for 1 hour. 3 samples of the radiolabelled peptide with no cells will be used as standard. The supernatant is removed, and cells are washed once with ice-cold PBS. The cells were then washed twice with washes with 200 μL of ice-cold 0.2 M Acetic Acid, 0.5 M NaCl, pH2.6. The washings were combined and measured, constituting the membrane bound portion of peptide. The cells are washed again with ice-cold PBS, trypsinized, collected and measured, constituting the internalized fraction of the peptide. Standards, membrane bound fraction and cells are counted on the Wizard gamma counter. Analysis is performed using GraphPad Prism.

Cell Culture

The Daudi B lymphoblast cell line (ATCC® CCL-213) and PC-3 prostate adenocarcinoma (ATCC® CRL-1435) were purchased from the American Type Culture Collection and tested for potential rodent pathogens and *mycoplasma* contamination using the IMPACT test (IDEXX BioAnalytics). The CHO:CXCR4 cell line was a kind gift from Drs. David McDermott and Xiaoyuan Chen (National Institutes of Health). The GRANTA519, Jeko1 and Z138 cells were a kind gift from Dr. Christian Steidl. The Daudi, GRANTA519, Jeko1, Z138, PC-3 and CHO:CXCR4 cells were cultured in a 5% $CO_2$ atmosphere at 37° C. in a humidified incubator.

The Daudi and GRANTA519 cells were cultured with RPMI-1640 medium (Life Technologies Corporations) supplemented with 10% fetal bovine serum (Sigma-Aldrich), 100 I.U./mL penicillin, and 100 μg/mL streptomycin (Penicillin-Streptomycin Solution). The Jeko1 cells were cultured with RPMI-1640 medium (Life Technologies Corporations) supplemented with 20% fetal bovine serum (Sigma-Aldrich), 100 I.U./mL penicillin, and 100 μg/mL streptomycin (Penicillin-Streptomycin Solution). The Z138 cells were cultured with Iscove's Modified Dulbecco's Medium (IMDM) supplemented with 10% fetal bovine serum (Sigma-Aldrich), 100 I.U./mL penicillin, and 100 μg/mL streptomycin (Penicillin-Streptomycin Solution). The CHO:CXCR4 cells and PC-3 cells were cultured with F12K medium (Life Technologies Corporations) supplemented with 10% fetal bovine serum (Sigma-Aldrich), 100 I.U./mL penicillin, and 100 μg/mL streptomycin (Penicillin-Streptomycin Solution).

Animal Models

Animal experiments were performed in accordance with guidelines established by the Canadian Council on Animal Care, under a research protocol approved by the Animal Ethics Committee of the University of British Columbia. For Daudi, Z138, GRANTA519 and Jeko1 xenografts, male NOD.Cg-Rag1$^{tm1Mom}$Il2rg$^{tm1Wjl}$/SzJ (NRG) mice were subcutaneously inoculated on the left flank with 5×10$^6$ cells (100 μL; 1:1 ratio of PBS/Matrigel) and tumors were grown to a size of 200-500 mm$^3$. For PC-3 xenografts, male NOD.Cg-Rag1$^{tm1Mom}$Il2rg$^{tm1Wjl}$/SzJ (NRG) mice were subcutaneously inoculated on the left flank with 5×10$^6$ PC-3 cells (100 μL; 1:1 ratio of PBS/Matrigel) and tumors were grown to a size of 200-400 mm$^3$.

PET/CT Imaging

PET and CT scans were performed on a Siemens Inveon microPET/CT with body temperature maintained by a heating pad. Tumor-bearing mice were briefly sedated with isoflurane (2-2.5% isoflurane in 2 L/min 02) for i.v. injection of 4-7 MBq of each PET radiotracer. As a blocking control, mice received intraperitoneal (i.p.) injection of 7.5 μg LY2510924 15 minutes prior to radiotracer administration. The animals were allowed to roam freely during the uptake period (50 or 110 minutes), after which they were sedated and scanned. The CT scan was obtained for attenuation correction and anatomical localization (80 kV; 500 pA; 3 bed positions; 34% overlap; 220° continuous rotation) followed by a 10 min PET acquisition at 1 or 2 h p.i. of the radiotracer. PET data were acquired in list mode, reconstructed using 3-dimensional ordered-subsets expectation maximization (2 iterations) followed by a fast maximum a priori algorithm (18 iterations) with CT-based attenuation correction. Images were analyzed using the Inveon Research Workplace software (Siemens Healthineers).

Biodistribution

Under isoflurane anesthesia (2-2.5% isoflurane in 2 L/min $O_2$), the mice were injected intravenously with 0.8-3.0 MBq of each radiotracer. Additional groups of mice received 7.5 μg LY2510924 as a blocking control i.p. 15 min before radiotracer injection. The mice were euthanized via $CO_2$ inhalation while anesthetized with isoflurane. Tissues were harvested, washed in PBS, blotted dry, weighed, and measured on a Hidex AMG Automatic Gamma Counter. The radioactivity counts were decay corrected, converted to absolute units using a calibration curve, and expressed as the percent injected dose per gram of tissue (% ID/g).

In Vivo Stability

Radiolabeled peptides (10-30 MBq) was intravenously injected into male NRG mice. After a 5-min, 24-hour or 120-hour uptake period, mice were sedated/euthanized, and blood was collected. The plasma was isolated and analyzed with analytical radio-HPLC following published procedures (Lin et al., *Cancer Res.* 2015, 75:387-393).

Dosimetry

The multi-time-point organ uptake obtained from biodistribution data of $^{177}$Lu-labeled analogs was decayed to their appropriate time-point, fitted to a mono-exponential or bi-exponential model (fit chosen based on R2 and residuals) in Python (version 3.7). The area under the curve was used to compute residence times which were multiplied by model organ mass for human (NURBS model) and mouse (25 g MOBY mouse phantom) for use in OLINDA/EXM software (Hermes Medical Solution; version 2.0) that calculated dosimetry for an average mouse (Stabin et al., *J Nucl Med.* 2005, 46:1023-1027; Keenan et al., *J Nucl Med.* 2010, 51:471-476) and extrapolated to an average human male (Segars et al., *J Nucl Med.* 2001, 42:7; Stabin et al., *J Nucl Med.* 2012, 53:1807-13).

Results

Figure 2:
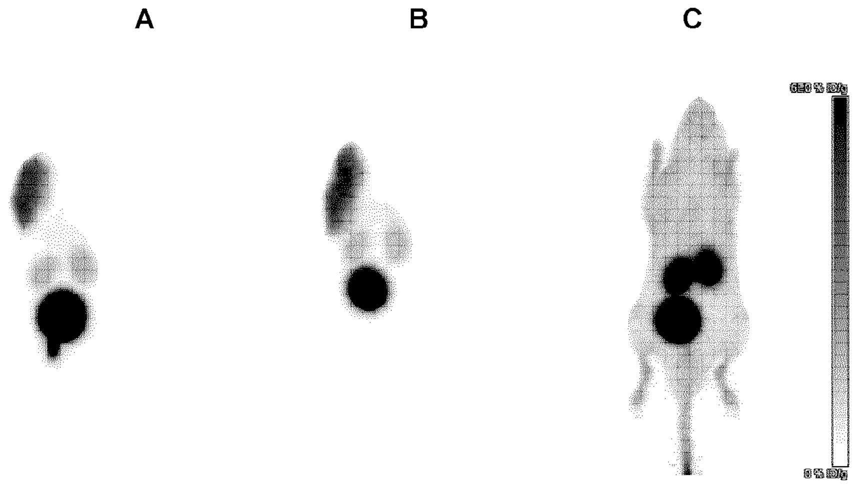
FIG. 2 shows maximal intensity projection PET images of [$^{68}$Ga]Ga-BL02 at A) 1 and B) 2 h post-injection in mice bearing Daudi Burkitt's lymphoma xenografts. C) Blocking study was performed by pre-injection of 7.5 μg of LY2510924 (i.p.) 15 minutes before tracer administration. The scale bar is in units of % ID/g from 0 to 6.
Figure 3:
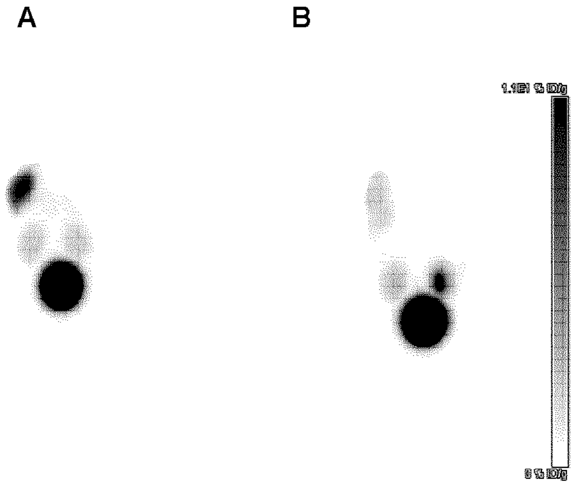
FIG. 3 shows maximal intensity projection PET images of [$^{68}$Ga]Ga-BL02 at A) 1 h post-injection in mice bearing Z138 mantle cell lymphoma xenografts. B) Blocking study was performed by pre-injection of 7.5 μg of LY2510924 (i.p.) 15 minutes before tracer administration. The scale bar is in units of % ID/g from 0 to 11.
Figure 4:
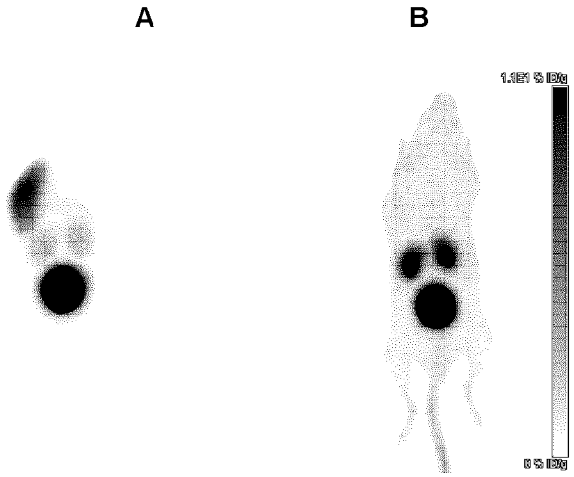
FIG. 4 shows maximal intensity projection PET images of [$^{68}$Ga]Ga-BL02 at A) 1 h post-injection in mice bearing Jeko1 mantle cell lymphoma xenografts. B) Blocking study was performed by pre-injection of 7.5 μg of LY2510924 (i.p.) 15 minutes before tracer administration. The scale bar is in units of % ID/g from 0 to 11.
Figure 5:
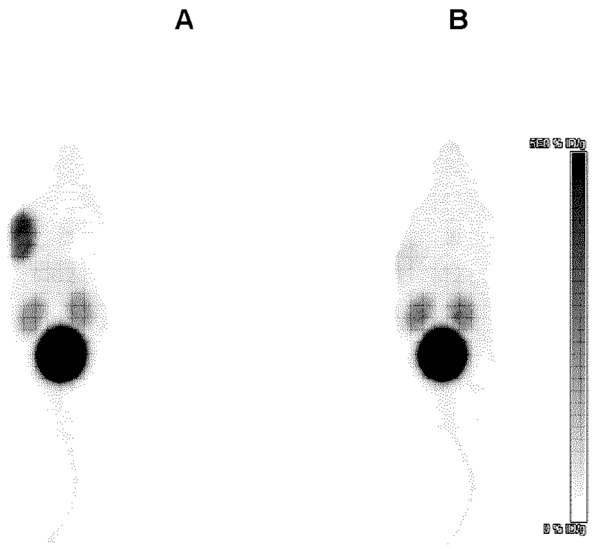
FIG. 5 shows maximal intensity projection PET images of [$^{68}$Ga]Ga-BL02 at A) 1 h post-injection in mice bearing GRANTA519 mantle cell lymphoma xenografts. B) Blocking study was performed by pre-injection of 7.5 μg of LY2510924 (i.p.) 15 minutes before tracer administration. The scale bar is in units of % ID/g from 0 to 5.
Figure 6:
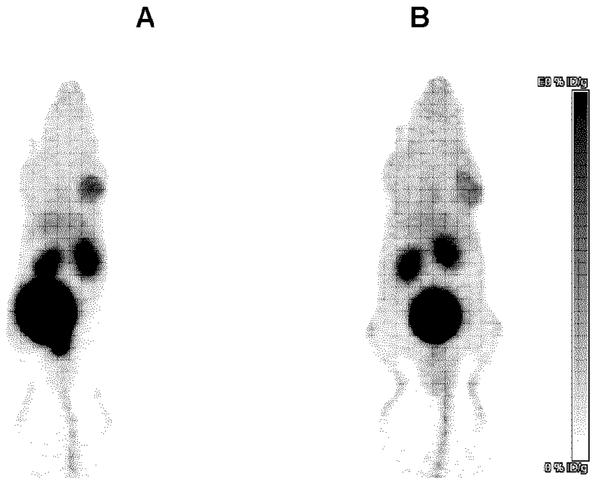
FIG. 6 shows maximal intensity projection PET images of [$^{68}$Ga]Ga-BL02 at A) 1 h post-injection in mice bearing PC3 prostate adenocarcinoma xenografts. B) Blocking study was performed by pre-injection of 7.5 μg of LY2510924 (i.p.) 15 minutes before tracer administration. The scale bar is in units of % ID/g from 0 to 1.5.
Figure 7:
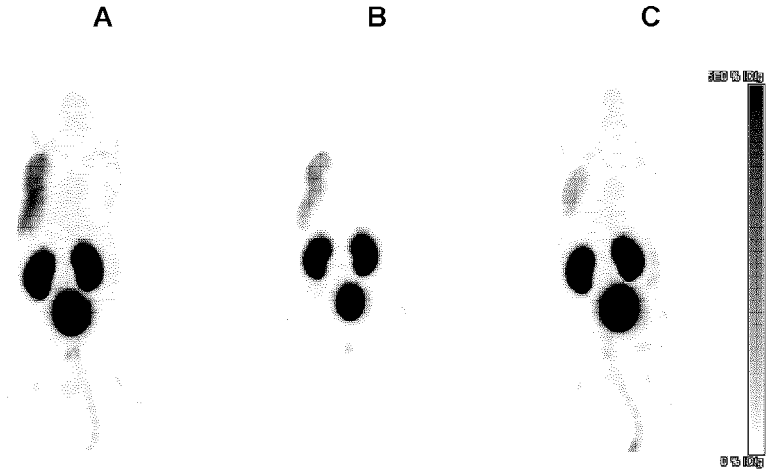
FIG. 7 shows maximal intensity projection PET images of [$^{18}$F]F-BL04 at A) 1 and B) 2 h post-injection in mice bearing Daudi Burkitt's lymphoma xenografts. C) Blocking study was performed by pre-injection of 7.5 μg of LY2510924 15 min (i.p.) before tracer administration. The scale bar is in units of % ID/g from 0 to 5.
Figure 8:
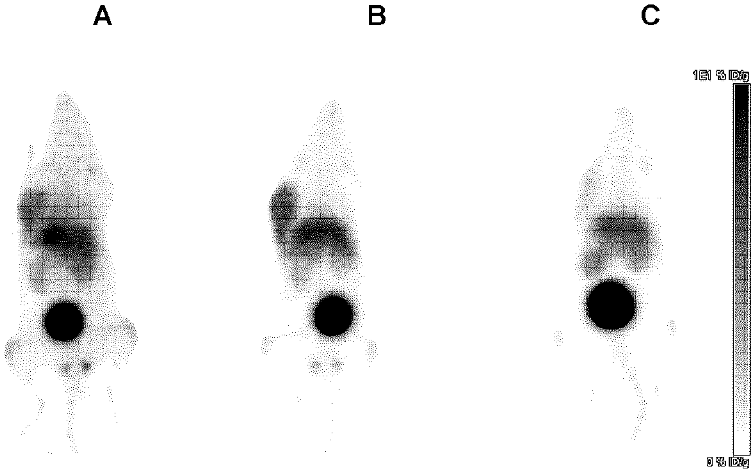
FIG. 8 shows maximal intensity projection PET images of [$^{68}$Ga]Ga-BL06 at A) 1 and B) 2 h post-injection in mice bearing Daudi Burkitt's lymphoma xenografts. C) Blocking study was performed by pre-injection of 7.5 μg of LY2510924 15 min (i.p.) before tracer administration. The scale bar is in units of % ID/g from 0 to 10.
Figure 9:
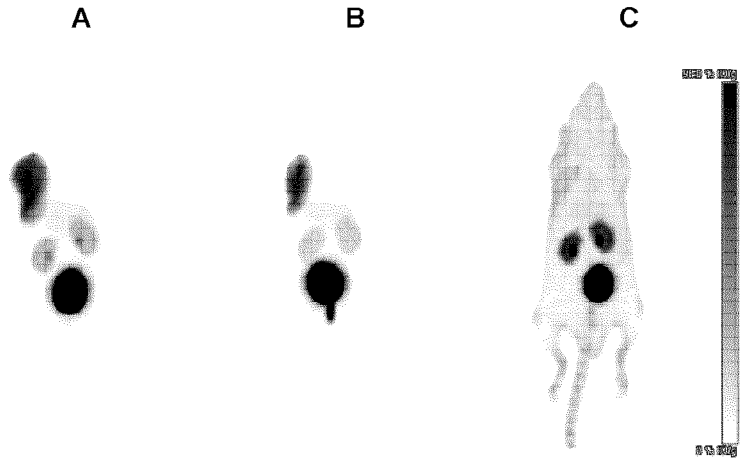
FIG. 9 shows maximal intensity projection PET images of [$^{18}$F]F-BL08 at A) 1 and B) 2 h post-injection in mice bearing Daudi Burkitt's lymphoma xenografts. C) Blocking study was performed by pre-injection of 7.5 μg of LY2510924 15 min (i.p.) before tracer administration. The scale bar is in units of % ID/g from 0 to 9.
Figure 10:
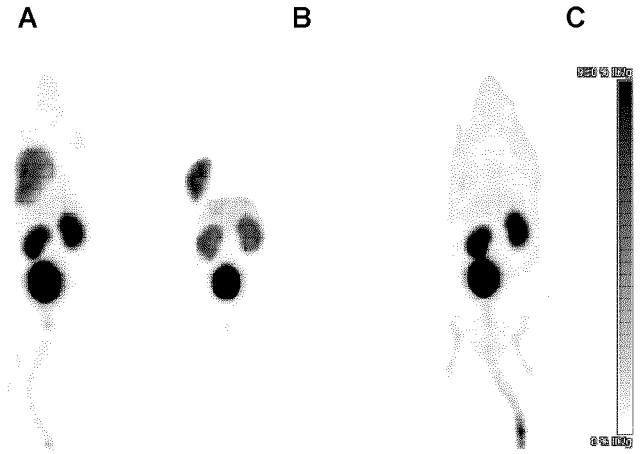
FIG. 10 shows maximal intensity projection PET images of [$^{18}$F]F-BL09 at A) 1 and B) 2 h post-injection in mice bearing Daudi Burkitt's lymphoma xenografts. C) Blocking study was performed by pre-injection of 7.5 μg of LY2510924 15 min (i.p.) before tracer administration. The scale bar is in units of % ID/g from 0 to 9.
Figure 11:
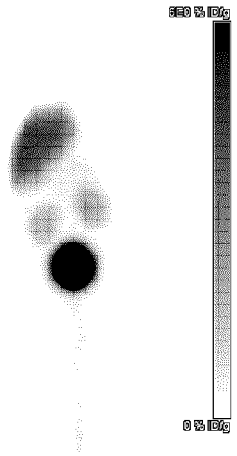
FIG. 11 shows a maximal intensity projection PET image of [$^{68}$Ga]Ga-BL17 at 1 h post-injection in mice bearing Daudi Burkitt's lymphoma xenografts. The scale bar is in units of % ID/g from 0 to 6.

As shown in Tables 1-23 and FIGS. 1-11, an anionic linker increases internalization (longer/sustained retention in tumor) and/or facilitates background clearance. This enhances tumor-to-background contrast for improved imaging and therapeutic agents compared to compounds that have a cationic linker, or a neutral linker (i.e. lysine amide conjugation or simple maleimide conjugation). This enhances tumor-to-background contrast for improved imaging and therapeutic agents. The albumin binder extends the circulatory half-life of the compounds in the mouse models, allowing for sustained uptake of the radiotracer into the tumor. As shown in Table 24-33, the Lu-177 labeled compounds delivered high radiation dose to tumor xenografts but minimal radiation dose to normal tissues/organs, leading to excellent tumor-to-normal tissue/organ therapeutic indexes. The in vivo stability of various compounds is shown in Table 34.

TABLE 1

List of the binding affinities in half maximal inhibitory constants ($IC_{50}$) in the competitive binding assay for CXCR4 of select compounds

| Compound | $IC_{50}$ (nM) | n |
|---|---|---|
| Ga-BL02 | 27.9 ± 12.5 | 3 |
| BL04 | 63.0 ± 9.0 | 3 |
| BL08 | 11.62 ± 7.0 | 4 |
| BL09 | 13.4 ± 2.3 | 4 |
| Ga-BL17 | 13.0 ± 8.6 | 3 |
| Lu-BL18 | 29.4 ± 8.7 | 4 |
| Lu-BL19 | 17.24 ± 8.5 | 4 |
| Ga-BL25 | 21.3 ± 0.1 | 2 |

TABLE 2

The internalization of [$^{68}$Ga]Ga-BL02 in CHO:CXCR4 and CHO:WT cells

| Cell Line | Blocking | % Internalized | n |
|---|---|---|---|
| CHO:CXCR4 | No | 52.4 ± 1.2 | 3 |
| CHO:CXCR4 | Yes | 11.6 ± 8.8 | 3 |
| CHO:WT | No | 13.3 ± 6.4 | 3 |
| CHO:WT | Yes | 9.2 ± 7.3 | 3 |

TABLE 3

Biodistribution data (% ID/g) of [$^{68}$Ga]Ga-BL02 in Daudi tumor-bearing mice at selected time points. Mice in the 1 h blocked group received an injection of 7.5 μg of LY2510924 (i.p.) 15 min before tracer administration.

| | 1 h | | | 1 h blocked | | | 2 h | | |
|---|---|---|---|---|---|---|---|---|---|
| [$^{68}$Ga]Ga-BL02 | Mean | S.Dev | n | Mean | S.Dev | n | Mean | S.Dev | n |
| Blood | 0.31 | 0.09 | 6 | 0.50 | 0.17 | 8 | 0.08 | 0.04 | 9 |
| Fat | 0.05 | 0.03 | 6 | 0.07 | 0.04 | 8 | 0.02 | 0.01 | 9 |
| Testes | 0.11 | 0.01 | 5 | 0.15 | 0.05 | 8 | 0.05 | 0.01 | 9 |
| Intestine | 0.22 | 0.03 | 5 | 0.31 | 0.07 | 8 | 0.12 | 0.04 | 9 |
| Stomach | 0.07 | 0.03 | 6 | 0.07 | 0.03 | 8 | 0.07 | 0.05 | 9 |
| Spleen | 0.53 | 0.22 | 6 | 0.23 | 0.07 | 8 | 0.24 | 0.10 | 9 |
| Liver | 0.59 | 0.07 | 6 | 0.55 | 0.09 | 8 | 0.54 | 0.04 | 8 |
| Pancreas | 0.18 | 0.14 | 5 | 0.12 | 0.05 | 8 | 0.05 | 0.02 | 9 |
| Adrenals | 0.36 | 0.10 | 5 | 0.32 | 0.19 | 8 | 0.21 | 0.07 | 9 |
| Kidney | 4.18 | 0.68 | 6 | 4.63 | 1.05 | 8 | 3.40 | 0.51 | 9 |
| Lung | 0.48 | 0.05 | 6 | 0.58 | 0.16 | 8 | 0.27 | 0.09 | 9 |
| Heart | 0.13 | 0.02 | 6 | 0.14 | 0.03 | 7 | 0.05 | 0.01 | 9 |
| Muscle | 0.10 | 0.03 | 5 | 0.09 | 0.03 | 7 | 0.04 | 0.01 | 9 |
| Bone | 0.19 | 0.06 | 6 | 0.20 | 0.07 | 8 | 0.09 | 0.03 | 9 |
| Brain | 0.02 | 0.00 | 6 | 0.02 | 0.01 | 8 | 0.01 | 0.01 | 9 |
| Daudi | 8.52 | 2.70 | 6 | 0.80 | 0.21 | 8 | 7.78 | 1.44 | 9 |
| Ratios | | | | | | | | | |
| Tumor: Blood | 30.57 | 15.01 | 6 | 1.71 | 0.60 | 8 | 114.6 | 44.60 | 9 |
| Tumor: Liver | 14.30 | 3.37 | 6 | 1.47 | 0.34 | 8 | 14.47 | 2.52 | 9 |
| Tumor: Spleen | 17.18 | 6.54 | 6 | 3.57 | 0.72 | 8 | 36.06 | 14.92 | 9 |
| Tumor: Muscle | 80.77 | 25.39 | 5 | 9.23 | 4.05 | 7 | 216.0 | 57.47 | 9 |
| Tumor: Bone | 48.04 | 21.87 | 6 | 4.44 | 1.62 | 8 | 87.81 | 21.69 | 9 |
| Tumor: Lung | 18.07 | 5.77 | 6 | 1.43 | 0.39 | 8 | 31.68 | 11.48 | 9 |

TABLE 4

Biodistribution data (% ID/g) of [$^{68}$Ga]Ga-BL02 in Z138 tumor-bearing mice at selected time points. Mice in the 1 h blocked group received an injection of 7.5 μg of LY2510924 (i.p.) 15 min before tracer administration.

| | 1 h | | | 1 h blocked | | |
|---|---|---|---|---|---|---|
| [$^{68}$Ga]Ga-BL02 | Mean | S.Dev | n | Mean | S.Dev | n |
| Blood | 0.30 | 0.03 | 5 | 0.83 | 0.37 | 6 |
| Fat | 0.04 | 0.01 | 4 | 0.14 | 0.07 | 6 |
| Testes | 0.11 | 0.02 | 5 | 0.26 | 0.12 | 5 |
| Intestine | 0.19 | 0.04 | 5 | 0.61 | 0.27 | 6 |
| Stomach | 0.07 | 0.05 | 4 | 0.16 | 0.09 | 6 |
| Spleen | 0.33 | 0.05 | 5 | 0.43 | 0.16 | 6 |
| Liver | 0.48 | 0.04 | 5 | 0.55 | 0.14 | 6 |
| Pancreas | 0.08 | 0.01 | 5 | 0.21 | 0.09 | 6 |
| Adrenals | 0.14 | 0.04 | 5 | 0.59 | 0.61 | 6 |
| Kidney | 3.48 | 0.29 | 5 | 7.86 | 4.68 | 6 |
| Lung | 0.50 | 0.08 | 5 | 0.85 | 0.33 | 6 |
| Heart | 0.11 | 0.01 | 5 | 0.24 | 0.10 | 6 |
| Muscle | 0.05 | 0.01 | 5 | 0.15 | 0.08 | 6 |
| Bone | 0.08 | 0.02 | 5 | 0.20 | 0.12 | 6 |
| Brain | 0.01 | 0.01 | 5 | 0.02 | 0.01 | 6 |
| Z138 | 12.94 | 1.28 | 5 | 2.86 | 0.94 | 6 |
| Ratios | | | | | | |
| Tumor: Blood | 43.12 | 2.57 | 5 | 3.94 | 1.58 | 6 |
| Tumor: Liver | 26.89 | 0.69 | 5 | 5.23 | 1.14 | 6 |
| Tumor: Spleen | 39.22 | 5.34 | 5 | 7.40 | 2.71 | 6 |
| Tumor: Muscle | 240.96 | 32.87 | 5 | 21.59 | 8.59 | 6 |
| Tumor: Bone | 163.06 | 54.42 | 5 | 19.08 | 11.43 | 6 |
| Tumor: Lung | 26.39 | 3.20 | 5 | 3.65 | 1.20 | 6 |

TABLE 5

Biodistribution data (% ID/g) of [$^{68}$Ga]Ga-BL02 in Jeko1 tumor-bearing mice at selected time points. Mice in the 1 h blocked group received an injection of 7.5 μg of LY2510924 (i.p.) 15 min before tracer administration.

| | 1 h | | | 1 h blocked | | |
|---|---|---|---|---|---|---|
| [$^{68}$Ga]Ga-BL02 | Mean | S.Dev | n | Mean | S.Dev | n |
| Blood | 0.38 | 0.10 | 7 | 1.08 | 0.67 | 6 |
| Fat | 0.05 | 0.02 | 7 | 0.14 | 0.06 | 6 |
| Testes | 0.14 | 0.06 | 7 | 0.29 | 0.11 | 6 |
| Intestine | 0.19 | 0.03 | 7 | 0.44 | 0.14 | 6 |
| Stomach | 0.06 | 0.03 | 7 | 0.13 | 0.07 | 6 |
| Spleen | 0.70 | 0.33 | 7 | 0.57 | 0.36 | 6 |
| Liver | 0.77 | 0.16 | 7 | 0.55 | 0.13 | 6 |
| Pancreas | 0.09 | 0.02 | 7 | 0.26 | 0.12 | 6 |
| Adrenals | 0.23 | 0.17 | 7 | 0.47 | 0.56 | 6 |
| Kidney | 3.32 | 0.41 | 7 | 8.91 | 6.31 | 6 |
| Lung | 0.74 | 0.09 | 7 | 1.05 | 0.37 | 6 |
| Heart | 0.13 | 0.02 | 7 | 0.35 | 0.13 | 6 |
| Muscle | 0.06 | 0.02 | 5 | 0.20 | 0.10 | 6 |
| Bone | 0.47 | 0.34 | 7 | 0.18 | 0.06 | 6 |
| Brain | 0.02 | 0.00 | 7 | 0.03 | 0.01 | 6 |
| Jeko1 | 11.45 | 1.14 | 7 | 1.32 | 0.40 | 6 |
| Ratios | | | | | | |
| Tumor: Blood | 31.30 | 7.38 | 7 | 1.74 | 1.23 | 6 |
| Tumor: Liver | 15.41 | 3.01 | 7 | 2.59 | 1.26 | 6 |
| Tumor: Spleen | 19.78 | 9.26 | 7 | 3.10 | 1.96 | 6 |
| Tumor: Muscle | 180.39 | 34.73 | 5 | 8.71 | 6.61 | 6 |
| Tumor: Bone | 37.23 | 22.85 | 7 | 8.83 | 4.89 | 6 |
| Tumor: Lung | 15.76 | 2.88 | 7 | 1.48 | 0.86 | 6 |

TABLE 6

Biodistribution data (% ID/g) of [$^{68}$Ga]Ga-BL02 in GRANTA519 tumor-bearing mice at selected time points. Mice in the 1 h blocked group received an injection of 7.5 μg of LY2510924 (i.p.) 15 min before tracer administration.

| | 1 h | | | 1 h blocked | | |
|---|---|---|---|---|---|---|
| [$^{68}$Ga]Ga-BL021 | Mean | S. Dev | n | Mean | S. Dev | n |
| Blood | 0.41 | 0.11 | 6 | 0.83 | 0.34 | 6 |
| Fat | 0.05 | 0.02 | 5 | 0.10 | 0.05 | 6 |
| Testes | 0.16 | 0.04 | 6 | 0.20 | 0.04 | 6 |
| Intestine | 0.22 | 0.04 | 6 | 0.46 | 0.16 | 6 |
| Stomach | 0.05 | 0.02 | 5 | 0.12 | 0.05 | 5 |
| Spleen | 0.49 | 0.05 | 6 | 0.53 | 0.11 | 6 |
| Liver | 0.09 | 0.03 | 6 | 0.19 | 0.09 | 6 |
| Pancreas | 0.20 | 0.08 | 6 | 0.34 | 0.16 | 6 |
| Adrenals | 3.48 | 0.47 | 6 | 7.40 | 4.53 | 6 |
| Kidney | 0.62 | 0.11 | 6 | 0.81 | 0.30 | 6 |
| Lung | 0.12 | 0.01 | 5 | 0.25 | 0.11 | 6 |
| Heart | 0.49 | 0.05 | 5 | 0.53 | 0.11 | 6 |
| Muscle | 0.07 | 0.02 | 6 | 0.14 | 0.05 | 6 |
| Bone | 0.16 | 0.12 | 6 | 0.25 | 0.20 | 6 |
| Brain | 0.01 | 0.00 | 6 | 0.02 | 0.01 | 6 |
| GRANTA519 | 5.50 | 0.95 | 6 | 0.72 | 0.18 | 6 |
| Ratios | | | | | | |
| Tumor: Blood | 13.83 | 1.47 | 6 | 0.94 | 0.30 | 6 |
| Tumor: Liver | 11.28 | 1.73 | 6 | 1.37 | 0.21 | 6 |
| Tumor: Spleen | 15.86 | 1.94 | 6 | 1.78 | 0.26 | 6 |
| Tumor: Muscle | 83.17 | 15.89 | 6 | 5.36 | 1.51 | 6 |
| Tumor: Bone | 45.39 | 20.98 | 6 | 4.27 | 2.51 | 6 |
| Tumor: Lung | 9.12 | 0.55 | 5 | 0.96 | 0.31 | 6 |

TABLE 7

Biodistribution data (% ID/g) of [$^{68}$Ga]Ga-BL02 in PC3 tumor-bearing mice at selected time points. Mice in the 1 h blocked group received an injection of 7.5 μg of LY2510924 (i.p.) 15 min before tracer administration.

| | 1 h | | | 1 h blocked | | | 2h | | |
|---|---|---|---|---|---|---|---|---|---|
| [$^{68}$Ga]Ga-BL02 | Mean | S.Dev | n | Mean | S.Dev | n | Mean | S.Dev | n |
| Blood | 0.33 | 0.06 | 3 | 0.54 | 0.18 | 2 | 0.06 | 0.02 | 3 |
| Fat | 0.20 | 0.25 | 3 | 0.16 | 0.02 | 2 | 0.01 | 0.00 | 3 |
| Testes | 0.18 | 0.05 | 3 | 0.35 | 0.15 | 2 | 0.06 | 0.02 | 3 |
| Intestine | 0.18 | 0.05 | 3 | 0.25 | 0.10 | 2 | 0.14 | 0.08 | 3 |
| Stomach | 0.05 | 0.02 | 3 | 0.06 | 0.02 | 2 | 0.06 | 0.02 | 3 |
| Spleen | 0.28 | 0.01 | 3 | 0.37 | 0.06 | 2 | 0.25 | 0.04 | 3 |
| Liver | 0.55 | 0.04 | 3 | 0.50 | 0.13 | 2 | 0.73 | 0.28 | 3 |
| Pancreas | 0.10 | 0.02 | 3 | 0.12 | 0.04 | 2 | 0.04 | 0.01 | 3 |
| Adrenals | 0.18 | 0.02 | 3 | 0.18 | 0.01 | 2 | 0.10 | 0.02 | 3 |
| Kidney | 3.60 | 0.36 | 3 | 3.75 | 1.72 | 2 | 4.67 | 2.19 | 3 |
| Lung | 0.50 | 0.03 | 3 | 0.60 | 0.15 | 2 | 0.33 | 0.11 | 3 |
| Heart | 0.14 | 0.02 | 3 | 0.21 | 0.06 | 2 | 0.06 | 0.02 | 3 |
| Muscle | 0.08 | 0.03 | 3 | 0.11 | 0.03 | 2 | 0.03 | 0.01 | 3 |
| Bone | 0.12 | 0.03 | 3 | 0.15 | 0.07 | 2 | 0.11 | 0.05 | 3 |
| Brain | 0.01 | 0.00 | 3 | 0.02 | 0.00 | 2 | 0.01 | 0.00 | 3 |
| PC3 | 1.83 | 0.44 | 3 | 0.75 | 0.26 | 2 | 1.41 | 0.37 | 3 |
| Ratios | | | | | | | | | |
| Tumor: Blood | 5.74 | 1.67 | 3 | 1.56 | 1.01 | 2 | 25.33 | 3.89 | 3 |
| Tumor: Liver | 3.31 | 0.74 | 3 | 1.62 | 0.94 | 2 | 1.99 | 0.25 | 3 |
| Tumor: Spleen | 6.62 | 1.69 | 3 | 2.16 | 1.10 | 2 | 5.63 | 0.61 | 3 |
| Tumor: Muscle | 23.74 | 9.95 | 3 | 7.68 | 4.58 | 2 | 55.01 | 0.87 | 3 |
| Tumor: Bone | 15.68 | 5.15 | 3 | 6.16 | 4.62 | 2 | 13.96 | 3.28 | 3 |
| Tumor: Lung | 3.71 | 1.15 | 3 | 1.36 | 0.77 | 2 | 4.36 | 0.39 | 3 |

TABLE 8

Biodistribution data (% ID/g) of [$^{18}$F]F-BL04 in Daudi tumor-bearing mice at selected time points. Mice in the 1 h blocked group received an injection of 7.5 μg of LY2510924 (i.p.) 15 min before tracer administration.

| | 1 h | | | 1 h blocked | | | 2 h | | |
|---|---|---|---|---|---|---|---|---|---|
| [$^{18}$F]F-BL04 | Mean | S. Dev | n | Mean | S.Dev | n | Mean | S.Dev | n |
| Blood | 0.34 | 0.06 | 7 | 0.44 | 0.15 | 7 | 0.08 | 0.02 | 7 |
| Fat | 0.05 | 0.03 | 6 | 0.06 | 0.03 | 7 | 0.02 | 0.02 | 7 |
| Testes | 0.21 | 0.15 | 7 | 0.13 | 0.04 | 7 | 0.04 | 0.01 | 7 |
| Intestine | 0.20 | 0.02 | 7 | 0.25 | 0.04 | 7 | 0.11 | 0.03 | 7 |
| Stomach | 0.06 | 0.05 | 7 | 0.06 | 0.04 | 7 | 0.03 | 0.01 | 7 |
| Spleen | 0.27 | 0.34 | 7 | 0.17 | 0.08 | 7 | 0.10 | 0.03 | 7 |
| Liver | 0.20 | 0.03 | 7 | 0.21 | 0.03 | 7 | 0.15 | 0.02 | 7 |
| Pancreas | 0.10 | 0.03 | 7 | 0.11 | 0.04 | 7 | 0.04 | 0.01 | 7 |
| Adrenals | 0.27 | 0.26 | 7 | 0.26 | 0.11 | 7 | 0.22 | 0.20 | 7 |
| Kidney | 18.39 | 2.43 | 7 | 21.72 | 4.14 | 7 | 15.30 | 2.30 | 7 |
| Lung | 0.35 | 0.06 | 7 | 0.40 | 0.14 | 7 | 0.20 | 0.04 | 7 |
| Heart | 0.11 | 0.03 | 7 | 0.13 | 0.04 | 7 | 0.05 | 0.01 | 7 |
| Muscle | 0.07 | 0.01 | 7 | 0.10 | 0.06 | 7 | 0.04 | 0.03 | 7 |
| Bone | 0.21 | 0.02 | 7 | 0.22 | 0.06 | 7 | 0.18 | 0.05 | 7 |
| Brain | 0.01 | 0.00 | 7 | 0.01 | 0.00 | 7 | 0.01 | 0.00 | 7 |
| Daudi | 3.08 | 0.59 | 7 | 0.47 | 0.23 | 7 | 2.16 | 0.89 | 7 |
| Ratios | | | | | | | | | |
| Tumor Blood | 7.92 | 3.63 | 7 | 1.20 | 0.72 | 7 | 28.97 | 14.55 | 7 |
| Tumor:Liver | 15.64 | 1.97 | 7 | 2.29 | 1.07 | 7 | 14.67 | 5.66 | 7 |
| Tumor:Spleen | 19.99 | 8.97 | 7 | 2.87 | 1.26 | 7 | 23.89 | 11.64 | 7 |
| Tumor:Muscle | 45.63 | 7.15 | 7 | 5.81 | 3.63 | 7 | 61.14 | 27.56 | 7 |
| Tumor:Bone | 14.84 | 3.45 | 7 | 2.44 | 1.47 | 7 | 12.77 | 6.25 | 7 |
| Tumor:Lungs | 8.93 | 1.26 | 7 | 1.31 | 0.76 | 7 | 10.75 | 3.76 | 7 |

TABLE 9

Biodistribution data (% ID/g) of [$^{68}$Ga]Ga-BL06 in Daudi tumor-bearing mice at selected time points. Mice in the 1 h blocked group received an injection of 7.5 μg of LY2510924 (i.p.) 15 min before tracer administration.

| | 1 h | | | 1 h blocked | | | 2 h | | |
|---|---|---|---|---|---|---|---|---|---|
| [$^{68}$Ga]Ga-BL06 | Mean | S.Dev | n | Mean | S.Dev | n | Mean | S.Dev | n |
| Blood | 2.78 | 0.46 | 6 | 1.17 | 0.26 | 7 | 1.11 | 0.24 | 8 |
| Fat | 0.35 | 0.10 | 6 | 0.16 | 0.09 | 7 | 0.19 | 0.04 | 8 |
| Testes | 0.61 | 0.10 | 6 | 0.34 | 0.06 | 7 | 0.46 | 0.02 | 8 |
| Intestine | 1.07 | 0.13 | 6 | 0.70 | 0.18 | 7 | 0.68 | 0.11 | 8 |
| Stomach | 0.29 | 0.08 | 6 | 0.14 | 0.04 | 7 | 0.21 | 0.07 | 8 |
| Spleen | 15.53 | 1.83 | 6 | 3.30 | 0.73 | 7 | 9.14 | 1.60 | 8 |
| Liver | 8.60 | 0.77 | 6 | 9.25 | 0.94 | 6 | 10.35 | 0.40 | 8 |
| Pancreas | 0.70 | 0.09 | 6 | 0.29 | 0.08 | 7 | 0.39 | 0.07 | 7 |
| Adrenals | 3.61 | 1.14 | 5 | 0.80 | 0.33 | 7 | 3.19 | 1.11 | 8 |
| Kidney | 6.25 | 1.05 | 6 | 8.26 | 2.79 | 7 | 4.82 | 0.61 | 8 |
| Lung | 15.00 | 2.06 | 6 | 2.20 | 0.55 | 7 | 7.18 | 0.86 | 8 |
| Heart | 1.73 | 0.25 | 6 | 0.48 | 0.11 | 7 | 0.93 | 0.17 | 8 |
| Muscle | 0.41 | 0.11 | 6 | 0.19 | 0.04 | 7 | 0.21 | 0.06 | 8 |
| Bone | 1.84 | 0.65 | 6 | 0.82 | 0.26 | 7 | 1.11 | 0.25 | 8 |
| Brain | 0.06 | 0.00 | 6 | 0.03 | 0.01 | 7 | 0.03 | 0.00 | 8 |
| Daudi | 10.26 | 1.29 | 6 | 2.06 | 0.62 | 7 | 11.32 | 1.44 | 8 |
| Ratios | | | | | | | | | |
| Tumor:Blood | 3.75 | 1.18 | 6 | 1.84 | 0.74 | 7 | 10.35 | 1.33 | 8 |
| Tumor:Liver | 1.19 | 0.56 | 6 | 0.21 | 0.05 | 6 | 1.10 | 0.14 | 8 |
| Tumor:Spleen | 0.67 | 0.17 | 6 | 0.64 | 0.19 | 7 | 1.25 | 0.13 | 8 |
| Tumor:Muscle | 25.59 | 4.15 | 6 | 10.97 | 2.86 | 7 | 57.98 | 13.51 | 8 |
| Tumor:Bone | 6.04 | 1.30 | 6 | 2.77 | 1.10 | 7 | 10.56 | 2.36 | 8 |
| Tumor:Lungs | 0.69 | 0.21 | 6 | 0.95 | 0.26 | 7 | 1.59 | 0.21 | 8 |

TABLE 10

Ex vivo biodistribution data of [$^{18}$F]F-BL08 (% ID/g) in Daudi xenograft bearing mice. The mice in the 1 h blocked group received an intraperitoneal injection of 7.5 μg of LY2510924 15 minutes prior to radiotracer administration.

| | 1 h | | | 1 h blocked | | | 2 h | | |
|---|---|---|---|---|---|---|---|---|---|
| [$^{18}$F]F-BL08 | Mean | S.Dev | n | Mean | S. Dev | n | Mean | S. Dev | n |
| Blood | 0.36 | 0.05 | 6 | 0.83 | 0.46 | 8 | 0.09 | 0.05 | 7 |
| Fat | 0.04 | 0.01 | 6 | 0.13 | 0.08 | 8 | 0.01 | 0.00 | 5 |
| Testes | 0.14 | 0.02 | 6 | 0.67 | 1.30 | 8 | 0.04 | 0.02 | 7 |
| Intestine | 0.19 | 0.03 | 6 | 0.32 | 0.19 | 7 | 0.09 | 0.03 | 7 |
| Stomach | 0.053 | 0.052 | 6 | 0.12 | 0.05 | 8 | 0.02 | 0.01 | 7 |
| Spleen | 0.32 | 0.17 | 7 | 0.72 | 0.28 | 8 | 0.13 | 0.03 | 7 |
| Liver | 0.62 | 0.02 | 6 | 0.18 | 0.11 | 8 | 0.41 | 0.09 | 7 |
| Pancreas | 0.08 | 0.01 | 6 | 0.42 | 0.42 | 8 | 0.03 | 0.02 | 7 |
| Adrenals | 0.23 | 0.16 | 6 | 6.70 | 3.21 | 8 | 0.12 | 0.10 | 7 |
| Kidney | 3.47 | 0.46 | 6 | 0.86 | 0.48 | 8 | 2.15 | 0.46 | 7 |
| Lung | 0.61 | 0.17 | 6 | 0.24 | 0.13 | 8 | 0.27 | 0.12 | 7 |
| Heart | 0.13 | 0.01 | 6 | 0.72 | 0.28 | 8 | 0.04 | 0.02 | 7 |
| Muscle | 0.07 | 0.01 | 5 | 0.14 | 0.08 | 8 | 0.03 | 0.02 | 5 |
| Bone | 0.18 | 0.05 | 6 | 0.32 | 0.16 | 8 | 0.12 | 0.04 | 7 |
| Brain | 0.01 | 0.01 | 6 | 0.02 | 0.01 | 8 | 0.01 | 0.00 | 7 |
| Daudi | 7.60 | 1.38 | 6 | 1.17 | 0.71 | 8 | 5.67 | 1.25 | 7 |
| Ratios | | | | | | | | | |
| Tumour: Blood | 21.53 | 6.49 | 6 | 2.01 | 2.13 | 8 | 71.90 | 19.76 | 7 |
| Tumour:Liver | 13.05 | 4.05 | 6 | 1.88 | 1.54 | 8 | 14.04 | 2.99 | 7 |
| Tumour: Spleen | 25.81 | 4.57 | 6 | 3.87 | 3.28 | 8 | 43.46 | 7.98 | 7 |
| Tumour:Muscle | 107.7 | 24.86 | 5 | 12.30 | 13.85 | 8 | 339.0 | 81.39 | 5 |
| Tumour: Bone | 45.87 | 17.31 | 6 | 4.49 | 4.18 | 8 | 52.27 | 12.27 | 7 |
| Tumour:Lung | 13.18 | 3.88 | 6 | 1.85 | 1.88 | 8 | 23.08 | 5.57 | 7 |

TABLE 11

Ex vivo biodistribution data of [$^{18}$F]F-BL09 (% ID/g) in Daudi xenograft bearing mice. The mice in the 1 h blocked group received an intraperitoneal injection of 7.5 μg of LY2510924 15 minutes prior to radiotracer administration.

| | 1 h | | | 1 h blocked | | | 2 h | | |
|---|---|---|---|---|---|---|---|---|---|
| [$^{18}$F]F-BL09 | Mean | S. Dev | n | Mean | S. Dev | n | Mean | S. Dev | n |
| Blood | 0.44 | 0.11 | 7 | 0.53 | 0.30 | 7 | 0.10 | 0.03 | 7 |
| Fat | 0.05 | 0.02 | 7 | 0.10 | 0.06 | 7 | 0.01 | 0.00 | 7 |
| Testes | 0.21 | 0.06 | 7 | 0.21 | 0.16 | 7 | 0.05 | 0.02 | 7 |
| Intestine | 0.23 | 0.08 | 7 | 0.26 | 0.12 | 7 | 0.14 | 0.08 | 6 |
| Stomach | 0.06 | 0.02 | 7 | 0.09 | 0.04 | 7 | 0.01 | 0.00 | 7 |
| Spleen | 0.31 | 0.08 | 7 | 0.24 | 0.12 | 7 | 0.12 | 0.03 | 7 |
| Liver | 0.56 | 0.09 | 7 | 0.50 | 0.20 | 7 | 0.35 | 0.05 | 6 |
| Pancreas | 0.11 | 0.05 | 6 | 0.14 | 0.08 | 7 | 0.03 | 0.01 | 6 |
| Adrenals | 0.34 | 0.32 | 7 | 0.17 | 0.09 | 7 | 0.06 | 0.03 | 7 |
| Kidney | 9.74 | 1.47 | 7 | 8.65 | 3.23 | 7 | 7.59 | 1.00 | 7 |
| Lung | 0.54 | 0.15 | 7 | 0.53 | 0.24 | 7 | 0.20 | 0.03 | 6 |
| Heart | 0.16 | 0.04 | 7 | 0.18 | 0.10 | 7 | 0.04 | 0.01 | 6 |
| Muscle | 0.08 | 0.03 | 6 | 0.07 | 0.02 | 5 | 0.03 | 0.01 | 6 |
| Bone | 0.34 | 0.23 | 7 | 0.29 | 0.28 | 7 | 0.16 | 0.09 | 7 |
| Brain | 0.02 | 0.00 | 7 | 0.02 | 0.02 | 7 | 0.01 | 0.00 | 7 |
| Daudi | 6.61 | 2.07 | 6 | 0.79 | 0.65 | 7 | 5.83 | 0.92 | 7 |
| Ratios | | | | | | | | | |
| Tumour: Blood | 15.42 | 2.27 | 6 | 1.87 | 1.44 | 7 | 64.36 | 19.84 | 7 |
| Tumour:Liver | 11.82 | 2.94 | 6 | 1.58 | 1.05 | 7 | 17.07 | 3.01 | 6 |
| Tumour: Spleen | 21.79 | 5.29 | 6 | 3.82 | 2.87 | 7 | 49.37 | 10.59 | 7 |
| Tumour:Muscle | 83.21 | 19.44 | 5 | 11.15 | 8.52 | 5 | 238.60 | 71.96 | 6 |
| Tumour: Bone | 25.95 | 11.94 | 6 | 4.61 | 3.95 | 7 | 49.94 | 26.98 | 7 |
| Tumour:Lung | 12.59 | 2.04 | 6 | 1.70 | 1.23 | 7 | 29.99 | 9.45 | 6 |

TABLE 12

Biodistribution data (% ID/g) of [$^{68}$Ga]Ga-BL17 in Daudi tumor-bearing mice at selected time points. Mice in the 1 h blocked group received an injection of 7.5 μg of LY2510924 (i.p.) 15 min before tracer administration.

| | 1 h | | | 1 h blocked | | | 2 h | | |
|---|---|---|---|---|---|---|---|---|---|
| [$^{68}$Ga]Ga-BL17 | Mean | S. Dev | n | Mean | S. Dev | n | Mean | S. Dev | n |
| Blood | 0.41 | 0.12 | 4 | 1.40 | 0.14 | 2 | 0.09 | 0.01 | 4 |
| Fat | 0.04 | 0.01 | 4 | 0.32 | 0.01 | 2 | 0.02 | 0.01 | 4 |
| Testes | 0.20 | 0.05 | 4 | 0.53 | 0.16 | 2 | 0.06 | 0.01 | 4 |
| Intestine | 0.21 | 0.07 | 4 | 0.65 | 0.08 | 2 | 0.15 | 0.07 | 4 |
| Stomach | 0.05 | 0.03 | 4 | 0.18 | 0.02 | 2 | 0.03 | 0.02 | 4 |
| Spleen | 0.33 | 0.07 | 4 | 0.81 | 0.20 | 2 | 0.30 | 0.05 | 4 |
| Liver | 0.50 | 0.07 | 4 | 0.84 | 0.13 | 2 | 0.47 | 0.08 | 4 |
| Pancreas | 0.10 | 0.03 | 4 | 0.38 | 0.05 | 2 | 0.04 | 0.02 | 4 |
| Adrenals | 0.16 | 0.07 | 4 | 0.79 | 0.25 | 2 | 0.20 | 0.12 | 4 |
| Kidney | 3.30 | 0.41 | 4 | 15.17 | 8.21 | 2 | 3.28 | 0.34 | 4 |
| Lung | 0.51 | 0.12 | 4 | 1.35 | 0.20 | 2 | 0.25 | 0.03 | 4 |
| Heart | 0.14 | 0.04 | 4 | 0.45 | 0.05 | 2 | 0.06 | 0.01 | 4 |
| Muscle | 0.10 | 0.03 | 4 | 0.25 | 0.00 | 2 | 0.03 | 0.01 | 4 |
| Bone | 0.09 | 0.03 | 4 | 0.31 | 0.05 | 2 | 0.09 | 0.03 | 4 |
| Brain | 0.02 | 0.01 | 4 | 0.03 | 0.00 | 2 | 0.01 | 0.00 | 4 |
| Daudi | 6.32 | 0.67 | 4 | 0.68 | 0.00 | 2 | 6.40 | 1.60 | 4 |
| Ratios | | | | | | | | | |
| Tumour: Blood | 16.94 | 6.57 | 4 | 0.49 | 0.05 | 2 | 69.33 | 18.61 | 4 |
| Tumour:Liver | 12.66 | 0.79 | 4 | 0.81 | 0.13 | 2 | 13.69 | 4.46 | 4 |
| Tumour: Spleen | 19.76 | 3.57 | 4 | 0.87 | 0.22 | 2 | 21.11 | 6.42 | 4 |
| Tumour:Muscle | 67.93 | 16.71 | 4 | 2.74 | 0.05 | 2 | 256.87 | 72.49 | 4 |
| Tumour: Bone | 76.60 | 21.25 | 4 | 2.24 | 0.35 | 2 | 79.15 | 32.79 | 4 |
| Tumour:Lung | 12.64 | 2.48 | 4 | 0.51 | 0.07 | 2 | 25.37 | 6.19 | 4 |

TABLE 13

Biodistribution data (% ID/g) of [$^{68}$Ga]Ga-BL20 in Daudi tumor-bearing mice at selected time points. Mice in the 1 h blocked group received an injection of 7.5 μg of LY2510924 (i.p.) 15 min before tracer administration.

| | 1 h | | | 1 h blocked | | | 2 h | | |
|---|---|---|---|---|---|---|---|---|---|
| [$^{68}$Ga]Ga-BL17 | Mean | S. Dev | n | Mean | S. Dev | n | Mean | S. Dev | n |
| Blood | 0.42 | 0.12 | 3 | 0.65 | na | 1 | 0.08 | 0.02 | 4 |
| Fat | 0.06 | 0.03 | 3 | 0.12 | na | 1 | 0.01 | 0.01 | 4 |
| Testes | 0.15 | 0.03 | 3 | 0.20 | na | 1 | 0.05 | 0.01 | 4 |
| Intestine | 0.21 | 0.02 | 3 | 0.37 | na | 1 | 0.25 | 0.25 | 4 |
| Stomach | 0.05 | 0.01 | 3 | 0.24 | na | 1 | 0.05 | 0.03 | 4 |
| Spleen | 0.49 | 0.07 | 3 | 0.30 | na | 1 | 0.21 | 0.06 | 4 |
| Liver | 0.58 | 0.07 | 3 | 0.44 | na | 1 | 0.51 | 0.04 | 4 |
| Pancreas | 0.11 | 0.03 | 3 | 0.16 | na | 1 | 0.04 | 0.01 | 4 |
| Adrenals | 0.35 | 0.20 | 3 | 0.35 | na | 1 | 0.27 | 0.17 | 4 |
| Kidney | 3.58 | 0.26 | 3 | 5.92 | na | 1 | 3.02 | 0.22 | 4 |
| Lung | 0.51 | 0.08 | 3 | 0.71 | na | 1 | 0.22 | 0.04 | 4 |
| Heart | 0.15 | 0.03 | 3 | 0.22 | na | 1 | 0.05 | 0.01 | 4 |
| Muscle | 0.08 | 0.02 | 3 | 0.13 | na | 1 | 0.02 | 0.00 | 4 |
| Bone | 0.17 | 0.00 | 3 | 0.15 | na | 1 | 0.05 | 0.03 | 4 |
| Brain | 0.01 | 0.00 | 3 | 0.02 | na | 1 | 0.01 | 0.00 | 4 |
| Daudi | 9.07 | 0.76 | 3 | 0.59 | na | 1 | 8.01 | 1.39 | 4 |
| Ratios | | | | | | | | | |
| Tumour: Blood | 22.78 | 7.35 | 3 | 0.90 | na | 1 | 113.17 | 45.03 | 4 |
| Tumour: Liver | 15.68 | 0.90 | 3 | 1.34 | na | 1 | 15.57 | 1.73 | 4 |
| Tumour:Spleen | 18.55 | 1.38 | 3 | 1.96 | na | 1 | 41.58 | 13.90 | 4 |
| Tumour:Muscle | 125.40 | 54.59 | 3 | 4.49 | na | 1 | 346.93 | 81.84 | 4 |
| Tumour: Bone | 54.57 | 6.00 | 3 | 3.88 | na | 1 | 189.39 | 109.18 | 4 |
| Tumour:Lung | 18.12 | 3.56 | 3 | 0.82 | na | 1 | 37.40 | 8.71 | 4 |

TABLE 14

Biodistribution data (%ID/g) of [$^{68}$Ga]Ga-BL25 in Daudi tumor-bearing mice at selected time points.

| | 2 h | | |
|---|---|---|---|
| [$^{68}$Ga]Ga-BL25 | Mean | S.Dev | n |
| Blood | 0.18 | 0.01 | 4 |
| Fat | 0.02 | 0.01 | 4 |
| Testes | 0.07 | 0.00 | 4 |
| Intestine | 0.13 | 0.03 | 4 |
| Stomach | 0.03 | 0.02 | 4 |
| Spleen | 0.19 | 0.03 | 4 |
| Liver | 0.47 | 0.04 | 4 |
| Pancreas | 0.05 | 0.01 | 4 |
| Adrenals | 0.10 | 0.01 | 4 |
| Kidney | 1.92 | 0.07 | 4 |
| Lung | 0.37 | 0.11 | 4 |
| Heart | 0.07 | 0.00 | 4 |
| Muscle | 0.04 | 0.00 | 4 |
| Bone | 0.06 | 0.02 | 4 |
| Brain | 0.01 | 0.00 | 4 |
| Daudi | 5.53 | 0.29 | 4 |
| Ratios | | | |
| Tumor:Blood | 30.77 | 1.18 | 4 |
| Tumor:Liver | 12.05 | 0.76 | 4 |
| Tumor:Spleen | 30.72 | 3.73 | 4 |
| Tumor:Muscle | 159.64 | 19.97 | 4 |
| Tumor:Bone | 103.83 | 33.98 | 4 |
| Tumor:Lung | 16.13 | 4.21 | 4 |

TABLE 15

Biodistribution data (% ID/g) of [$^{68}$Ga]Ga-BL22 in Daudi tumor-bearing mice at selected time points.

| | 1 h | | | 3 h | | |
|---|---|---|---|---|---|---|
| [$^{68}$Ga]Ga-BL22 | Mean | S. Dev | n | Mean | S. Dev | n |
| Blood | 14.23 | 0.62 | 4 | 12.89 | 0.70 | 4 |
| Fat | 0.74 | 0.10 | 4 | 0.81 | 0.09 | 4 |
| Testes | 1.73 | 0.36 | 4 | 2.26 | 0.30 | 4 |
| Intestine | 1.39 | 0.18 | 4 | 1.21 | 0.13 | 4 |
| Stomach | 0.51 | 0.15 | 4 | 0.56 | 0.16 | 4 |
| Spleen | 2.76 | 0.37 | 4 | 2.64 | 0.56 | 4 |
| Liver | 3.23 | 0.43 | 4 | 3.50 | 0.29 | 4 |
| Pancreas | 1.38 | 0.08 | 4 | 1.36 | 0.12 | 4 |
| Adrenals | 2.96 | 0.42 | 4 | 3.04 | 0.61 | 4 |
| Kidney | 5.18 | 0.16 | 4 | 4.90 | 0.29 | 4 |
| Lung | 9.83 | 0.85 | 4 | 7.51 | 0.84 | 4 |
| Heart | 2.81 | 0.16 | 4 | 2.89 | 0.09 | 4 |
| Muscle | 1.08 | 0.18 | 4 | 0.98 | 0.02 | 4 |
| Bone | 0.96 | 0.23 | 4 | 1.16 | 0.15 | 4 |
| Brain | 0.19 | 0.02 | 4 | 0.18 | 0.01 | 4 |
| Daudi | 3.93 | 0.67 | 4 | 9.04 | 0.41 | 4 |
| Ratios | | | | | | |
| Tumor:Blood | 0.28 | 0.05 | 4 | 0.70 | 0.05 | 4 |
| Tumor:Liver | 1.26 | 0.21 | 4 | 2.60 | 0.34 | 4 |
| Tumor:Spleen | 1.49 | 0.38 | 4 | 3.54 | 0.73 | 4 |
| Tumor:Muscle | 3.84 | 1.04 | 4 | 9.23 | 0.31 | 4 |
| Tumor:Bone | 4.42 | 1.54 | 4 | 7.90 | 1.41 | 4 |
| Tumor:Lung | 0.41 | 0.04 | 4 | 1.21 | 0.11 | 4 |

TABLE 16

Biodistribution data (% ID/g) of [$^{68}$Ga]Ga-BL23 in Daudi tumor-bearing mice at selected time points.

| | 1 h | | | 3 h | | |
|---|---|---|---|---|---|---|
| [$^{68}$Ga]Ga-BL23 | Mean | S. Dev | n | Mean | S. Dev | n |
| Blood | 9.93 | 0.27 | 4 | 4.48 | 0.45 | 4 |
| Fat | 0.55 | 0.08 | 4 | 0.28 | 0.02 | 4 |
| Testes | 1.29 | 0.08 | 4 | 1.08 | 0.35 | 4 |
| Intestine | 0.96 | 0.12 | 4 | 0.53 | 0.01 | 4 |
| Stomach | 0.31 | 0.06 | 4 | 0.18 | 0.02 | 4 |
| Spleen | 2.42 | 0.36 | 4 | 1.43 | 0.08 | 4 |
| Liver | 2.83 | 0.17 | 4 | 1.84 | 0.09 | 4 |
| Pancreas | 1.13 | 0.09 | 4 | 0.58 | 0.03 | 4 |
| Adrenals | 2.40 | 0.47 | 4 | 1.22 | 0.36 | 4 |
| Kidney | 6.08 | 0.22 | 4 | 4.97 | 0.38 | 4 |
| Lung | 5.82 | 1.23 | 4 | 2.93 | 0.49 | 4 |
| Heart | 2.37 | 0.11 | 4 | 1.08 | 0.03 | 4 |
| Muscle | 0.73 | 0.07 | 4 | 0.39 | 0.03 | 4 |
| Bone | 0.95 | 0.17 | 4 | 0.47 | 0.05 | 4 |
| Brain | 0.14 | 0.01 | 4 | 0.08 | 0.01 | 4 |
| Daudi | 7.59 | 1.17 | 4 | 10.88 | 0.80 | 4 |
| Ratios | | | | | | |
| Tumor:Blood | 0.84 | 0.17 | 4 | 2.46 | 0.42 | 4 |
| Tumor:Liver | 2.96 | 0.73 | 4 | 5.92 | 0.40 | 4 |
| Tumor:Spleen | 3.45 | 0.73 | 4 | 7.63 | 0.94 | 4 |
| Tumor:Muscle | 11.38 | 2.40 | 4 | 27.82 | 3.88 | 4 |
| Tumor:Bone | 8.81 | 1.98 | 4 | 23.23 | 4.02 | 4 |
| Tumor:Lung | 1.49 | 0.52 | 4 | 3.79 | 0.68 | 4 |

TABLE 17

Biodistribution data (% ID/g) of [$^{68}$Ga]Ga-BL27 in Daudi tumor-bearing mice at selected time points.

| | 1 h | | | 3 h | | |
|---|---|---|---|---|---|---|
| [$^{68}$Ga]Ga-BL27 | Mean | S. Dev | n | Mean | S. Dev | n |
| Blood | 4.60 | 0.50 | 4 | 0.95 | 0.12 | 4 |
| Fat | 0.35 | 0.04 | 4 | 0.09 | 0.03 | 4 |
| Testes | 0.80 | 0.11 | 4 | 0.31 | 0.03 | 4 |
| Intestine | 0.85 | 0.11 | 4 | 0.36 | 0.07 | 4 |
| Stomach | 0.19 | 0.07 | 4 | 0.12 | 0.05 | 4 |
| Spleen | 2.82 | 0.64 | 4 | 1.06 | 0.20 | 4 |
| Liver | 2.61 | 0.04 | 4 | 2.64 | 0.33 | 4 |
| Pancreas | 0.62 | 0.09 | 4 | 0.26 | 0.12 | 4 |
| Adrenals | 1.66 | 0.32 | 4 | 0.58 | 0.04 | 4 |
| Kidney | 6.21 | 0.49 | 4 | 4.77 | 0.43 | 4 |
| Lung | 7.23 | 0.88 | 4 | 2.10 | 0.61 | 4 |
| Heart | 1.27 | 0.25 | 4 | 0.32 | 0.09 | 4 |
| Muscle | 0.43 | 0.07 | 4 | 0.13 | 0.04 | 4 |

TABLE 17-continued

Biodistribution data (% ID/g) of [$^{68}$Ga]Ga-BL27 in Daudi tumor-bearing mice at selected time points.

| | 1 h | | | 3 h | | |
|---|---|---|---|---|---|---|
| [$^{68}$Ga]Ga-BL27 | Mean | S. Dev | n | Mean | S. Dev | n |
| Bone | 0.66 | 0.06 | 4 | 0.27 | 0.02 | 4 |
| Brain | 0.07 | 0.01 | 4 | 0.03 | 0.01 | 4 |
| Daudi | 8.78 | 1.36 | 4 | 10.37 | 1.70 | 4 |
| Ratios | | | | | | |
| Tumor:Blood | 1.99 | 0.44 | 4 | 10.85 | 0.82 | 4 |
| TumonLiver | 3.46 | 0.49 | 4 | 3.91 | 0.22 | 4 |
| Tumor:Spleen | 3.37 | 1.01 | 4 | 10.08 | 2.23 | 4 |
| Tumor:Muscle | 21.47 | 5.50 | 4 | 83.68 | 16.22 | 4 |
| Tumor:Bone | 13.68 | 2.10 | 4 | 38.31 | 6.36 | 4 |
| Tumor:Lung | 1.27 | 0.27 | 4 | 5.59 | 3.03 | 4 |

TABLE 18

Biodistribution data (% ID/g) of [$^{68}$Ga]Ga-BL28 in Daudi tumor-bearing mice at selected time points.

| | 1 h | | | 3 h | | |
|---|---|---|---|---|---|---|
| [$^{68}$Ga]Ga-BL28 | Mean | S. Dev | n | Mean | S. Dev | n |
| Blood | 14.70 | 1.47 | 4 | 11.59 | 0.33 | 4 |
| Fat | 0.64 | 0.20 | 4 | 0.56 | 0.09 | 4 |
| Testes | 1.73 | 0.24 | 4 | 2.05 | 0.24 | 4 |
| Intestine | 1.21 | 0.12 | 4 | 1.00 | 0.05 | 4 |
| Stomach | 0.47 | 0.07 | 4 | 0.38 | 0.05 | 4 |
| Spleen | 2.21 | 0.08 | 4 | 2.34 | 0.34 | 4 |
| Liver | 2.92 | 0.52 | 4 | 2.92 | 0.34 | 4 |
| Pancreas | 1.49 | 0.22 | 4 | 1.21 | 0.08 | 4 |
| Adrenals | 2.53 | 0.70 | 4 | 2.46 | 0.78 | 4 |
| Kidney | 5.41 | 0.60 | 4 | 4.76 | 0.42 | 4 |
| Lung | 7.11 | 1.01 | 4 | 5.35 | 0.19 | 4 |
| Heart | 3.21 | 0.37 | 4 | 2.29 | 0.14 | 4 |
| Muscle | 0.96 | 0.14 | 4 | 0.76 | 0.09 | 4 |
| Bone | 1.14 | 0.25 | 4 | 0.94 | 0.15 | 4 |
| Brain | 0.19 | 0.02 | 4 | 0.17 | 0.02 | 4 |
| Daudi | 4.59 | 1.16 | 4 | 7.82 | 0.51 | 4 |
| Ratios | | | | | | |
| Tumor:Blood | 0.31 | 0.04 | 4 | 0.68 | 0.05 | 4 |
| Tumor:Liver | 1.59 | 0.30 | 4 | 2.71 | 0.44 | 4 |
| Tumor:Spleen | 2.08 | 0.43 | 4 | 3.38 | 0.44 | 4 |
| Tumor:Muscle | 4.82 | 0.56 | 4 | 10.49 | 1.90 | 4 |
| Tumor:Bone | 4.12 | 0.81 | 4 | 8.55 | 1.86 | 4 |
| Tumor:Lung | 0.65 | 0.13 | 4 | 1.46 | 0.10 | 4 |

TABLE 19

Biodistribution data (% ID/g) of [$^{177}$Lu]Lu-BL02 in Z138 tumor-bearing mice at selected time points.

| | 1 h | | | 1 h blocked | | | 4 h | | | 24 h | | | 72 h | | |
|---|---|---|---|---|---|---|---|---|---|---|---|---|---|---|---|
| [$^{177}$Lu]Lu-BL02 | Mean | S. Dev | n | Mean | S. Dev | n | Mean | S. Dev | n | Mean | S. Dev | n | Mean | S. Dev | n |
| Blood | 0.44 | 0.07 | 6 | 2.06 | 1.96 | 6 | 0.03 | 0.00 | 7 | 0.010 | 0.001 | 7 | 0.007 | 0.003 | 5 |
| Fat | 0.07 | 0.03 | 6 | 0.19 | 0.06 | 6 | 0.03 | 0.06 | 7 | 0.011 | 0.002 | 7 | 0.008 | 0.003 | 6 |
| Testes | 0.18 | 0.02 | 6 | 0.39 | 0.15 | 6 | 0.04 | 0.00 | 6 | 0.032 | 0.013 | 7 | 0.029 | 0.006 | 6 |
| Intestine | 0.27 | 0.05 | 6 | 0.75 | 0.31 | 6 | 0.09 | 0.02 | 6 | 0.126 | 0.184 | 7 | 0.023 | 0.003 | 6 |
| Stomach | 0.12 | 0.07 | 6 | 0.20 | 0.09 | 6 | 0.07 | 0.07 | 7 | 0.052 | 0.028 | 7 | 0.022 | 0.007 | 6 |
| Spleen | 0.56 | 0.20 | 6 | 0.56 | 0.15 | 6 | 0.33 | 0.08 | 7 | 0.277 | 0.036 | 7 | 0.288 | 0.122 | 6 |
| Liver | 0.93 | 0.14 | 6 | 0.99 | 0.25 | 6 | 0.92 | 0.09 | 7 | 0.703 | 0.030 | 7 | 0.436 | 0.073 | 6 |
| Pancreas | 0.14 | 0.02 | 6 | 0.31 | 0.10 | 6 | 0.04 | 0.01 | 7 | 0.034 | 0.003 | 7 | 0.016 | 0.002 | 6 |
| Adrenals | 0.46 | 0.29 | 6 | 0.47 | 0.30 | 6 | 0.13 | 0.10 | 7 | 0.117 | 0.072 | 7 | 0.073 | 0.024 | 6 |
| Kidney | 3.87 | 0.66 | 6 | 10.90 | 6.47 | 6 | 3.27 | 0.40 | 7 | 1.433 | 0.204 | 7 | 0.560 | 0.078 | 6 |
| Lung | 0.83 | 0.19 | 6 | 1.57 | 0.89 | 6 | 0.26 | 0.04 | 7 | 0.176 | 0.046 | 7 | 0.184 | 0.091 | 6 |
| Heart | 0.18 | 0.03 | 6 | 0.46 | 0.24 | 6 | 0.05 | 0.01 | 7 | 0.035 | 0.005 | 7 | 0.022 | 0.003 | 6 |

TABLE 19-continued

Biodistribution data (% ID/g) of [$^{177}$Lu]Lu-BL02 in Z138 tumor-bearing mice at selected time points.

| | 1 h | | | 1 h blocked | | | 4 h | | | 24 h | | | 72 h | | |
|---|---|---|---|---|---|---|---|---|---|---|---|---|---|---|---|
| [$^{177}$Lu]Lu-BL02 | Mean | S. Dev | n | Mean | S. Dev | n | Mean | S. Dev | n | Mean | S. Dev | n | Mean | S. Dev | n |
| Muscle | 0.10 | 0.02 | 6 | 0.45 | 0.48 | 6 | 0.03 | 0.01 | 7 | 0.019 | 0.004 | 7 | 0.010 | 0.002 | 6 |
| Bone | 0.25 | 0.11 | 6 | 0.49 | 0.32 | 6 | 0.11 | 0.02 | 7 | 0.085 | 0.027 | 7 | 0.053 | 0.010 | 6 |
| Brain | 0.02 | 0.00 | 6 | 0.04 | 0.01 | 6 | 0.01 | 0.00 | 7 | 0.003 | 0.001 | 7 | 0.001 | 0.000 | 6 |
| Z138 | 17.17 | 3.04 | 6 | 3.75 | 0.83 | 6 | 15.57 | 2.59 | 7 | 8.791 | 1.215 | 6 | 3.574 | 0.645 | 6 |
| Ratios | | | | | | | | | | | | | | | |
| Tumour: Blood | 38.98 | 3.01 | 6 | 2.74 | 1.22 | 6 | 627.62 | 129.95 | 7 | 873.49 | 84.55 | 7 | 613.24 | 330.77 | 5 |
| Tumour: Liver | 18.53 | 2.34 | 6 | 3.84 | 0.40 | 6 | 16.93 | 1.54 | 7 | 12.51 | 1.72 | 7 | 8.32 | 1.60 | 6 |
| Tumour:Spleen | 33.05 | 8.73 | 6 | 6.87 | 1.25 | 6 | 49.43 | 10.83 | 7 | 31.90 | 3.61 | 7 | 13.86 | 5.15 | 6 |
| Tumour:Muscle | 166.59 | 14.05 | 6 | 13.22 | 5.59 | 6 | 503.09 | 126.87 | 7 | 463.22 | 90.14 | 7 | 358.55 | 59.03 | 6 |
| Tumour:Bone | 74.82 | 20.30 | 6 | 9.53 | 3.81 | 6 | 145.11 | 15.72 | 7 | 109.48 | 29.98 | 7 | 68.39 | 12.84 | 6 |
| Tumour:Lung | 21.08 | 2.76 | 6 | 2.75 | 0.89 | 6 | 60.62 | 13.42 | 7 | 52.72 | 16.22 | 7 | 21.59 | 5.59 | 6 |

TABLE 20

Biodistribution data (% ID/g) of [$^{177}$Lu]Lu-BL02 in GRANTA519 tumor-bearing mice at selected time points.

| | 1 h | | | 1 h blocked | | | 4 h | | | 24 h | | | 72 h | | |
|---|---|---|---|---|---|---|---|---|---|---|---|---|---|---|---|
| [$^{177}$Lu]Lu-BL02 | Mean | S. Dev | n | Mean | S. Dev | n | Mean | S. Dev | n | Mean | S. Dev | n | Mean | S. Dev | n |
| Blood | 0.50 | 0.13 | 6 | 1.14 | 0.45 | 6 | 0.02 | 0.00 | 6 | 0.006 | 0.001 | 5 | 0.002 | 0.000 | 5 |
| Fat | 0.08 | 0.03 | 6 | 0.16 | 0.08 | 6 | 0.01 | 0.00 | 7 | 0.008 | 0.002 | 7 | 0.006 | 0.001 | 5 |
| Testes | 0.21 | 0.06 | 6 | 0.32 | 0.11 | 6 | 0.04 | 0.01 | 7 | 0.034 | 0.005 | 7 | 0.034 | 0.020 | 5 |
| Intestine | 0.28 | 0.02 | 6 | 0.58 | 0.23 | 6 | 0.09 | 0.04 | 7 | 0.046 | 0.011 | 5 | 0.017 | 0.005 | 6 |
| Stomach | 0.10 | 0.03 | 6 | 0.19 | 0.09 | 6 | 0.05 | 0.02 | 7 | 0.206 | 0.297 | 7 | 0.021 | 0.010 | 5 |
| Spleen | 0.49 | 0.10 | 6 | 0.48 | 0.17 | 6 | 0.28 | 0.07 | 7 | 0.321 | 0.139 | 7 | 0.198 | 0.008 | 6 |
| Liver | 0.96 | 0.15 | 6 | 1.07 | 0.29 | 6 | 0.87 | 0.16 | 7 | 0.635 | 0.061 | 7 | 0.413 | 0.047 | 6 |
| Pancreas | 0.17 | 0.05 | 6 | 0.30 | 0.11 | 6 | 0.04 | 0.00 | 7 | 0.028 | 0.008 | 7 | 0.015 | 0.003 | 6 |
| Adrenals | 0.39 | 0.23 | 6 | 0.48 | 0.23 | 6 | 0.10 | 0.03 | 6 | 0.094 | 0.065 | 7 | 0.346 | 0.517 | 6 |
| Kidney | 3.91 | 0.46 | 6 | 8.63 | 4.34 | 6 | 2.98 | 0.42 | 7 | 1.329 | 0.162 | 7 | 0.573 | 0.095 | 6 |
| Lung | 0.77 | 0.19 | 6 | 1.16 | 0.44 | 6 | 0.27 | 0.08 | 7 | 0.117 | 0.036 | 7 | 0.060 | 0.028 | 6 |
| Heart | 0.19 | 0.05 | 6 | 0.40 | 0.16 | 6 | 0.05 | 0.02 | 7 | 0.034 | 0.006 | 7 | 0.022 | 0.003 | 6 |
| Muscle | 0.13 | 0.05 | 6 | 0.34 | 0.21 | 6 | 0.04 | 0.01 | 7 | 0.015 | 0.003 | 7 | 0.007 | 0.001 | 6 |
| Bone | 0.24 | 0.04 | 6 | 0.41 | 0.18 | 6 | 0.09 | 0.01 | 7 | 0.090 | 0.011 | 7 | 0.061 | 0.007 | 6 |
| Brain | 0.02 | 0.01 | 6 | 0.04 | 0.02 | 6 | 0.01 | 0.00 | 7 | 0.003 | 0.001 | 7 | 0.001 | 0.001 | 6 |
| GRANTA519 | 6.83 | 1.26 | 6 | 0.84 | 0.31 | 6 | 3.22 | 0.49 | 7 | 1.090 | 0.125 | 7 | 0.353 | 0.025 | 6 |
| Ratios | | | | | | | | | | | | | | | |
| Tumour:Blood | 14.18 | 2.52 | 6 | 0.77 | 0.17 | 6 | 119.44 | 45.07 | 6 | 206.07 | 47.16 | 5 | 126.69 | 44.62 | 5 |
| Tumour:Liver | 7.10 | 0.96 | 6 | 0.78 | 0.14 | 6 | 3.75 | 0.43 | 7 | 1.72 | 0.19 | 7 | 0.86 | 0.08 | 6 |
| Tumour:Spleen | 14.20 | 2.50 | 6 | 1.77 | 0.17 | 6 | 11.98 | 2.92 | 7 | 3.78 | 1.04 | 7 | 1.53 | 0.54 | 5 |
| Tumour:Muscle | 56.86 | 20.00 | 6 | 3.18 | 1.51 | 6 | 90.57 | 26.90 | 7 | 76.90 | 17.73 | 7 | 50.64 | 6.85 | 6 |
| Tumour:Bone | 28.95 | 2.63 | 6 | 2.16 | 0.54 | 6 | 34.26 | 4.03 | 7 | 12.33 | 2.00 | 7 | 5.88 | 0.57 | 6 |
| Tumour:Lung | 9.08 | 1.96 | 6 | 0.74 | 0.09 | 6 | 12.56 | 2.64 | 7 | 9.91 | 2.64 | 7 | 6.60 | 1.87 | 6 |

TABLE 21

Biodistribution data (% ID/g) of [$^{177}$Lu]Lu-BL18 in Daudi tumor-bearingmice at selected time points.

| | 1 h | | | 4 h | | | 24 h | | | 72 h | | | 120 h | | |
|---|---|---|---|---|---|---|---|---|---|---|---|---|---|---|---|
| [$^{177}$Lu]Lu-BL18 | Mean | S. Dev | n | Mean | S. Dev | n | Mean | S. Dev | n | Mean | S. Dev | n | Mean | S. Dev | n |
| Blood | 30.38 | 4.39 | 4 | 18.25 | 1.37 | 4 | 13.49 | 1.15 | 4 | 6.12 | 0.56 | 4 | 3.35 | 0.76 | 4 |
| Fat | 1.18 | 0.12 | 4 | 1.30 | 0.23 | 4 | 0.73 | 0.14 | 4 | 0.63 | 0.23 | 4 | 0.43 | 0.16 | 4 |
| Testes | 4.02 | 0.75 | 4 | 3.96 | 0.36 | 4 | 4.28 | 0.53 | 4 | 4.45 | 0.81 | 4 | 3.88 | 0.61 | 4 |
| Intestine | 2.76 | 0.53 | 4 | 1.53 | 0.20 | 4 | 1.55 | 0.14 | 4 | 0.94 | 0.27 | 4 | 0.50 | 0.09 | 4 |
| Stomach | 0.89 | 0.29 | 4 | 0.96 | 0.36 | 4 | 1.4 | 10.12 | 4 | 0.73 | 0.29 | 4 | 0.45 | 0.19 | 4 |
| Spleen | 6.35 | 2.44 | 4 | 4.04 | 0.79 | 4 | 5.76 | 0.52 | 4 | 6.47 | 1.52 | 4 | 6.34 | 1.49 | 4 |
| Liver | 7.12 | 1.92 | 4 | 5.64 | 0.94 | 4 | 4.66 | 0.67 | 4 | 3.18 | 0.83 | 4 | 2.04 | 0.14 | 4 |
| Pancreas | 3.84 | 0.79 | 4 | 2.19 | 0.12 | 4 | 1.83 | 0.17 | 4 | 1.42 | 0.41 | 4 | 0.85 | 0.11 | 4 |
| Adrenals | 8.47 | 3.21 | 4 | 5.25 | 1.57 | 4 | 6.20 | 0.91 | 4 | 7.82 | 2.06 | 4 | 4.94 | 1.38 | 4 |
| Kidney | 8.68 | 2.01 | 4 | 5.98 | 0.23 | 4 | 4.78 | 0.27 | 4 | 2.99 | 0.79 | 4 | 1.72 | 0.25 | 4 |

TABLE 21-continued

Biodistribution data (% ID/g) of [$^{177}$Lu]Lu-BL18 in Daudi tumor-bearingmice at selected time points.

| | 1 h | | | 4 h | | | 24 h | | | 72 h | | | 120 h | | |
|---|---|---|---|---|---|---|---|---|---|---|---|---|---|---|---|
| [$^{177}$Lu]Lu-BL18 | Mean | S. Dev | n | Mean | S. Dev | n | Mean | S. Dev | n | Mean | S. Dev | n | Mean | S. Dev | n |
| Lung | 21.59 | 5.79 | 4 | 11.30 | 1.42 | 4 | 8.94 | 0.34 | 4 | 5.59 | 1.94 | 4 | 3.0 | 10.49 | 4 |
| Heart | 7.3 | 11.47 | 4 | 4.88 | 0.70 | 4 | 3.87 | 0.18 | 4 | 2.6 | 10.59 | 4 | 1.73 | 0.15 | 4 |
| Muscle | 1.32 | 0.37 | 4 | 1.56 | 0.06 | 4 | 1.16 | 0.17 | 4 | 0.85 | 0.25 | 4 | 0.45 | 0.07 | 4 |
| Bone | 2.87 | 0.85 | 4 | 1.44 | 0.25 | 4 | 1.71 | 0.33 | 4 | 1.19 | 0.37 | 4 | 0.95 | 0.35 | 4 |
| Brain | 0.4 | 10.06 | 4 | 0.30 | 0.02 | 4 | 0.21 | 0.02 | 4 | 0.13 | 0.04 | 4 | 0.06 | 0.01 | 4 |
| Daudi | 3.49 | 1.04 | 4 | 5.79 | 0.64 | 4 | 18.6 | 0.45 | 4 | 23.06 | 2.05 | 3 | 18.3 | 3.64 | 4 |
| Ratios | | | | | | | | | | | | | | | |
| Tumour:Blood | 0.12 | 0.03 | 4 | 0.32 | 0.05 | 4 | 1.38 | 0.09 | 4 | 4.10 | 0.87 | 3 | 5.76 | 1.89 | 4 |
| Tumour: Liver | 0.53 | 0.23 | 4 | 1.05 | 0.24 | 4 | 4.05 | 0.62 | 4 | 7.88 | 0.64 | 3 | 8.97 | 1.48 | 4 |
| Tumour:Spleen | 0.59 | 0.22 | 4 | 1.49 | 0.40 | 4 | 3.25 | 0.36 | 4 | 3.90 | 0.41 | 3 | 2.95 | 0.60 | 4 |
| Tumour:Muscle | 2.69 | 0.69 | 4 | 3.72 | 0.54 | 4 | 16.26 | 2.40 | 4 | 29.58 | 9.82 | 3 | 41.40 | 7.23 | 4 |
| Tumour: Bone | 1.28 | 0.44 | 4 | 4.17 | 1.12 | 4 | 11.24 | 2.40 | 4 | 21.36 | 3.97 | 3 | 21.28 | 7.69 | 4 |
| Tumour: Lung | 0.17 | 0.06 | 4 | 0.52 | 0.12 | 4 | 2.08 | 0.12 | 4 | 4.50 | 1.31 | 3 | 6.18 | 1.24 | 4 |

TABLE 22

Biodistribution data (% ID/g) of [$^{177}$Lu]Lu-BL19 in Daudi tumor-bearing mice at selected time points.

| | 1 h | | | 4 h | | | 24 h | | | 72 h | | | 120 h | | |
|---|---|---|---|---|---|---|---|---|---|---|---|---|---|---|---|
| [$^{177}$Lu]Lu-BL19 | Mean | S. Dev | n | Mean | S. Dev | n | Mean | S. Dev | n | Mean | S. Dev | n | Mean | S. Dev | n |
| Blood | 29.42 | 2.52 | 4 | 20.08 | 0.59 | 4 | 12.75 | 1.21 | 4 | 5.66 | 0.30 | 2 | 3.08 | 0.47 | 2 |
| Fat | 0.77 | 0.10 | 4 | 1.15 | 0.23 | 4 | 0.85 | 0.43 | 4 | 0.57 | 0.08 | 2 | 0.42 | 0.05 | 2 |
| Testes | 3.42 | 0.79 | 4 | 4.02 | 0.43 | 4 | 4.31 | 1.14 | 4 | 4.49 | 0.49 | 2 | 3.97 | 0.12 | 2 |
| Intestine | 2.68 | 0.17 | 4 | 1.75 | 0.16 | 4 | 1.27 | 0.05 | 4 | 0.81 | 0.03 | 2 | 0.46 | 0.03 | 2 |
| Stomach | 0.64 | 0.15 | 4 | 0.98 | 0.24 | 4 | 1.14 | 0.15 | 4 | 0.68 | 0.20 | 2 | 0.33 | 0.04 | 2 |
| Spleen | 5.39 | 1.34 | 4 | 3.89 | 0.03 | 4 | 3.94 | 0.45 | 4 | 5.05 | 0.10 | 2 | 5.18 | 0.11 | 2 |
| Liver | 6.02 | 1.06 | 4 | 4.3 | 10.57 | 4 | 5.24 | 2.31 | 4 | 2.54 | 0.27 | 2 | 2.04 | 0.09 | 2 |
| Pancreas | 3.20 | 0.27 | 4 | 2.52 | 0.10 | 4 | 1.77 | 0.26 | 4 | 1.28 | 0.09 | 2 | 0.84 | 0.01 | 2 |
| Adrenals | 6.71 | 1.84 | 4 | 5.12 | 1.66 | 4 | 5.36 | 1.42 | 4 | 7.48 | 1.55 | 2 | 3.85 | 0.72 | 2 |
| Kidney | 10.59 | 1.05 | 4 | 6.48 | 0.51 | 4 | 4.65 | 0.79 | 4 | 2.62 | 0.05 | 2 | 1.78 | 0.03 | 2 |
| Lung | 17.49 | 3.30 | 4 | 11.48 | 1.18 | 4 | 8.07 | 1.22 | 4 | 4.87 | 0.12 | 2 | 2.85 | 0.08 | 2 |
| Heart | 7.43 | 0.65 | 4 | 4.77 | 0.21 | 4 | 3.79 | 1.29 | 4 | 2.53 | 0.09 | 2 | 1.76 | 0.10 | 2 |
| Muscle | 1.30 | 0.20 | 4 | 1.52 | 0.15 | 4 | 1.47 | 0.74 | 4 | 0.78 | 0.06 | 2 | 0.42 | 0.03 | 2 |
| Bone | 2.20 | 0.32 | 4 | 1.99 | 0.65 | 4 | 0.94 | 0.16 | 4 | 1.37 | 0.03 | 2 | 0.86 | 0.07 | 2 |
| Brain | 0.45 | 0.03 | 4 | 0.29 | 0.04 | 4 | 0.23 | 0.07 | 4 | 0.11 | 0.00 | 2 | 0.07 | 0.00 | 2 |
| Daudi | 2.15 | 0.43 | 4 | 5.44 | 0.43 | 4 | 15.33 | 2.23 | 4 | 16.63 | 0.14 | 2 | 12.20 | 1.75 | 2 |
| Ratios | | | | | | | | | | | | | | | |
| Tumour:Blood | 0.07 | 0.01 | 4 | 0.27 | 0.01 | 4 | 1.20 | 0.09 | 4 | 2.94 | 0.18 | 2 | 3.97 | 0.04 | 2 |
| Tumour:Liver | 0.37 | 0.12 | 4 | 1.27 | 0.15 | 4 | 3.36 | 1.54 | 4 | 6.58 | 0.76 | 2 | 6.01 | 1.13 | 2 |
| Tumour:Spleen | 0.42 | 0.13 | 4 | 1.40 | 0.10 | 4 | 3.92 | 0.65 | 4 | 3.30 | 0.09 | 2 | 2.35 | 0.29 | 2 |
| Tumour:Muscle | 1.67 | 0.25 | 4 | 3.60 | 0.51 | 4 | 11.63 | 3.32 | 4 | 21.33 | 1.46 | 2 | 28.67 | 2.03 | 2 |
| Tumour:Bone | 0.98 | 0.16 | 4 | 3.07 | 1.44 | 4 | 16.89 | 4.91 | 4 | 12.15 | 0.18 | 2 | 14.11 | 0.83 | 2 |
| Tumour:Lung | 0.13 | 0.04 | 4 | 0.48 | 0.06 | 4 | 1.91 | 0.19 | 4 | 3.42 | 0.06 | 2 | 4.28 | 0.49 | 2 |

TABLE 23

Biodistribution data (% ID/g) of [$^{177}$Lu]Lu-BL23 in Daudi tumor-bearing mice at selected time points.

| | 1 h | | | 1 h blocked | | | 4 h | | | 24 h | | | 72 h | | |
|---|---|---|---|---|---|---|---|---|---|---|---|---|---|---|---|
| [$^{177}$Lu]Lu-BL23 | Mean | S. Dev | n | Mean | S. Dev | n | Mean | S. Dev | n | Mean | S. Dev | n | Mean | S. Dev | n |
| Blood | 13.32 | 0.89 | 4 | 4.98 | 0.30 | 4 | 0.11 | 0.04 | 4 | 0.03 | 0.01 | 4 | 0.01 | 0.00 | 4 |
| Fat | 0.68 | 0.08 | 4 | 0.30 | 0.01 | 4 | 0.06 | 0.01 | 4 | 0.04 | 0.01 | 4 | 0.02 | 0.01 | 4 |
| Testes | 2.01 | 0.26 | 4 | 1.42 | 0.23 | 4 | 0.34 | 0.08 | 4 | 0.05 | 0.01 | 4 | 0.14 | 0.08 | 4 |
| Intestine | 1.32 | 0.10 | 4 | 0.79 | 0.31 | 4 | 0.13 | 0.02 | 4 | 0.27 | 0.02 | 4 | 0.03 | 0.01 | 4 |
| Stomach | 0.43 | 0.08 | 4 | 0.29 | 0.09 | 4 | 0.17 | 0.03 | 4 | 0.09 | 0.01 | 4 | 0.02 | 0.00 | 4 |
| Spleen | 5.81 | 0.18 | 4 | 4.80 | 1.59 | 4 | 4.45 | 1.54 | 4 | 5.73 | 0.64 | 4 | 5.51 | 1.20 | 4 |
| Liver | 5.72 | 0.89 | 4 | 3.97 | 0.67 | 4 | 3.82 | 1.90 | 4 | 3.23 | 0.19 | 4 | 2.57 | 0.25 | 4 |
| Pancreas | 1.55 | 0.10 | 4 | 0.69 | 0.05 | 4 | 0.11 | 0.02 | 4 | 0.07 | 0.01 | 4 | 0.04 | 0.00 | 4 |

TABLE 23-continued

Biodistribution data (% ID/g) of [$^{177}$Lu]Lu-BL23 in Daudi tumor-bearing mice at selected time points.

| | 1 h | | | 1 h blocked | | | 4 h | | | 24 h | | | 72 h | | |
|---|---|---|---|---|---|---|---|---|---|---|---|---|---|---|---|
| [$^{177}$Lu]Lu-BL23 | Mean | S. Dev | n | Mean | S. Dev | n | Mean | S. Dev | n | Mean | S. Dev | n | Mean | S. Dev | n |
| Adrenals | 5.84 | 1.97 | 4 | 1.99 | 0.65 | 4 | 1.04 | 0.53 | 4 | 1.24 | 0.85 | 4 | 0.42 | 0.17 | 4 |
| Kidney | 7.23 | 1.23 | 4 | 5.14 | 0.47 | 4 | 1.86 | 0.47 | 4 | 0.95 | 0.46 | 4 | 0.40 | 0.05 | 4 |
| Lung | 17.52 | 2.71 | 4 | 3.82 | 0.22 | 4 | 0.86 | 0.39 | 4 | 0.53 | 0.29 | 4 | 0.25 | 0.15 | 4 |
| Heart | 3.22 | 0.36 | 4 | 1.32 | 0.16 | 4 | 0.21 | 0.05 | 4 | 0.13 | 0.02 | 4 | 0.07 | 0.00 | 4 |
| Muscle | 1.09 | 0.09 | 4 | 0.48 | 0.03 | 4 | 0.07 | 0.03 | 4 | 0.04 | 0.01 | 4 | 0.02 | 0.00 | 4 |
| Bone | 1.36 | 0.09 | 4 | 0.55 | 0.10 | 4 | 0.29 | 0.11 | 4 | 0.33 | 0.09 | 4 | 0.19 | 0.04 | 4 |
| Brain | 0.19 | 0.03 | 4 | 0.08 | 0.00 | 4 | 0.01 | 0.00 | 4 | 0.00 | 0.00 | 4 | 0.00 | 0.00 | 4 |
| Daudi | 8.38 | 0.97 | 4 | 13.24 | 0.85 | 4 | 11.50 | 0.40 | 4 | 6.50 | 0.08 | 4 | 3.17 | 0.23 | 4 |
| Ratios | | | | | | | | | | | | | | | |
| Tumour:Blood | 0.63 | 0.05 | 4 | 2.67 | 0.27 | 4 | 95.35 | 23.25 | 4 | 284.24 | 36.85 | 4 | 362.04 | 40.25 | 4 |
| Tumour:Liver | 1.51 | 0.39 | 4 | 3.43 | 0.74 | 4 | 2.55 | 0.60 | 4 | 2.24 | 0.12 | 4 | 1.24 | 0.12 | 4 |
| Tumour:Spleen | 1.45 | 0.20 | 4 | 3.04 | 1.14 | 4 | 2.79 | 0.94 | 4 | 1.26 | 0.22 | 4 | 0.60 | 0.14 | 4 |
| Tumour:Muscle | 7.65 | 0.41 | 4 | 27.88 | 3.60 | 4 | 150.51 | 33.19 | 4 | 182.80 | 41.44 | 4 | 202.59 | 26.09 | 4 |
| Tumour:Bone | 6.17 | 0.86 | 4 | 24.71 | 5.02 | 4 | 33.91 | 5.10 | 4 | 22.16 | 7.72 | 4 | 17.44 | 4.28 | 4 |
| Tumour: Lung | 0.48 | 0.07 | 4 | 3.47 | 0.23 | 4 | 11.31 | 2.30 | 4 | 16.32 | 8.16 | 4 | 15.83 | 7.24 | 4 |

TABLE 24

Absorbed Doses in mGy/MBq for the Mouse 25 g model with isotope Lu-177 based on [$^{177}$Lu]Lu-BL02 in Z138 xenograft mice.

| Organ | Lu-177 |
|---|---|
| Brain | 0.0246 |
| Large Intestine | 0.0691 |
| Small Intestine | 0.0767 |
| Stomach | 0.163 |
| Heart | 0.137 |
| Kidneys | 0.887 |
| Liver | 0.573 |
| Lungs | 0.363 |
| Pancreas | 0.155 |
| Bone | 0.72 |
| Spleen | 0.533 |
| Testes | 0.0615 |
| Thyroid | 0.0403 |
| Bladder | 0.0314 |
| Remainder of the Body | 0.107 |
| Z138 Tumor | 528.22 |

TABLE 25

Absorbed Doses in mGy/MBq for the Human Extrapolated from Mouse Model with isotope Lu-177 based on [$^{177}$Lu]Lu-BL02 in Z138 xenograft mice.

| Organs | Lu-177 |
|---|---|
| Adrenals | 0.00413 |
| Brain | 4.5e−05 |
| Esophagus | 0.000564 |
| Eyes | 0.000296 |
| Gallbladder Wall | 0.000923 |
| Left colon | 0.000755 |
| Small Intestine | 0.000691 |
| Stomach Wall | 0.000883 |
| Right colon | 0.000642 |
| Rectum | 0.000473 |
| Heart | 0.00148 |
| Kidneys | 0.0332 |
| Liver | 0.0183 |
| Lungs | 0.0126 |
| Pancreas | 0.00105 |
| Prostate | 0.000336 |

TABLE 25-continued

Absorbed Doses in mGy/MBq for the Human Extrapolated from Mouse Model with isotope Lu-177 based on [$^{177}$Lu]Lu-BL02 in Z138 xenograft mice.

| Organs | Lu-177 |
|---|---|
| Salivary Glands | 0.00031 |
| Red Marrow | 0.000377 |
| Skeleton | 0.000457 |
| Spleen | 0.0193 |
| Testes | 0.00168 |
| Thymus | 0.000454 |
| Thyroid | 0.000396 |
| Urin Blad | 0.00032 |
| Remainder of the Body | 0.00117 |

TABLE 26

Absorbed Doses in mGy/MBq for the Mouse 25 g model with isotope Lu-177, based on [$^{177}$Lu]Lu-BL02 in GRANTA519 xenograft mice.

| Organ | Lu-177 |
|---|---|
| Brain | 0.0253 |
| Large Intestine | 0.0874 |
| Small Intestine | 0.0968 |
| Stomach | 0.137 |
| Heart | 0.133 |
| Kidneys | 0.836 |
| Liver | 0.577 |
| Lungs | 0.169 |
| Pancreas | 0.15 |
| Bone | 0.662 |
| Spleen | 0.28 |
| Testes | 0.0809 |
| Thyroid | 0.0397 |
| Bladder | 0.0331 |
| Remainder of the Body | 0.106 |
| GRANTA519 | 68.7 |

TABLE 27

Absorbed Doses in mGy/MBq for the Human Extrapolated from Mouse Model with isotope Lu-177, based on $[^{177}Lu]$Lu-BL02 in GRANTA519 xenograft mice.

| Organ | Lu-177 |
|---|---|
| Adrenals | 0.00757 |
| Brain | 7.33e−05 |
| Esophagus | 0.00043 |
| Eyes | 0.000245 |
| Gallbladder Wall | 0.000863 |
| Left colon | 0.00141 |
| Small Intestine | 0.00131 |
| Stomach Wall | 0.000464 |
| Right colon | 0.00095 |
| Rectum | 0.000761 |
| Heart | 0.00148 |
| Kidneys | 0.0311 |
| Liver | 0.0185 |
| Lungs | 0.00333 |
| Pancreas | 0.000976 |
| Prostate | 0.000284 |
| Salivary Glands | 0.000254 |
| Red Marrow | 0.000343 |
| Skeleton | 0.000444 |
| Spleen | 0.00859 |
| Testes | 0.00245 |
| Thymus | 0.000336 |
| Thyroid | 0.00029 |
| Urin Blad | 0.000269 |
| Remainder of the Body | 0.000952 |

TABLE 28

Absorbed Doses in mGy/MBq for the Mouse 25 g model with isotope Lu-177, based on $[^{177}Lu]$Lu-BL18 in Daudi xenograft mice.

| Organ | Lu-177 |
|---|---|
| Brain | 1.91 |
| Large Intestine | 3.41 |
| Small Intestine | 3.42 |
| Stomach | 3.75 |
| Heart | 5.48 |
| Kidneys | 5.77 |
| Liver | 6.17 |
| Lungs | 7.63 |
| Pancreas | 4.2 |
| Bone | 1.27e+02 |
| Spleen | 11.3 |
| Testes | 8.79 |
| Thyroid | 2.55 |
| Bladder | 2.8 |
| Remainder of the Body | 2.88 |
| Daudi | 2044.55 |

TABLE 29

Absorbed Doses in mGy/MBq for the Human Extrapolated from Mouse Model with isotope Lu-177, based on $[^{177}Lu]$Lu-BL18 in Daudi xenograft mice.

| Organ | Lu-177 |
|---|---|
| Adrenals | 0.341 |
| Brain | 0.00596 |
| Esophagus | 0.025 |
| Eyes | 0.0198 |
| Gallbladder Wall | 0.0256 |
| Left colon | 0.0594 |

TABLE 29-continued

Absorbed Doses in mGy/MBq for the Human Extrapolated from Mouse Model with isotope Lu-177, based on $[^{177}Lu]$Lu-BL18 in Daudi xenograft mice.

| Organ | Lu-177 |
|---|---|
| Small Intestine | 0.0563 |
| Stomach Wall | 0.034 |
| Right colon | 0.0409 |
| Rectum | 0.0384 |
| Heart | 0.27 |
| Kidneys | 0.129 |
| Liver | 0.139 |
| Lungs | 0.229 |
| Pancreas | 0.0598 |
| Prostate | 0.0211 |
| Salivary Glands | 0.0204 |
| Red Marrow | 0.0733 |
| Skeleton | 0.044 |
| Spleen | 0.38 |
| Testes | 0.274 |
| Thymus | 0.0249 |
| Thyroid | 0.022 |
| Urin Blad | 0.021 |
| Remainder of the Body | 0.0341 |

TABLE 30

Absorbed Doses in mGy/MBq for the Mouse 25 g model with isotope Lu-177, based on $[^{177}Lu]$Lu-BL19 in Daudi xenograft mice.

| Organ | Lu-177 |
|---|---|
| Brain | 1.8 |
| Large Intestine | 3.18 |
| Small Intestine | 3.19 |
| Stomach | 3.39 |
| Heart | 5.29 |
| Kidneys | 5.43 |
| Liver | 5.71 |
| Lungs | 7.18 |
| Pancreas | 3.97 |
| Bone | 1.19e+02 |
| Spleen | 8.76 |
| Testes | 7.62 |
| Thyroid | 2.41 |
| Bladder | 2.6 |
| Remainder of the Body | 2.69 |
| Daudi | 1587.55 |

TABLE 31

Absorbed Doses in mGy/MBq for the Human Extrapolated from Mouse Model with isotope Lu-177, based on $[^{177}Lu]$Lu-BL19 in Daudi xenograft mice.

| Organ | Lu-177 |
|---|---|
| Adrenals | 0.245 |
| Brain | 0.00581 |
| Esophagus | 0.0242 |
| Eyes | 0.0193 |
| Gallbladder Wall | 0.0247 |
| Left colon | 0.056 |
| Small Intestine | 0.0532 |
| Stomach Wall | 0.0313 |
| Right colon | 0.0389 |
| Rectum | 0.0366 |
| Heart | 0.258 |
| Kidneys | 0.123 |
| Liver | 0.128 |

TABLE 31-continued

| Absorbed Doses in mGy/MBq for the Human Extrapolated from Mouse Model with isotope Lu-177, based on [$^{177}$Lu]Lu-BL19 in Daudi xenograft mice. | |
|---|---|
| Organ | Lu-177 |
| Lungs | 0.215 |
| Pancreas | 0.0594 |
| Prostate | 0.0206 |
| Salivary Glands | 0.0199 |
| Red Marrow | 0.0688 |
| Skeleton | 0.0417 |
| Spleen | 0.279 |
| Testes | 0.232 |
| Thymus | 0.0241 |
| Thyroid | 0.0214 |
| Urin Blad | 0.0205 |
| Remainder of the Body | 0.0326 |

TABLE 32

| Absorbed Doses in mGy/MBq for the Mouse 25 g model with isotope Lu-177, based on [$^{177}$Lu]Lu-BL23 in Daudi xenograft mice. | |
|---|---|
| Organ | Lu-177 |
| Brain | 0.219 |
| Large Intestine | 0.54 |
| Small Intestine | 0.627 |
| Stomach | 1.27 |
| Heart | 1.1 |
| Kidneys | 1.9 |
| Liver | 4.71 |
| Lungs | 1.58 |
| Pancreas | 1.13 |
| Bone | 8.97 |
| Spleen | 9.06 |
| Testes | 0.562 |
| Thyroid | 0.338 |
| Bladder | 0.289 |
| Remainder of the Body | 0.806 |
| Daudi | 709.31 |

TABLE 33

| Absorbed Doses in mGy/MBq for the Human Extrapolated from Mouse Model with isotope Lu-177, based on [$^{177}$Lu]Lu-BL23 in Daudi xenograft mice. | |
|---|---|
| Organ | Lu-177 |
| Adrenals | 0.0379 |
| Brain | 0.000494 |
| Esophagus | 0.00347 |
| Eyes | 0.00176 |
| Gallbladder Wall | 0.00665 |
| Left colon | 0.00724 |
| Small Intestine | 0.00665 |
| Stomach Wall | 0.00491 |
| Right colon | 0.00536 |
| Rectum | 0.00406 |
| Heart | 0.0196 |
| Kidneys | 0.0501 |
| Liver | 0.152 |
| Lungs | 0.0365 |
| Pancreas | 0.00671 |
| Prostate | 0.00199 |
| Salivary Glands | 0.00184 |
| Red Marrow | 0.00529 |
| Skeleton | 0.00412 |
| Spleen | 0.363 |

TABLE 33-continued

| Absorbed Doses in mGy/MBq for the Human Extrapolated from Mouse Model with isotope Lu-177, based on [$^{177}$Lu]Lu-BL23 in Daudi xenograft mice. | |
|---|---|
| Organ | Lu-177 |
| Testes | 0.0149 |
| Thymus | 0.00268 |
| Thyroid | 0.0022 |
| Urin Blad | 0.00191 |
| Total Body | 0.00753 |

TABLE 34

The in vivo stability of select peptides

| Peptide | Time Point | % Intact Peptide | n |
|---|---|---|---|
| [$^{68}$Ga]Ga-BL02 | 5 mins | >99% | 3 |
| [$^{18}$F]F-BL08 | 5 mins | >99% | 3 |
| [$^{18}$F]F-BL09 | 5 mins | >99% | 3 |
| [$^{177}$Lu]Lu-BL19 | 24 Hrs | >98% | 3 |
| [$^{177}$Lu]Lu-BL19 | 120 Hrs | >93% | 3 |

The present invention has been described with regard to one or more embodiments. However, it will be apparent to persons skilled in the art that a number of variations and modifications can be made without departing from the scope of the invention as defined herein.

What is claimed is:

1. A compound of Formula I or a salt or solvate of Formula I $$[\text{targeting peptide}]\text{-N}(R^1)\text{—}X^1(R^2)L^1\text{-}[\text{linker}]\text{-}R^{X}_{n1} \quad \text{(I)},$$

wherein:

the targeting peptide is cyclo [L-Phe-L-Tyr-L-Lys(iPr)-D-Arg-L-2-Nal-Gly-D-Glu]-L-Lys(iPr) which is C-terminally bonded to —N($R^1$)—;

$R^1$ is H or methyl;

$X^1$ is a linear, branched, or cyclic $C_1$-$C_{15}$ alkylenyl, alkenylenyl or alkynylenyl wherein 0-6 carbons are independently replaced by N, S, or O heteroatoms, and substituted with 0-3 groups independently selected from one or a combination of oxo, hydroxyl, sulfhydryl, halogen, guanidino, carboxylic acid, sulfonic acid, sulfinic acid, or phosphoric acid;

$R^2$ is C(O)OH or C(O)$NH_2$;

$L^1$ is —S—, —NHC(O)—, —C(O)NH—, —N($CH_3$)C(O)—, —C(O)N($CH_3$)—,

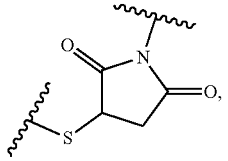

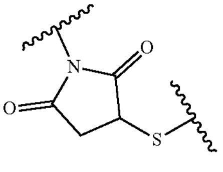
,

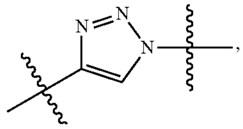
, or

-continued

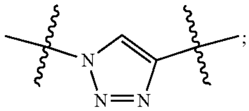;

the linker is a linear or branched chain of 1-10 units of $X^2L^2$ or $X^2(L^2)_2$, wherein:

each $X^2$ is, independently, a linear, branched, or cyclic $C_1$-$C_{15}$ alkylenyl, alkenylenyl or alkynylenyl wherein 0-6 carbons are independently replaced by N, S, or O heteroatoms, and substituted with 0-3 groups independently selected from one or a combination of oxo, hydroxyl, sulfhydryl, halogen, guanidino, carboxylic acid, sulfonic acid, sulfinic acid, or phosphoric acid;

each $L^2$ is independently —S—, —NHC(O)—, —C(O)NH—, —$N(CH_3)C(O)$—, —$C(O)N(CH_3)$—,

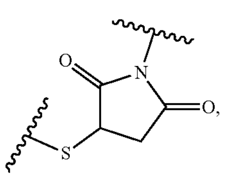, 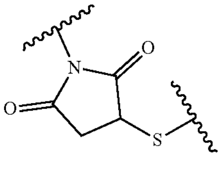,

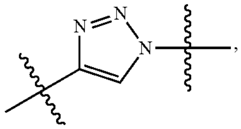, or

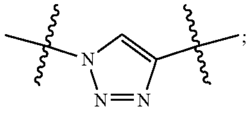;

the linker comprises at least one carboxylic acid, sulfonic acid, sulfinic acid, or phosphoric acid, and has a net negative charge at physiological pH;

the linker optionally further comprises an albumin binder bonded to an $L^2$ of the linker, wherein the albumin binder is: —$(CH_2)_{n2}$—$CH_3$ wherein n2 is 8-20; —$(CH_2)_{n3}$—C(O)OH wherein n3 is 8-20, or

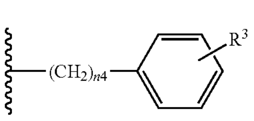

wherein n4=1-4 and $R^3$ is I, Br, F, Cl, H, OH, $OCH_3$, $NH_2$, $NO_2$ or $CH_3$;

n1 is 1 or 2; and each $R^X$ is a radiolabelling group linked through a separate $L_2$ of the linker, and is independently selected from: a metal chelator in complex with a radiometal or radioisotope-bound metal; a prosthetic group containing trifluoroborate ($BF_3$); or a prosthetic group containing a silicon-fluorine-acceptor moiety.

2. The compound of claim 1, wherein $X^1$ is a linear, branched, or cyclic $C_1$-$C_{15}$ alkylenyl.

3. The compound of claim 2, wherein $X^1$ is

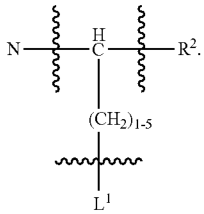.

4. The compound of claim 1, wherein —$N(R^1)$—$X^1(R^2)L^1$- forms a sidechain-linked amino acid residue selected from Lys, ornithine, 2,3-diaminopropionic acid (Dap), 2,4-diaminobutyric acid (Dab), Glu, Asp, or 2-aminoadipic acid (2-Aad).

5. The compound of claim 1, wherein $R^1$ is H.

6. The compound of claim 1, wherein $L^1$ is —NHC(O)— or —C(O)NH—.

7. The compound of claim 1, wherein the linker consists of 1-8 units of $X^2L^2$ and 0-2 units of $X^2(L^2)_2$.

8. The compound of claim 1, wherein each $X^2$ is independently a linear, branched, cyclic $C_1$-$C_{15}$ alkylenyl.

9. The compound of claim 6, wherein each $X^2$ is independently:

—CH—;

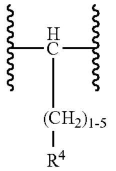

wherein each $R^4$ is independently carboxylic acid, sulfonic acid, sulfinic acid, or phosphoric acid; or

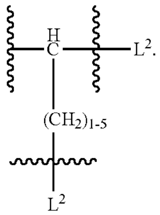.

10. The compound of claim 9, wherein each $L^2$ between two $X^2$ groups is independently —NHC(O)—, —C(O)NH—, —$N(CH_3)C(O)$—, or —$C(O)N(CH_3)$—, and each $L^2$ linking an $R^X$ is independently —S—, —NHC(O)—, —C(O)NH—, —$N(CH_3)C(O)$—, —$C(O)N(CH_3)$—,

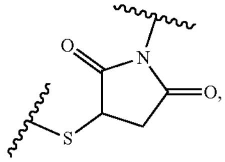, 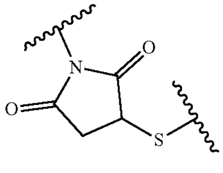,

-continued

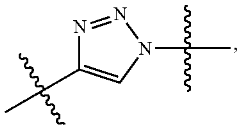

, or

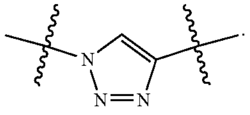

11. The compound of claim 1, wherein the linker is a linear or branched peptide of 2-7 amino acid residues selected from one or a combination of proteinogenic amino acid residues or nonproteinogenic amino acid residues, wherein the nonproteinogenic amino acid residue is selected from D-Ala, D-Arg, D-Asn, D-Asp, D-Cys, D-Glu, D-Gln, D-His, D-Ile, D-Leu, D-Lys, D-Met, D-Phe, D-Pro, D-Ser, D-Thr, D-Trp, D-Tyr, D-Val, ornithine, 3-(1-naphtyl) alanine, 3-(2-naphtyl) alanine, α-aminobutyric acid, norvaline, norleucine, homonorleucine, beta-(1,2,3-triazol-4-yl)-L-alanine, 1,2,4-triazole-3-alanine, Phe (4-F), Phe (4-Cl), Phe (4-Br), Phe (4-I), Phe (4-$NH_2$), Phe (4-$NO_2$), homoarginine, 4-(2-aminoethyl)-1-carboxymethyl-piperazine, 2-(5'-azidopentyl) alanine, 2-(6'-azidohexyl) alanine, 2-amino-4-guanidinobutyric acid, 2-amino-3-guanidinopropionic acid, β-alanine, 4-aminobutyric acid, 5-aminovaleric acid, 6-aminohexanoic acid, 7-aminoheptanoic acid, 8-aminooctanoic acid, 9-aminononanoic acid, 10-aminodecanoic acid, 2-aminooctanoic acid, 2-amino-3-(anthracen-2-yl) propanoic acid, 2-amino-3-(anthracen-9-yl) propanoic acid, 2-amino-3-(pyren-1-yl) propanoic acid, Trp (5-Br), Trp (5-$OCH_3$), Trp (6-F), Trp (5-OH), Trp (CHO), 2-aminoadipic acid, 3-aminoadipic acid, propargylglycine, homopropargylglycine, beta-homopropargylglycine, 2,3-diaminopropionic acid, 2,4-diaminobutyric acid, azidolysine, azido-ornithine, amino-4-azidobutanoic acid, Dab ($N_3$), tranexamic acid, 4-amino-1-carboxymethyl-piperidine, $NH_2(CH_2)2O(CH_2)^2$ C(O)OH, $NH_2(CH_2)_2[O(CH_2)_2]C(O)OH$, $NH_2(CH_2)_2[O(CH_2)_2]_3C(O)OH$, $NH_2(CH_2)_2[O(CH_2)_2]_4C(O)OH$, $NH_2(CH_2)_2[O(CH_2)_2]_5C(O)OH$, or $NH_2(CH_2)_2[O(CH_2)_2]_6C(O)OH$;

wherein each $L^2$ between two $X^2$ groups is methylated or unmethylated, and wherein each $L^2$ linking an $R^X$ is independently —S—, —NHC(O)—, —C(O)NH—, —$N(CH_3)C(O)$—, —$C(O)N(CH_3)$—

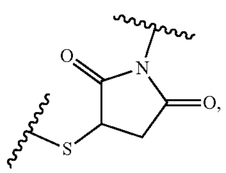

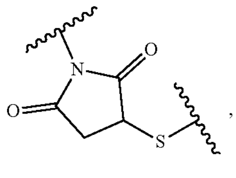

,

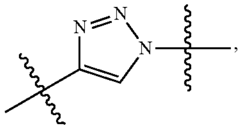

, or

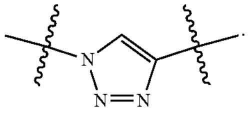

12. The compound of claim 11, wherein each $L^2$ between two $X^2$ groups is an unmethylated amide.

13. The compound of claim 1, wherein the linker comprises 2 or 3 amino acids selected from one or a combination of: Glu, Asp, or 2-aminoadipic acid (2-Aad).

14. The compound of claim 13, wherein the linker comprises 3 consecutive Glu residues.

15. The compound of claim 1, wherein the linker has a net negative charge of −2 to −5 at physiological pH.

16. The compound of claim 1, wherein the linker further comprises the albumin binder.

17. The compound of claim 1, wherein each $L^2$ linking an $R^X$ is independently —NHC(O)—, —C(O)NH—,

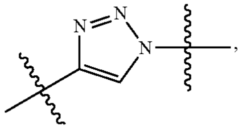

, or

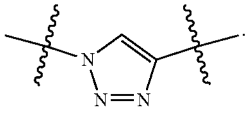

18. The compound of claim 1, wherein n1 is 1.

19. The compound of claim 1, wherein n1 is 2.

20. The compound of claim 19, comprising both the metal chelator and the prosthetic group containing $BF_3$.

21. The compound of claim 19, comprising two prosthetic groups each containing a $BF_3$.

22. The compound of claim 1, wherein a prosthetic group containing $BF_3$ is —$R^6R^7BF_3$ wherein $R^6$ is —$(CH_2)_{1-5}$— and —$R^7BF_3$ is selected from Table 3 or 4 or is wherein each $R^8$

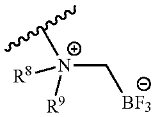

and each $R^9$ are independently a branched or linear $C_1$-$C_5$ alkyl.

23. The compound of claim 22, wherein —$R^7BF_3$ is

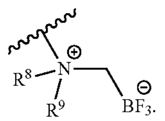

24. The compound of claim 23, wherein $R^8$ and $R^9$ are each methyl.

25. The compound of claim 1, wherein the prosthetic group containing $BF_3$ comprises $^{18}F$.

26. The compound of claim 1, wherein at least one $R^X$ is a metal chelator in complex with a radiometal or radioisotope-bound metal.

27. The compound of claim 26, wherein the metal chelator is a polyaminocarboxylate chelator.

28. The compound of claim 27, wherein the metal chelator is DOTA or a DOTA derivative.

29. The compound of claim 1, which has the structure selected from:

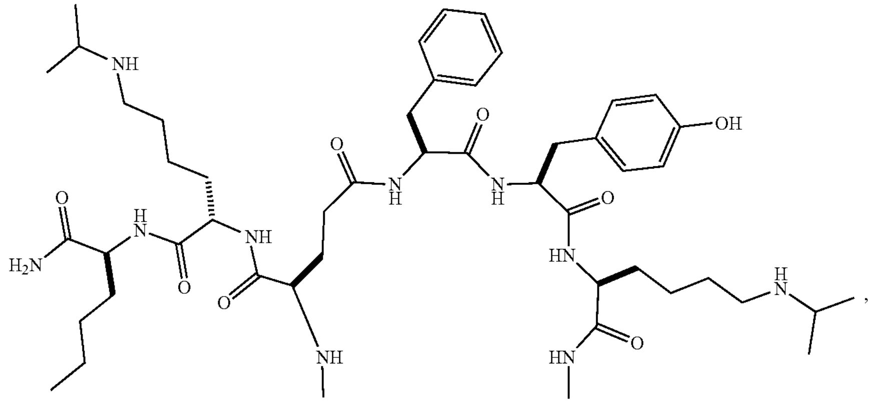,
(BL02)
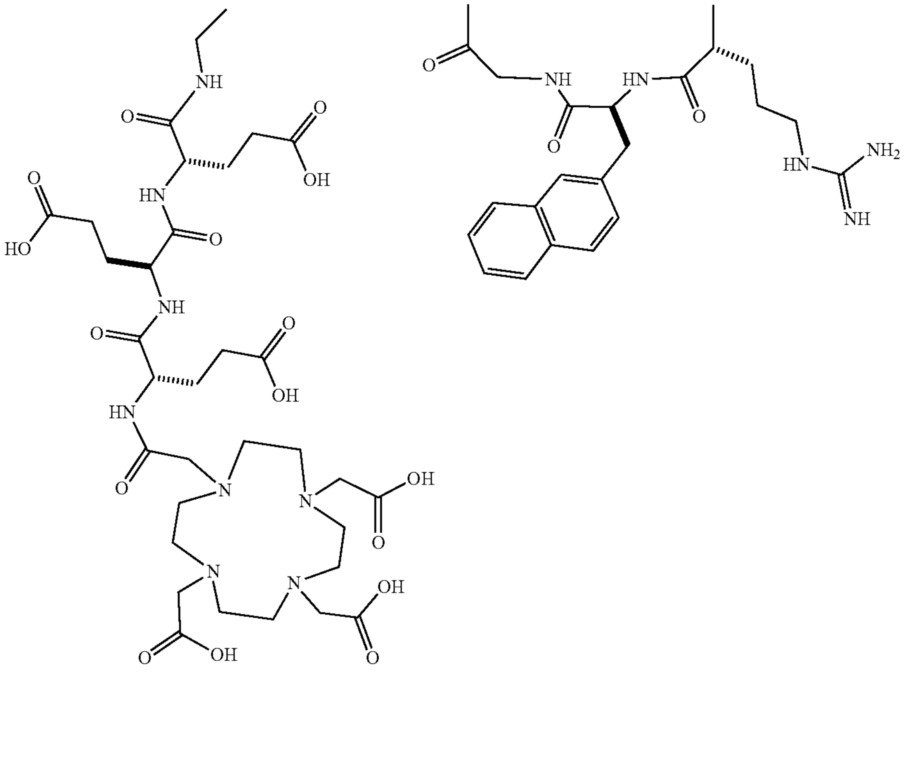

-continued
(BL03)
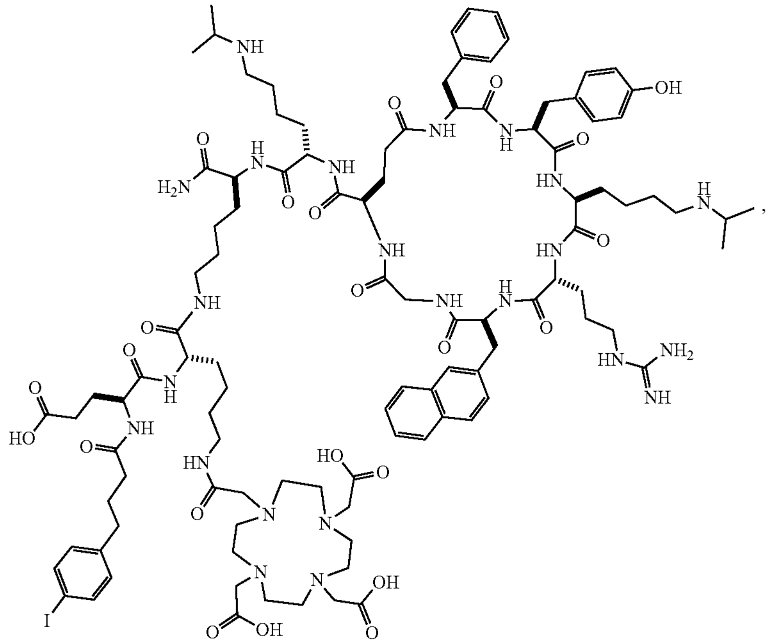
(BL04)
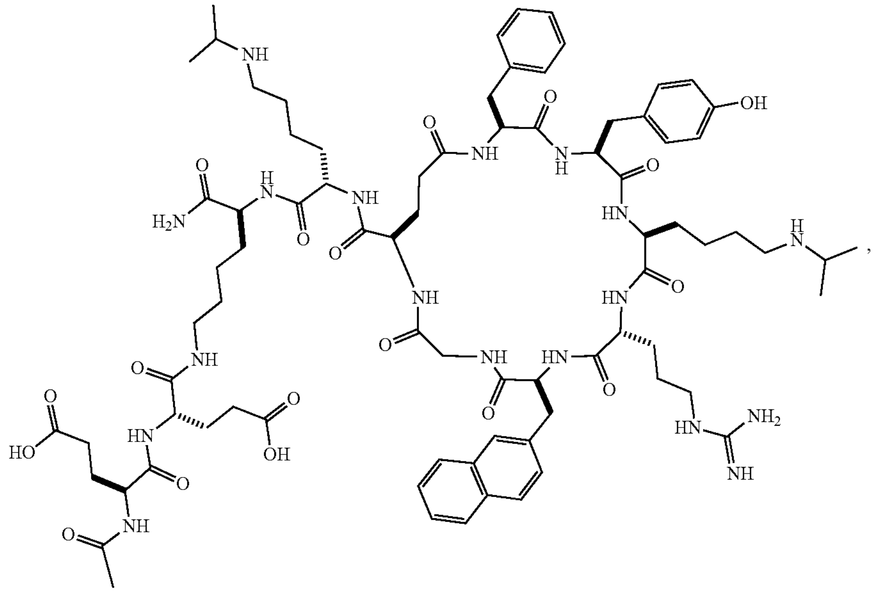

-continued
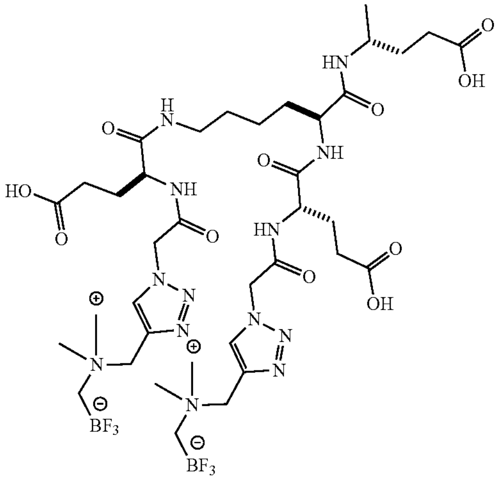
(BL07)
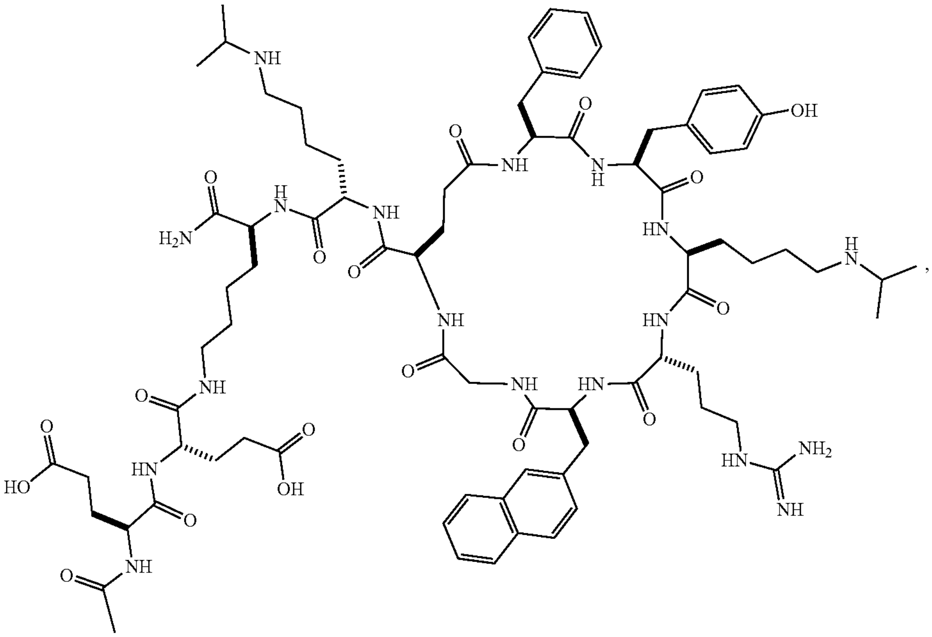
,

-continued
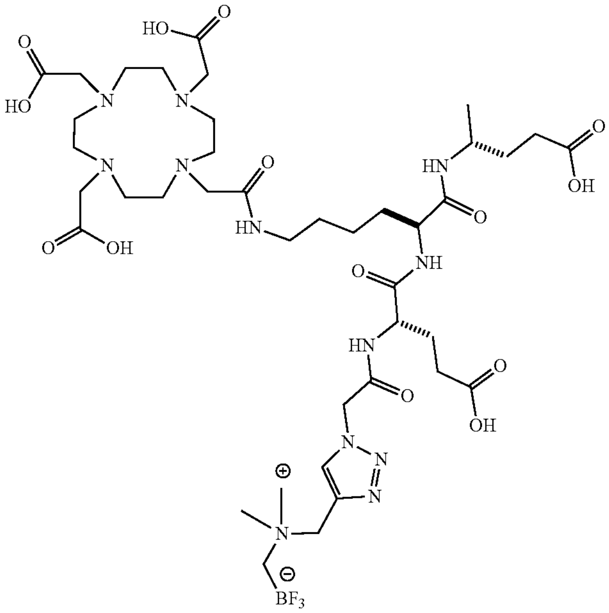
(BL08)
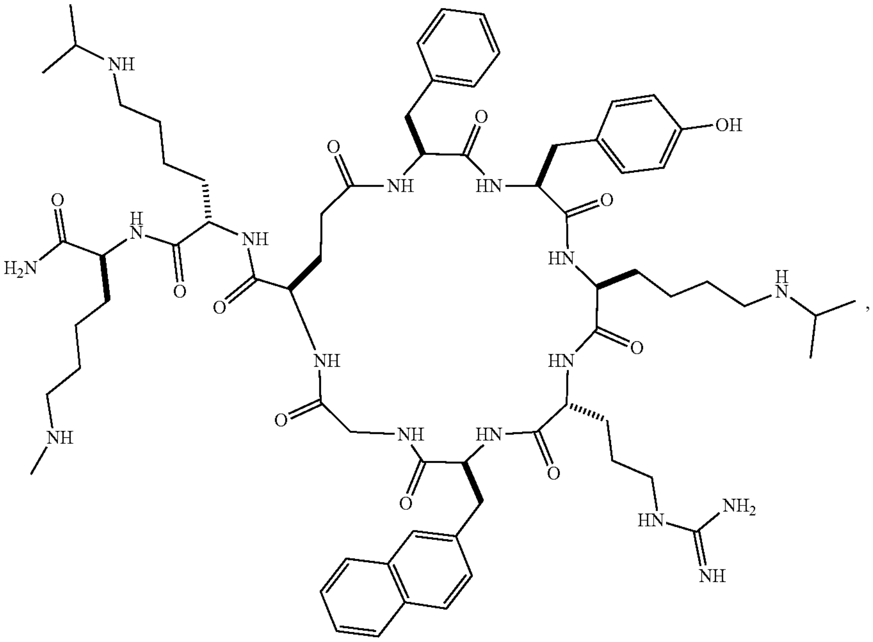
,

-continued
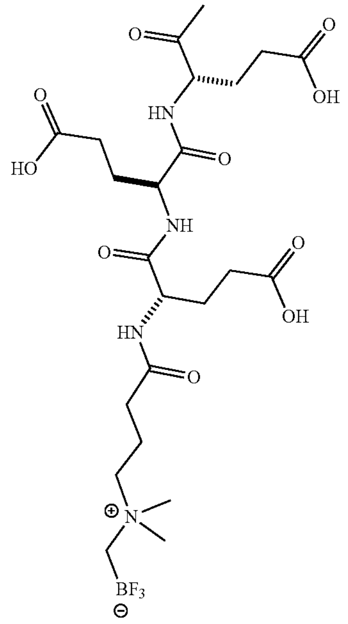
(BL09)
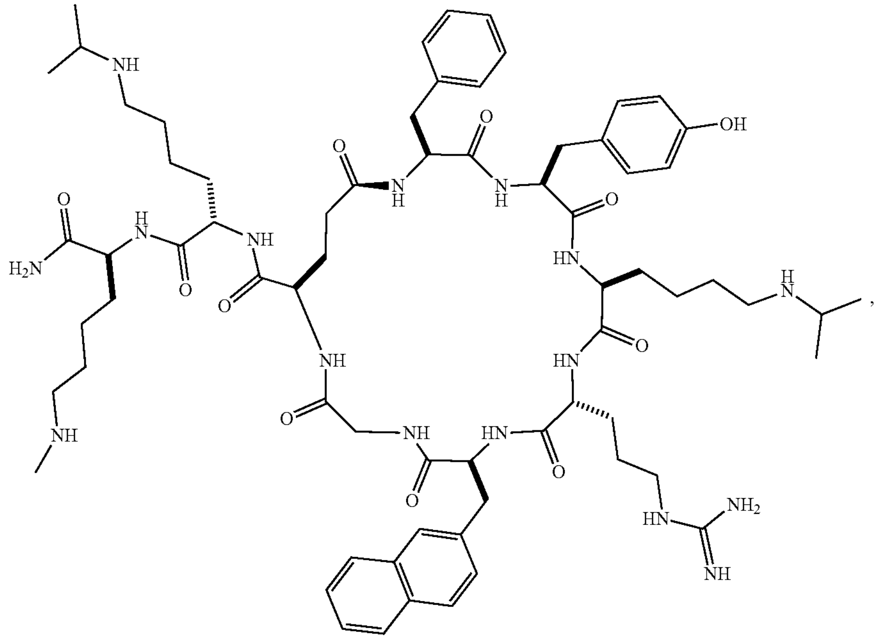
,

-continued
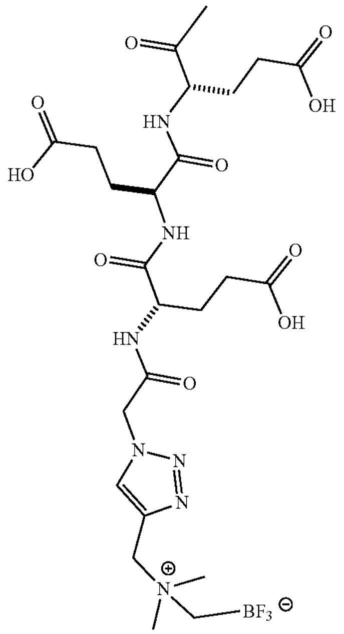
(BL017)
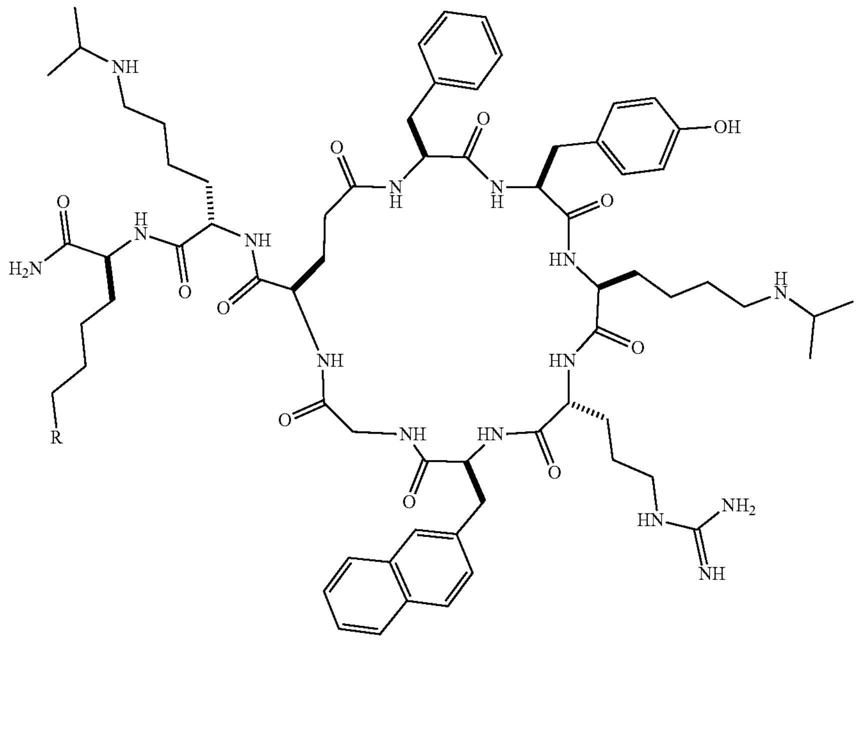

-continued
R =
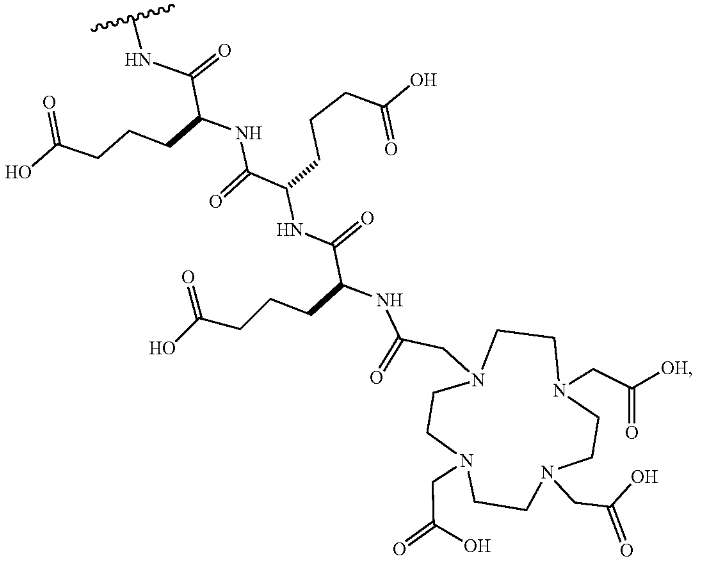
(BL18)
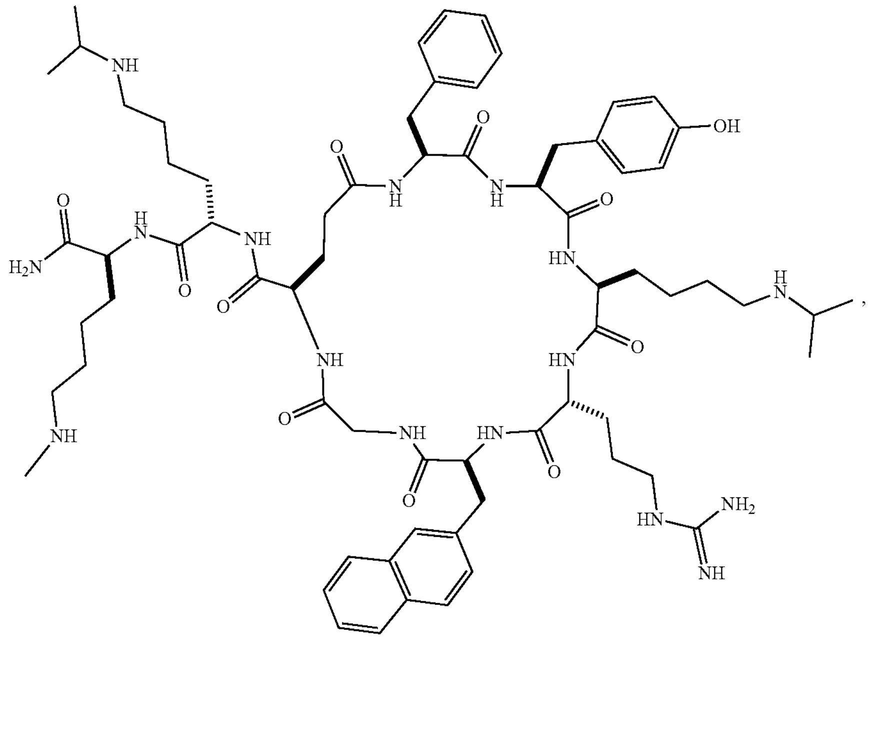
,

-continued
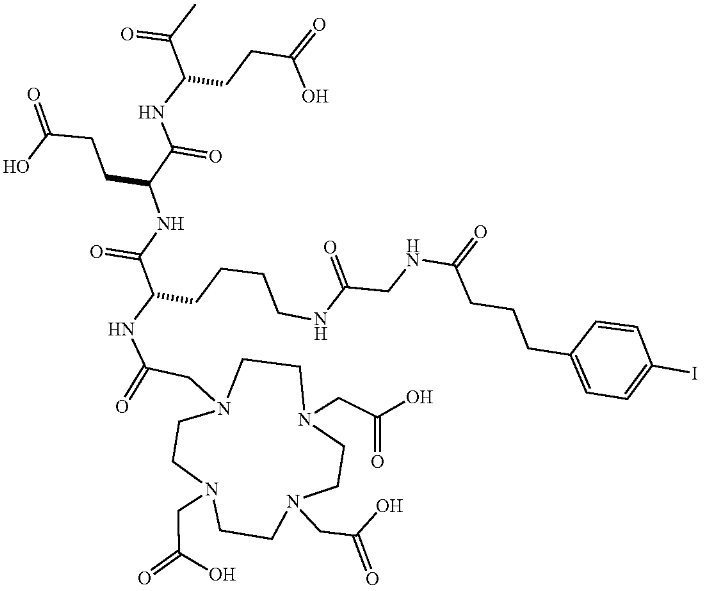
(BL19)
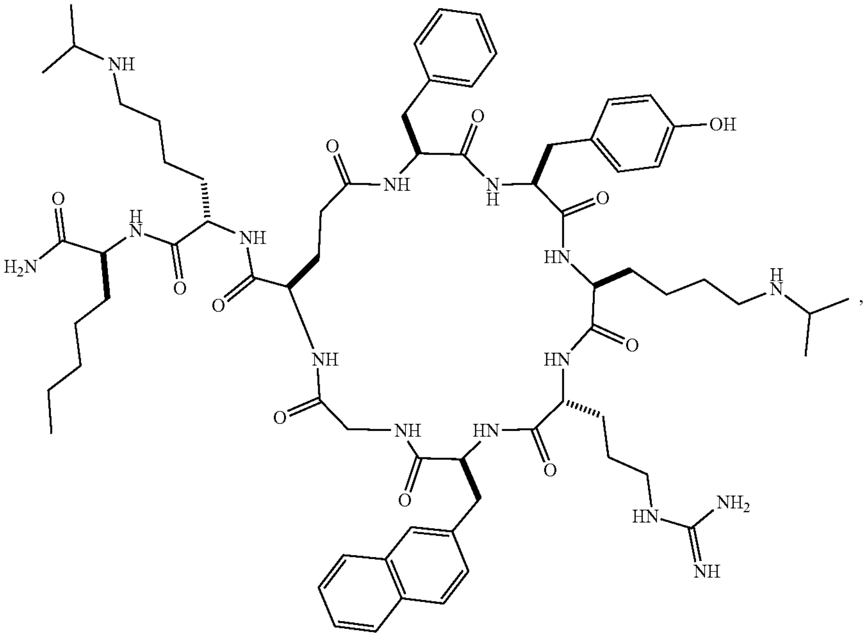
,

-continued
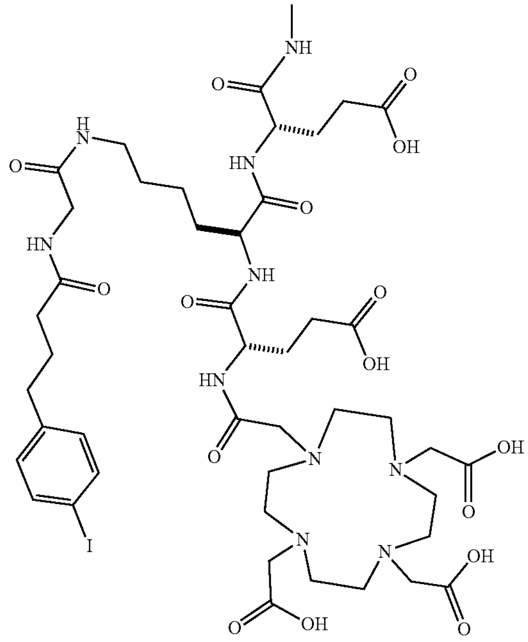
(BL020)
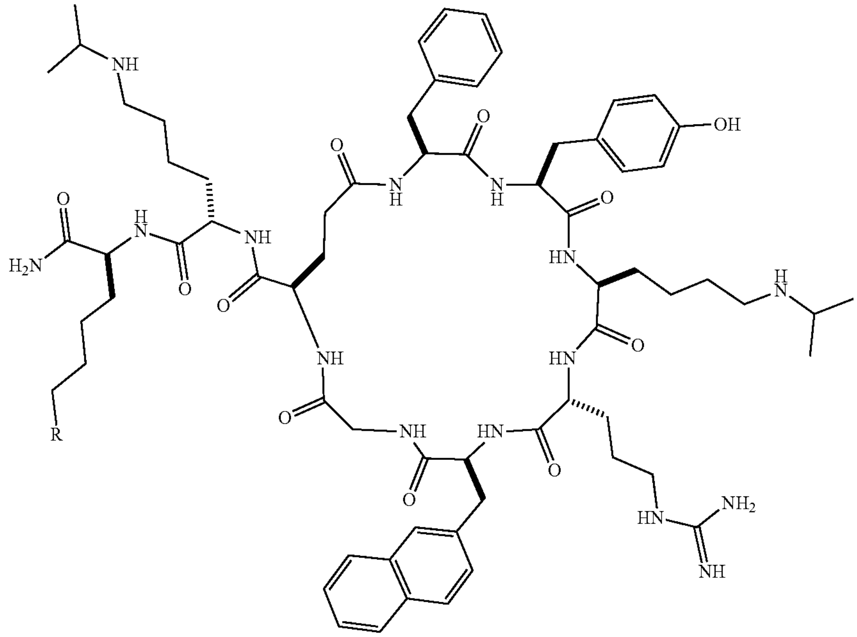

-continued
R = 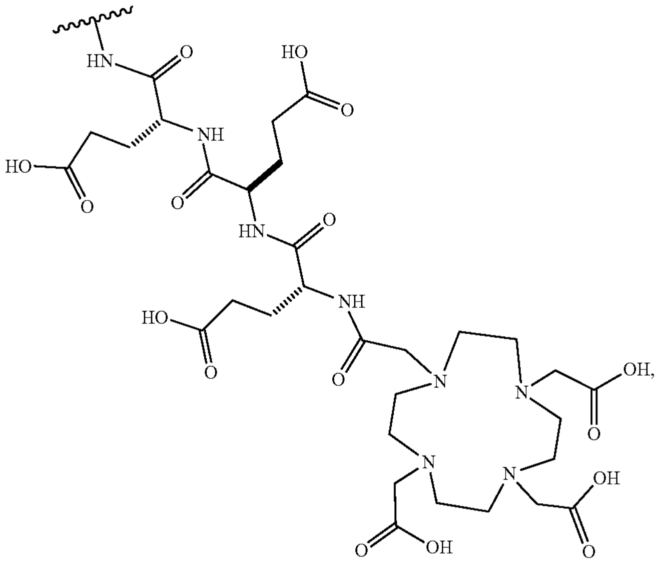
(BL21)
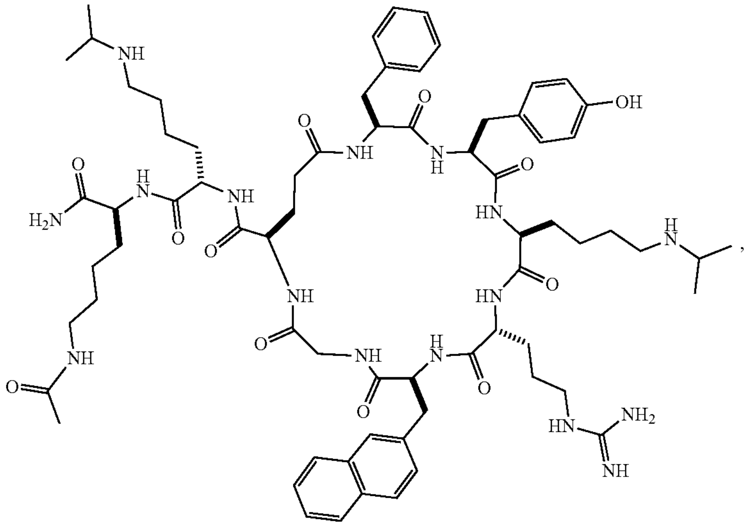
,
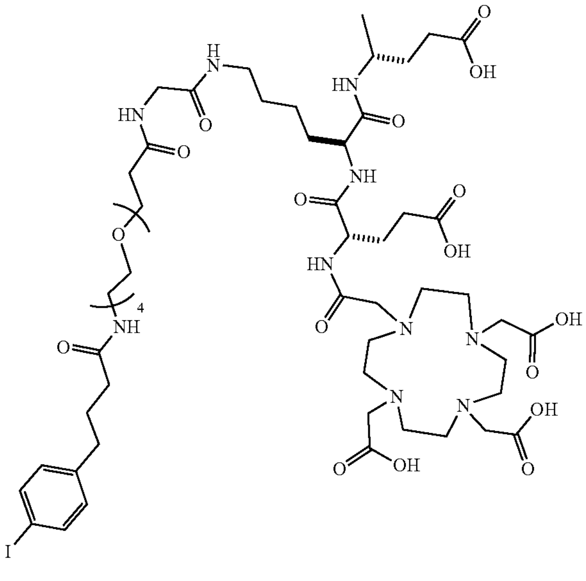

-continued
(BL22)
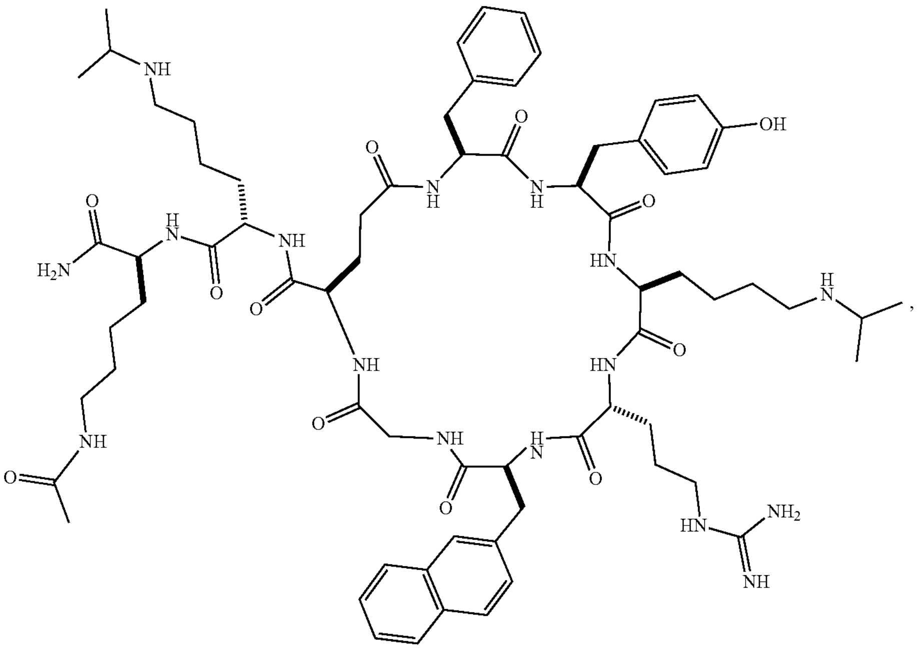
,
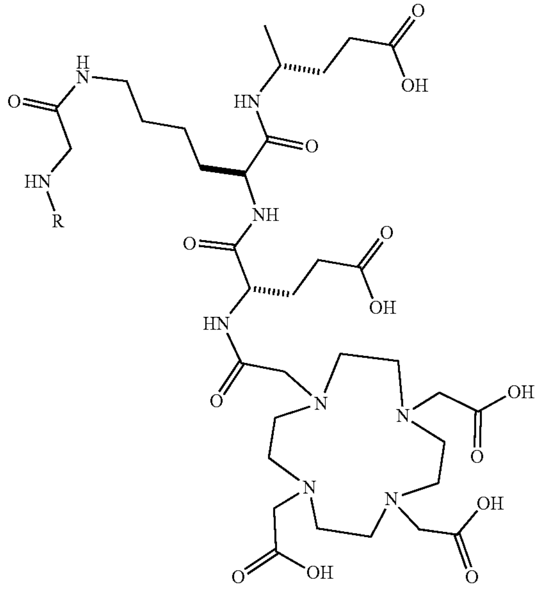
R =
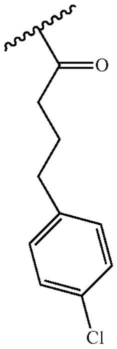

(BL23)
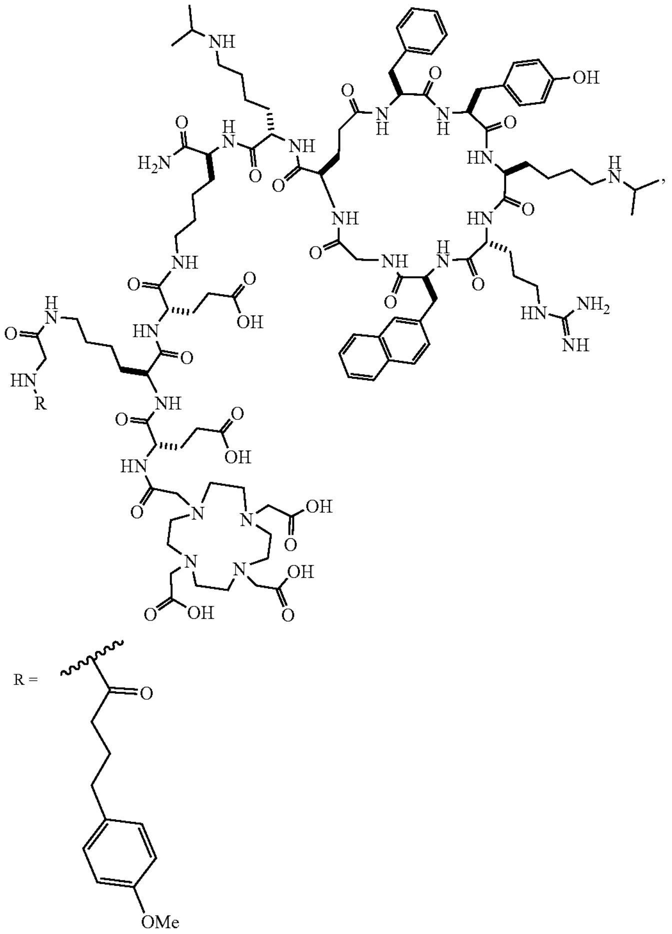
(BL24)
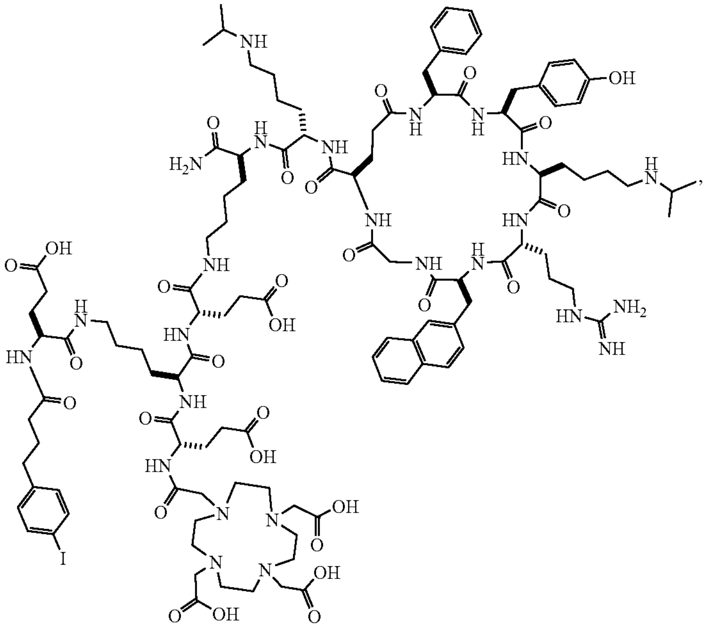

-continued
(BL25)
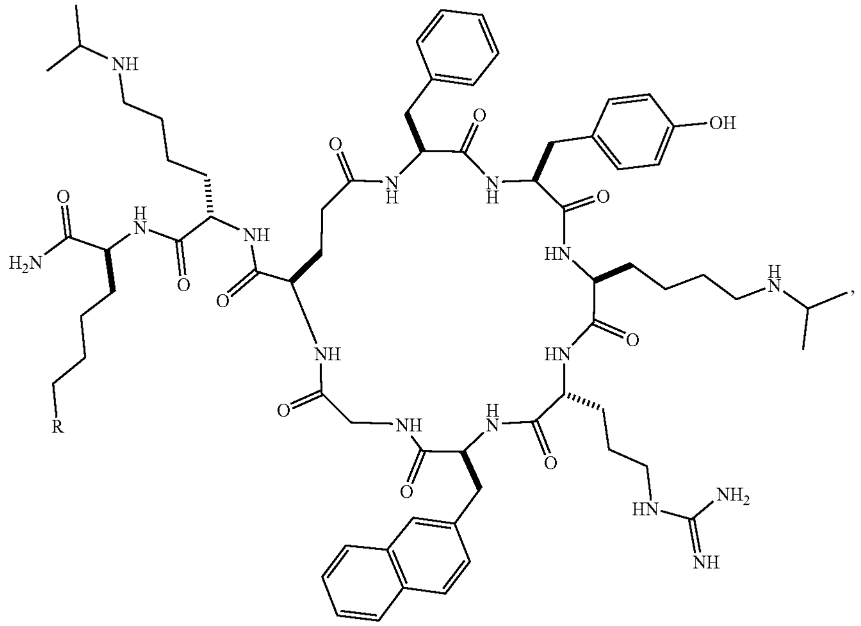
R =
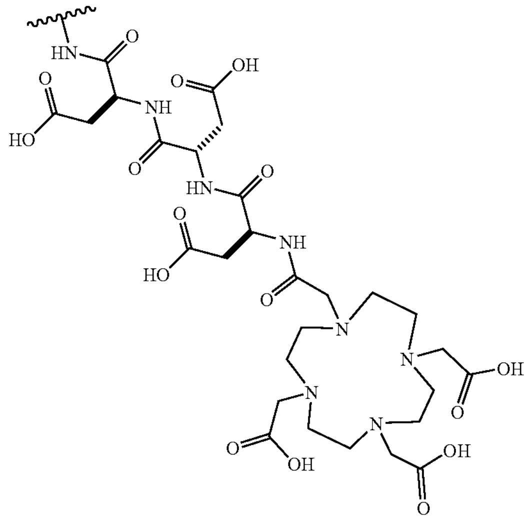

-continued
(BL26)
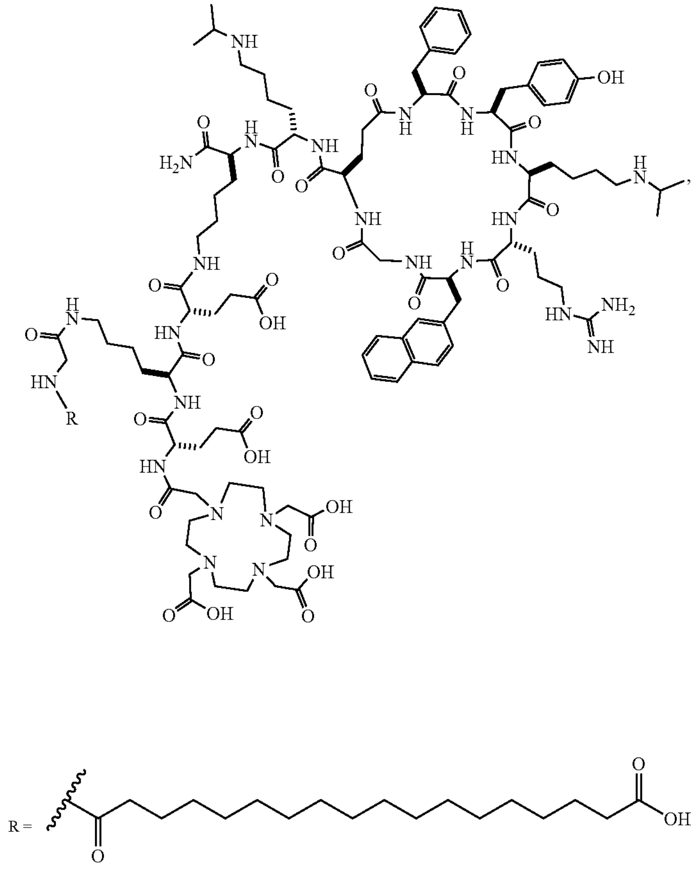
(BL27)
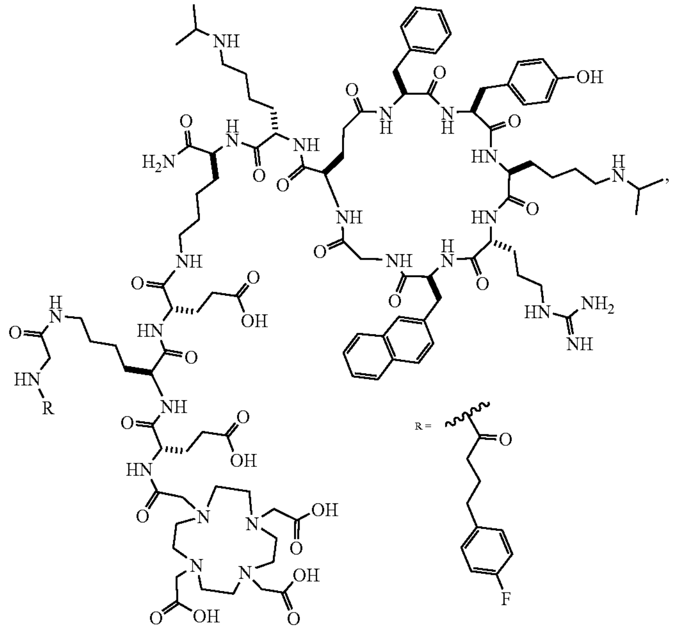

-continued
(BL28)
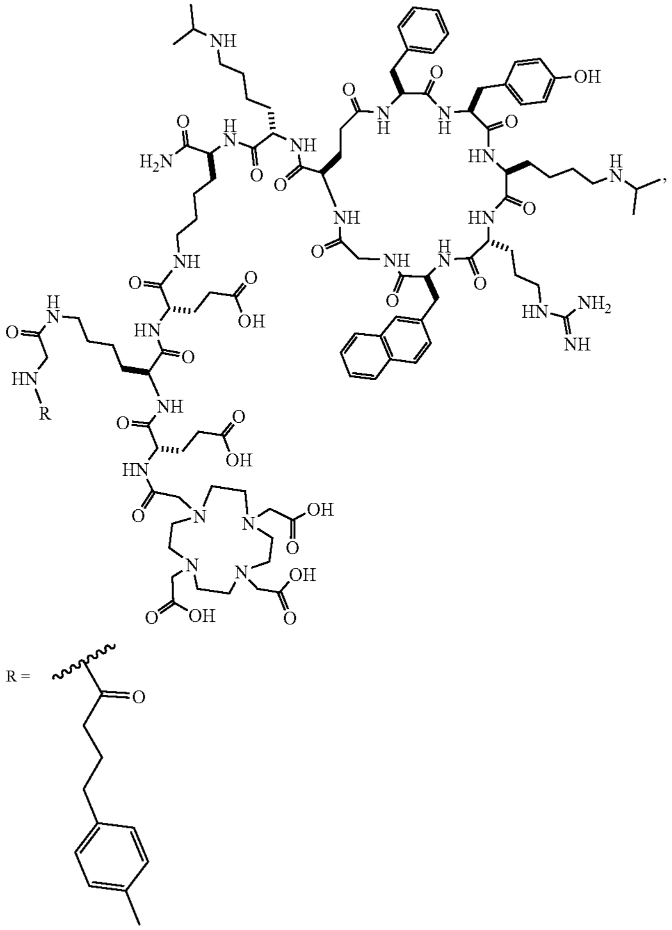
, or
(BL29)
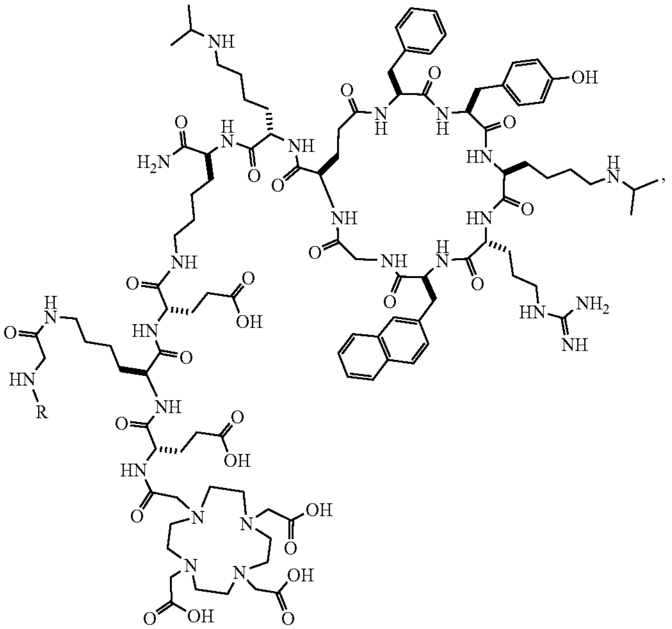
,

-continued

R = 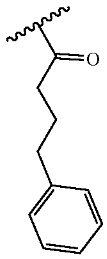

or a salt or solvate thereof, wherein DOTA is in complex with a radioisotope or wherein the prosthetic group containing $BF_3$ comprises $^{18}F$.

30. A method of imaging a CXCR4-expressing tissue or imaging an inflammatory condition or disease in a subject, comprising administering to the patient in need of imaging an effective amount of a compound of claim 1; and imaging the CXCR-4 expressing tissue or the inflammatory condition or disease;

wherein at least one $R^X$ comprises or is complexed with an imaging radioisotope; and wherein the inflammatory condition or disease is selected from the group consisting of infectious bone diseases, urinary tract infections, myocardial infarctions, ischemic strokes, rheumatoid arthritis, non-Hodgkin lymphoma, lymphoma, multiple myeloma, leukemia, adrenocortical cancer, lung cancer, breast cancer, renal cell cancer, prostate cancer, and colorectal cancer.

31. A method of treating a disease or condition characterized by expression of CXCR4 in a subject, comprising administering to the patient in need thereof a therapeutically effective amount of a compound of claim 1;

wherein at least one $R^X$ comprises or is complexed with a therapeutic radioisotope; and wherein the disease or condition is selected from the group consisting of infectious bone diseases, urinary tract infections, myocardial infarctions, ischemic strokes, rheumatoid arthritis, non-Hodgkin lymphoma, lymphoma, multiple myeloma, leukemia, adrenocortical cancer, lung cancer, breast cancer, renal cell cancer, prostate cancer, and colorectal cancer.

* * * * *